US011279928B2

(12) United States Patent
Yin et al.

(10) Patent No.: US 11,279,928 B2
(45) Date of Patent: Mar. 22, 2022

(54) COMPOSITIONS COMPRISING NUCLEIC ACIDS AND METHODS OF USING THE SAME

(71) Applicant: Massachusetts Institute of Technology, Cambridge, MA (US)

(72) Inventors: Hao Yin, Cambridge, MA (US); Daniel G. Anderson, Framingham, MA (US); Robert Samuel Langer, Newton, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 0 days.

(21) Appl. No.: 15/741,211

(22) PCT Filed: Jun. 29, 2016

(86) PCT No.: PCT/US2016/040221
§ 371 (c)(1),
(2) Date: Dec. 29, 2017

(87) PCT Pub. No.: WO2017/004279
PCT Pub. Date: Jan. 5, 2017

(65) Prior Publication Data

US 2018/0187186 A1 Jul. 5, 2018

Related U.S. Application Data

(60) Provisional application No. 62/290,907, filed on Feb. 3, 2016, provisional application No. 62/243,589, filed on Oct. 19, 2015, provisional application No. 62/186,358, filed on Jun. 29, 2015.

(51) Int. Cl.

| | |
|---|---|
| ***C12N 15/11*** | (2006.01) |
| ***C12N 9/22*** | (2006.01) |
| ***A61K 48/00*** | (2006.01) |
| ***C12N 9/96*** | (2006.01) |
| ***C12N 15/90*** | (2006.01) |
| ***C07H 21/02*** | (2006.01) |
| ***C07H 21/04*** | (2006.01) |

(52) U.S. Cl.
CPC ............ *C12N 15/11* (2013.01); *A61K 48/005* (2013.01); *C07H 21/02* (2013.01); *C07H 21/04* (2013.01); *C12N 9/22* (2013.01); *C12N 9/96* (2013.01); *C12N 15/907* (2013.01); *C12N 2310/20* (2017.05); *C12N 2310/322* (2013.01); *C12N 2800/80* (2013.01)

(58) Field of Classification Search
None
See application file for complete search history.

(56) References Cited

U.S. PATENT DOCUMENTS

| | | | | |
|---|---|---|---|---|
| 2014/0068797 | A1 | 3/2014 | Doudna et al. | |
| 2014/0142160 | A1 | 5/2014 | Lee et al. | |
| 2014/0242664 | A1* | 8/2014 | Zhang | C12N 15/01 435/188 |
| 2014/0273232 | A1 | 9/2014 | Zhang et al. | |
| 2015/0059010 | A1* | 2/2015 | Cigan | C12N 15/8213 800/260 |
| 2015/0128300 | A1 | 5/2015 | Warming et al. | |
| 2015/0232883 | A1* | 8/2015 | Dahlman | C12N 9/22 435/462 |
| 2016/0024524 | A1* | 1/2016 | Joung | C12N 9/22 435/462 |
| 2017/0044536 | A1* | 2/2017 | Collingwood | C12N 15/111 |
| 2019/0048338 | A1 | 2/2019 | Yin et al. | |
| 2019/0233816 | A1 | 8/2019 | Langer et al. | |

FOREIGN PATENT DOCUMENTS

| | | | |
|---|---|---|---|
| WO | 2013/176772 | A1 | 11/2013 |
| WO | 2014/204578 | A1 | 12/2014 |
| WO | 2015/191693 | A2 | 12/2015 |
| WO | 2016/089433 | A1 | 6/2016 |
| WO | 2016/100951 | A2 | 6/2016 |
| WO | 2016/123230 | A1 | 8/2016 |
| WO | 2016/164356 | A1 | 10/2016 |
| WO | 2016/186745 | A1 | 11/2016 |
| WO | 2017/004261 | A1 | 1/2017 |
| WO | 2017/004279 | A2 | 1/2017 |
| WO | 2017/068377 | A1 | 4/2017 |

(Continued)

OTHER PUBLICATIONS

International Preliminary Report on Patentability and Written Opinion for PCT/US 2016/040221 dated Jan. 2, 2018, pp. 1-18.
U.S. Appl. No. 16/256,006, filed Jan. 24, 2019, Pending.
Handel et al., Chemically modified guide RNAs enhance CRISPR-Cas genome editing in human primary cells. Nat Biotechnol. Sep. 2015;33(9):985-989.
Mir et al., Heavily and fully modified RNAs guide efficient SpyCas9-mediated genome editing. Nat Commun. Jul. 6, 2018;9(1):2641, 9 pages.

(Continued)

*Primary Examiner* — Antonio Galisteo Gonzalez
(74) *Attorney, Agent, or Firm* — McCarter & English, LLP

(57) ABSTRACT

The disclosure relates to compositions comprising and methods for chemical modification of single guide RNA (sgRNA), tracrRNA and/or crRNA used individually or in combination with one another or Cas system components. Compositions comprising modified ribonucleic acids have been designed with chemical modification for even higher efficiency as unmodified native strand of sgRNA. Administration of modified ribonucleic acids will allow decreased immune response when administered to a subject, increased stability, increased editing efficiency and facilitated in vivo delivery of sgRNA via various delivery platforms. The disclosure also relates to methods of decreasing off-target effect of CRISPR and a CRISPR complex.

20 Claims, 48 Drawing Sheets

Specification includes a Sequence Listing.

(56) References Cited

FOREIGN PATENT DOCUMENTS

| | | |
|---|---|---|
| WO | 2017/136794 A1 | 8/2017 |
| WO | 2018/057946 A2 | 3/2018 |
| WO | 2018/107028 A1 | 6/2018 |

OTHER PUBLICATIONS

Rahdar et al., Synthetic CRISPR RNA-Cas9-guided genome editing in human cells. Proc Natl Acad Sci U S A. Dec. 22, 2015;112(51):E7110-7.
Ueda et al., Establishment of rat embryonic stem cells and making of chimera rats. PLoS One. Jul. 30, 2008;3(7):e2800, 9 pages.
Yin et al., Partial DNA-guided Cas9 enables genome editing with reduced off-target activity. Nat Chem Biol. Mar. 2018;14(3):311-316.
International Search Report and Written Opinion for Application No. PCT/US2019/014865, dated Apr. 26, 2019, 16 pages.
International Search Report for Application No. PCT/US2016/040221, dated Jan. 9, 2017, 6 pages.
International Search Report and Written Opinion for Application No. PCT/US2017/016608, dated Jun. 21, 2017, 20 pages.

* cited by examiner

GFP-1 (sgRNA1; no modification RNA requence from 5' to 3')
GGGCGAGGAGCUGUUCACCGGUUUUAGAGCUAGAAAUAGCAAGUUAAAAUAAGG
CUAGUCCGUUAUCAACUUGAAAAAGUGGCACCGAGUCGGUGCUUUUU
(SEQ ID NO:1)

GFP-2 (sgRNA2; 2 F modification RNA at 3 end: Uf and Cf at 3 end)
GGGCGAGGAGCUGUUCACCGGUUUUAGAGCUAGAAAUAGCAAGUUAAAAUAAGG
CUAGUCCGUUAUfCfAACfUfUfGAAAAAGUfGGCfACfCfGAGUfCfGGUfGCfUfUfUfUfUf
(SEQ ID NO:2)

GFP-3 (sgRNA3; 2 F modification RNA at 5 end: Gf, Uf, and Cf at 5 end)
GfGfGfCfGfAGGAGCfUfGUfUfCACCGGUUUUAGAGCUAGAAAUAGCAAGUUAAAAU
AAGGCUAGUCCGUUAUCAACUUGAAAAAGUGGCACCGAGUCGGUGCUUUUU
(SEQ ID NO:3)

FIG. 2

GFP-4 (2 F modification RNA at middle: Uf and Cf at middle)
GGGCGAGGAGCUGUUCACCGGUfUfUfUfAGAGCfUfAGAAAUfAGCfAAGUfUfAAAAUfAAGGCfUfAGUfCfCfGUUAUCAACUUGAAAAAGUGGCACCGAGUCGGUGCUUUUU
(SEQ ID NO: 4)

GFP-5 (2 F modification RNA at middle and 3' end: Uf and Cf at middle and 3' end)
GGGCGAGGAGCUGUUCACCGGUfUfUfUfAGAGCfUfAGAAAUfAGCfAAGUfUfAAAAUfAAGGCfUfAGUfCfCfGUfUfAUfCfAACfUfUfGAAAAAGUfGGCfACfCfGAGUfCfGGUfGCfUfUfUfUfUf
(SEQ ID NO: 5)

GFP-6 (2 F modification RNA at 5' end: Gf, Uf, and Cf at 5' end with seed)
GfGfGfCfGAGGAGCfUfGUfUfCfACfCfGGUUUUAGAGCUAGAAAUAGCAAGUUAAAAUAAGGCUAGUCCGUUAUCAACUUGAAAAAGUGGCACCGAGUCGGUGCUUUUU
(SEQ ID NO: 6)

GFP-7 (2 F modification RNA; all with Uf and Cf)
GfGfGfCfGAGGAGCfUfGUfUfCfACfCfGGUfUfUfUfAGAGCfUfAGAAAUfAGCfAAGUfUfAAAAUfAAGGCfUfAGUfCfCfGUfUfAUfCfAACfUfUfGAAAAAGUfGGCfACfCfGAGUfCfGGUfGCfUfUfUfUfUf
(SEQ ID NO: 7)

GFP-8 (2 F modification RNA at 3' end and 5' end)
GfGfGfCfGAGGAGCfUfGUfUfCACCGGUUUUAGAGCUAGAAAUAGCAAGUUAAAAUAAGGCUAGUCCGUUAUfCfAACfUfUfGAAAAAGUfGGCfACfCfGAGUfCfGGUfGCfUfUfUfUfUf
(SEQ ID NO: 8)

GFP-9 (u and c: 2'-O-methyl modification RNA)
GGGCGAGGAGCUGUUCACCGGUUUUAGAGCUAGAAAUAGCAAGUUAAAAUAAGGCUAGUCCGuuAucAAcuuGAAAAAGuGGcAccGAGucGGuGcuuuuu
(SEQ ID NO: 9)

GFP-10 (u and c: 2'-O-methyl modification RNA)
GGGCGAGGAGCUGUUCACCGGUUUUAGAGcuaGaaAuagCAAGUUAAAAUAAGGCUAGUCCGUUAUCAacuugaaaaaguGGCACCGAGUCGGUGCUUUUU
(SEQ ID NO: 10)

FIG. 5B

Cas9 programmed by crRNA:tracrRNA duplex
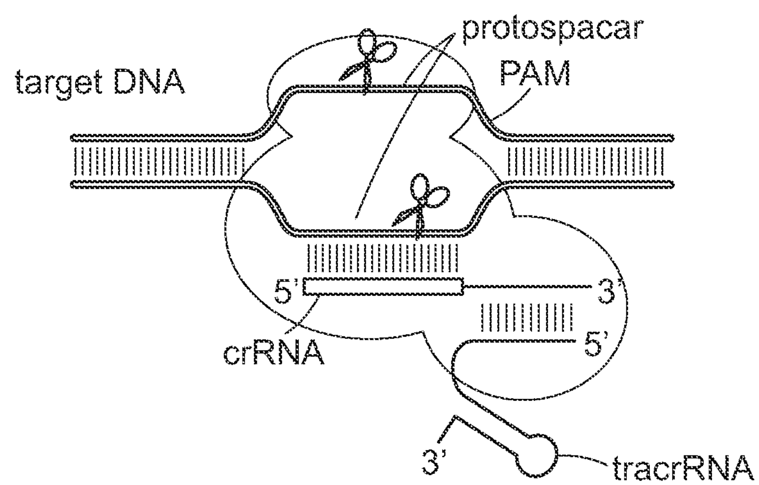
Cas9 programmed by single chimeric RNA
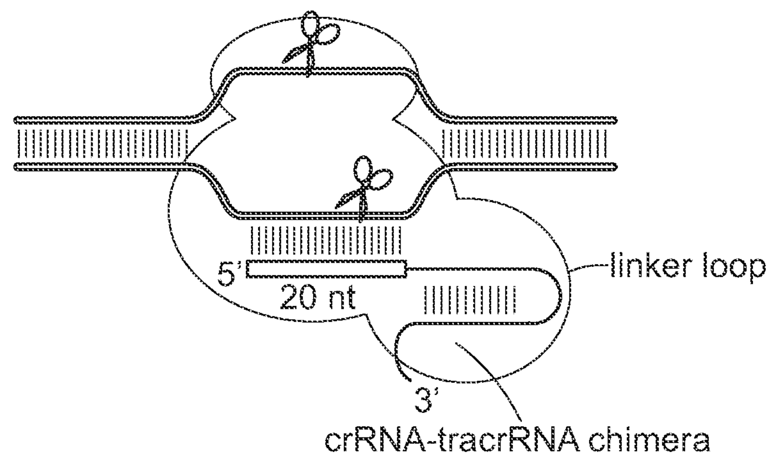
FIG. 7 crRNA-GFP-1 (SEQ ID NO: 31)
GGGCGAGGAGCUGUUCACCGGUUUUAGAGCUAUGCUGUUUUG

TracrRNA (SEQ ID NO: 32)
AAACAGCAUAGCAAGUUAAAAUAAGGCUAGUCCGUUAUCAACUUGAAAAAGUGGCACCGAGUCGG
UGCUUUUUUU crRNA-GFP-3: All DNA (SEQ ID NO: 33)
GGGCGAGGAGCTGTTCACCGrGrUrUrUrUrArGrArGrCrUrArUrGrCrUrGrUrUrUrUrG crRNA-GFP-4: 10 nt DNA (SEQ ID NO: 34)
GGGCGAGGAGrCrUrGrUrUrCrArCrCrGrGrUrUrUrUrArGrArGrCrUrArUrGrCrUrGrUrUrUrUrG crRNA-GFP-7 (SEQ ID NO: 35)
GGGCGAGGAGCTGTTCACrCrGrGrUrUrUrUrArGrArGrCrUrArUrGrCrUrGrUrUrUrUrG crRNA-GFP-8 (SEQ ID NO: 36)
GGGCGAGGAGCTGTTCrArCrCrGrGrUrUrUrUrArGrArGrCrUrArUrGrCrUrGrUrUrUrUrG crRNA-GFP-9 (SEQ ID NO: 37)
GGGCGAGGAGCTGTrUrCrArCrCrGrGrUrUrUrUrArGrArGrCrUrArUrGrCrUrGrUrUrUrUrG crRNA-GFP-10 (SEQ ID NO: 38)
GGGCGAGGAGCTrGrUrUrCrArCrCrGrGrUrUrUrUrArGrArGrCrUrArUrGrCrUrGrUrUrUrUrG crRNA-GFP-11 (SEQ ID NO: 39)
GGGCGAGGrArGrCrUrGrUrUrCrArCrCrGrGrUrUrUrUrArGrArGrCrUrArUrGrCrUrGrUrUrUrUrG crRNA-GFP-12 (SEQ ID NO: 40)
GGGCGArGrGrArGrCrUrGrUrUrCrArCrCrGrGrUrUrUrUrArGrArGrCrUrArUrGrCrUrGrUrUrUrUrG crRNA-GFP-13 (SEQ ID NO: 41)
GGGCrGrArGrGrArGrCrUrGrUrUrCrArCrCrGrGrUrUrUrUrArGrArGrCrUrArUrGrCrUrGrUrUrUrUrG crRNA-GFP-14 (SEQ ID NO: 42)
GgrGrCrGrArGrGrArGrCrUrGrUrUrCrArCrCrGrGrUrUrUrUrArGrArGrCrUrArUrGrCrUrGrUrUrUrUrG

FIG. 8

SgRNA of GFP-1 Sequence:

Underlined region is fixed region

Grey region is variable region of DNA-binding domain

5'-
GGGCGAGGAGCUGUUCACCGGUUUUAGAGCUAGAAAUAGCA
AGUUAAAAUAAGGCUAGUCCGUUAUCAACUUGAAAAAGUG
GCACCGAGUCGGUGCUUUUU-3' (SEQ ID NO:1)

FIG. 10A

GFP-1 (no modification RNA sequence from 5' to 3')
GGGCGAGGAGCUGUUCACCGGUUUUAGAGCUAGAAAUAGCAAGUUAAAAUAAGGCUAGUCCGUUAUCAACUUGAAAAAGUGGCACCGAGUCGGUGCUUUUU (SEQ ID NO:1)

GFP-4 (2 F modification RNA at middle: Uf and Cf at middle)
GGGCGAGGAGCUGUUCACCGGUfUfUfUfAGAGCfUfAGAAAUfAGCfAAGUfUfAAAAUfAAGGCfUfAGUfCfCfGUUAUCAACUUGAAAAAGUGGCACCGAGUCGGUGCUUUUU (SEQ ID NO:4)

GFP-5 (2 F modification RNA at middle and 3 end: Uf and Cf at middle and 3 end)
GGGCGAGGAGCUGUUCACCGGUfUfUfUfAGAGCfUfAGAAAUfAGCfAAGUfUfAAAAUfAAGGCfUfAGUfCfCfGUfUfAUfCfAACfUfUfGAAAAAGUfGGCfACfCfGAGUfCfGGUfGCfUfUfUfUfUf (SEQ ID NO: 5)

GFP-10 (u and c: 2'-O-methyl modification RNA)
GGGCGAGGAGCUGUUCACCGGUUUUAGAGcuaGaaAuagCAAGUUAAAAUAAGGCUAGUCCGUUAUCAacuugaaaaaguGGCACCGAGUCGGUGCUUUUU (SEQ ID NO:10)

GFP-12 (2 F modification RNA; Uf and Cf and Af and Gf)
GGGCGAGGAGCUGUUCACCGGUUUUAGAGCfUfAfGAfAfAUfAfGfCAAGUUAAAAUAAGGCUAGUCCGUUAUCAAfCfUfUfGfAfAfAfAfAfGfUfGGCfACfCfGAGUfCfGGUfGCfUfUfUfUfUf (SEQ ID NO:43)

GFP-33 (s: phosphorothioat; N: RNA residues: RNA)
GGGCGAGGAGCUGUUCACCGGsUsUsUsUsAsGsAsGsCsUsAsGsAsAsAsUsAsGsCsAsAsGsUsUsAsAsAsAsUsAsAsGsGsCsUsAsGsUsCsCsGsUsUsAsUsCsAsAsCsUsUsGsAsAsAsAsAsGsUsGsGsCsAsCsCsGsAsGsUsCsGsGsUsGsCsUsUsUsUsU (SEQ ID NO:44)

GFP-35 (n: 2'-O-methyl modification RNA; N: RNA residues: RNA)
GGGCGAGGAGCUGUUCACCGguuuuagagcuagaaauagcaaguuaaaauaaggcuaguccguuaucaacuugaaaaaguggcaccgagucggugcuuuuu (SEQ ID NO:46)

GFP-36 (n: 2'-O-methyl modification RNA; N: RNA residues: RNA)
GGGCGAGGAGCUGUUCACCGgUUUUAGagcuagaaauagcaaGUUaAaAuAaggcuaGUccGUUAucAAcuugaaaaagugGcaccgagucggugcuuuuu (SEQ ID NO:47)

GFP-39 (N: RNA residues: RNA; s: phosphorothioat)
GGGCGAGGAGCUGUUCACCGGUUUUAGAGCUAGAAAUAGCAAGUUAAAAUAAGGCUAGUCCGUUAUCAACsUsUsGsAsAsAsAsAsGUGGsCAsCsCsGsAsGsUsCGsGsUsGsCsUsUsUsUsU (SEQ ID NO:48)

GFP-40 (n: 2'-O-methyl modification RNA; N: RNA residues: RNA; s: phosphorothioat)
GGGCGAGGAGCUGUUCACCGgUUUUAGagcuagaaauagcaaGUUaAaAuAaggcuaGUccGUUAucAAcsusugsasasasasasgugGscascscsgsasgsuscgsgsusgscsusususu (SEQ ID NO:49)

GFP-CS(n: 2'-O-methyl modification RNA; N: RNA residues: RNA)
GGGCGAGGAGCUGUUCACCGGuuuuagAGCUAGAAAUAGCAAguuAaAaUaAGGCUAguCCguuaUCaaCUUGAAAAAGUGgCACCGAGUCGGUGCUUUUU (SEQ ID NO:50)

FIG. 10B

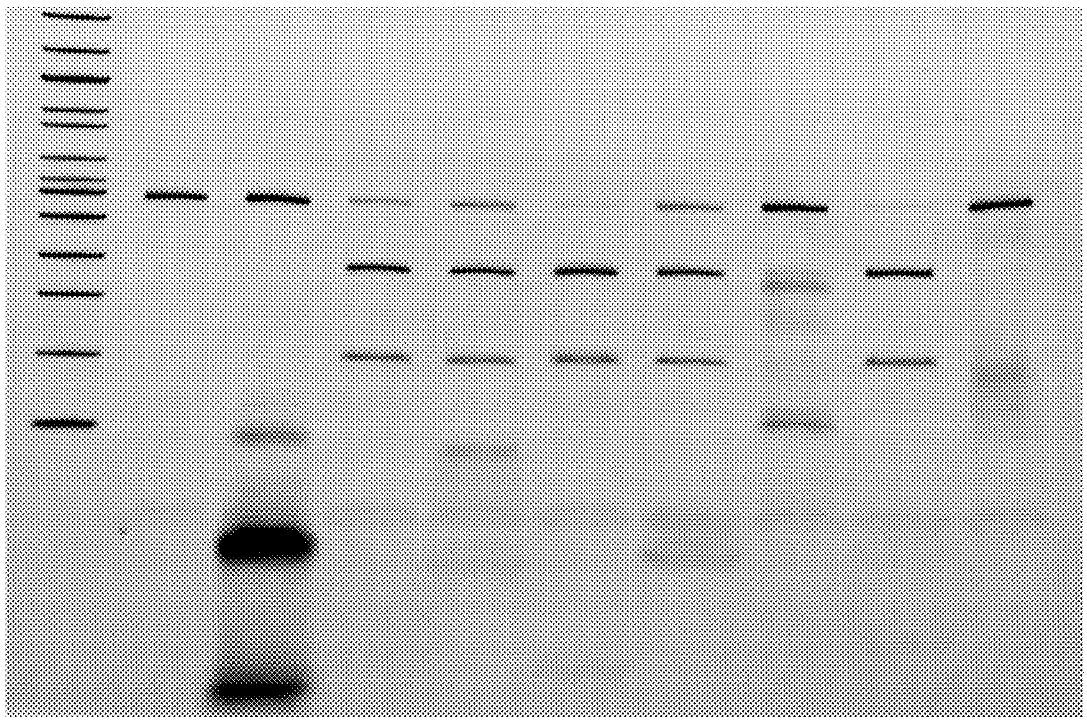
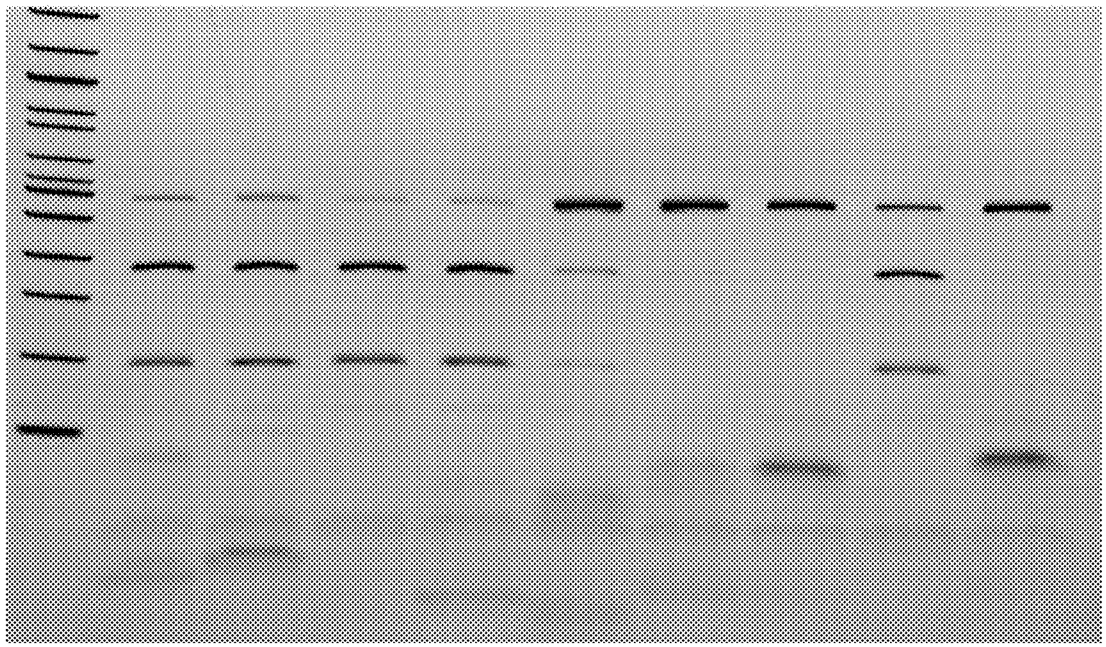
FIG. 10H

GFP-17 (n: 2'-O-methyl modification RNA; N: RNA residues: RNA)
gggcgaggagcuguucaccgGUUUUAGAGCUAUGCUGUUUUG (SEQ ID NO:51)
GFP-18 (n: 2'-O-methyl modification RNA; N: RNA residues: RNA)
GGGCGAGGAGcuguucaccgGUUUUAGAGCUAUGCUGUUUUG (SEQ ID NO:52)
GFP-19 (n: 2'-O-methyl modification RNA; N: RNA residues: RNA)
gggcgaggagCUGUUCACCGGUUUUAGAGCUAUGCUGUUUUG (SEQ ID NO:53)
GFP-20 (n: 2'-O-methyl modification RNA; N: RNA residues)
GggCGAGgagcUguUCacCGGUUUUAGAGCUAUGCUGUUUUG (SEQ ID NO:54)
GFP-21 (n: 2'-O-methyl modification RNA; N: RNA residues: RNA)
gGGcgagGAGCuGUucACcgGUUUUAGAGCUAUGCUGUUUUG (SEQ ID NO:55)
GFP-22 (Nf: 2 F modification RNA)
GfGfGfCfGfAfGfGfAfGfCfUfGfUfUfCfAfCfCfGfGUUUUAGAGCUAUGCUGUUUUG (SEQ ID NO:56)
GFP-23 (Nf: 2 F modification RNA)
GGGCGAGGAGCfUfGfUfUfCfAfCfCfGfGUUUUAGAGCUAUGCUGUUUUG (SEQ ID NO:57)
GFP-24 (Nf: 2 F modification RNA)
GfGfGfCfGfAfGfGfAfGfCUGUUCACCGGUUUUAGAGCUAUGCUGUUUUG (SEQ ID NO:58)
GFP-25 (Nf: 2 F modification RNA)
GGfGfCGAGGfAfGfCfUGfUfUCAfCfCGGUUUUAGAGCUAUGCUGUUUUG (SEQ ID NO:59)
GFP-26 (Nf: 2 F modification RNA)
GfGGCfGfAfGfGAGCUfGUUfCfACCfGfGUUUUAGAGCUAUGCUGUUUUG (SEQ ID NO:60)
GFP-27 (s: phosphorothioat; N: RNA residues: RNA)
GsGsGsCsGsAsGsGsAsGsCsUsGsUsUsCsAsCsCsGGUUUUAGAGCUAUGCUGUUUUG (SEQ ID NO:61)
GFP-28 (s: phosphorothioat; N: RNA residues: RNA)
GGsGCGAsGsGsAsGsCUGUUCACCGGUUUUAGAGCUAUGCUGUUUUG (SEQ ID NO:62)
GFP-29 (s: phosphorothioat; N: RNA residues: RNA)
GsGGsCsGsAGGAGCsUsGUUCACCGGUUUUAGAGCUAUGCUGUUUUG (SEQ ID NO:63)
GFP-30 (N: RNA residues: RNA)
GGGCGAGGAGCUGUUCACCGGUUUUAGAGCUAUGCUGUUUUG (SEQ ID NO:64)
GFP-31 (s: phosphorothioat; n: 2'-O-methyl modification RNA; N: RNA residues: RNA)
GgsgCGAsGsgsasgscUguUCacCGGUUUUAGAGCUAUGCUGUUUUG (SEQ ID NO:65)
GFP-32 (s: phosphorothioat; Nf: 2 F modification RNA; N: RNA residues: RNA)
GGfsGfCGAsGsGfsAfsGfsCfUGfUfUCAfCfCGGUUUUAGAGCUAUGCUGUUUUG (SEQ ID NO:66)

FIG. 11A

HY-VEGFA
GACCCCCUCCACCCCGCCUCGUUUUAGAGCUAUGCUGUUUUG (SEQ ID NO:67)
HY-VEGFA_M
GAfsCfCCCsCsUfsCfsCfsAfCCfCfCGCfCfUCGUUUUAGAGCUAUGCUGUUUUG (SEQ ID NO:68)
HY-EMX1
GAGUCCGAGCAGAAGAAGAAGUUUUAGAGCUAUGCUGUUUUG (SEQ ID NO:69)
HY-EMX1_M
GAfsGfUCCsGsAfsGfsCfsAfGAfAfGAAfGfAAGUUUUAGAGCUAUGCUGUUUUG (SEQ ID NO:70)
HY-HBB
CUUGCCCCACAGGGCAGUAAGUUUUAGAGCUAUGCUGUUUUG (SEQ ID NO:71)
HY-HBB_M
CUfsUfGCCsCsCfsAfsCfsAfGGfGfCAGfUfAAGUUUUAGAGCUAUGCUGUUUUG (SEQ ID NO:72)

Grey is the guide sequence region crRNA tracrRNA

293 HEK cells containing

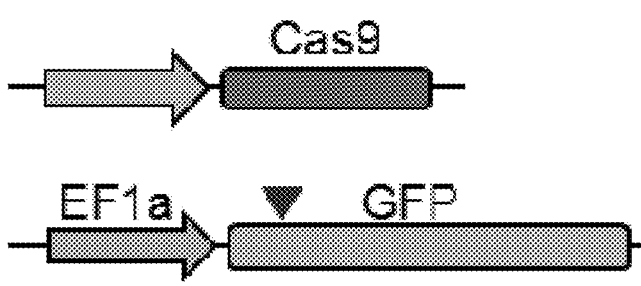

FIG. 11A continued

Published "light modification"

GFP-42
gsgsgsCGAGGAGCUGUUCACCGGUUUUAGAGCUAGAAAUAGCAAGUUAAAAUAA GGCUAGUCCGUUAUCAACUUGAAAAAGUGGCACCGAGUCGGUGCUusususU (SEQ ID NO:73)

*Our modification:*

GFP- 43 (s: phosphorothioate; Nf: 2 F modification RNA; N: RNA residues: RNA; n: 2'-O-methyl modification RNA)

GGfsGfCGAsGsGfsAfsGfsCfUGfUfUCAfCfCGgUUUUAGagcuagaaauagcaaGUUaAaAu AaggcuaGUccGUUAucAAcsususgsasasasasasgugGscascscsgsasgsuscgsgsusgscsus usususu (SEQ ID NO:74)

Published: 6% of nt (6 out of 101) has been modified

Our modification: 73% of nt (73 out of 101) has been modified

FIG. 12A

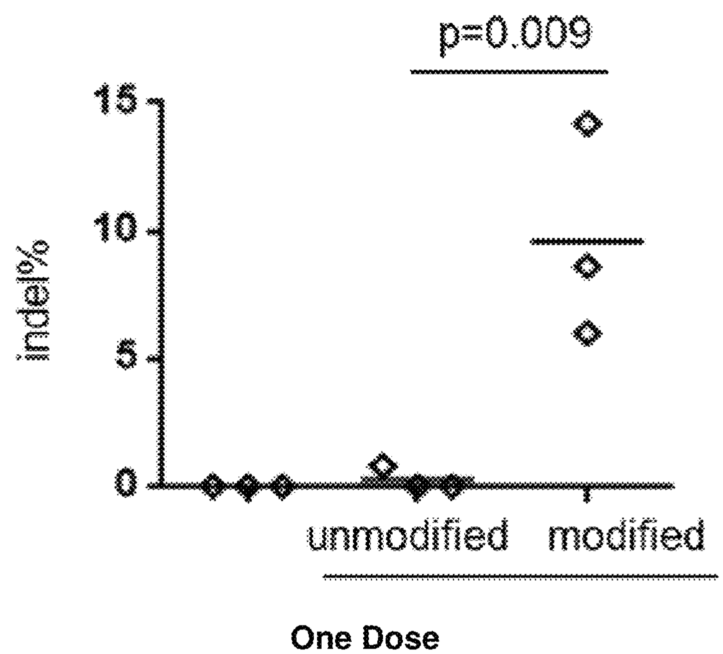
One Dose
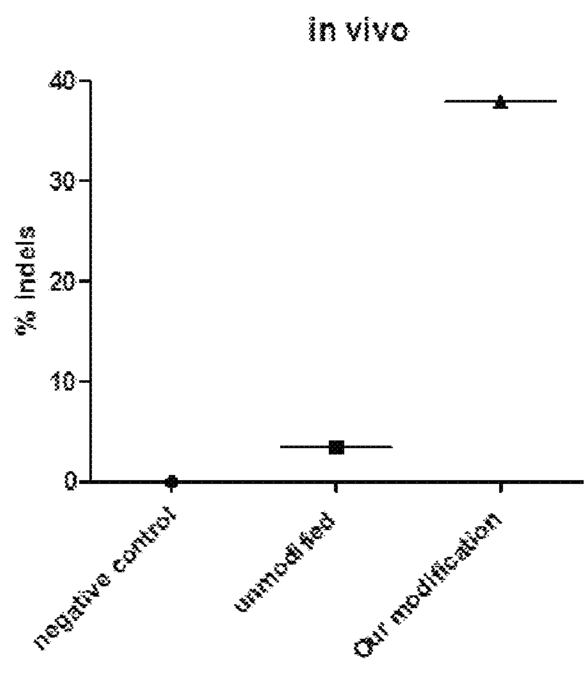
Two Doses
FIG. 12D

COMPOSITIONS COMPRISING NUCLEIC ACIDS AND METHODS OF USING THE SAME

RELATED APPLICATIONS

This application is a National Stage application filed under 35 U.S.C. § 371 of International Application No. PCT/US2016/040221, filed on Jun. 29, 2016, which claims priority to U.S. Provisional Ser. No. 62/186,358, filed Jun. 29, 2015, U.S. Provisional Ser. No. 62/243,589, filed Oct. 19, 2015, and U.S. Provisional Ser. No. 62/290,907, filed Feb. 3, 2016, each of which is incorporated by reference in its entirety.

SEQUENCE LISTING

The instant application contains a Sequence Listing which has been submitted electronically in ASCII format and is hereby incorporated by reference in its entirety. Said ASCII copy, created Dec. 22, 2020, is named 127299_00301_Second_Revised_Sequence_Listing.txt and is 49,265 bytes in size.

FIELD OF DISCLOSURE

The disclosure relates to compositions comprising modified nucleic acid sequence and methods of making, using and administering such modified nucleic acid sequences to, among other things, stabilize components of the CRISPR/Cas system.

BACKGROUND

The type II bacterial clustered, regularly interspaced, palindromic repeats (CRISPR)-associated (Cas) system has been engineered into a powerful genome editing tool consisting of the Cas9 nuclease and a single guide RNA (sgRNA). The sgRNA targets *S. pyogenes* Cas9 (spCas9) to genomic regions that are complementary to the 20-nucleotide (nt) target region of the sgRNA and that contain a 5'-NGG-3' protospacer-adjacent motif (PAM). Double-stranded DNA breaks generated by Cas9 at target loci are repaired by non-homologous end-joining or homology-directed repair (HDR). The efficient delivery of the CRISPR-Cas9 system is a key challenge for its therapeutic application. The clinical use of CRISPR-Cas9 requires the discovery and development of safer and more effective delivery systems. Toward this end, we now develop methods of chemical modifications of sgRNAs to allow applications for different types of in vitro and ex vivo applications, for embryo injections, as well as for in vivo delivery applications. Such modifications of sgRNA can be used for different CRISPR systems, such as *Staphylococcus aureus* Cas9 (saCas9), *Streptococcus thermophiles* Cas9 (stCas9) or different Cas systems which uses sgRNAs (e.g. Cas1-9). Such chemical modifications also applied to endogenous crRNA and tracrRNA system.

SUMMARY

The present disclosure relates to a nucleic acid sequence comprising at least one or a combination of domains from a 5' to 3' orientation: a DNA-binding domain, a Cas protein-binding domain, and a transcription terminator domain, wherein the DNA-binding domain comprises from about 40% to about 80% chemically modified ribonucleotides or deoxyribonucleotides. The present disclosure also relates to a nucleic acid sequence comprising at least one or a combination of domains from a 5' to 3' orientation: a DNA-binding domain, a Cas-protein binding domain, and a transcription terminator domain, wherein the DNA-binding domain comprises from about 40% to about 80% modified ribonucleotides and/or the transcription terminator domain comprises from about 40% to about 80% modified ribonucleotides. The present disclosure also relates to a nucleic acid sequence comprising at least one or a combination of domains from a 5' to 3' orientation: a DNA-binding domain, a Cas-protein binding domain, and a transcription terminator domain, wherein the DNA-binding domain comprises from about 1% to about 100% modified ribonucleotides and/or the transcription terminator domain comprises from about 1% to about 100% modified ribonucleotides; and the Cas-protein binding domain comprises from about 1 to about 150 nucleotides and at least one or a combination of nucleotides are conserved at positions: 2, 3, 4, 23, 24, 25, 27, 31, 38, 42, 43, 44, 45, 48 according to the sequence of FIG. 1. The present disclosure also relates to a nucleic acid sequence comprising at least one or a combination of domains from a 5' to 3' orientation: a DNA-binding domain, a Cas-protein binding domain, and a transcription terminator domain, wherein the DNA-binding domain comprises from about 1% to about 100% modified ribonucleotides and/or the transcription terminator domain comprises from about 1% to about 100% modified ribonucleotides; and the Cas-protein binding domain comprises from about 1 to about 150 nucleotides and at least one or a combination of nucleotides are conserved at the C1 of the nucleic acid sugar position of positions: 2, 3, 4, 23, 24, 25, 27, 31, 38, 42, 43, 44, 45, 48 according to the sequence of FIG. 1. The present disclosure also relates to a nucleic acid sequence comprising at least one or a combination of domains from a 5' to 3' orientation: a DNA-binding domain, a Cas-protein binding domain, and a transcription terminator domain, wherein the DNA-binding domain comprises from about 1% to about 100% modified ribonucleotides and/or the transcription terminator domain comprises from about 1% to about 100% modified ribonucleotides; and the Cas-protein binding domain comprises from about 1 to about 150 nucleotides and at least one or a combination of nucleotides are conserved at the C2 position of the nucleic acid sugar positions: 2, 3, 4, 23, 24, 25, 27, 31, 38, 42, 43, 44, 45, 48 according to the sequence of FIG. 1. The present disclosure also relates to a nucleic acid sequence comprising at least one or a combination of domains from a 5' to 3' orientation: a DNA-binding domain, a Cas-protein binding domain, and a transcription terminator domain, wherein the DNA-binding domain comprises from about 1% to about 100% modified ribonucleotides and/or the transcription terminator domain comprises from about 1% to about 100% modified ribonucleotides; and the Cas-protein binding domain comprises from about 1 to about 150 nucleotides and at least one or a combination of nucleotides are conserved at the C3 position of the nucleic acid sugar of positions: 2, 3, 4, 23, 24, 25, 27, 31, 38, 42, 43, 44, 45, 48 according to the sequence of FIG. 1. The present disclosure also relates to a nucleic acid sequence comprising at least one or a combination of domains from a 5' to 3' orientation: a DNA-binding domain, a Cas-protein binding domain, and a transcription terminator domain, wherein the DNA-binding domain comprises from about 1% to about 100% modified ribonucleotides and/or the transcription terminator domain comprises from about 1% to about 100% modified ribonucleotides; and the Cas-protein binding domain comprises from about 1 to about 150 nucleotides and at least one or a combination of nucleotides are conserved at the C4 position of the nucleic acid sugar of positions: 2, 3, 4, 23, 24, 25, 27, 31, 38, 42, 43, 44, 45, 48 according to the sequence of FIG. 1. The present disclosure also relates to a nucleic acid sequence comprising at least one or a combination of domains from a 5' to 3' orientation: a DNA-binding domain, a Cas-protein binding domain, and a transcription terminator domain, wherein the DNA-binding domain comprises from about 1% to about 100% modified ribonucleotides and/or the transcription terminator domain comprises from about 1% to about 100% modified ribonucleotides; and the Cas-protein binding domain comprises from about 1 to about 150 nucleotides and at least one or a combination of nucleotides are conserved at the C5 position of the nucleic acid sugar of positions: 2, 3, 4, 23, 24, 25, 27, 31, 38, 42, 43, 44, 45, 48 according to the sequence of FIG. 1.

The present disclosure also relates to a nucleic acid sequence comprising at least one or a combination of domains from a 5' to 3' orientation: a DNA-binding domain, a Cas-protein binding domain, and a transcription terminator domain, wherein the DNA-binding domain comprises and/or the transcription terminator domain comprises from about 1% to about 99% modified ribonucleotides except the first 3 nucleotides of the 5' end of the DNA-binding domain if there are modifications in the DNA-binding domain and the last 3 nucleotides of the 3' end of the transcription terminator domain; if there are modifications in the transcription terminator domain; and the Cas-protein binding domain comprises from about 1 to about 150 nucleotides and at least one or a combination of nucleotides are conserved at positions: 2, 3, 4, 23, 24, 25, 27, 31, 38, 42, 43, 44, 45, 48 according to the sequence of FIG. 1. The present disclosure also relates to a nucleic acid sequence comprising at least one or a combination of domains from a 5' to 3' orientation: a DNA-binding domain, a Cas-protein binding domain, and a transcription terminator domain, wherein the DNA-binding domain comprises from about 40% to about 60% fluorinated ribonucleotides at the 2'carbon position of a pentose sugar and/or the transcription terminator domain comprises from about 40% to about 60% fluorinated ribonucleotides at the 2'carbon position of a pentose sugar.

The present disclosure also relates to a nucleic acid sequence comprising at least one or a combination of domains from a 5' to 3' orientation: a DNA-binding domain, a Cas-protein binding domain, and a transcription terminator domain, wherein the DNA-binding domain comprises from about 1% to about 99% modified ribonucleotides and/or deoxyribonucleotides and/or the transcription terminator domain comprises from about 1% to about 99% modified ribonucleotides and/or deoxyribonucleotides; and the Cas-protein binding domain comprises from about 1 to about 150 nucleotides and at least one or a combination of nucleotides are conserved at positions: 2, 3, 4, 23, 24, 25, 27, 31, 38, 42, 43, 44, 45, 48 according to the sequence of FIG. 1. The present disclosure also relates to a nucleic acid sequence comprising at least one or a combination of domains from a 5' to 3' orientation: a DNA-binding domain, a Cas protein-binding domain, and a transcription terminator domain; wherein the DNA-binding domain comprises from about 1% to about 99% modified ribonucleotides and/or deoxyribonucleotides and/or the transcription terminator domain comprises from about 1% to about 99% modified ribonucleotides and/or deoxyribonucleotides; and the Cas-protein binding domain comprises from about 1 to about 150 nucleotides and at least one or a combination of 2'-oxygen within the nucleotides which are conserved at positions: 2, 3, 4, 23, 24, 25, 27, 31, 38, 42, 43, 44, 45, 48 according to the sequence of FIG. 1. In some embodiments, while one or a combination of 2' carbon substituents in the ribose or deoxyribose sugar may be conserved at a given nucleotide of FIG. 1, other functional groups of the nucleotide may be modified in some embodiments. For instance, any of the modifications listed in this application may be incorporated into a modified nucleotide, either a deoxyribonucleotide or ribonucleotide. In one non-limiting example, any of the nucleotides identified at positions: 2, 3, 4, 23, 24, 25, 27, 31, 38, 42, 43, 44, 45, 48 according to the sequence of FIG. 1 comprise a conserved 2' carbon substituent (oxygen atom or hydroxyl, or hydrogen in the case of a deoxyribonucleic acid) but may contain a modified functional group at the 3' position.

In some embodiments, the disclosure relates to composition comprising a nucleic acid sequence, wherein the nucleic acid sequence comprises a modified Cas-binding domain with between 1%-99% sequence homology with SEQ ID NO: 11, wherein one or any combination of nucleic acids at position 2, 3, 4, 23, 24, 25, 27, 31, 38, 42, 43, 44, 45, 48 are unmodified. In some embodiments, the disclosure relates to composition comprising a nucleic acid sequence, wherein the nucleic acid sequence comprises a modified Cas-binding domain with between 1%-99% sequence homology with SEQ ID NO: 11, wherein one or any combination of functional groups with nucleic acids at position 2, 3, 4, 23, 24, 25, 27, 31, 38, 42, 43, 44, 45, 48 are unmodified. In some embodiments, the functional group left unmodified is the 2'-oxygen or the hydroxyl group at the 2' carbon of any such positions.

In some embodiments, the disclosure relates to composition comprising a nucleic acid sequence, wherein the nucleic acid sequence comprises a modified Cas-binding domain with between 1%-99% sequence homology with SEQ ID NO: 11, wherein one or any combination of nucleic acids at position 2, 3, 4, 23, 24, 25, 27, 31, 38, 42, 43, 44, 45, 48 are unmodified in the 2' OH position. In some embodiments, the disclosure relates to composition comprising a nucleic acid sequence, wherein the nucleic acid sequence comprises a modified Cas-binding domain with between 1%-99% sequence homology with SEQ ID NO: 11, wherein one or any combination of functional groups with nucleic acids at position 2, 3, 4, 23, 24, 25, 27, 31, 38, 42, 43, 44, 45, 48 are unmodified. In some embodiments, the functional group left unmodified is the oxygen at the 2' carbon position.

In some embodiments, the disclosure relates to a composition comprising a nucleic acid sequence, wherein the nucleic acid sequence comprises a DNA-binding domain comprising at least one fluorinated nucleic acid. In some embodiments, the Cas-protein binding domain comprises at least one fluorinated nucleic acid. In some embodiments, the transcription terminator domain comprises at least one fluorinated nucleic acid. In some embodiments, the nucleic acid sequence consists of from about 25 to about 250 ribonucleotides. In some embodiments, the nucleic acid sequence consists of from about 25 to about 200 ribonucleotides. In some embodiments the nucleic acid consists of from about 25 to about 150 nucleotides, wherein at least one or pluralities of nucleotides are modified. In some embodiments, the nucleic acid sequence consists of from about 25 to about 140 ribonucleotides. In some embodiments, the nucleic acid sequence consists of from about 25 to about 130 ribonucleotides. In some embodiments, the nucleic acid sequence consists of from about 25 to about 120 ribonucleotides. In some embodiments, the nucleic acid sequence consists of from about 25 to about 110 ribonucleotides. In some embodiments, the nucleic acid sequence consists of from about 25 to about 100 ribonucleotides.

The present disclosure relates to a composition comprising one or plurality of sgRNA molecules. In some embodiments, the composition comprises at least one sgRNA molecule comprising GUUUUAGAGCUAGAAAUAGCAAGUUAAAAUAAGGCUAGUC CG (SEQ ID NO:11). In some embodiments, the composition comprises a plurality of domains from a 5' to 3' orientation: a DNA-binding domain, a Cas-protein binding domain, and a transcription terminator domain, wherein the DNA-binding domain comprises from about 1% to about 99% modified ribonucleotides and/or the transcription terminator domain comprises from about 1% to about 99% modified ribonucleotides; and the Cas-protein binding domain comprises from about 42 to about 150 nucleotides comprising SEQ ID NO:11 or a nucleotide sequence in which position 2 of SEQ ID NO:11 is a uracil. In some embodiments, the composition comprises a plurality of domains from a 5' to 3' orientation: a DNA-binding domain, a Cas-protein binding domain, and a transcription terminator domain, wherein the DNA-binding domain comprises from about 1% to about 99% modified ribonucleotides and/or the transcription terminator domain comprises from about 1% to about 99% modified ribonucleotides; and the Cas-protein binding domain comprises from about 42 to about 150 nucleotides comprising SEQ ID NO:11 or a nucleotide sequence in which position 3 of SEQ ID NO:11 is a uracil.

In some embodiments, all or a portion of the nucleic acid sequence comprises or consists of synthetically assembled nucleotides. In some embodiments, the nucleic acid sequence is an sgRNA molecule free of recombinantly assembled nucleotides. In some embodiments, the nucleic acid sequence is an sgRNA molecule manufactured by polymerase by synthesizing at least one of the nucleotides.

In some embodiments, the DNA-binding domain consists of from about 20 to about 25 contiguous nucleotides; wherein the Cas-protein binding domain consists of from about 38 to about 42 contiguous nucleotides; wherein the transcription terminator domain consists of from about 38 to about 42 contiguous nucleotides. In some embodiments, the DNA-binding domain consists of from about 20 to about 25 contiguous ribonucleotides; wherein the Cas-protein binding domain consists of from about 38 to about 42 contiguous ribonucleotides; wherein the transcription terminator domain consists of from about 38 to about 42 contiguous ribonucleotides. In some embodiments, the DNA-binding domain consists of from about 20 to about 250 contiguous nucleotides; wherein the Cas-protein binding domain consists of from about 38 to about 250 contiguous nucleotides; wherein the transcription terminator domain consists of from about 38 to about 250 contiguous nucleotides. In some embodiments, the DNA-binding domain consists of from about 20 to about 250 contiguous ribonucleotides; wherein the Cas-protein binding domain consists of from about 38 to about 250 contiguous ribonucleotides; wherein the transcription terminator domain consists of from about 38 to about 200 contiguous ribonucleotides.

The disclosure relates to a Cas-protein binding domain with at least 70% homology to SEQ ID NO:2 and binds a target sequence of a DNA molecule in the presence of a Cas protein. In some embodiments, the Cas-binding domain is at least 70% homologous to SEQ ID NO:2 and binds a target sequence of a DNA molecule in the presence of a concentration of Cas protein sufficient to cause hybridization of the DNA-binding domain. In some embodiments, the Cas-protein binding domain is at least 70% homologous to SEQ ID NO:2 and binds a target sequence of a DNA molecule in the presence of a Cas9 protein. In some embodiments, the Cas9 binding domain is at least 70% homologous to SEQ ID NO:2 and binds a target sequence of a DNA molecule in the presence of a concentration of Cas protein sufficient to cause hybridization of the DNA-binding domain.

The disclosure relates to a Cas-protein binding domain with at least 70% homology to SEQ ID NO:3 and binds a target sequence of a DNA molecule in the presence of a Cas protein. In some embodiments, the Cas-binding domain is at least 70% homologous to SEQ ID NO:3 and binds a target sequence of a DNA molecule in the presence of a concentration of Cas protein sufficient to cause hybridization of the DNA-binding domain. In some embodiments, the transcription terminator domain is at least 70% homologous to SEQ ID NO:3 and wherein the nucleic acid sequence binds a target sequence of a DNA molecule in the presence of a Cas9 protein. In some embodiments, the Cas9 binding domain is at least 70% homologous to SEQ ID NO:3 and binds a target sequence of a DNA molecule in the presence of a concentration of Cas9 protein sufficient to cause hybridization of the DNA-binding domain to the target sequence.

In some embodiments, the transcription terminator domain is at least 70% homologous to SEQ ID NO:3 and wherein the nucleic acid sequence binds a target sequence of a DNA molecule in the presence of a Cas protein. In some embodiments, the Cas binding domain is at least 70% homologous to SEQ ID NO:3 and binds a target sequence of a DNA molecule in the presence of a concentration of Cas protein sufficient to cause hybridization of the DNA-binding domain to the target sequence.

In some embodiments, the nucleic acid sequence is at least 70% homologous to SEQ ID NO:4 and wherein the nucleic acid sequence binds a target sequence of a DNA molecule in the presence of a Cas9 protein. In some embodiments, the Cas9 binding domain is at least 70% homologous to SEQ ID NO:4 and binds a target sequence of a DNA molecule in the presence of a concentration of Cas9 protein sufficient to cause hybridization of the DNA-binding domain to the target sequence.

In some embodiments, the nucleic acid sequence is at least 70% homologous to SEQ ID NO:4 and wherein the nucleic acid sequence binds a target sequence of a DNA molecule in the presence of a Cas protein. In some embodiments, the Cas binding domain is at least 70% homologous to SEQ ID NO:4 and binds a target sequence of a DNA molecule in the presence of a concentration of Cas protein sufficient to cause hybridization of the DNA-binding domain to the target sequence.

In some embodiments, the DNA-binding domain comprises from about 15% to about 85% fluorinated ribonucleotides at the 2'carbon position of a pentose sugar. In some embodiments, the transcription terminator comprises from about 60% to about 85% fluorinated ribonucleotides at the 2'carbon position of a pentose sugar. In some embodiments, the transcription terminator comprises from about 70% to about 85% fluorinated ribonucleotides at the 2'carbon position of a pentose sugar. In some embodiments, the transcription terminator comprises from about 85% to about 95% fluorinated ribonucleotides at the 2'carbon position of a pentose sugar.

In some embodiments, the DNA-binding domain consists of a sequence a RNA sequence at least 90% complementary to a DNA target sequence and contiguous with SEQ ID NO:6. In some embodiments, the transcription terminator domain consists of SEQ ID NO:7.

The present disclosure also relates to a composition comprising: (a) a nucleic acid sequence comprising a regulatory element operable in a eukaryotic cell operably linked to at least one nucleotide sequence encoding a Cas protein or functional fragment thereof; and (b) any guide sequence disclosed herein, wherein the DNA-domain hybridizes with a target sequence of a DNA sequence in a eukaryotic cell that contains the DNA sequence, wherein the DNA sequence encodes and the eukaryotic cell expresses at least one gene product. In some embodiments, the nucleic acid sequence comprising a regulatory element operable in a eukaryotic cell operably linked to at least one nucleotide sequence encoding a Cas protein or functional fragment thereof is on a first nucleic acid molecule and the guide sequence is a component of a second nucleic acid molecule, optionally comprising one or a plurality of regulatory elements operable in a eukaryotic cell. Pharmaceutical compositions comprising any one or more nucleic acid sequences are contemplated by this disclosure.

The present disclosure also relates to a composition comprising: (a) a nucleic acid sequence comprising a regulatory element operable in a eukaryotic cell operably linked to at least one nucleotide sequence encoding a deactivated Cas protein; and (b) any one or plurality of guide sequences disclosed herein wherein the DNA-domain hybridizes with a target sequence of a DNA sequence in a eukaryotic cell that contains the DNA sequence, wherein the DNA sequence encodes and the eukaryotic cell expresses at least one gene product.

The present disclosure also relates to a composition comprising: (a) a nucleic acid sequence comprising a regulatory element operable in a eukaryotic cell operably linked to at least one nucleotide sequence encoding a Cas protein; and (b) a nucleic acid molecule comprising any DNA-binding domain described herein, wherein the DNA-binding domain is capable of hybridizing with a target sequence within a DNA sequence in a eukaryotic cell that contains the DNA sequence, wherein the DNA sequence encodes and the eukaryotic cell expresses at least one gene product. In some embodiments, the composition further comprises a lipid or polymer that encapsulates any of the nucleic acids disclosed herein, including any ribonucleotide described herein. In some embodiments, the composition further comprises a pharmaceutically acceptable carrier.

The present disclosure also relates to a composition comprising: (a) a nucleic acid sequence comprising a regulatory element operable in a eukaryotic cell operably linked to at least one nucleotide sequence encoding a Type-II Cas9 protein; and (b) a ribonucleotide of any of claims 1-13 wherein the DNA-domain hybridizes with a target sequence of a DNA sequence in a eukaryotic cell that contains the DNA sequence, wherein the DNA sequence encodes and the eukaryotic cell expresses at least one gene product. In some embodiments, the composition further comprises a lipid or polymer that encapsulates the ribonucleotide described herein. In some embodiments, the composition further comprises a pharmaceutically acceptable carrier.

The present disclosure also relates to a kit comprising: (a) one or more vectors comprising: a first regulatory element operable in a eukaryotic cell operably linked to a nucleotide sequence encoding a Cas protein; and (b) any nucleic acid sequence described herein. In some embodiments, the one or more vectors and any nucleic acid sequence described herein are lyophilized or desiccated. The present disclosure also relates to a kit comprising: (a) one or more vectors comprising: a first regulatory element operable in a eukaryotic cell operably linked to a nucleotide sequence encoding a Type-II Cas9 protein; and (b) any nucleic acid sequence described herein. In some embodiments, the one or more vectors and any nucleic acid sequence described herein are lyophilized or desiccated. In some embodiments, the kit further comprises at least one container comprising a reconstitution fluid.

The present disclosure also relates to a method of chemically synthesizing a small guide ribonucleic acid molecule comprising integrating a modification into a nucleic acid. The present disclosure also relates to a method of chemically synthesizing a small guide ribonucleic acid molecule comprising integrating a modification into a ribonucleic acid or a deoxyribonucleic acid. The present disclosure also relates to a method of chemically synthesizing a small guide ribonucleic acid molecule comprising integrating a fluorine atom into or reacting compound comprising a fluorine atom with a nucleic acid sequence.

The present disclosure also relates to a method of altering expression of at least one gene product in a cell comprising introducing into a cell an engineered, non-naturally occurring Clustered Regularly Interspaced Short Palindromic Repeats (CRISPR)-CRISPR associated (Cas) (CRISPR-Cas) system comprising: (a) a vector comprising a nucleotide sequence encoding a Type-II Cas9 protein; and (b) a nucleic acid described herein, wherein components (a) and (b) are located on same or different vectors of the system; wherein the cell contains and expresses a DNA molecule having a target sequence and encoding the gene product; and wherein the guide RNA targets and, at concentration sufficient to hybridize the DNA target sequence, hybridizes with a DNA target sequence and the Cas9 protein cleaves the DNA molecule, whereby expression of the at least one gene product is altered. The present disclosure also relates to a method of altering expression of at least one gene product in a cell comprising introducing into a cell an engineered, non-naturally occurring CRISPR-Cas system comprising: (a) a vector comprising a nucleotide sequence encoding a Cas protein; and (b) a nucleic acid described herein, wherein components (a) and (b) are located on same or different vectors of the system; wherein the cell contains and expresses a DNA molecule having a target sequence and encoding the gene product; and wherein the guide RNA targets and, at concentration sufficient to hybridize the DNA target sequence, hybridizes with a DNA target sequence and the Cas protein cleaves the DNA molecule, whereby expression of the at least one gene product is altered.

In some embodiments, the DNA-binding domain comprises from about 40% to about 60% fluorinated ribonucleotides at the 2'carbon position of a pentose sugar. In some embodiments, the transcription terminator domain comprises from about 40% to about 60% fluorinated ribonucleotides at the 2'carbon position of a pentose sugar. In some embodiments, the DNA-binding domain consists of a sequence a RNA sequence at least 90% complementary to a DNA target sequence and contiguous with SEQ ID NO:6. In some embodiments, the transcription terminator domain consists of SEQ ID NO:7.

The present disclosure also relates to a method of improving the enzymatic efficiency of a Cas protein comprising: exposing the Cas protein to a chemically modified nucleic acid sequence comprising at least one fluorinated nucleotide. In some embodiments, the enzymatic efficiency is increased by no less than from about 5% to about 10%. In some embodiments, the transcription terminator domain is at least 70% homologous to SEQ ID NO:7.

The present disclosure also relates to a method of reducing off-target enzyme activity of a Cas protein comprising: exposing the Cas protein to a chemically modified nucleic acid sequence comprising at least one fluorinated nucleotide. In some embodiments, the off-target enzyme activity is reduced no less than about 5%. In some embodiments, the transcription terminator domain is at least 70% homologous to SEQ ID NO:7.

The present disclosure also relates to a method of introducing a mutation in the genomic DNA of a eukaryotic cell comprising contacting said cell with a nucleic acid sequence or guide sequence described herein or any composition described herein. In some embodiments, the step of contacting is performed in vitro, ex vivo, or in vivo. In some embodiments, the eukaryotic cell is a stem cell or cancer cell. In some embodiments, the step of contacting is performed in vivo. In some embodiments, the cell is a lymphocyte isolated from a subject. In some embodiments, the cell is a cultured T-cell or CAR T cell. In some embodiments, the cell is a cell from the liver, lung, neuron, skin, intestine, stomach, breast, or colon.

BRIEF DESCRIPTION OF THE DRAWINGS

FIG. 2 depicts three chemically synthesized sgRNAs. The GFP-1 sgRNA is not chemically modified (native strand). The GFP-2 sgRNA is with 2'-Fluoro modified RNA at the 40-nt-long transcription terminator hairpin region. The GFP-3 sgRNA is with 2'Fluoro modified RNA at the 20-nt-long base-pairing region for specific DNA binding. The grey highlighted section is the Cas9 protein binding region.

FIG. 4A depicts a gel showing the specific cutting of sgRNA1, sgRNA2, and sgRNA3 at a concentration of 1.0 ug. FIG. 4B depicts a gel showing the specific cutting of sgRNA1, sgRNA2, and sgRNA3 at a concentration of 0.5 ug. FIG. 4C depicts a gel showing the specific cutting of sgRNA1, sgRNA2, and sgRNA3 at a concentration of 0.25 ug. FIG. 4D depicts a gel showing the specific cutting of sgRNA1, sgRNA2, and sgRNA3 at a concentration of 0.05 ug. FIG. 4E is a combination graph of the results from FIGS. 4A, 4B, 4C, and 4D. At different concentrations of sgRNA, sgRNA2 is more efficient that both sgRNA1 and sgRNA3 in generating GFP negative cells.

FIGS. 5A and 5B depict the sgRNA structure and modified sgRNAs. FIG. 5A depicts the published structure of sgRNA-Cas9. Some positions of the sgRNA (e.g. position 6, 7, 8 of the base-paring region) can be modified due to less interaction with the Cas9 protein. Other positions of the sgRNA (e.g. positions 2, 3, 4, and 23 of the Cas9 binding domain etc.) have 2' interactions with the Cas9 protein and may not be 2' modified. FIG. 5B depicts the design of 7 new sgRNA modified sequences. Sequences shown in FIG. 5A are SEQ ID NO: 136 and SEQ ID NO: 137.

FIG. 6A depicts a bar graph showing that chemical modifications at certain positions enhance sgRNA efficiency while modification at other positions abolishes its effect. sgRNAs with minimal or no 2F or 2OMe modifications on key positions maintain or enhance its activity, while sgRNAs with multiple 2F or 2OMe modifications on key positions abolish its effect. FIG. 6B depicts a gel showing the specific cutting of sgRNAs 1, 4, 5, 6, 7, 8, 9, and 10. FIG. 6C depicts a graph showing dose titration of sgRNAs 1, 6, 8, and 10 targeting GFPs. At various concentrations, sgRNA 8 and 10 are more potent than sgRNA 1 at generating GFP negative cells, indicating various chemical modifications improve efficiency of sgRNA.

FIG. 7 depicts crRNA targeting genomic DNA. The crRNA use 20-nucleotide (nt) target region in RNA format to target genomic DNA. It duplexes with tracrRNA, and binds to Cas9 protein to perform genome editing. A sgRNA is a crRNA-tracrRNA chimera.

FIG. 8 depicts several crRNA modifications. Highlighted is 20 nt guide sequence. The design of crRNA modifications: cRNA-GFP-1 is a chemically synthesized crRNA targeting EGFP protein. It is in native RNA format. TracrRNA is chemically synthesized to allow co-delivery with different crRNAs. crRNA-GFP-3 replaces all 20 RNA in crRNA target region with DNA, crRNA-GFP-7, 8, 9, 10, 4, 11, 12, 13, 14 replaces 18, 16, 14, 12, 10, 8, 6, 4 and 2 ribonucleotides in crRNA genomic target region with deoxyribonucleotides, respectively, starting at 5' end.

FIGS. 10A-10H depict nucleotide sequences and data exploring the rules of chemical modification of sgRNA. FIG. 10A depicts the variable and fixed regions of sgRNA. FIG. 10B depicts several sgRNA sequences both with and without modifications. FIG. 10C depicts the engineering of HEK293 cells to express EGFP and spCas9. FIG. 10D depicts graphs showing the diminished GFP signature of various sequences compared to GFP-1 (SEQ ID NO:1). FIG. 10E depicts an overview of the structure-guided design for sgRNA. The first panel of 10E is a structural figure from *Science,* 348, 1477 (2015); and the second panel of 10E (10E continued) is a structural figure from *Cell,* 156, 935-949, Feb. 27, 2014.

FIG. 10F depicts a graph showing the increased GFP signature in GFP-10. FIG. 10G depicts a graph showing the increased GFP signature in sequences having 2' O-Methyl and/or phosphorothioate modifications at sites in the sequence that do not interact with Cas9, and the abolishment of GFP signature in sequences have the same modifications at sites in the sequence that do interact with Cas9. FIG. 10H depicts pictures of gels showing that in vitro cleavage activity is consistent with HEK293 activity. Sequence shown in FIG. 10E is SEQ ID NO: 138.

FIGS. 11A-11F depict nucleotide sequences and data exploring the rules of chemical modification at the variable region of the guide sequences. FIG. 11A depicts several sgRNA sequences both with and without modifications. FIG. 11B depicts a graph showing the GFP signature of various sgRNA sequences, notably the positive results from sequences with 2' O-Methyl modification at the tail region and/or no modification at specific cautious sites. FIG. 11C depicts a graph showing the GFP signature of various sgRNA sequences where the 2' O-Methyl modification was replaced with a 2'-Fluoro modification. FIG. 11D depicts a graph showing the GFP signature of various sgRNA sequences where the 2' O-Methyl modification was replaced with a phosphorothioate modification. FIG. 11E depicts a graph showing the GFP signature of various sgRNA sequences with various combinations of modifications. FIG. 11F depicts a graph showing the effects of various modification on additional crRNA sequences.

FIGS. 12A-12E depict nucleotide sequences and data exploring the combination of modification at both the variable and the fixed region. FIG. 12A depicts both an unmodified sgRNA with 2' O-Methyl and phosphorothioate modification at 3 nucleotides at the 5' end and 3' end respectively (GFP-42; SEQ ID NO:73), and a further modified sequence (GFP-43; SEQ ID NO:74). FIG. 12B depicts a graph showing the GFP signature of GFP-43 is greater than GFP-42. FIG. 12C depicts the in vivo delivery of GFP-43 in Cas9-expressing mice. FIG. 12D depicts graphs showing a higher percentage of indels with GFP-43 compared to GFP-42 with both one injection dose and two injection doses. FIG. 12E depicts immunohistochemical staining of antibodies bound to tissue expressing GFP in mice liver. The circled region is an area in which GFP is not expressed due to insertion of the gene in vivo.

DETAILED DESCRIPTION

Figure 1:
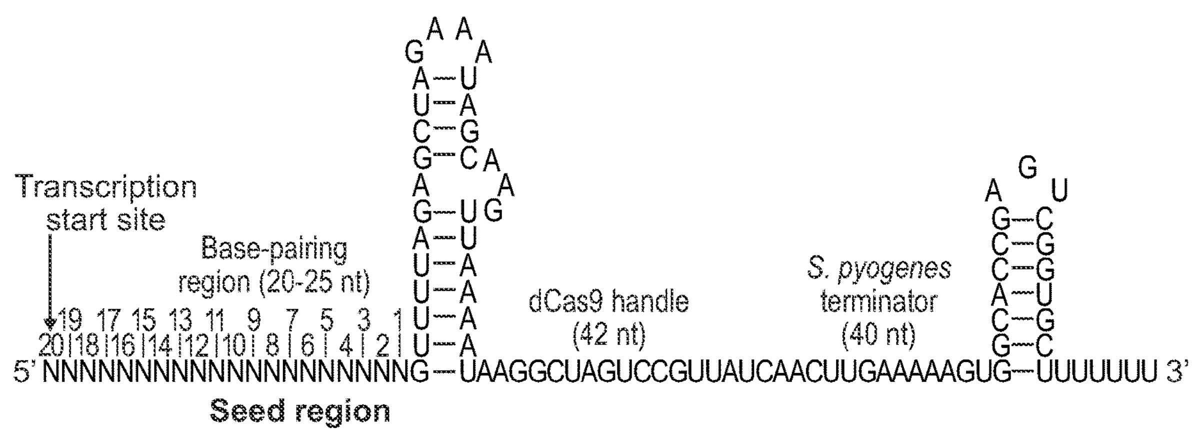
FIG. 1 depicts an example of sgRNA of spCas9. This sgRNA can be separated into three regions based on functionality: a 20-25 nt-long base-paring region for specific DNA binding, a 42 nt-long dCas9 handle hairpin for Cas9 protein binding, and a 40 nt-long transcription terminator hairpin derived from *S. pyogenes*. The sequence shown is SEQ ID NO: 112.

The disclosure relates to the Clustered Regularly Interspaced Short Palindromic Repeats (CRISPR) and CRISPR associated (Cas) proteins (CRISPR/Cas) system to drive both non-homologous end joining (NHEJ) based gene disruption and homology directed repair (HDR) based precise gene editing to achieve highly efficient and simultaneous targeting of multiple nucleic acid sequences in cells and nonhuman mammals.

The term "about" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, "either," "one of," "only one of," or "exactly one of" "Consisting essentially of," when used in the claims, shall have its ordinary meaning as used in the field of patent law.

As used herein, "activity" in the context of CRISPR/Cas activity, Cas protein activity, Cas9 activity, sgRNA activity, sgRNA: nuclease activity and the like refers to the ability of a nucleic acid and/or protein to bind to a target sequence and/or label or cleave the target sequence. Such activity can be measured in a variety of ways as known in the art. For example, expression, activity, or level of a reporter gene can be measured, and sgRNA: nucleases targeting the reporter gene sequence can be assayed for their ability to reduce the expression, activity, or level of the reporter gene. For example, a cell can be transfected with an expression cassette encoding a green fluorescent protein under the control of a constitutive promoter. The fluorescence intensity can be measured and compared to the intensity of the cell after transfection with Cas9 and candidate sgRNAs to identify optimized sgRNAs.

The term "analog" as used herein refers to compounds that are similar but not identical in chemical formula and share the same or substantial function of the compound with the similar chemical formula.

The terms "biophysically effective amount" refers to an amount of nucleic acid in a system under physiological conditions (such as temperature, pH, exposure to percent oxygen, etc.) sufficient to associate to or bind a Cas protein or functional fragment thereof in the presence of a Cas protein or functional fragment thereof. In some embodiments, the nucleic acid is a sgRNA, or a crRNA/tracr RNA duplex. In some embodiments, the Cas protein or functional fragment thereof is chosen from any of the sequences of Tables D or E or functional fragments thereof.

As used herein, "conservative" amino acid substitutions may be defined as set out in Tables A, B, or C below. The polypeptides of the disclosure include those wherein conservative substitutions (from either nucleic acid or amino acid sequences) have been introduced by modification of polynucleotides encoding polypeptides. In some embodiments, these polypeptides comprise or consist or enzymes (such as those enzymes capable to forming a complex with one or a plurality of sgRNA sequences) or functional fragments thereof. Amino acids can be classified according to physical properties and contribution to secondary and tertiary protein structure. A conservative substitution is recognized in the art as a substitution of one amino acid for another amino acid that has similar properties. In some embodiments, the conservative substitution is recognized in the art as a substitution of one nucleic acid for another nucleic acid that has similar properties, or, when encoded, has similar binding affinities or. Exemplary conservative substitutions are set out in Table A.

TABLE A

Conservative Substitutions I

| Side Chain Characteristics | Amino Acid |
|---|---|
| Aliphatic | |
| Non-polar | G A P I L V F |
| Polar-uncharged | C S T M N Q |
| Polar-charged | D E K R |
| Aromatic | H F W Y |
| Other | N Q D E |

Alternately, conservative amino acids can be grouped as described in Lehninger, (Biochemistry, Second Edition; Worth Publishers, Inc. NY, N.Y. (1975), pp. 71-77) as set forth in Table B.

TABLE B

Conservative Substitutions II

| Side Chain Characteristic | Amino Acid |
|---|---|
| Non-polar (hydrophobic) | |
| Aliphatic: | A L I V P |
| Aromatic: | F W Y |
| Sulfur-containing: | M |
| Borderline: | G Y |
| Uncharged-polar | |
| Hydroxyl: | S T Y |
| Amides: | N Q |
| Sulfhydryl: | C |
| Borderline: | G Y |
| Positively Charged (Basic): | K R H |
| Negatively Charged (Acidic): | D E |

Alternately, exemplary conservative substitutions are set out in Table C.

TABLE C

Conservative Substitutions III

| Original Residue | Exemplary Substitution |
|---|---|
| Ala (A) | Val Leu Ile Met |
| Arg (R) | Lys His |
| Asn (N) | Gln |
| Asp (D) | Glu |
| Cys (C) | Ser Thr |
| Gln (Q) | Asn |
| Glu (E) | Asp |
| Gly (G) | Ala Val Leu Pro |
| His (H) | Lys Arg |
| Ile (I) | Leu Val Met Ala Phe |
| Leu (L) | Ile Val Met Ala Phe |
| Lys (K) | Arg His |
| Met (M) | Leu Ile Val Ala |
| Phe (F) | Trp Tyr Ile |
| Pro (P) | Gly Ala Val Leu Ile |
| Ser (S) | Thr |
| Thr (T) | Ser |
| Trp (W) | Tyr Phe Ile |
| Tyr (Y) | Trp Phe Thr Ser |
| Val (V) | Ile Leu Met Ala |

It should be understood that the enzymes (such as the Cas9 enzyme) or any functional fragments thereof described herein are intended to include amino acid sequences comprising polypeptides bearing one or more insertions, deletions, or substitutions, or any combination thereof, of amino acid residues as well as modifications other than insertions, deletions, or substitutions of amino acid residues.

"Cas binding domain" refers to a nucleic acid element or domain within a nucleic acid sequence or polynucleotide sequence that, in a biophysically effective amount, will bind or have an affinity for one or a plurality of proteins (or functional fragments thereof) encoded by one or a plurality of CRISPR-associated genes. In some embodiments, in the presence of a the one or a plurality of proteins (or functional fragments thereof) and a target sequence, the one or plurality of proteins and the nucleic acid element forms a biologically active CRISPR complex and/or can be enzymatically active on a target sequence. The terms "CRISPR-associated genes" refer to any nucleic acid that encodes a regulatory or expressible gene that regulates a component or encodes a component of the CRISPR system. In some embodiments, the terms "CRISPR-associated genes" refer to any nucleic acid sequence that encodes any of the proteins in Table D or Table E (or functional fragments or variants thereof that are at least about 70, 75, 80, 85, 90, 95, 96, 97, 98, or 99% homologous to the sequences disclosed in either Table). In some embodiments, the terms "Cas-binding domain" or "Cas protein-binding domain" refers to a nucleic acid element or domain within a nucleic acid sequence or polynucleotide sequence that, in a biophysically effective amount, will bind to or have an affinity for one or a plurality of proteins in Table D or Table E (or functional fragments or variants thereof that are at least about 70, 75, 80, 85, 90, 95, 96, 97, 98, or 99% homologous to the sequences disclosed in either Table). In some embodiments, the Cas binding domain consists of no more than about 10, 11, 12, 13, 14, 15, 16, 17 18, 19, 20, 25, 30, 35, 40, 41, 42, 43, 44, 45, 50, 60, 70, 80, 90, 100, 110, 120, 130, 140, 150, 160, 170, 180, 190, 200, 210, 220, 230, 240, 250 or more nucleotides in length and comprises at least one sequence that is capable of forming a hairpin or duplex that partially associates or binds to a biologically active CRISPR system at a concentration and within microenvironment suitable for CRISPR system formation. In some embodiments, the composition or pharmaceutical compositions comprises one or a combination of sgRNA, crRNA, and tracrRNA that consists of no more than about 25, 30, 35, 40, 45, 50, 60, 70, 80, 90, 100, 110, 120, 130, 140, 150, 160, 170, 180, 190, 200, 210, 220, 230, 240, 250 or more nucleotides in length and comprises at least one sequence that is capable of forming a hairpin or duplex that partially associates or binds to a biologically active amino acid sequence (or functional fragment disclosed herein) disclosed in Table E at a concentration and within microenvironment suitable for CRISPR system formation and CRISPR enzymatic activity on a target sequence. In some embodiments, the Cas protein derived from the Cas9 family of Cas proteins or a functional fragment thereof.

The terms "transcription terminator domain" refers to a nucleic acid element or domain within a nucleic acid sequence (or polynucleotide sequence) that, in a biophysically effective amount, prevents bacterial transcription when the CRISPR complex is in a bacterial species and/or creates a secondary structure that stabilizes the association of the nucleic acid sequence to one or a plurality of Cas proteins (or functional fragments thereof) encoded by one or a plurality of CRISPR-associated genes such that, in the presence of the one or a plurality of proteins (or functional fragments thereof), the one or plurality of Cas proteins and the nucleic acid element forms a biologically active CRISPR complex and/or can be enzymatically active on a target sequence in the presence of such a target sequence and a DNA-binding domain. In some embodiments, the transcription terminator domain consists of no more than about 25, 30, 35, 40, 45, 50, 60, 70, 80, 90, 100, 110, 120, 130, 140, 150, 160, 170, 180, 190, 200, 210, 220, 230, 240, 250 or more nucleotides in length and comprises at least one sequence that is capable of forming a hairpin or duplex that partially drives association of the nucleic acid sequence (sgRNA, crRNA with tracrRNA, or other nucleic acid sequence) to a biologically active CRISPR complex at a concentration and microenvironment suitable for CRISPR complex formation.

The terms "DNA-binding domain" refer to an element or refers to a nucleic acid element or domain within a nucleic acid sequence or sgRNA that is complementary to a target sequence. In some embodiments, in a biophysically effective amount upstream from a Cas-binding domain, the DNA-binding domain will bind or have an affinity for one or a plurality of target nucleic acid sequences such that, in the presence of a biologically active CRISPR complex, one or plurality of Cas proteins can be enzymatically active on the target sequence. In some embodiments, the DNA binding domain consists of no more than about 25, 30, 35, 40, 45, 50, 60, 70, 80, 90, 100, 110, 120, 130, 140, 150, 160, 170, 180, 190, 200, 210, 220, 230, 240, 250 or more nucleotides in length and comprises at least one sequence that is capable of forming Watson Crick basepairs with a target sequence as part of a biologically active CRISPR system at a concentration and microenvironment suitable for CRISPR system formation.

"CRISPR system" refers collectively to transcripts or synthetically produced transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or other sequences and transcripts from a CRISPR locus. In some embodiments, one or more elements of a CRISPR system is derived from a type I, type II, or type III CRISPR system. In some embodiments, one or more elements of a CRISPR system is derived from a particular organism comprising an endogenous CRISPR system, such as *Streptococcus pyogenes*. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a nucleic acid sequence to which a guide sequence is designed to have complementarity, where hybridization between a target sequence and a guide sequence promotes the formation of a CRISPR complex. Full complementarity is not necessarily required, provided there is sufficient complementarity to cause hybridization and promote formation of a CRISPR complex. A target sequence may comprise any polynucleotide, such as DNA or RNA polynucleotides. In some embodiments, the target sequence is a DNA polynucleotide and is referred to a DNA target sequence. In some embodiments, a target sequence comprises at least three nucleic acid sequences that are recognized by a Cas-protein when the Cas protein is associated with a CRISPR complex or system which comprises at least one sgRNA or one tracrRNA/crRNA duplex at a concentration and within an microenvironment suitable for association of such a system. In some embodiments the target DNA comprises at least one or more proto-spacer adjacent motifs which sequences are known in the art and are dependent upon the Cas protein system being used in conjunction with the sgRNA or crRNA/tracrRNAs employed by this work. In some embodiments, the target DNA comprises NNG, where G is an guanine and N is any naturally occurring nucleic acid. In some embodiments the target DNA comprises any one or combination of NNG, NNA, GAA, NNAGAAW and NGGNG, where G is an guanine, A is adenine, and N is any naturally occurring nucleic acid In some embodiments, a target sequence is located in the nucleus or cytoplasm of a cell. In some embodiments, the target sequence may be within an organelle of a eukaryotic cell, for example, mitochondrion or chloroplast. A sequence or template that may be used for recombination into the targeted locus comprising the target sequences is referred to as an "editing template" or "editing polynucleotide" or "editing sequence". In aspects of the disclosure, an exogenous template polynucleotide may be referred to as an editing template. In an aspect of the disclosure the recombination is homologous recombination. In some embodiments, a composition disclosed herein comprises a recombination template. A recombination template may be a component of another vector as described herein, contained in a separate vector, or provided as a separate polynucleotide. In some embodiments, a recombination template is designed to serve as a template in homologous recombination, such as within or near a target sequence nicked or cleaved by a CRISPR enzyme (or equivalently a "Cas protein") as a part of a CRISPR complex. A template polynucleotide may be of any suitable length, such as about or more than about 10, 15, 20, 25, 50, 75, 100, 150, 200, 500, 1000, or more nucleotides in length. In some embodiments, the template polynucleotide is complementary to a portion of a polynucleotide comprising the target sequence. When optimally aligned, a template polynucleotide might overlap with one or more nucleotides of a target sequences (e.g. about or more than about 1, 5, 10, 15, 20, 25, 30, 35, 40, 45, 50, 60, 70, 80, 90, 100 or more nucleotides). In some embodiments, when a template sequence and a polynucleotide comprising a target sequence are optimally aligned, the nearest nucleotide of the template polynucleotide is within about 1, 5, 10, 15, 20, 25, 50, 75, 100, 200, 300, 400, 500, 1000, 5000, 10000, or more nucleotides from the target sequence.

Typically, in the context of an endogenous CRISPR system, formation of a CRISPR complex (comprising a guide sequence hybridized to a target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. Without wishing to be bound by theory, the tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to the guide sequence. In some embodiments, the tracr sequence has sufficient complementarity to a tracr mate sequence to hybridize and participate in formation of a CRISPR complex. As with the target sequence, it is believed that complete complementarity is not needed, provided there is sufficient to be functional (bind the Cas protein or functional fragment thereof). In some embodiments, the tracr sequence has at least 50%, 60%, 70%, 80%, 90%, 95% or 99% of sequence complementarity along the length of the tracr mate sequence when optimally aligned. In some embodiments, one or more vectors driving expression of one or more elements of a CRISPR system are introduced into a host cell such that the presence and/or expression of the elements of the CRISPR system direct formation of a CRISPR complex at one or more target sites. For example, a Cas enzyme, a guide sequence linked to a tracr-mate sequence, and a tracr sequence could each be operably linked to separate regulatory elements on separate vectors. Alternatively, two or more of the elements expressed from the same or different regulatory elements, may be combined in a single vector, with one or more additional vectors providing any components of the CRISPR system not included in the first vector. With at least some of the modification contemplated by this disclosure, in some embodiments, the guide sequence or RNA or DNA sequences that form a CRISPR complex are at least partially synthetic. The CRISPR system elements that are combined in a single vector may be arranged in any suitable orientation, such as one element located 5' with respect to ("upstream" of) or 3' with respect to ("downstream" of) a second element. In some embodiments, the disclosure relates to a composition comprising a chemically synthesized guide sequence. In some embodiments, the chemically synthesized guide sequence is used in conjunction with a vector comprising a coding sequence that encodes a CRISPR enzyme, such as a type II Cas9 protein. In some embodiments, the chemically synthesized guide sequence is used in conjunction with one or more vectors, wherein each vector comprises a coding sequence that encodes a CRISPR enzyme, such as a type II Cas9 protein. The coding sequence of one element may be located on the same or opposite strand of the coding sequence of a second element, and oriented in the same or opposite direction. In some embodiments, a single promoter drives expression of a transcript encoding a CRISPR enzyme and one or more additional (second, third, fourth, etc.) guide sequences, tracr mate sequence (optionally operably linked to the guide sequence), and a tracr sequence embedded within one or more intron sequences (e.g. each in a different intron, two or more in at least one intron, or all in a single intron). In some embodiments, the CRISPR enzyme, one or more additional guide sequence, tracr mate sequence, and tracr sequence are each a component of different nucleic acid sequences. For instance, in the case of a tracr and tracr mate sequences and in some embodiments, the disclosure relates to a composition comprising at least a first and second nucleic acid sequence, wherein the first nucleic acid sequence comprises a tracr sequence and the second nucleic acid sequence comprises a tracr mate sequence, wherein the first nucleic acid sequence is at least partially complementary to the second nucleic acid sequence such that the first and second nucleic acid for a duplex and wherein the first nucleic acid and the second nucleic acid either individually or collectively comprise a DNA-targeting domain, a Cas protein binding domain, and a transcription terminator domain. In some embodiments, the CRISPR enzyme, one or more additional guide sequence, tracr mate sequence, and tracr sequence are operably linked to and expressed from the same promoter. In some embodiments, the disclosure relates to compositions comprising any one or combination of the disclosed domains on one guide sequence or two separate tracrRNA/crRNA sequences with or without any of the disclosed modifications. Any methods disclosed herein also relate to the use of tracrRNA/crRNA sequence interchangeably with the use of a guide sequence, such that a composition may comprise a single synthetic guide sequence and/or a synthetic tracrRNA/crRNA with any one or combination of modified domains disclosed herein.

One or a plurality of vectors may also be components in any system or composition provided herein. In some embodiments, a vector comprises one or more insertion sites, such as a restriction endonuclease recognition sequence (also referred to as a "cloning site"). In some embodiments, one or more insertion sites (e.g. about or more than about 1, 2, 3, 4, 5, 6, 7, 8, 9, 10, or more insertion sites) are located upstream and/or downstream of one or more sequence elements of one or more vectors. In some embodiments, a vector comprises an insertion site upstream of a tracr mate sequence, and optionally downstream of a regulatory element operably linked to the tracr mate sequence, such that following insertion of a guide sequence into the insertion site and upon expression, the guide sequence directs sequence-specific binding of a CRISPR complex to a target sequence in a eukaryotic cell. In some embodiments, a vector comprises two or more insertion sites, each insertion site being located between two tracr mate sequences so as to allow insertion of a guide sequence at each site. In such an arrangement, the two or more guide sequences may comprise two or more copies of a single guide sequence, two or more different guide sequences, or combinations of these. When multiple, different guide sequences are used, a single expression construct may be used to target CRISPR activity to multiple, different, corresponding target sequences within a cell. For example, a single vector may comprise about or more than about 1, 2, 3, 4, 5, 6, 7, 8, 9, 10, 15, 20, or more guide sequences. In some embodiments, about or more than about 1, 2, 3, 4, 5, 6, 7, 8, 9, 10, or more such guide-sequence-containing vectors may be provided, and optionally delivered to a cell. The disclosure relates to any composition comprising any of the aforementioned elements and one or more artificially synthesized guide sgRNA described herein.

Another aspect of the disclosure relates to a CRISPR system comprising a modified CRISPR enzyme (or "Cas protein") or a nucleotide sequence encoding one or more Cas proteins. Any protein capable of enzymatic activity in cooperation with a guide sequence is a Cas protein. In some embodiments, the disclosure relates to a system comprises a vector comprising a regulatory element operably linked to an enzyme-coding sequence encoding a CRISPR enzyme, such as a Cas protein from the Cas family of enzymes. In some embodiments, the disclosure relates to a system, composition, or pharmaceutical composition comprising any one or plurality of Cas proteins either individually or in combination with one or a plurality of guide sequences. Compositions of one or a plurality of Cas proteins may be admistered to a subject with any of the disclosed guide sequences sqeuntially or contemporaneously. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, type V CRISPR-Cas systems, variants and fragments thereof, or modified versions thereof having at least 70% homology to the sequences of Table E. These enzymes are known; for example, the amino acid sequence of *S. pyogenes* Cas9 protein may be found in the SwissProt database under accession number Q99ZW2. In some embodiments, the unmodified CRISPR enzyme has DNA cleavage activity, such as Cas9. In some embodiments the CRISPR enzyme is Cas9, and may be Cas9 from *S. pyogenes* or *S. pneumoniae*. In some embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, a vector encodes a CRISPR enzyme or Cas protein that is mutated to with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (cleaves a single strand). Other examples of mutations that render Cas9 a nickase include, without limitation, H840A, N854A, and N863A. In some embodiments, a Cas9 nickase may be used in combination with guide sequenc(es), e.g., two guide sequences, which target respectively sense and antisense strands of the DNA target. This combination allows both strands to be nicked and used to induce NHEJ.

As a further example, two or more catalytic domains of Cas9 (RuvC I, RuvC II, and RuvC III) may be mutated to produce a mutated Cas9 substantially lacking all DNA cleavage activity. In some embodiments, a D10A mutation is combined with one or more of H840A, N854A, or N863A mutations to produce a Cas9 enzyme substantially lacking all DNA cleavage activity. In some embodiments, a CRISPR enzyme is considered to substantially lack all DNA cleavage activity when the DNA cleavage activity of the mutated enzyme is less than about 25%, 10%, 5%, 1%, 0.1%, 0.01%, or lower with respect to its non-mutated form. Other mutations may be useful; where the Cas9 or other CRISPR enzyme is from a species other than *S. pyogenes*, mutations in corresponding amino acids may be made to achieve similar effects.

In some embodiments, an enzyme coding sequence encoding a CRISPR enzyme is codon optimized for expression in particular cells, such as eukaryotic cells. The eukaryotic cells may be those of or derived from a particular organism or a particular subject, such as a mammal, including but not limited to human, mouse, rat, rabbit, dog, or non-human primate. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database", and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, Pa.), are also available. In some embodiments, one or more codons (e.g. 1, 2, 3, 4, 5, 10, 15, 20, 25, 50, or more, or all codons) in a sequence encoding a CRISPR enzyme correspond to the most frequently used codon for a particular amino acid.

TABLE D

| CRISPR enzymes (Cas proteins or Cas-like proteins) organized by Family | | | | | | |
|---|---|---|---|---|---|---|
| Proposed gene name‡ | System type or subtype | Name from Haft et al.§ | Name from Brouns et al.‖ | Structure of encoded protein (PDB accessions)¶ | Families (and superfamily) of encoded protein#** | Representatives |
| cas1 | Type I Type II Type III | cas1 | cas1 | 3GOD, 3LFX and 2YZS | COG1518 | SERP2463, SPy1047 and ygbT |
| cas2 | Type I Type II Type III | cas2 | cas1 | 2IVY, 2I8E and 3EXC | COG1343 and COG3512 | SERP2462, SPy1048, SPy1723 (N-terminal domain) and ygbF |
| cas3' | Type I‡‡ | cas3 | cas3 | NA | COG1203 | APE1232 and ygcB |
| cas3" | Subtype I-A Subtype I-B | NA | NA | NA | COG2254 | APE1231 and BH0336 |
| cas4 | Subtype I-A Subtype I-B Subtype I-C Subtype I-D Subtype II-B | cas4 and csa1 | NA | NA | COG1468 | APE1239 and BH0340 |
| cas5 | Subtype I-A Subtype I-B Subtype I-C Subtype I-E | cas5a, cas5d, cas5e, cas5h, cas5p, cas5t and cmx5 | casD | 3KG4 | COG1688 (RAMP) | APE1234, BH0337, devS and ygcI |
| cas6 | Subtype I-A Subtype I-B Subtype I-D Subtype III-A Subtype III-B | cas6 and cmx6 | NA | 3I4H | COG1583 and COG5551 (RAMP) | PF1131 and slr7014 |
| cas6e | Subtype I-E | cse3 | casE | 1WJ9 | (RAMP) | ygcH |
| cas6f | Subtype I-F | csy4 | NA | 2XLJ | (RAMP) | y1727 |
| cas7 | Subtype I-A Subtype I-B Subtype I-C Subtype I-E | csa2, csd2, cse4, csh2, csp1 and cst2 | casC | NA | COG1857 and COG3649 (RAMP) | devR and ygcJ |
| cas8a1 | Subtype I-A‡‡ | cmx1, cst1, csx8, csx13 and CXXC-CXXC | NA | NA | BH0338-like | LA3191§§ and PG2018§§ |
| cas8a2 | Subtype I-A‡‡ | csa4 and csx9 | NA | NA | PH0918 | AF0070, AF1873, MJ0385, PF0637, PH0918 and SSO1401 |
| cas8b | Subtype I-B‡‡ | csh1 and TM1802 | NA | NA | BH0338-like | MTH1090 and TM1802 |
| cas8c | Subtype I-C‡‡ | csd1 and csp2 | NA | NA | BH0338-like | BH0338 |
| cas9 | Type II‡‡ | csn1 and csx12 | NA | NA | COG3513 | FTN_0757 and SPy1046 |
| cas10 | Type III‡‡ | cmr2, csm1 and csx11 | NA | NA | COG1353 | MTH326, Rv2823c§§ and TM1794§§ |
| cas10d | Subtype I-D‡‡ | csc3 | NA | NA | COG1353 | slr7011 |
| csy1 | Subtype I-F‡‡ | csy1 | NA | NA | y1724-like | y1724 |
| csy2 | Subtype I-F | csy2 | NA | NA | (RAMP) | y1725 |
| csy3 | Subtype I-F | csy3 | NA | NA | (RAMP) | y1726 |
| cse1 | Subtype I-E‡‡ | cse1 | casA | NA | YgcL-like | ygcL |
| cse2 | Subtype I-E | cse2 | casB | 2ZCA | YgcK-like | ygcK |
| csc1 | Subtype I-D | csc1 | NA | NA | alr1563-like (RAMP) | alr1563 |
| csc2 | Subtype I-D | csc1 and csc2 | NA | NA | COG1337 (RAMP) | slr7012 |
| csa5 | Subtype I-A | csa5 | NA | NA | AF1870 | AF1870, MJ0380, PF0643 and SSO1398 |

TABLE D-continued

CRISPR enzymes (Cas proteins or Cas-like proteins) organized by Family

| Proposed gene name‡ | System type or subtype | Name from Haft et al.§ | Name from Brouns et al.‖ | Structure of encoded protein (PDB accessions)¶ | Families (and superfamily) of encoded protein#** | Representatives |
|---|---|---|---|---|---|---|
| csn2 | Subtype II-A | csn2 | NA | NA | SPy1049-like | SPy1049 |
| csm2 | Subtype III-A‡‡ | csm2 | NA | NA | COG1421 | MTH1081 and SERP2460 |
| csm3 | Subtype III-A | csc2 and csm3 | NA | NA | COG1337 (RAMP) | MTH1080 and SERP2459 |
| csm4 | Subtype III-A | csm4 | NA | NA | COG1567 (RAMP) | MTH1079 and SERP2458 |
| csm5 | Subtype III-A | csm5 | NA | NA | COG1332 (RAMP) | MTH1078 and SERP2457 |
| csm6 | Subtype III-A | APE2256 and csm6 | NA | 2WTE | COG1517 | APE2256 and SSO1445 |
| cmr1 | Subtype III-B | cmr1 | NA | NA | COG1367 (RAMP) | PF1130 |
| cmr3 | Subtype III-B | cmr3 | NA | NA | COG1769 (RAMP) | PF1128 |
| cmr4 | Subtype III-B | cmr4 | NA | NA | COG1336 (RAMP) | PF1126 |
| cmr5 | Subtype III-B‡‡ | cmr5 | NA | 2ZOP and 2OEB | COG3337 | MTH324 and PF1125 |
| cmr6 | Subtype III-B | cmr6 | NA | NA | COG1604 (RAMP) | PF1124 |
| csb1 | Subtype I-U | GSU0053 | NA | NA | (RAMP) | Balac_1306 and GSU0053 |
| csb2 | Subtype I-U§§ | NA | NA | NA | (RAMP) | Balac_1305 and GSU0054 |
| csb3 | Subtype I-U | NA | NA | NA | (RAMP) | Balac_1303§§ |
| csx17 | Subtype I-U | NA | NA | NA | NA | Btus_2683 |
| csx14 | Subtype I-U | NA | NA | NA | NA | GSU0052 |
| csx10 | Subtype I-U | csx10 | NA | NA | (RAMP) | Caur_2274 |
| csx16 | Subtype III-U | VVA1548 | NA | NA | NA | VVA1548 |
| csaX | Subtype III-U | csaX | NA | NA | NA | SSO1438 |
| csx3 | Subtype III-U | csx3 | NA | NA | NA | AF1864 |
| csx1 | Subtype III-U | csa3, csx1, csx2, DXTHG, NE0113 and TIGR02710 | NA | 1XMX and 2I71 | COG1517 and COG4006 | MJ1666, NE0113, PF1127 and TM1812 |
| csx15 | Unknown | NA | NA | NA | TTE2665 | TTE2665 |

In some embodiments, a vector encodes a CRISPR enzyme comprising one or more nuclear localization sequences (NLSs), such as about (or more than about) 1, 2, 3, 4, 5, 6, 7, 8, 9, 10, or more NLSs. In some embodiments, the CRISPR enzyme comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g. one or more NLS at the amino-terminus and one or more NLS at the carboxy terminus). When more than one NLS is present, each may be selected independently of the others, such that a single NLS may be present in more than one copy and/or in combination with one or more other NLSs present in one or more copies. In a preferred embodiment of the disclosure, the CRISPR enzyme comprises at most 6 NLSs. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. Typically, an NLS consists of one or more short sequences of positively charged lysines or arginines exposed on the protein surface, but other types of NLS are known. Non-limiting examples of NLSs include an NLS sequence derived from: the NLS of the SV40 virus large T-antigen, having the amino acid sequence PKKKRKV (SEQ ID NO: 75); the NLS from nucleoplasmin (e.g. the nucleoplasmin bipartite NLS with the sequence KRPAATKKAGQAKKKK (SEQ ID NO:76)); the c-myc NLS having the amino acid sequence PAAKRVKLD (SEQ ID NO:77) or RQRRNELKRSP (SEQ ID NO:78); the hRNPAI M9 NLS having the sequence NQSSNFGPMKGGNFGGRSSGPYGGGGQYFAK-PRNQGGY (SEQ ID NO:79); the sequence RMRIZFKNKGKDTAELRRRRVEVSVELRKAKKD-EQILKRRNV (SEQ ID NO:80) of the IBB domain from importin-alpha; the sequences VSRKRPRP (SEQ ID NO:81) and PPKKARED (SEQ ID NO:82) of the myoma T protein; the sequence PQPKKKPL (SEQ ID NO:83) of human p53; the sequence SALIKKKKKMAP (SEQ ID NO:84) of mouse c-abl IV; the sequences DRLRR (SEQ ID NO:14) and PKQKKRK (SEQ ID NO:15) of the influenza virus NS1; the sequence RKLKKKIKKL (SEQ ID NO:16) of the Hepatitis virus delta antigen; the sequence REKKKFLKRR (SEQ ID NO:17) of the mouse Mx protein; the sequence KRKGDEVDGVDEVAKKKSKK (SEQ ID NO:18) of the human poly(ADP-ribose) polymerase; and the sequence RKCLQAGMNLEARKTKK (SEQ ID NO:19) of the steroid hormone receptors (human) glucocorticoid. In general, the one or more NLSs are of sufficient strength to drive accumulation of the CRISPR enzyme in a detectable amount in the nucleus of a eukaryotic cell. Strength of nuclear localization activity may derive from the number of NLSs in the CRISPR enzyme, the particular NLS(s) used, or a combination of these factors. Detection of accumulation in the nucleus may be performed by any suitable technique. For example, a detectable marker may be fused to the CRISPR enzyme, such that location within a cell may be visualized, such as in combination with a means for detecting the location of the nucleus (e.g. a stain specific for the nucleus such as DAPI). Examples of detectable markers include fluorescent proteins (such as Green fluorescent proteins, or GFP; RFP; CFP), and epitope tags (HA tag, flag tag, SNAP tag). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of CRISPR complex formation (e.g. assay for DNA cleavage or mutation at the target sequence, or assay for altered gene expression activity affected by CRISPR complex formation and/or CRISPR enzyme activity), as compared to a control no exposed to the CRISPR enzyme or complex, or exposed to a CRISPR enzyme lacking the one or more NLSs.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The terms "functional fragment" means any portion of a polypeptide or nucleic acid sequence from which the respective full-length polypeptide or nucleic acid relates that is of a sufficient length and has a sufficient structure to confer a biological affect that is at least similar or substantially similar to the full-length polypeptide or nucleic acid upon which the fragment is based. In some embodiments, a functional fragment is a portion of a full-length or wild-type nucleic acid sequence that encodes any one of the nucleic acid sequences disclosed herein, and said portion encodes a polypeptide of a certain length and/or structure that is less than full-length but encodes a domain that still biologically functional as compared to the full-length or wild-type protein. In some embodiments, the functional fragment may have a reduced biological activity, about equivalent biological activity, or an enhanced biological activity as compared to the wild-type or full-length polypeptide sequence upon which the fragment is based. In some embodiments, the functional fragment is derived from the sequence of an organism, such as a human. In such embodiments, the functional fragment may retain 99%, 98%, 97%, 96%, 95%, 94%, 93%, 92%, 91%, or 90% sequence identity to the wild-type human sequence upon which the sequence is derived. In some embodiments, the functional fragment may retain 85%, 80%, 75%, 70%, 65%, or 60% sequence homology to the wild-type sequence upon which the sequence is derived.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence.

The present disclosure also relates to isotopically-enriched compounds, which are structurally similar to the nucleic acid sequences disclosed herein, but for the fact that one or more atoms are replaced by an atom having an atomic mass or mass number different from the atomic mass or mass number usually found in nature. Examples of isotopes that can be incorporated into compounds of the disclosure include isotopes of hydrogen, carbon, nitrogen, oxygen, phosphorous, fluorine and chlorine, such as $^{2}H$, $^{3}H$, $^{13}C$, $^{14}C$, $^{15}N$, $^{16}O$, $^{17}O$, $^{31}P$, $^{32}P$, $^{35}S$, $^{18}F$, and $^{36}Cl$. Nucleic acids of the present disclosures that contain the aforementioned isotopes and/or other isotopes of other atoms are within the scope of this disclosure. Certain isotopically-labelled compounds of the present disclosure, for example those into which radioactive isotopes such as 3H and 14C are incorporated, are useful in drug and/or substrate tissue distribution assays. Tritiated, i.e., 3H, and carbon-14, i.e., 14C, isotopes are particularly preferred for their ease of preparation and detection. Further, substitution with heavier isotopes such as deuterium, i.e., 2H, can afford certain therapeutic advantages resulting from greater metabolic stability, for example increased in vivo half-life or reduced dosage requirements and, hence, may be preferred in some circumstances. Isotopically enriched compounds of this disclosure can generally be prepared by substituting a readily available isotopically labeled reagent for a non-isotopically enriched reagent. The disclosure relates to nucleic acids disclosed herein unsolvated forms as well as solvated forms, including hydrated forms. The compounds of the disclosure also are capable of forming both pharmaceutically acceptable salts, including but not limited to acid addition and/or base addition salts. Furthermore, compounds of the present disclosure may exist in various solid states including an amorphous form (noncrystalline form), and in the form of clathrates, prodrugs, polymorphs, bio-hydrolyzable esters, racemic mixtures, non-racemic mixtures, or as purified stereoisomers including, but not limited to, optically pure enantiomers and diastereomers. In general, all of these forms can be used as an alternative form to the free base or free acid forms of the compounds, as described above and are intended to be encompassed within the scope of the present disclosure.

"Nucleobase" means a heterocyclic moiety capable of non-covalently pairing with another nucleobase.

"Nucleoside" means a nucleobase linked to a sugar moiety.

"Nucleotide" means a nucleoside having a phosphate group covalently linked to the sugar portion of a nucleoside. In some embodiments, the nucleotide is characterized as being modified if the 3' phosphate group is covalently linked to a contiguous nucleotide by any linkage other than a phosphodiester bond.

"Compound comprising a modified oligonucleotide consisting of a number of linked nucleosides means a compound that includes a modified oligonucleotide having the specified number of linked nucleosides. Thus, the compound may include additional substituents or conjugates. Unless otherwise indicated, the compound does not include any additional nucleosides beyond those of the modified oligonucleotide.

"Modified oligonucleotide" means an oligonucleotide having one or more modifications relative to a naturally occurring terminus, sugar, nucleobase, and/or internucleoside linkage. A modified oligonucleotide may comprise unmodified nucleosides.

"Single-stranded modified oligonucleotide" means a modified oligonucleotide which is not hybridized to a complementary strand.

"Modified nucleoside" means a nucleoside having any change from a naturally occurring nucleoside. A modified nucleoside may have a modified sugar, and an unmodified nucleobase. A modified nucleoside may have a modified sugar and a modified nucleobase. A modified nucleoside may have a natural sugar and a modified nucleobase. In certain embodiments, a modified nucleoside is a bicyclic nucleoside. In certain embodiments, a modified nucleoside is a non-bicyclic nucleoside.

A "polymorph" refers to solid crystalline forms of a compound. In some embodiments, one or more nucleic acids disclosed herein are in polymorph form. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Different physical properties of polymorphs can affect their processing.

The guide sequences, nucleic acid sequences, proteins or other agents of the present disclosure can be administered, inter alia, as pharmaceutically acceptable salts, esters, or amides. The term "salts" refers to inorganic and organic salts of compounds of the present disclosure. The salts can be prepared in situ during the final isolation and purification of a compound, or by separately reacting a purified compound in its free base or acid form with a suitable organic or inorganic base or acid and isolating the salt thus formed. Representative salts include the hydrobromide, hydrochloride, sulfate, bisulfate, nitrate, acetate, oxalate, palmitate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. The salts may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, S. M. Berge, et al., "Pharmaceutical Salts," J Pharm Sci, 66: 1-19 (1977).

The terms "polynucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after synthesis or polymerization, such as by conjugation with a labeling component.

The oligonucleotides of the disclosure also include those nucleic acid sequences disclosed herein that comprise nucleosides connected by charged linkages, and/or whose sequences are divided into at least two subsequences. In some embodiments, a first, second, and third subsequence or domains include a nucleotide binding domain (or DNA-binding domain), a Cas-binding domain, and a transcription terminator domain. In some embodiments, a first, second, and third subsequence or domains include a nucleotide binding domain, a Cas-binding domain, and a transcription terminator sequence, but, if any two domains are present the they must be oriented such that the nucleotide binding domain precedes the Cas-binding domain which, in turn precedes the transcription terminator domain in a 5' to 3' orientation. Any of the nucleosides within any of the domains may be 2'-substituted-nucleosides linked by a first type of linkage. The second subsequence includes nucleosides linked by a second type of linkage. In some embodiments, there exists a third subsequence whose nucleosides are selected from those selectable for the first subsequence, and the second subsequence is positioned between the first and the third subsequences. Such oligonucleotides of the disclosure are known as "chimeras," or "chimeric" or "gapped" oligonucleotides.

In the context of this disclosure, the term "oligonucleotide" also refers to a plurality of nucleotides joined together in a specific sequence from naturally and non-naturally occurring nucleobases. Nucleobases of the disclosure are joined through a sugar moiety via phosphorus linkages, and include any one or combination of adenine, guanine, cytosine, uracil, thymine, xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thiolalkyl guanines, 8-hydroxyl guanine and other 8-substituted guanines, other aza and deaza uracils, other aza and deaza thymidines, other aza and deaza cytosines, other aza and deaza adenines, other aza and deaza guanines, 5-trifluoromethyl uracil and 5-trifluoro cytosine. The sugar moiety may be deoxyribose or ribose. The sugar moiety may be a modified deoxyribose or ribose with one or more modifications on the $C_1$, $C_2$, $C_3$, $C_4$, and/or $C_5$ carbons. The oligonucleotides of the disclosure may also comprise modified nucleobases or nucleobases having other modifications consistent with the spirit of this disclosure, and in particular modifications that increase their nuclease resistance in order to facilitate their use as therapeutic, diagnostic or research reagents.

The terms "polypeptide", "peptide" and "protein" are used interchangeably herein to refer to polymers of amino acids of any length. The polymer may be linear or branched, it may comprise modified amino acids, and it may be interrupted by non-natural amino acids or chemical groups that are not amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics.

As used herein, "more than one" or "two or more" 2, 3, 4, 5, 6, 7, 8, 9, or 10 or more. In some embodiments, "more than one" means 2, 3, 4, or 5 of the amino acids or nucleic acids or mutations described herein. In some embodiments, "more than one" means 2, 3, or 4 of the amino acids or nucleic acids or mutations described herein. In some embodiments, "more than one" means 2 or 3 of the amino acids or nucleic acids or mutations described herein. In some embodiments, "more than one" means 2 of the amino acids or nucleic acids or mutations described herein.

"Sugar moiety" means a naturally occurring furanosyl or a modified sugar moiety.

"Modified sugar moiety" means a substituted sugar moiety or a sugar surrogate.

"Substituted sugar moiety" means a furanosyl that is not a naturally occurring furanosyl. Substituted sugar moieties include, but are not limited to sugar moieties comprising modifications at the 2'-position, the 5'-position and/or the 4'-position of a naturally occurring furanosyl. Certain substituted sugar moieties are bicyclic sugar moieties.

"Sugar surrogate" means a structure that does not comprise a furanosyl and that is capable of replacing the naturally occurring furanosyl of a nucleoside, such that the resulting nucleoside is capable of (1) incorporation into an oligonucleotide and (2) hybridization to a complementary nucleoside. Such structures include relatively simple changes to the furanosyl, such as rings comprising a different number of atoms (e.g., 4, 6, or 7-membered rings); replacement of the oxygen of the furanosyl with a non-oxygen atom (e.g., carbon, sulfur, or nitrogen); or both a change in the number of atoms and a replacement of the oxygen. Such structures may also comprise substitutions corresponding with those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholines, cyclohexenyls and cyclohexitols.

The terms "therapeutically effective amount" mean a quantity sufficient to achieve a desired therapeutic and/or prophylactic effect, for example, an amount which results in the prevention or amelioration of or a decrease in the symptoms associated with a disease that is being treated. The amount of composition administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The regimen of administration can affect what constitutes an effective amount. The compound of the disclosure can be administered to the subject either prior to or after the onset of disease or disorder. Further, several divided dosages, as well as staggered dosages, can be administered daily or sequentially, or the dose can be continuously infused, or can be a bolus injection. Further, the dosages of the compound(s) of the disclosure can be proportionally increased or decreased as indicated by the exigencies of the therapeutic or prophylactic situation. Typically, an effective amount of the compounds of the present disclosure, sufficient for achieving a therapeutic or prophylactic effect, range from about 0.000001 mg per kilogram body weight per day to about 10,000 mg per kilogram body weight per day. Preferably, the dosage ranges are from about 0.0001 mg per kilogram body weight per day to about 100 mg per kilogram body weight per day. A therapetucially effective amount of a pharmaceutical composition comprising any one or a plurality of any of the guide sequences disclosed herein (and, optionally, any nucleic acid sequence encoding a Cas protein of the present disclosure) can also be administered in combination with each other, or with one or more additional therapeutic compounds. Those skilled in the art will recognize and determine a therapeutically effective amount of any of the guide sequences disclosed herein whether calculated when administered alone or part of a therapeutic regimen that includes one or more other beta-catenin nuclear translocation inhibitors and/or one or more one or more other therapeutic agents and/or one or more other therapeutic treatments or interventions. Generally, therapeutically effective amount refers to an amount of a guide sequence (such as an sgRNA) that, in combination with one or a plurality of CRISPR system components causes a mutation in a target sequence sufficient to ameliorate symptoms, or reverse, prevent or reduce the rate of progress of disease, or extend life span of a subject when administered alone or in combination with other therapeutic agents or treatments as compared to the symptoms, rate of progress of disease, or life span of an individual not receiving a therapeutically effective amount an sgRNA disclosed herein. In some embodiments, the therapeutically effective amount thereof is the amount of sgRNA needed to form a CRISPR complex with any disclosed Cas protein and cause the Cas protein within the complex to adequately perform its enzymatic function at or proximate to the target sequence.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Alkyl is not cyclized. Examples of saturated hydrocarbon radicals include, but are not limited to, groups such as methyl, ethyl, n-propyl, isopropyl, n-butyl, t-butyl, isobutyl, sec-butyl, (cyclohexyl) methyl, homologs and isomers of, for example, n-pentyl, n-hexyl, n-heptyl, n-octyl, and the like. An unsaturated alkyl group is one having one or more double bonds or triple bonds (e.g. alkene, alkyne). Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —$CH_2CH_2$—. Typically, an alkyl (or alkylene) group will have from about 1 to about 24 carbon atoms, with those groups having 10 or fewer carbon atoms being preferred in the present disclosure. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. Heteroalkyl is not cyclized. The heteroatom(s) 0, N, P, S, and Si may be placed at any interior position of the heteroalkyl group or at the position at which the alkyl group is attached to the remainder of the molecule. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—$S(O)_2$—$CH_3$, —CH═CH—O—$CH_3$, —$Si(CH_3)_3$, —$CH_2$—CH═N—$OCH_3$, —CH═CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—$Si(CH_3)_3$.

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —$C(O)_2R'$— represents both —$C(O)_2R'$— and —$R'C(O)_2$—. As described above, heteroalkyl groups, as used herein, include those groups that are attached to the remainder of the molecule through a heteroatom, such as —C(O)R', —C(O)NR', —NR'R", —OR', —SR', and/or —$SO_2R'$. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Additionally, for heterocycloalkyl, a heteroatom can occupy the position at which the heterocycle is attached to the remainder of the molecule. Cycloalkyl and heterocycloalkyl are non-aromatic. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl.

Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substitutents described herein.

The term "oxo," as used herein, means an oxygen that is double bonded to a carbon atom.

The term "alkylsulfonyl," as used herein, means a moiety having the formula —$S(O_2)$—R', where R' is a substituted or unsubstituted alkyl group as defined above. R' may have a specified number of carbons (e.g., "$C_1$-$C_4$ alkylsulfonyl").

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', ═O, ═NR', ═N—OR', —NR'R", —SR', -halogen, —SiR'R"R"', —OC(O)R', —C(O)R', —$CO_2$R', —CONR'R", —OC(O)NR'R", —NR"C(O)R', —NR'—C(O)NR"R"', —NR"C$(O)_2$R', —NR—C(NR'R"R"')═NR", —NR—C(NR'R")═NR"', —S(O)R', —$S(O)_2$R', —$S(O)_2$NR'R", —$NRSO_2$R', —NR'NR"R"', —ONR'R", —NR'C═(O)NR"NR"'R"", —CN, —$NO_2$, monophosphate (or derivatives thereof), diphosphate (or derivatives thereof), triphosphate (or derivatives thereof), in a number ranging from zero to (2m'+1), where m' is the total number of carbon atoms in such radical. R, R', R", R"', and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the disclosure includes more than one R group, for example, each of the R groups is independently selected as are each R', R", R"', and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R"', —OC(O)R', —C(O)R', —$CO_2$R', —CONR'R", —OC(O)NR'R", —NR"C(O)R', —NR'—C(O)NR"R"', —NR"C$(O)_2$R', —NR—C(NR'R"R"')═NR", —NR—C(NR'R")═NR"', —S(O)R', —$S(O)_2$R', —$S(O)_2$NR'R", —$NRSO_2$R', —NR'NR"R"', —ONR'R", —NR'C, (O)NR"NR"'R"", —CN, —$NO_2$, —R', —$N_3$, —CH$(Ph)_2$, fluoro($C_1$-$C_4$)alkoxy, and fluoro($C_1$-$C_4$)alkyl, in a number ranging from zero to the total number of open valences on the aromatic ring system; and where R', R", R"', and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the disclosure includes more than one R group, for example, each of the R groups is independently selected as are each R', R", R"', and R"" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In embodiments, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')q-U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-$(CH_2)$r-B—, wherein A and B are independently —CRR'—, —O—, —NR—, —S—, —S(O)—, —$S(O)_2$—, —$S(O)_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')s-X'—(C"R"R"')d-, where s and d are independently integers of from 0 to 3, and X' is —O—, —NR'—, —S—, —S(O)—, —$S(O)_2$—, or —$S(O)_2$NR'—. The substituents R, R', R", and R"' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties: (A) oxo, halogen, —$CF_3$, —CN, —OH, —$NH_2$, —COOH, —$CONH_2$, —$NO_2$, —SH, —$SO_2$Cl, —$SO_3$H, —$SO_4$H, —$SO_2NH_2$, —$NHNH_2$, —$ONH_2$, —NHC═(O)$NHNH_2$, —NHC═(O)$NH_2$, —$NHSO_2$H, —NHC═(O)H, —NHC(O)—OH, —NHOH, —$OCF_3$, —$OCHF_2$, —$NHSO_2CH_3$, —$N_3$, unsubstituted alkyl, unsubstituted heteroalkyl, unsubstituted cycloalkyl, unsubstituted heterocycloalkyl, unsubstituted aryl, unsubstituted heteroaryl, monophosphate (or derivatives thereof), diphosphate (or derivatives thereof), or triphosphate (or derivatives thereof), and (B) alkyl, heteroalkyl, cycloalkyl, heterocycloalkyl, aryl, heteroaryl, substituted with at least one substituent selected from:

(i) oxo, halogen, —$CF_3$, —CN, —OH, —$NH_2$, —COOH, —$CONH_2$, —$NO_2$, —SH, —$SO_2$Cl, —$SO_3$H, —$SO_4$H, —$SO_2NH_2$, —$NHNH_2$, —$ONH_2$, —NHC═(O)$NHNH_2$, —NHC═(O) $NH_2$, —$NHSO_2$H, —NHC═(O)H, —NHC(O)—OH, —NHOH, —$OCF_3$, —$OCHF_2$, —$NHSO_2CH_3$, —$N_3$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, heteroaryl, substituted with at least one substituent selected from:

(a) oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC═(O)$NHNH_2$, —NHC═(O) $NH_2$, —$NHSO_2H$, —NHC═(O)H, —NHC(O)—OH, —NHOH, —$OCF_3$, —$OCHF_2$, —$NHSO_2CH_3$, —$N_3$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cyclo alkyl, heterocycloalkyl, aryl, heteroaryl, monophosphate (or derivatives thereof), diphosphate (or derivatives thereof), or triphosphate (or derivatives thereof), substituted with at least one substituent selected from: oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC═(O)$NHNH_2$, —NHC═(O) $NH_2$, —$NHSO_2H$, —NHC═(O)H, —NHC(O)—OH, —NHOH, —$OCF_3$, —$OCHF_2$, —$NHSO_2CH_3$, —$N_3$, unsubstituted alkyl, unsubstituted heteroalkyl, unsubstituted cycloalkyl, unsubstituted heterocycloalkyl, unsubstituted aryl, unsubstituted heteroaryl, A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In embodiments, each substituted group described in the compounds herein is substituted with at least one substituent group. More specifically, In embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds, compositions and pharmaceutical compositions disclosed herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In embodiments herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In embodiments, the compound is a chemical species set forth in the Examples section below.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those which are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another. It will be apparent to one skilled in the art that the compositions of this disclosure comprise nucleic acid sequences or molecules with nucleic acids that may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by 13C- or 14C-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium (3H), iodine-125 (125I), or carbon-14 (14C) including the radioisotopes of Table 2. All isotopic variations of the compounds of the present disclosure, whether radioactive or not, are encompassed within the scope of the present disclosure.

The symbol "-" denotes the point of attachment of a chemical moiety to the remainder of a molecule or chemical formula.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The symbol "∿∿" denotes the point of attachment of a chemical moiety to the remainder of a molecule or chemical formula. The symbol "∿∿" denotes one or more than one modified or unmodified contiguous nucleotide.

A "base," as used herein, means a group selected from the following: adenine, guanine, cytosine, uracil, thymine, uridine, pyrimidine, purine, pseudouridine, inosine, hypoxanthine, rhodamine, fluroscein, 2-aminopurine, cytidine, 2'-deoxycytidine, 1,3-Diaza-2-oxophenothiazine, dihydrouridine, queuosine, wyosine, cyanophage S-2L diaminopurine, isoguanine, isocytosine, diaminopyrimidine, 2,4-difluorotoluene, 4-methylbenzimidazole, isoquinoline, pyrrolo[2,3-b]pyridine, 2-amino-6-(2-thienyl)purine, pyrrole-2-carbaldehyde, 2,6-bis(ethylthiomethyl)pyridine, pyridine-2,6-dicarboxamide, 2'-deoxyinosine, 2-amino-8-(2-thienyl)purine, pyridine-2-one, 7-(2-thienyl)imidazo[4,5-b] pyridine, pyrrole-2-carbaldehyde, 4-[3-(6-aminohexanamido)-1-propynyl]-2-nitropyrrole, or modfied derivative thereof.

The term "phosphodiester," by itself or as part of another substituent, means, unless otherwise stated, —O—$P(O)_2$—O—, wherein the phosphate atom is doubly bonded to one oxygen atom and bound to other substituents through the adjacent oxygen atoms.

The term "LNA," as used herein, means any nucleic acid analog disclosed herein comprising a cyclic structure between the C2 and C4 carbon of the sugar moiety of a nucleic acid. In some embodiments, the LNA has the structure below:

LNA

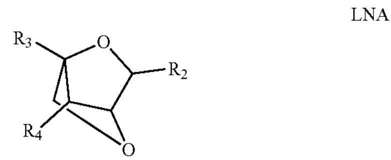

wherein $R_2$ is independently selected from: any base or nucleobase, adenine, guanine, cytosine, uracil, thymine, uridine, pyrimidine, purine, pseudouridine, inosine, or hypoxanthine;

wherein $R_3$ is independently selected from a: phosphodiester, phosphorothioate, aldehyde, carboxyl, carbonyl, ether, ester, or amino; wherein $R_4$ is independently selected from a: phosphodiester, phosphorothioate, aldehyde, carboxyl, carbonyl, ether, ester, or amino;

or a pharmaceutically active salt thereof.

In some embodiments, the present disclosure provides a composition comprising a nucleic acid sequence comprising at least one nucleic acid having Formula W:

W

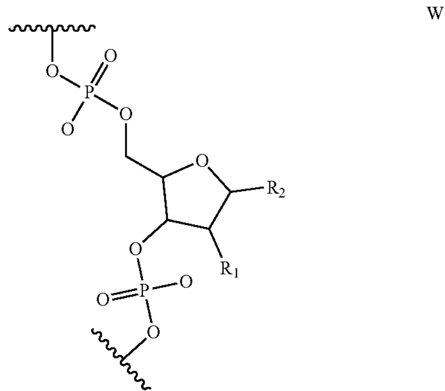

wherein $R_1$ is independently selected from: hydrogen, hydroxyl, halogen, alkyl, alkenyl, alkynyl, acyl, ester, sulfonyl, amide, amine, alkyloxy, methoxyethyl, or DNP (2,4'-dinitrophenol);

wherein $R_2$ is independently selected from: hydrogen, hydroxyl, halogen, alkyl, alkenyl, alkynyl, acyl, a base or nucleobase, adenine, guanine, cytosine, uracil, thymine, uridine, pyrimidine, purine, pseudouridine, inosine, or hypoxanthine;

or a pharmaceutically active salt thereof.

In some embodiments, the present disclosure provides a composition comprising a compound having Formula X:

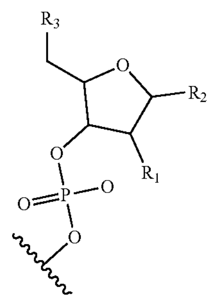

wherein $R_1$ is independently selected from: hydrogen, hydroxyl, halogen, alkyl, alkenyl, alkynyl, acyl, ester, sulfonyl, amide, amine, alkyloxy, methoxyethyl, or DNP (2,4'-dinitrophenol);

wherein $R_2$ is independently selected from: hydrogen, hydroxyl, halogen, alkyl, alkenyl, alkynyl, acyl, adenine, guanine, cytosine, uracil, thymine, uridine, pyrimidine, purine, pseudouridine, inosine, or hypoxanthine;

wherein $R_3$ is independently selected from a: alkylphosphonate, phosphotriester, phosphorodithioate, phosphoramidate, ketone, sulfone, carbonate thioamidate, phosphodiester, phosphorothioate, aldehyde, carboxyl, carbonyl, ether, ester, or amine; wherein, in some embodiments, the alkylphosphonate, phosphotriester, phosphorodithioate, phosphoramidate, ketone, sulfone, carbonate thioamidate, phosphodiester, aldehyde, carboxyl, carbonyl, ether, ester, or amine is bonded to a contiguous nucleic acid or nucleside, such that the formula reads

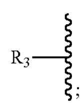

or a pharmaceutically active salt thereof.

In some embodiments, the present disclosure provides a composition comprising a compound having Formula Y:

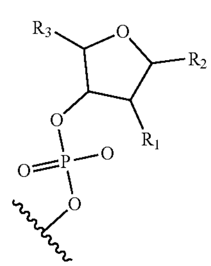

wherein $R_1$ is independently selected from: hydrogen, hydroxyl, halogen, alkyl, alkenyl, alkynyl, acyl, ester, sulfonyl, amide, amine, alkyloxy, methoxyethyl, or DNP (2,4'-dinitrophenol);

wherein $R_2$ is independently selected from: hydrogen, hydroxyl, halogen, alkyl, alkenyl, alkynyl, acyl, adenine, guanine, cytosine, uracil, thymine, uridine, pyrimidine, purine, pseudouridine, inosine, or hypoxanthine;

wherein $R_3$ is independently selected from a: phosphorothioate, phosphodiester, aldehyde, carboxyl, carbonyl, ether, ester, or amine; and wherein, in some optional embodiments, the phosphodiester, aldehyde, carboxyl, carbonyl, ether, ester, or amine is bonded to a contiguous nucleic acid, such that $R_3$ reads

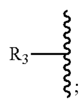

or a pharmaceutically active salt thereof.

In some embodiments, the present disclosure provides a composition comprising a compound having Formula Z:

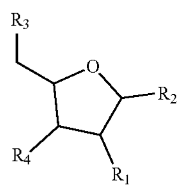

wherein $R_1$ is independently selected from: hydrogen, hydroxyl, halogen, alkyl, alkenyl, alkynyl, acyl, ester, sulfonyl, amide, amine, alkyloxy, methoxyethyl, or DNP (2,4'-dinitrophenol);

wherein $R_2$ is independently selected from: hydrogen, hydroxyl, halogen, alkyl, alkenyl, alkynyl, acyl, adenine, guanine, cytosine, uracil, thymine, uridine, any pyrimidine, any purine, pseudouridine, inosine, or hypoxanthine;

wherein $R_3$ is independently selected from a: alkylphosphonate, phosphotriester, phosphorodithioate, phosphoramidate, ketone, sulfone, carbonate thioamidate, phosphodiester, phosphorothioate, aldehyde, carboxyl, carbonyl, ether, ester, or amine phosphodiester, aldehyde, carboxyl, carbonyl, ether, ester, or amine; and, in some optional embodiments, the alkylphosphonate, phosphotriester, phosphorodithioate, phosphoramidate, ketone, sulfone, carbonate thioamidate, phosphodiester, aldehyde, carboxyl, carbonyl, ether, ester, or amine is bonded to a contiguous nucleic acid, such that $R_3$ reads

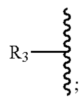

wherein $R_4$ is independently selected from a: alkylphosphonate, phosphotriester, phosphorodithioate, phosphoramidate, ketone, sulfone, carbonate thioamidate, phosphodiester, phosphorothioate, aldehyde, carboxyl, carbonyl, ether, ester, or amine; in some optional embodiments, the alkylphosphonate, phosphotriester, phosphorodithioate, phosphoramidate, ketone, sulfone, carbonate thioamidate, phosphodiester, aldehyde, carboxyl, carbonyl, ether, ester, or amine is bonded to one or a plurality of contiguous nucleic acids, such that $R_4$ reads $R_4$—;

or a pharmaceutically active salt thereof.

In some embodiments, the present disclosure provides a composition comprising a compound having Formula W:

W

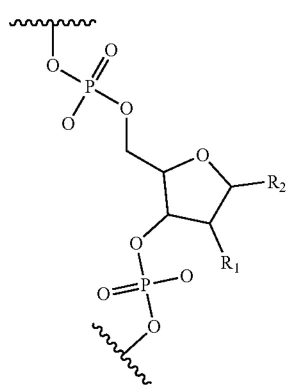

wherein $R_1$ is independently selected from a halogen, methyl, or methoxy ethyl;

wherein $R_2$ is independently selected from: hydrogen, hydroxyl, halogen, alkyl, alkenyl, alkynyl, acyl, a base, adenine, guanine, cytosine, uracil, thymine, uridine, pyrimidine, purine, pseudouridine, inosine, or hypoxanthine;

or a pharmaceutically active salt thereof.

In some embodiments, the present disclosure provides a composition comprising a compound having Formula X:

X

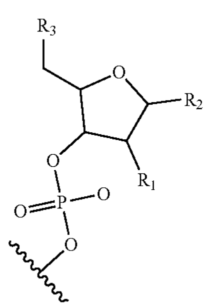

wherein $R_1$ is independently selected from a halogen, methyl, or methoxy ethyl;

wherein $R_2$ is independently selected from: any nucleobase, hydrogen, hydroxyl, halogen, alkyl, alkenyl, alkynyl, acyl, adenine, guanine, cytosine, uracil, thymine, uridine, a pyrimidine, a purine, pseudouridine, inosine, or hypoxanthine;

wherein $R_3$ is independently selected from a: alkylphosphonate, phosphotriester, phosphorodithioate, phosphoramidate, ketone, sulfone, carbonate thioamidate, phosphodiester, aldehyde, carboxyl, carbonyl, ether, ester, or amine; in some embodiments, the phosphodiester, alkylphosphonate, phosphotriester, phosphorodithioate, phosphoramidate, ketone, sulfone, carbonate thioamidate. aldehyde, carboxyl, carbonyl, ether, ester, or amine is bonded to a contiguous nucleic acid or nucleoside, such that the $R_3$ reads $R_3$—;

or a pharmaceutically active salt thereof.

In some embodiments, the present disclosure provides a composition comprising a compound having Formula Y:

Y

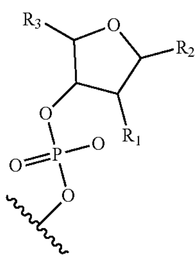

wherein $R_1$ is independently selected from: hydrogen, hydroxyl, halogen, methyl, or methoxy ethyl;

wherein $R_2$ is independently selected from: hydrogen, hydroxyl, halogen, alkyl, alkenyl, alkynyl, acyl, any base, adenine, guanine, cytosine, uracil, thymine, uridine, a pyrimidine, a purine, pseudouridine, inosine, or hypoxanthine;

wherein $R_3$ is independently selected from a: alkylphosphonate, phosphotriester, phosphorodithioate, phosphoramidate, ketone, sulfone, carbonate thioamidate. phosphorothioate, phosphodiester, aldehyde, carboxyl, carbonyl, ether, ester, amine or a CH2— bonded to a phosphodiester, aldehyde, carboxyl, carbonyl, ether, ester, amine;

wherein, in some optional, embodiments, the alkylphosphonate, phosphotriester, phosphorodithioate, phosphoramidate, ketone, sulfone, carbonate thioamidate, phosphodiester, aldehyde, carboxyl, carbonyl, ether, ester, or amine is bonded to a contiguous nucleic acid, such that the $R_3$ reads $R_3$—;

or a pharmaceutically active salt thereof.

In some embodiments, the present disclosure provides a composition comprising a compound having Formula Z:

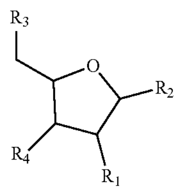

wherein $R_1$ is independently selected from: a hydrogen, a hydroxyl, a halogen, methyl, or methoxy ethyl;

wherein $R_2$ is independently selected from: hydrogen, hydroxyl, halogen, alkyl or heteroakyl, alkenyl, alkynyl, acyl, any base, pyrimidine, purine, adenine, guanine, cytosine, uracil, thymine, uridine, pseudouridine, inosine, or hypoxanthine;

wherein $R_3$ is independently selected from a: alkylphosphonate, phosphotriester, phosphorodithioate, phosphoramidate, ketone, sulfone, carbonate thioamidate, phosphorothioate, phosphodiester, aldehyde, carboxyl, carbonyl, ether, ester, or amine;

wherein $R_4$ is independently selected from a one or a combination of: alkylphosphonate, phosphotriester, phosphorodithioate, phosphoramidate, ketone, sulfone, carbonate thioamidate. phosphorothioate, phosphodiester, aldehyde, carboxyl, carbonyl, ether, ester, or amine;

or a pharmaceutically active salt thereof; wherein the compound X is positioned between or bonded to any one or plurality of unmodified or modified nucleotides at $R_3$ and/or $R_4$.

In some embodiments, the present disclosure provides a composition comprising a compound having Formula W:

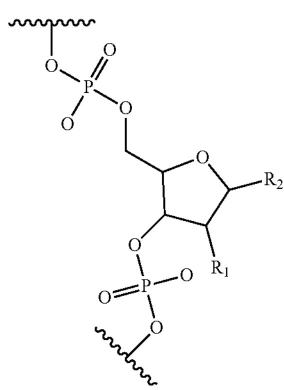

wherein $R_1$ is a hydrogen;

wherein $R_2$ is independently selected from: adenine, guanine, cytosine, uracil, thymine, uridine, pyrimidine, purine, pseudouridine, inosine, or hypoxanthine;

or a pharmaceutically active salt thereof.

In some embodiments, the present disclosure provides a composition comprising a compound having Formula X:

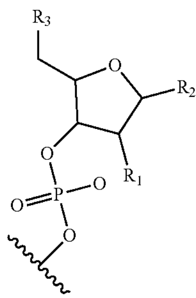

wherein $R_1$ is a hydrogen;

wherein $R_2$ is independently selected from: adenine, guanine, cytosine, uracil, thymine, uridine, pyrimidine, purine, pseudouridine, inosine, or hypoxanthine;

wherein $R_3$ is independently selected from a: phosphodiester, aldehyde, carboxyl, carbonyl, ether, ester, or amine;

or a pharmaceutically active salt thereof.

In some embodiments, the present disclosure provides a composition comprising a compound having Formula Y:

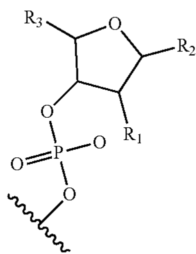

wherein $R_1$ is a hydrogen;

wherein $R_2$ is independently selected from: adenine, guanine, cytosine, uracil, thymine, uridine, pyrimidine, purine, pseudouridine, inosine, or hypoxanthine;

wherein $R_3$ is independently selected from a: alkylphosphonate, phosphotriester, phosphorodithioate, phosphoramidate, ketone, sulfone, carbonate thioamidate, phosphorothioate, phosphodiester, aldehyde, carboxyl, carbonyl, ether, ester, or amine;

or a pharmaceutically active salt thereof.

In some embodiments, the present disclosure provides a composition comprising a compound having Formula Z:

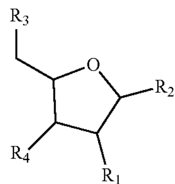

wherein $R_1$ independently selected from is a hydrogen, heteroakyl, methyl, methoxy ethyl, or halogen;

wherein $R_2$ is independently selected from: aryl, heteroaryl, cycloalkyl, heterocycloalkyl adenine, guanine, cytosine, uracil, thymine, uridine, pyrimidine, purine, pseudouridine, inosine, or hypoxanthine;

wherein $R_3$ is independently selected from a: alkylphosphonate, phosphotriester, phosphorodithioate, phosphoramidate, ketone, sulfone, carbonate thioamidate, phosphorothioate, phosphodiester, aldehyde, carboxyl, carbonyl, ether, ester, or amine;

wherein $R_4$ is independently selected from a: alkylphosphonate, phosphotriester, phosphorodithioate, phosphoramidate, ketone, sulfone, carbonate thioamidate, hydrogen, methyl, methoxy ethyl, phosphodiester, phosphorothioate, aldehyde, carboxyl, carbonyl, ether, ester, or amine; or or a pharmaceutically active salt thereof.

In some embodiments, the present disclosure provides a composition comprising a compound having Formula W:

W

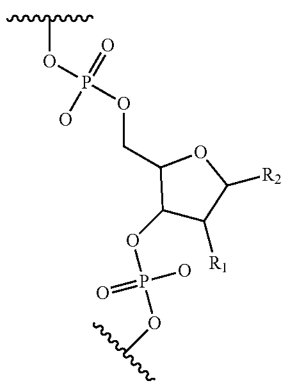

wherein $R_1$ is a hydroxyl;

wherein $R_2$ is independently selected from: adenine, guanine, cytosine, uracil, thymine, uridine, pyrimidine, purine, pseudouridine, inosine, or hypoxanthine;

or a pharmaceutically active salt thereof.

In some embodiments, the present disclosure provides a composition comprising a compound having Formula X:

X

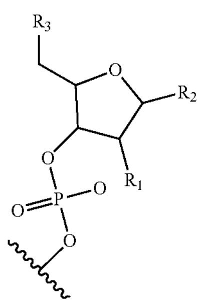

wherein $R_1$ is a hydroxyl;

wherein $R_2$ is independently selected from: adenine, guanine, cytosine, uracil, thymine, uridine, pyrimidine, purine, pseudouridine, inosine, or hypoxanthine;

wherein $R_3$ is independently selected from a: phosphorothioate, phosphodiester, aldehyde, carboxyl, carbonyl, ether, ester, or amine;

or a pharmaceutically active salt thereof.

In some embodiments, the present disclosure provides a composition comprising a compound having Formula Y:

Y

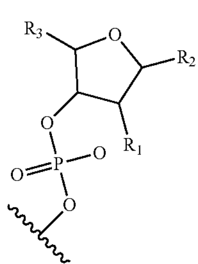

wherein $R_1$ is a hydroxyl;

wherein $R_2$ is independently selected from: adenine, guanine, cytosine, uracil, thymine, uridine, pyrimidine, purine, pseudouridine, inosine, or hypoxanthine;

wherein $R_3$ is independently selected from a: alkylphosphonate, phosphotriester, phosphorodithioate, phosphoramidate, ketone, sulfone, carbonate thioamidate, phosphorothioate, phosphodiester, aldehyde, carboxyl, carbonyl, ether, ester, or amine; wherein the groups are optionally further bound to one or a plurality of nucleotides or nucleosides, in deoxyribonucleic acid or ribonucleic acid forms.

or a pharmaceutically active salt thereof.

In some embodiments, the present disclosure provides a composition comprising a compound having Formula Z:

Z

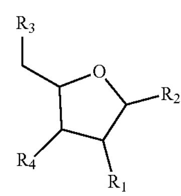

wherein $R_1$ is a hydroxyl;

wherein $R_2$ is independently selected from: hydrogen, hydroxyl, halogen, alkyl, alkenyl, alkynyl, acyl, any nucleobase, adenine, guanine, cytosine, uracil, thymine, uridine, pyrimidine, purine, pseudouridine, inosine, or hypoxanthine;

wherein $R_3$ is independently selected from a: alkylphosphonate, phosphotriester, phosphorodithioate, phosphoramidate, ketone, sulfone, carbonate thioamidate, phosphorothioate, phosphodiester, aldehyde, carboxyl, carbonyl, ether, ester, or amine optionally bound to one or a plurality or modified or unmodified nucleotides;

wherein $R_4$ is independently selected from a: phosphodiester, phosphorothioate aldehyde, carboxyl, carbonyl, ether, ester, or amine optionally bound to one or a plurality or modified or unmodified nucleotides and/or nucleosides; or a pharmaceutically active salt thereof.

In any of the forgoing formulae, any natural or non-natural nucleic acid may be one of several nucleic acids in a contiguous sequence within any of the disclosed sgRNAs, tracrRNAs, crRNAs, or other nucleic acid sequences disclosed herein, such that $R_3$ and/or $R_4$ are optionally comprising a substituent independently selected from one or a combination of: a alkylphosphonate, phosphotriester, phosphorodithioate, phosphoramidate, ketone, sulfone, carbonate thioamidate. phosphorothioate, phosphodiester, aldehyde, carboxyl, carbonyl, ether, ester, or amine is bonded to a contiguous nucleic acid, such that the $R_3$ and/or $R_4$ reads $R_3$— and/or $R_4$— respectively. In any of the forgoing formulae, any natural or non-natural nucleic acid may be one of several nucleic acids in a contiguous sequence within any of the disclosed sgRNAs, tracrRNAs, crRNAs, or other nucleic acid sequences disclosed herein, such that $R_1$ is free of an O-methyl group at positions within the nucleic acid sequence that bind or are capable of interacting with a Cas protein. In any of the forgoing formulae, any natural or non-natural nucleic acid may be one of several nucleic acids in a contiguous sequence within any of the disclosed sgRNAs, tracrRNAs, crRNAs, or other nucleic acid sequences disclosed herein, such that $R_1$ is a halogen at positions within the nucleic acid sequence that bind or are capable of interacting with a Cas protein. In any of the forgoing formulae, any natural or non-natural nucleic acid may be one of several nucleic acids in a contiguous sequence within any of the disclosed sgRNAs, tracrRNAs, crRNAs, or other nucleic acid sequences disclosed herein, such that $R_1$ is a fluorine at positions within the nucleic acid sequence that bind or are capable of interacting with a Cas protein. In any of the forgoing formulae, any natural or non-natural nucleic acid may be one of several nucleic acids in a contiguous sequence within any of the disclosed sgRNAs, tracrRNAs, crRNAs, or other nucleic acid sequences disclosed herein, such that $R_1$ is a halogen at positions within the nucleic acid sequence that bind or are capable of interacting with a Cas protein and wherein $R_3$ and/or $R_4$ are an internucleotide linkage comprising or selected from the group consisting of: a alkylphosphonate, phosphotriester, phosphorodithioate, phosphoramidate, ketone, sulfone, carbonate thioamidate, phosphorothioate, phosphodiester, aldehyde, carboxyl, carbonyl, ether, ester, or amine. In any of the forgoing formulae, any natural or non-natural nucleic acid may be one of several nucleic acids in a contiguous sequence within any of the disclosed sgRNAs, tracrRNAs, crRNAs, or other nucleic acid sequences disclosed herein, such that $R_1$ is a halogen at positions within the nucleic acid sequence that bind or are capable of interacting with a Cas protein and wherein $R_3$ and/or $R_4$ are an internucleotide linkage free of a phosphodiester bond. In any of the forgoing formulae, any natural or non-natural nucleic acid may be one of several nucleic acids in a contiguous sequence within any of the disclosed sgRNAs, tracrRNAs, crRNAs, or other nucleic acid sequences disclosed herein, such that $R_1$ is a fluorine at one or a plurality of positions within the nucleic acid sequence that bind or are capable of interacting with a Cas protein and wherein $R_3$ and/or $R_4$ are an phosphorothioate internucleotide linkage.

In some embodiments, the disclosure relates to a composition or pharmaceutical composition comprising a nucleic acid sequence comprising formulae W, X, Y, and Z in any contiguous or non-contiguous order or pattern, such that the total number of nucleic acids in the nucleic acid sequence is from about 15 to about 200. In some embodiments, the nucleic acid molecules of the disclosure comprise any one or combination of formulae W, X, Y, and Z, but wherein $R_1$ from any positions or all of the formula is free of a hydrogen or hydroxyl group in any one or more of its substituents. In some embodiments, the nucleic acid molecules of the disclosure comprise any one or combination of formulae W, X, Y, and Z, but wherein $R_1$ from any or all of the formula is free of a alkyl group and/or O-alkyl group.

In some embodiments, any natural or non-natural nucleic acid formula may be repeated across 1, 2, 3, 4, 5, 6, 7, 8, 9, 10 or more nucleic acids in contiguous nucleic acids or in a non-contiguous pattern across the length of the nucleic acid. In some embodiments, the disclosed nucleic acid sequences comprises 1, 2, 3, 4, 5, 6, 7, 8, 9, 10, 11, 12, 13, 14, 15, 16, 17, 18, 19, 20 or more contiguous or non-contiguous nucleic acids across a length of the nucleic acid.

In some embodiments, the composition or pharmaceutical composition disclosed herein comprises a nucleic acid disclosed herein that comprises ribonucleic acid and about 10%, 11%, 12%, 13%, 14%, 15%, 16%, 17%, 18%, 19%, 20%, 22%, 25%, 27%, 30%, 32%, 35%, 37%, 40%, 42%, 45%, 47%, 50%, 52%, 55%, 57%, 60%, 62%, or 65% deoxyribonucleic acid or variants or modified derivatives thereof.

In some embodiments, any of the forgoing formulae may comprise one or a plurality of LNA molecules positioned between or bound to one or a plurality of modified or unmodified nucleotides.

In some embodiments, the composition or pharmaceutical composition disclosed herein comprises a nucleic acid sequence comprising a total of about 50, 60, 70, 80, 90, 100, 150, or 200 nucleotides in length and comprising in 5' to 3' orientation: a nucleotide binding domain, a Cas protein binding domain (or Cas binding domain), and, optionally a transcription terminator domain; wherein each of the aforementioned domains independently consists of no more than about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, or 190 nucleotides; and wherein from about 1% to about 100% of the nucleotides are modified.

In some embodiments, the composition or pharmaceutical composition disclosed herein comprises a nucleic acid comprises a total of about 50, 60, 70, 80, 90, 100, 150, or 200 nucleotides in length and comprise in 5' to 3' orientation: a nucleotide binding domain, a Cas protein binding domain, and, optionally, a transcription terminator domain; wherein each of the aforementioned domains independently consists of no more than about 20, 30, 40, 50, 60, 70, 80, 90, 100, 110, 120, 130, 140, 150, 160, 170, 180, or 190 nucleotides; and wherein at least 10% of the nucleotides are modified at the 2' carbon position of the sugar moiety. In some embodiments, the composition or pharmaceutical composition disclosed herein comprises a nucleic acid comprises a total of about 50, 60, 70, 80, 90, 100, 150, or 200 nucleotides in length and comprise in 5' to 3' orientation: a nucleotide binding domain, a Cas protein binding domain, and, optionally, a transcription terminator domain; wherein each of the aforementioned domains independently consists of no more than about 20, 30, 40, 50, 60, 70, 80, 90, 100, 110, 120, 130, 140, 150, 160, 170, 180, or 190 nucleotides; and wherein at least 20% of the nucleotides are modified at the 2' carbon position of the sugar moiety. In some embodiments, the composition or pharmaceutical composition disclosed herein comprises a nucleic acid comprises a total of about 50, 60, 70, 80, 90, 100, 150, or 200 nucleotides in length and comprise in 5' to 3' orientation: a nucleotide binding domain, a Cas protein binding domain, and, optionally, a transcription terminator domain; wherein each of the aforementioned domains independently consists of no more than about 20, 30, 40, 50, 60, 70, 80, 90, 100, 110, 120, 130, 140, 150, 160, 170, 180, or 190 nucleotides; and wherein at least 30% of the nucleotides are modified at the 2' carbon position of the sugar moiety. In some embodiments, the composition or pharmaceutical composition disclosed herein comprises a nucleic acid comprises a total of about 50, 60, 70, 80, 90, 100, 150, or 200 nucleotides in length and comprise in 5' to 3' orientation: a nucleotide binding domain, a Cas protein binding domain, and, optionally, a transcription terminator domain; wherein each of the aforementioned domains independently consists of no more than about 20, 30, 40, 50, 60, 70, 80, 90, 100, 110, 120, 130, 140, 150, 160, 170, 180, or 190 nucleotides; and wherein at least 40% of the nucleotides are modified at the 2' carbon position of the sugar moiety. In some embodiments, the composition or pharmaceutical composition disclosed herein comprises a nucleic acid comprises a total of about 50, 60, 70, 80, 90, 100, 150, or 200 nucleotides in length and comprise in 5' to 3' orientation: a nucleotide binding domain, a Cas protein binding domain, and, optionally, a transcription terminator domain; wherein each of the aforementioned domains independently consists of no more than about 20, 30, 40, 50, 60, 70, 80, 90, 100, 110, 120, 130, 140, 150, 160, 170, 180, or 190 nucleotides; and wherein at least 50% of the nucleotides are modified at the 2' carbon position of the sugar moiety. In some embodiments, the composition or pharmaceutical composition disclosed herein comprises a nucleic acid comprises a total of about 50, 60, 70, 80, 90, 100, 150, or 200 nucleotides in length and comprise in 5' to 3' orientation: a nucleotide binding domain, a Cas protein binding domain, and, optionally, a transcription terminator domain; wherein each of the aforementioned domains independently consists of no more than about 20, 30, 40, 50, 60, 70, 80, 90, 100, 110, 120, 130, 140, 150, 160, 170, 180, or 190 nucleotides; and wherein at least 60% of the nucleotides are modified at the 2' carbon position of the sugar moiety. In some embodiments, the composition or pharmaceutical composition disclosed herein comprises a nucleic acid comprises a total of about 50, 60, 70, 80, 90, 100, 150, or 200 nucleotides in length and comprise in 5' to 3' orientation: a nucleotide or DNA binding domain, a Cas protein binding domain, and, optionally, a transcription terminator domain; wherein each of the aforementioned domains independently consists of no more than about 20, 30, 40, 50, 60, 70, 80, 90, 100, 110, 120, 130, 140, 150, 160, 170, 180, or 190 nucleotides; and wherein at least 70% of the nucleotides are modified at the 2' carbon position of the sugar moiety. In some embodiments, the composition or pharmaceutical composition disclosed herein comprises a nucleic acid sequence comprising total of about 50, 60, 70, 80, 90, 100, 150, or 200 nucleotides in length and comprise in 5' to 3' orientation: a nucleotide binding domain, a Cas protein binding domain, and, optionally, a transcription terminator domain; wherein each of the aforementioned domains independently consists of no more than about 20, 30, 40, 50, 60, 70, 80, 90, 100, 110, 120, 130, 140, 150, 160, 170, 180, or 190 nucleotides; and wherein at least 80% of the nucleotides are modified at the 2' carbon position of the sugar moiety. In some embodiments, the composition or pharmaceutical composition disclosed herein comprises a nucleic acid sequence comprising a total of about 50, 60, 70, 80, 90, 100, 150, or 200 nucleotides in length and comprise in 5' to 3' orientation: a nucleotide binding domain, a Cas protein binding domain, and, optionally, a transcription terminator domain; wherein each of the aforementioned domains independently consists of no more than about 20, 30, 40, 50, 60, 70, 80, 90, 100, 110, 120, 130, 140, 150, 160, 170, 180, or 190 nucleotides; and wherein at least 90% of the nucleotides are modified at the 2' carbon position of the sugar moiety. In some embodiments, the composition or pharmaceutical composition disclosed herein comprises a nucleic acid sequence comprising a total of about 50, 60, 70, 80, 90, 100, 150, or 200 nucleotides in length and comprise in 5' to 3' orientation: a nucleotide binding domain, a Cas protein binding domain, and, optionally, a transcription terminator domain; wherein each of the aforementioned domains independently consists of no more than about 20, 30, 40, 50, 60, 70, 80, 90, 100, 110, 120, 130, 140, 150, 160, 170, 180, or 190 nucleotides; and wherein at least 95% of the nucleotides are modified at the 2' carbon position of the sugar moiety. In some embodiments, the composition or pharmaceutical composition disclosed herein comprises a nucleic acid sequence comprising a total of about 50, 60, 70, 80, 90, 100, 150, or 200 nucleotides in length and comprise in 5' to 3' orientation: a nucleotide binding domain, a Cas protein binding domain, and, optionally, a transcription terminator domain; wherein each of the aforementioned domains independently consists of no more than about 20, 30, 40, 50, 60, 70, 80, 90, 100, 110, 120, 130, 140, 150, 160, 170, 180, or 190 nucleotides; and wherein at least 40%, 50%, 60%, 65%, 70%, 75%, 80%, 85%, 90%, or 95% of the nucleotides comprise halogens at the 2' carbon position of the sugar moiety. In any of the foregoing embodiments, the 2' carbon position may be a hydroxyl or hydrogen at any one or plurality of positions capable of interacting with or binding to a Cas protein in an active CRISPR complex. In any of the foregoing embodiments, the 2' carbon position may be a hydroxyl or hydrogen at any one or plurality of conserved positions capable of interacting with or binding to a Cas protein in an active CRISPR complex and identified in the Tables or Figures disclosed herein.

In some embodiments, the composition or pharmaceutical composition disclosed herein comprises a nucleic acid sequence comprising a total of about 50, 60, 70, 80, 90, 100, 150, or 200 nucleotides in length and comprising in 5' to 3' orientation: a nucleotide or DNA binding domain, a Cas protein binding domain, and, optionally, a transcription terminator domain; wherein each of the aforementioned domains independently consists of no more than about 20, 30, 40, 50, 60, 70, 80, 90, 100, 110, 120, 130, 140, 150, 160, 170, 180, or 190 nucleotides; and wherein at least 10% of the nucleotides are modified at the 2' carbon position of the sugar moiety, but one or a combination of the following positions within the domains comprise a hydroxyl group at the 2' carbon of the sugar moiety of the nucleotide: positions 1, 12, 15, 16, and/or 19 of the nucleotide-binding domain; positions 22, 23, 24, 25, 26, 27, 43, 44, 45, 47, 49, 51, 58, 59, and/or 62 of the Cas-binding domain;

positions 63, 64, 65, 68, 69, and/or 82 of the transcription terminator domain; wherein the position number 1 of the nucleic acid sequence corresponds to the first nucleotide in the nucleotide binding domain.

In some embodiments, the composition or pharmaceutical composition disclosed herein comprises a nucleic acid comprises a total of about 50, 60, 70, 80, 90, 100, 150, or 200 nucleotides in length and comprise in 5' to 3' orientation: a nucleotide binding domain, a Cas protein binding domain, and, optionally, a transcription terminator domain; wherein each of the aforementioned domains independently consists of no more than about 20, 30, 40, 50, 60, 70, 80, 90, 100, 110, 120, 130, 140, 150, 160, 170, 180, or 190 nucleotides;

and wherein at least 10% of the nucleotides are modified at the 2' carbon position of the sugar moiety, but one or a combination of the following positions within the domains consist of a hydroxyl group at the 2' carbon of the sugar moiety of the nucleotide: positions 1, 12, 15, 16, and/or 19 of the nucleotide-binding domain;

positions 22, 23, 24, 25, 26, 27, 43, 44, 45, 47, 49, 51, 58, 59, and/or 62 of the Cas-binding domain;

positions 63, 64, 65, 68, 69, and/or 82 of the transcription terminator domain; wherein the position number 1 of the nucleic acid sequence corresponds to the first nucleotide in the nucleotide binding domain.

In some embodiments, the composition or pharmaceutical composition disclosed herein comprises a nucleic acid sequence comprising a total of about 50, 60, 70, 80, 90, 100, 150, or 200 nucleotides in length and comprise in 5' to 3' orientation: a nucleotide binding domain, a Cas protein binding domain, and, optionally a transcription terminator domain; wherein each of the aforementioned domains independently consists of no more than about 20, 30, 40, 50, 60, 70, 80, 90, 100, 110, 120, 130, 140, 150, 160, 170, 180, or 190 nucleotides; and wherein at least 10% of the nucleotides are modified at the 3' carbon position carbon position of the sugar moiety.

In some embodiments, the composition or pharmaceutical composition disclosed herein comprises a nucleic acid comprising a total of about 50, 60, 70, 80, 90, 100, 150, or 200 nucleotides in length and comprising, in 5' to 3' orientation: a nucleotide binging domain, a Cas protein binding domain, and, optionally a transcription terminator domain; wherein each of the aforementioned domains independently consists of no more than about 20, 30, 40, 50, 60, 70, 80, 90, 100, 110, 120, 130, 140, 150, 160, 170, 180, or 190 nucleotides; and wherein at least 10% of the nucleotides are modified at the 4'carbon position of the sugar moiety. In some embodiments, the composition or pharmaceutical composition disclosed herein comprises a nucleic acid sequence comprising a total of about 50, 60, 70, 80, 90, 100, 150, or 200 nucleotides in length and comprise in 5' to 3' orientation: a nucleotide binding domain, a Cas protein binding domain, and, optionally a transcription terminator domain; wherein each of the aforementioned domains independently consists of no more than about 20, 30, 40, 50, 60, 70, 80, 90, 100, 110, 120, 130, 140, 150, 160, 170, 180, or 190 nucleotides; and wherein at least 10% of the nucleotides are modified at the 5'carbon position of the sugar moiety.

In some embodiments, the composition or pharmaceutical composition disclosed herein comprises a nucleic acid molecule comprising at least one or a combination of domains from a 5' to 3' orientation: a DNA-binding domain, a Cas-protein binding domain, and a transcription terminator domain.

In certain embodiments, the nucleic acid molecule comprising the DNA-binding domain is an sgRNA or a crRNA. The length of the DNA-binding domain may vary depending, for example, on the target sequence. In some embodiments, the DNA-binding domain comprises about 25, 30, 35, 40, 45, 50 or 55 nucleotides. Any of the these values may be used to define a range for the length of the DNA-binding domain. For example, in some embodiments, the DNA-binding domain comprises about 35-45, about 25-45, or about 25-55 nucleotides.

In some embodiments, one or more nucleotides in the DNA-binding domain are modified. For example, in some embodiments, about 5%, 10%, 15%, 25%, 30%, 35%, 40%, 45%, 50% or 55% of the nucleotides in the DNA-binding domain are modified. In some embodiments, less than 5%, 10%, 15%, 20%, 21%, 22%, 23%, 24% 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50% or 55% of the nucleotides in the DNA-binding domain are modified. Any of these values may be used to define a range for the percentage of nucleotides in the DNA-binding domain that are modified. For example, in some embodiments, 26% to 34%, 26% to 50%, or 21% to 50% of the nucleotides in the DNA-binding domain are modified. In some embodiments, fewer than 2, 3, 4, 5, 6, 7, 8, 9, 10, 11, 12, 13, 14 or 15 of the nucleotides in the DNA-binding domain are modified. Any of these values may be used to define a range for the number of nucleotides that are modified in the DNA-binding domain. For example, in some embodiments, 2 to 15, 7 to 15, or 13 to 15 of the nucleotides in the DNA-binding domain are modified.

In certain embodiments, the modification of the nucleotide in the DNA-binding domain is one or more of 2'-O-methyl, 2'-O-fluoro, or phosphorothioate. In certain embodiments, the nucleotide is modified at the 2' position of the sugar moiety. In certain embodiments, the modification at the 2' position of the sugar moiety is 2'-O-methyl or 2'-O-fluoro. In certain embodiments, the nucleotide is modified at the 3' position of the sugar moiety. In certain embodiments, the modification at the 3' position of the sugar moiety is phosphorothioate. In certain embodiments, the nucleotide is modified at both the 2' position of the sugar moiety and at the 3' position of the sugar moiety. In certain embodiments, the nucleotide is not modified at the 2' position of the sugar moiety. In certain embodiments, the nucleotide is not modified at the 3' position of the sugar moiety.

In certain embodiments, the nucleic acid molecule (e.g. an sgRNA or a crRNA) comprises a DNA-binding domain comprising about 25 to about 55 nucleotides, wherein the nucleotides of the nucleic acid sequence are modified at one or more of positions 1, 2, 3, 4, 5, 6, 7, 8, 9, 10, 11, 13, 14, 17 or 18 of the DNA-binding domain. In some embodiments, the nucleic acid molecule is modified at one or more of positions 1, 2, 3, 6, 7, 8, 9, 10, 11, 13, 14, 17 or 18 of the DNA-binding domain. In some embodiments, the nucleotide at one or more of positions 4, 5 and 12 of the DNA-binding domain is not modified. In some embodiments, the nucleotide at one or more of positions 1, 2, 3, 4 and 5 of the DNA-binding domain is not modified.

In a particular embodiment, the nucleic acid molecule (e.g. an sgRNA or a crRNA) comprises a DNA-binding domain comprising about 25 to about 55 nucleotides, wherein the nucleotides of the nucleic acid sequence are modified at one or more of positions 1, 2, 3, 6, 7, 8, 9, 10, 11, 13, 14, 17 or 18 of the DNA-binding domain, and wherein the nucleotide at one or more of positions 4, 5 and 12 of the DNA-binding domain is not modified.

In certain embodiments, the nucleic acid molecule is a crRNA and is combined with a second nucleic acid molecule comprising at least one transcription terminator domain. In certain embodiments, the second nucleic acid molecule is a tracrRNA.

In some embodiments, the nucleic acid molecule comprises a Cas-protein binding domain. In certain embodiments, the Cas-protein binding domain comprises about 30, 35, 40, 41, 42, 43, 44, 45, 46, 47, 48, 49, 50, 51, 52, 53, 54 or 55 nucleotides. Any of these values may be used to define a range for the length of the Cas-protein binding domain. For example, in some embodiments, the Cas-protein binding domain comprises about 30 to 55, about 40 to 45, or about 40 to 50 nucleotides. In a particular embodiment, the Cas-protein binding domain comprises about 41 nucleotides.

In certain embodiments, the Cas-protein binding domain comprises the nucleic acid sequence of SEQ ID NO: 112:

(SEQ ID NO: 112)
GUUUUAGAGCUAGAAAUAGCAAGUUAAAAUAAGGCUAGUCCG.

SEQ ID NO: 112 represents the Cas-protein binding domain shown in FIG. 1. In some embodiments, the Cas-protein binding domain comprises a nucleic acid sequence having at least 10, 20, 30, 40, 50, 60, 70, 75, 80, 85, 90, 95, 96, 97, 98 or 99% sequence identity to the nucleic acid sequence of SEQ ID NO: 112. In certain embodiments, the Cas-protein binding domain comprises a nucleic acid sequence in which at least one or a combination of nucleotides are conserved at positions: 2, 3, 4, 23, 24, 25, 27, 31, 38 and 42 of SEQ ID NO: 112. In certain embodiments, the Cas-protein binding domain comprises the sequence of SEQ ID NO: 113:

(SEQ ID NO: 113)
NUUUNNNNNNNNNNNNNNNNNNGUUNANNNANNNNNNGNNNG, wherein "N" may be any nucleotide.

In certain embodiments about 1, 2, 3, 4, 5, 6, 7, 8, 9, or 10 nucleotides in the Cas-protein binding domain are modified. In certain embodiments, fewer than 2, 3, 4, 5, 6, 7, 8, 9, or 10 nucleotides in the Cas-protein binding domain are modified. In a particular embodiment, 8 nucleotides in the Cas-protein binding domain are modified.

In certain embodiments, the modification of the nucleotide in the Cas-protein binding domain is one or more of 2'-O-methyl, 2'-O-fluoro, or phosphorothioate. In certain embodiments, the nucleotide is modified at the 2' position of the sugar moiety. In certain embodiments, the modification at the 2' position of the sugar moiety is 2'-O-methyl or 2'-O-fluoro. In certain embodiments, the nucleotide is modified at the 3' position of the sugar moiety. In certain embodiments, the modification at the 3' position of the sugar moiety is phosphorothioate. In certain embodiments, the nucleotide is modified at both the 2' position of the sugar moiety and at the 3' position of the sugar moiety. In certain embodiments, the nucleotide is not modified at the 2' position of the sugar moiety. In certain embodiments, the nucleotide is not modified at the 3' position of the sugar moiety.

In certain embodiments, the Cas-protein binding domain is modified at one or more of positions 10, 11, 12, 14, 15, 17, 18 and 19 of the Cas-protein binding domain (e.g. SEQ ID NO: 112).

In some embodiments, the nucleic acid molecule comprises a transcription terminator domain. In certain embodiments, the transcription terminator domain comprises about 15, 16, 17, 18, 19, 20, 25, 30, 35, 36, 37, 38, 39, 40, 41, 42, 43, 44 or 45 nucleotides. Any of these values may be used to define a range for the length of the transcription terminator domain. For example, in some embodiments, the transcription terminator domain comprises about 35 to 45, about 35 to 40, or about 17 to 45 nucleotides. In a particular embodiment, the transcription terminator domain comprises about 39 nucleotides.

In some embodiments, the transcription terminator domain comprises the nucleic acid sequence of SEQ ID NO: 114:

(SEQ ID NO: 114)
UUAUCAACUUGAAAAAGUGGCACCGAGUCGGUGCUUUUUU.

SEQ ID NO: 114 represents the transcription terminator domain shown in FIG. 1. In some embodiments, the transcription terminator domain comprises a nucleic acid sequence having at least 10, 20, 30, 40, 50, 60, 70, 75, 80, 85, 90, 95, 96, 97, 98 or 99% sequence identity to the nucleic acid sequence of SEQ ID NO: 114. In certain embodiments, the transcription terminator domain comprises a nucleic acid sequence in which at least one or a combination of nucleotides are conserved at positions 1, 2, 3 or 6 of the nucleic acid sequence of SEQ ID NO: 114. In certain embodiments, the transcription terminator domain comprises the nucleic acid sequence of SEQ ID NO: 115:

(SEQ ID NO: 115)
UUANNANNNNNNNNNNNNNNNNNNNNNNNNNNNNNNNNNN, wherein "N" may be any nucleotide.

In some embodiments, one or more nucleotides in the transcription terminator domain are modified. For example, in some embodiments, 1, 2, 3, 4, 5, 6, 7, 8, 9, 10, 11, 12, 13, 14, 15, 16, 17 or 18 nucleotides in the transcription terminator domain are modified. In some embodiments, fewer than 2, 3, 4, 5, 6, 7, 8, 9, 10, 11, 12, 13, 14, 15, 16, 17 or 18 nucleotides in the transcription terminator domain are modified. In certain embodiments, one or more nucleotides at positions 4, 5, 8, 9, 10, 20, 23, 25, 26, 30, 31, 34, 36 of the transcription terminator domain (e.g. SEQ ID NO: 114) are modified. In certain embodiment, one or more nucleotides at positions 4, 5, 8, 9, 10, 18, 21, 23, 24, 28, 29, 32, 33, 34, 35, or 36 of the transcription terminator domain (e.g. SEQ ID NO: 114) are modified.

In certain embodiments, the modification of a nucleotide in the transcription terminator domain is one or more of 2'-O-methyl, 2'-O-fluoro, or phosphorothioate. In a particular embodiment, the modification in the transcription terminator domain is 2'-O-fluoro. In certain embodiments, the nucleotide is modified at the 2' position of the sugar moiety. In certain embodiments, the modification at the 2' position of the sugar moiety is 2'-O-methyl or 2'-O-fluoro. In certain embodiments, the nucleotide is modified at the 3' position of the sugar moiety. In certain embodiments, the modification at the 3' position of the sugar moiety is phosphorothioate. In certain embodiments, the nucleotide is modified at both the 2' position of the sugar moiety and at the 3' position of the sugar moiety. In certain embodiments, the nucleotide is not modified at the 2' position of the sugar moiety. In certain embodiments, the nucleotide is not modified at the 3' position of the sugar moiety. In some embodiments, the nucleotide at one or more of positions 1, 2, 3, 4 and 5 of the transcription terminator domain (e.g. SEQ ID NO: 114) is not modified.

In a particular embodiment, the nucleic acid molecule comprises a transcription terminator domain comprising from about 17 to 45 nucleotides, wherein the transcription terminator domain has at least 70% sequence homology to the nucleic acid sequence of SEQ ID NO: 114, and wherein one or more of the nucleotides are modified.

In certain embodiments of the aforementioned nucleic acid molecules, only the DNA-binding domain comprises one or more modified nucleotides. In certain embodiments, only the Cas-protein binding domain of the nucleic acid molecule comprises one or more modified nucleotides. In certain embodiments, only the transcription terminator domain of the nucleic acid molecule comprises one or more modified nucleotides. In certain embodiments, both the DNA-binding domain and the Cas-protein binding domain of the nucleic acid molecule comprise one or more modified nucleotides. In certain embodiments, both the DNA-binding domain and the transcription terminator domain comprise one or more modified nucleotides. In certain embodiments, both the Cas-protein binding domain and the transcription terminator domain comprise one or more modified nucleotides. In certain embodiments, the DNA-binding domain, Cas-protein binding domain and transcription terminator domain each comprise one or more modified nucleotides.

In certain aspects, the invention also relates to a pharmaceutical composition comprising any of the aforementioned nucleic acid molecules. In certain embodiments, the pharmaceutical composition comprises a nanoparticle comprising any of the aforementioned nucleic acid molecules.

The pharmaceutical composition comprising the nucleic acid molecules may be administered to a subject to modify one or more target sequences. The dosage of the pharmaceutical composition administered to a subject may be optimized to maximize the percentage of target sequences in the subject that are modified by the nucleic acid molecules. In certain embodiments, the pharmaceutical composition is administered at a dosage sufficient to modify at least 4%, 5%, 6%, 7%, 8%, 9%, 10%, 11%, 12%, 13%, 14%, 15%, 16%, 17%, 18%, 19% or 20% of the target sequences. In a particular embodiment, the pharmaceutical composition is administered at a dosage sufficient to modify at least 4% of the target sequences. In certain embodiments, the pharmaceutical composition is administered to the subject at a dosage from about 100 μg/kg body weight of the subject to about 10 mg/kg body weight of the subject. In a particular embodiment, the pharmaceutical composition is administered at a dosage of about 1 mg/kg body weight of the subject.

In some embodiments, a small guide RNA (sgRNA) molecule is provided. The disclosure also relates to pharmaceutical compositions comprising any of the sgRNAs provided herein (including those sgRNA with percentages of deoxyribonucleic acids) or pharmaceutically acceptable salts thereof. sgRNAs contain a nucleotide binding region that determines the sequence specificity of the sgRNA and the sgRNA: nuclease complex, a 5' stem-loop region that, at least in part, participates in assembly and interaction with a sgRNA-mediated enzyme (such as a Cas protein-binding domain); and a transcription termination sequence. In some embodiments, the sgRNA or guide sequence comprises an intervening sequence between the transcription terminator domain and/or a 3' stem-loop region in the transcription terminator domain. In some embodiments, the intervening sequence is no more than about 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 60, 61, 62, 63, 63, 64, 65, 66, 67, 68, 69, 70, 71, 72, 73, 74, 75, 76, 77, 78, 79, 80, 81, 82, 83, 84, 85, 86, 87, 88, 89, 90, 91 92, 93, 94, 95, 96, 97, 98, 99, or 100 nucleotides in length.

The nucleotide binding region can be from about 5 to about 150 nucleotides long, or longer (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 60, 61, 62, 63, 63, 64, 65, 66, 67, 68, 69, 70, 71, 72, 73, 74, 75, 76, 77, 78, 79, 80, 81, 82, 83, 84, 85, 86, 87, 88, 89, 90, 91 92, 93, 94, 95, 96, 97, 98, 99, or 100 nucleotides in length, or longer). In some cases, the binding region is from about 15 to about 30 nucleotides in length (e.g., from about 15 to about 29, 15-26, 15-25; 16-30, 16-29, 16-26, 16-25; or about 18-30, 18-29, 18-26, or 18-25 nucleotides in length). Generally, the nucleotide binding region is designed to complement or substantially complement the target nucleic acid sequence or sequences, such as a DNA target sequence. In some cases, the nucleotide binding domain is also called a "DNA-binding region," and such terms are used equivalently in this application, because of its ability to bind to complementary or partially complementary target DNA sequences. Generally, for purposes of this application the nucleotide binding or DNA-binding domain is split between a seed region and a tail region. In most orientations and embodiments, the seed region is the 5' most portion of the nucleotide binding domain and the tail region is the 3' most portion of the nucleotide domain. The seed region can be no more than 6, 7, 8, 9, 10 or more contiguous nucleotides in length which is also contiguous with the tail region. In some embodiments, the tail region is also no more than 6, 7, 8, 9, 10 or more contiguous nucleotides in length. The position number of the nucleotides in the region is important in some embodiments because some positions of the nucleotide-binding portion of the sequences disclosed herein enhance the binding of the Cas protein to the nucleotide sequence and therefore enhance the enzymatic efficiency of the CRISPR complex.

The nucleotide binding domain can incorporate wobble or degenerate bases to bind multiple sequences. In some cases, the binding region can be altered to increase stability. For example, non-natural nucleotides, can be incorporated to increase RNA resistance to degradation. In some cases, the binding region can be altered or designed to avoid or reduce secondary structure formation in the binding region. In some cases, the binding region can be designed to optimize G-C content. In some cases, G-C content is from about 40% and about 60% (e.g., 40%, 45%, 50%, 55%, 60%). In some cases, the nucleotide binding region can contain modified nucleotides such as, without limitation, methylated, phosphorylated, fluorinated, or hydroxylated nucleotides. In some cases, the nucleotide binding region can contain modified nucleotides such as, without limitation, methylated, phosphorylated, fluorinated, or hydroxylated nucleotides; wherein if the nucleotide is fluorinated, the nucleotide may also be bound to one or more adjacent modified or unmodified nucleotides by a phosphorothioate bond, in either R or S orientation.

In some embodiments, the nucleotide binding region binds or is capable of hybridizing with DNA, RNA, or hybrid RNA/DNA sequences, such as any of those target sequences described herein. In some embodiments, any of the domains or elements comprises DNA, RNA, or hybrid RNA/DNA sequences. In some embodiments, the nucleotide binding region comprises from about 5% to about 100% modified nucleotides based upon the total number of the nucleotides in the element or domain or entire guide sequence. In some embodiments, the nucleotide binding region comprises from about 5% to about 90% modified nucleotides as compared to an unmodified or naturally occurring nucleotide sequence. In some embodiments, the nucleotide binding region comprises from about 5% to about 80% modified nucleotides. In some embodiments, the nucleotide binding region comprises from about 5% to about 70% modified nucleotides. In some embodiments, the nucleotide binding region comprises from about 5% to about 60% modified nucleotides. In some embodiments, the nucleotide binding region comprises from about 5% to about 50% modified nucleotides. In some embodiments, the nucleotide binding region comprises from about 5% to about 40% modified nucleotides. In some embodiments, the nucleotide binding region comprises from about 5% to about 30% modified nucleotides. In some embodiments, the nucleotide binding region comprises from about 5% to about 20% modified nucleotides. In some embodiments, the nucleotide binding region comprises from about 5% to about 10% modified nucleotides.

In some embodiments, the domain comprises hybrid RNA/DNA sequences of either unmodified or modified nucleotides. In some embodiments, the DNA-targeting domain comprises no less than about 250, 200, 150, 100, 50, 45, 40, 35, 30, 25, or 20 nucleotides, wherein no more than about 50, 45, 40, 35, 30, 25, 20, 15, 14, 13, 12, 11, 10, 9, 8, 7, 6, 5, 4, 3, 2, or 1 nucleotides is a modified or unmodified deoxyribonucleic acid. In some embodiments, the DNA-targeting domain comprises no less than about 250, 200, 150, 100, 50, 45, 40, 35, 30, 25, or 20 nucleotides, wherein no more than about 50, 45, 40, 35, 30, 25, 20, 15, 14, 13, 12, 11, 10, 9, 8, 7, 6, 5, 4, 3, 2, or 1 nucleotides from the 5' end of the guide sequence is a modified or unmodified deoxyribonucleic acid. In some embodiments, the Cas-binding domain comprises no less than about 250, 200, 150, 100, 50, 45, 40, 35, 30, 25, or 20 nucleotides, wherein no more than about 50, 45, 40, 35, 30, 25, 20, 15, 14, 13, 12, 11, 10, 9, 8, 7, 6, 5, 4, 3, 2, or 1 nucleotides is a modified or unmodified deoxyribonucleic acid. In some embodiments, the transcription terminator domain comprises no less than about 250, 200, 150, 100, 50, 45, 40, 35, 30, 25, or 20 nucleotides, wherein no more than about 50, 45, 40, 35, 30, 25, 20, 15, 14, 13 12, 11, 10, 9, 8, 7, 6, 5, 4, 3, 2, or 1 nucleotides is a modified or unmodified deoxyribonucleic acid. In some embodiments, the transcription terminator domain is free of modified or unmodified deoxyribonucleic acid. In some embodiments, the Cas-binding domain is free of modified or unmodified deoxyribonucleic acid.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part I, Second Chapter "Overview of principles of hybridization and the strategy of nucleic acid probe assay", Elsevier, N.Y.

The terms "subject," "individual," and "patient" are used interchangeably herein to refer to a vertebrate, preferably a mammal, more preferably a human. Mammals include, but are not limited to, murines, simians, humans, farm animals, cows, pigs, goats, sheep, horses, dogs, sport animals, and pets. Tissues, cells and their progeny obtained in vivo or cultured in vitro are also encompassed by the definition of the term "subject." The term "subject" is also used throughout the specification in some embodiments to describe an animal from which a cell sample is taken or an animal to which a disclosed cell or nucleic acid sequences have been administered. In some embodiment, the animal is a human. For treatment of those conditions which are specific for a specific subject, such as a human being, the term "patient" may be interchangeably used. In some instances in the description of the present disclosure, the term "patient" will refer to human patients suffering from a particular disease or disorder. In some embodiments, the subject may be a non-human animal from which an endothelial cell sample is isolated or provided. The term "mammal" encompasses both humans and non-humans and includes but is not limited to humans, non-human primates, canines, felines, murines, bovines, equines, caprines, and porcines.

"Variants" is intended to mean substantially similar sequences. For nucleic acid molecules, a variant comprises a nucleic acid molecule having deletions (i.e., truncations) at the 5' and/or 3' end; deletion and/or addition of one or more nucleotides at one or more internal sites in the native polynucleotide; and/or substitution of one or more nucleotides at one or more sites in the native polynucleotide. As used herein, a "native" nucleic acid molecule or polypeptide comprises a naturally occurring nucleotide sequence or amino acid sequence, respectively. For nucleic acid molecules, conservative variants include those sequences that, because of the degeneracy of the genetic code, encode the amino acid sequence of one of the polypeptides of the disclosure. Variant nucleic acid molecules also include synthetically derived nucleic acid molecules, such as those generated, for example, by using site-directed mutagenesis but which still encode a protein of the disclosure. Generally, variants of a particular nucleic acid molecule of the disclosure will have at least about 70%, 75%, 80%, 85%, 90%, 91%, 92%, 93%, 94%, 95%, 96%, 97%, 98%, 99% or more sequence identity to that particular polynucleotide as determined by sequence alignment programs and parameters as described elsewhere herein. Variants of a particular nucleic acid molecule of the disclosure (i.e., the reference DNA sequence) can also be evaluated by comparison of the percent sequence identity between the polypeptide encoded by a variant nucleic acid molecule and the polypeptide encoded by the reference nucleic acid molecule. Percent sequence identity between any two polypeptides can be calculated using sequence alignment programs and parameters described elsewhere herein. Where any given pair of nucleic acid molecule of the disclosure is evaluated by comparison of the percent sequence identity shared by the two polypeptides that they encode, the percent sequence identity between the two encoded polypeptides is at least about 70%, 75%, 80%, 85%, 90%, 91%, 92%, 93%, 94%, 95%, 96%, 97%, 98%, 99% or more sequence identity. In some embodiments, the term "variant" protein is intended to mean a protein derived from the native protein by deletion (so-called truncation) of one or more amino acids at the N-terminal and/or C-terminal end of the native protein; deletion and/or addition of one or more amino acids at one or more internal sites in the native protein; or substitution of one or more amino acids at one or more sites in the native protein. Variant proteins encompassed by the present disclosure are biologically active, that is they continue to possess the desired biological activity of the native protein as described herein. Such variants may result from, for example, genetic polymorphism or from human manipulation. Biologically active variants of a protein of the disclosure will have at least about 70%, 75%, 80%, 85%, 90%, 91%, 92%, 93%, 94%, 95%, 96%, 97%, 98%, 99% or more sequence identity to the amino acid sequence for the native protein as determined by sequence alignment programs and parameters described elsewhere herein. A biologically active variant of a protein of the disclosure may differ from that protein by as few as 1-15 amino acid residues, as few as 1-10, such as 6-10, as few as 5, as few as 4, 3, 2, or even 1 amino acid residue. The proteins or polypeptides of the disclosure may be altered in various ways including amino acid substitutions, deletions, truncations, and insertions. Methods for such manipulations are generally known in the art. For example, amino acid sequence variants and fragments of the proteins can be prepared by mutations in the nucleic acid sequence that encode the amino acid sequence recombinantly.

"Internucleotide linkage" refers to any group, molecules or atoms that covalently or noncovalently join two nucleosides. Unmodified internucleotide linkages are phosphodiester bonds. In some embodiments, the nucleic acid sequence or guide sequence comprises at least about 10%, 20%, 30%, 40%, 50%, 60%, 70%, 75%, 80%, 85%, 90%, 91%, 92%, 93%, 94%, 95%, 96%, 97%, 98%, 99% or more modified internucleotide linkages. Modified internucleotide linkages are set forth in the U.S. Pat. No. 8,133,669 and WO1994002499, each of which is incorporated herein in its entirety. Examples of such well known modified linkages, for which conventional synthesis schemes are known, include alkylphosphonate, phosphodiester, phosphotriester, phosphorothioate, phosphorodithioate, phosphoramidate, ketone, sulfone, carbonate and thioamidate linkages.

"2'-O-methyl sugar" or "2'-OMe sugar" means a sugar having a O-methyl modification at the 2' position.

"2'-O-methoxyethyl sugar" or "2'-MOE sugar" means a sugar having a O-methoxy ethyl modification at the 2' position.

"2'-O-fluoro" or "2'-F" means a sugar having a fluoro modification of the 2' position.

Compositions

The CRISPR/Cas or the CRISPR-Cas system (both terms are used interchangeably throughout this application) does not require the generation of customized proteins to target specific sequences but rather a single Cas protein (or CRISPR enzyme) can be programmed by a short RNA molecule to recognize a specific DNA target, in other words the Cas enzyme (such as a type II Cas9 protein) can be recruited to a specific DNA target using a short RNA molecule complementary to at least a portion of such specific DNA target. One aspect of the disclosure is a modified guide sequence. Adding the guide sequence to the repertoire of genome sequencing techniques and analysis methods may significantly simplify the methodology and accelerate the ability to catalog, map genetic factors associated with a diverse range of biological functions and diseases and treat disease. To utilize the CRISPR-Cas system effectively for genome editing without deleterious effects, it is critical to understand aspects of engineering and optimization of these genome engineering tools, which are aspects of the disclosure.

In some embodiments, the disclosure relates to a nucleic acid sequence and compositions comprising the same. In another aspect, the disclosure relates to a nucleic acid sequence disclosed herein and compositions comprising the same with or without a vector that comprises a CRISPR enzyme or functional fragment thereof. In some embodiments, the nucleic acid sequence is a ribonucleic sequence or an sgRNA sequence that comprises from about 1% to about 99% modified nucleic acids in one, two or three domains which, in the 5' to 3' orientation, are: a DNA-binding domain, a Cas protein-binding domain, and a transcription terminator domain. Any combination or sequence of Formulae W, X, Y and Z are comtemplated in this disclosure. As a non-limiting example, compositions of the disclosure can comprise a guide sequence of $N'—[Z]_n—N''$; wherein N' is any modified or unmodified 5' terminal nucleotide; N" is any modified or unmodified 3' terminal nucleotide; any n is any positive integer from about 1 to about 250, wherein each position of Z in the formula may have an independently selected positions at their respective $R_1$, $R_2$, $R_3$, and $R_4$, subgroups; wherein, if a Z is at a position that binds to or interacts with a Cas protein in an active CRISPR complex, then $R_1$ is a hydroxyl or hydrogen; and $R_3$ and $R_4$ are natural or phosphosdiester linkages; and wherein, if a Z is at a position that does bind to or interact with a Cas protein in an active CRISPR complex, then at least 10%, 20%, 30%, 40%, 50%, 60%, 70%, 75%, 80%, 85%, 90%, 91%, 92%, 93%, 94%, 95%, 96%, 97%, 98%, 99% of Z comprise: an $R_1$ is free of hydroxyl or hydrogen; and $R_3$ and $R_4$ are free of natural or phosphosdiester internucleotide linkages. As a non-limiting example, compositions of the disclosure relate to a guide sequence of $N'—[Z]_n—N''$; wherein N' is any modified or unmodified 5' terminal nucleotide; N" is any modified or unmodified 3' terminal nucleotide; any n is any positive integer from about 1 to about 102, wherein each position of Z in the formula may have an independently selected positions at their respective $R_1$, $R_2$, $R_3$, and $R_4$, subgroups; wherein, if a Z is at a position that binds to or interacts with a Cas protein in an active CRISPR complex, then $R_1$ is a hydroxyl or hydrogen; and $R_3$ and/or $R_4$ are phosphosdiester linkages; and wherein, if a Z is at a position that does bind to or interact with a Cas protein in an active CRISPR complex, then at least 10%, 20%, 30%, 40%, 50%, 60%, 70%, 75%, 80%, 85%, 90%, 91%, 92%, 93%, 94%, 95%, 96%, 97%, 98%, or 99% of the $R_1$ is free of hydroxyl or hydrogen; and each $R_3$ and/or each $R_4$ are independently selected as an internucleotide linkage chosen from: an alkylphosphonate, phosphotriester, phosphorothioate, phosphorodithioate, phosphoramidate, ketone, sulfone, carbonate, aldehyde, carboxyl, carbonyl, ether, ester except a (phosphoester bond), amine and thioamidate. As a another non-limiting example, compositions of the disclosure may comprise a guide sequence of $N'—[Z]_n—N''$; wherein N' is any modified or unmodified 5' terminal nucleotide; N" is any modified or unmodified 3' terminal nucleotide; any n is any positive integer from about 1 to about 100, wherein each position of Z in the guide sequence may have an independently selected positions at their respective $R_1$, $R_2$, $R_3$, and $R_4$, subgroups; wherein, if a Z is at position that sufficiently binds to or interacts with a Cas protein to form an active CRISPR complex, then at least one of the Z has a hydroxyl or hydrogen at $R_1$; a phosphosester linkage at $R_3$ and/or $R_4$; and wherein, if a Z is at a position that does bind to or interact with a Cas protein to form an active CRISPR complex (each a non-binding Z), then at least 10%, 20%, 30%, 40%, 50%, 60%, 70%, 75%, 80%, 85%, 90%, 91%, 92%, 93%, 94%, 95%, 96%, 97%, 98%, or 99% of the non-binding Z is: (i) free of hydroxyl or hydrogen at the $R_1$ position; and (ii) each $R_3$ and/or each $R_4$ are independently selected as an internucleotide linkage chosen from: an alkylphosphonate, phosphotriester, phosphorothioate, phosphorodithioate, phosphoramidate, ketone, sulfone, carbonate, aldehyde, carboxyl, carbonyl, ether, ester except a (phosphoester bond), amine and thioamidate. As a another non-limiting example, compositions of the disclosure may comprise a guide sequence of $N'—[Z]_n—N''$; wherein N' is any modified or unmodified 5' terminal nucleotide; N" is any modified or unmodified 3' terminal nucleotide; any n is any positive integer from about 1 to about 100, wherein each position of Z in the guide sequence may have an independently selected positions at their respective $R_1$, $R_2$, $R_3$, and $R_4$, subgroups; wherein, if a Z is at position that binds to or interacts with a Cas protein to form an active CRISPR complex (a "binding-Z"), then at least one of the binding-Z has a hydroxyl or hydrogen at $R_1$; a phosphosester linkage at $R_3$ and/or $R_4$; and wherein, if a Z is at a position that does bind to or interact with a Cas protein to form an active CRISPR complex (each a non-binding Z), then at least 10%, 20%, 30%, 40%, 50%, 60%, 70%, 75%, 80%, 85%, 90%, 91%, 92%, 93%, 94%, 95%, 96%, 97%, 98%, or 99% of the non-binding Z is: (i) a halogen at its $R_1$; and (ii) each $R_3$ and/or each $R_4$ are independently selected as an internucleotide linkage chosen from: an alkylphosphonate, phosphorothioate, phosphorodithioate, phosphoramidite, and thioamidate. In some embodiments, any one or plurality of Z of the guide sequence of N'—$[Z]_n$—N" may be replaced with one or a plurality of contiguous or noncontiguous, modified or unmodified nucleotides chosen from Formula W, X, and/or Y. In some embodiments, the non-binding Zs are at positions chosen from any position other than one or a plurality of positions on Tables 1, 5 and 6. In some embodiments, the guide sequence comprises one or a plurality of binding Zs at positions chosen from any one or plurality of positions identified on Tables 1, 5 or 6. As a another non-limiting example, compositions of the disclosure may comprise a guide sequence of N'—$[Z]_n$—N"; wherein N' is any modified or unmodified 5' terminal nucleotide; N" is any modified or unmodified 3' terminal nucleotide; any n is any positive integer from about 1 to about 100, wherein the guide sequence comprises the following domains in the 5' to 3' orientation: a nucleotide-binding domain; a Cas-binding domain; and a transcription terminator domain; and wherein each position of Z ($Z_1$ through $Z_{100}$) in the guide sequence may have an independently selectable substituents at their respective $R_1$, $R_2$, $R_3$, and $R_4$, subgroups; wherein, if a Z is at position that binds to or interacts with a Cas protein to form an active CRISPR complex (a "binding-Z"), then at least one of the binding-Z has a hydroxyl or hydrogen at $R_1$; a phosphosester linkage at $R_3$ and/or $R_4$; and wherein, if a Z is at a position that does bind to or interact with a Cas protein to form an active CRISPR complex (each a non-binding Z), then at least 10%, 20%, 30%, 40%, 50%, 60%, 70%, 75%, 80%, 85%, 90%, 91%, 92%, 93%, 94%, 95%, 96%, 97%, 98%, or 99% of the non-binding Z is: (i) a halogen at its $R_1$; and (ii) each $R_3$ and/or each $R_4$ are phosphorothioate. In some embodiments, any one or plurality of Z ($Z_1$ through $Z_n$) of the guide sequence of N'—$[Z]_n$—N" may be replaced with one or a plurality of contiguous or noncontiguous, modified or unmodified nucleotides chosen from Formula W, X, and/or Y. In some embodiments, the non-binding Zs are at positions chosen from any position other than one or a plurality of positions on Tables 1, 5 and 6. In some embodiments, the guide sequence comprises one or a plurality of binding Zs at positions chosen from any one or plurality of positions identified on Tables 1, 5 and/or 6.

In general, a "guide sequence" is any polynucleotide sequence having sufficient complementarity with a target polynucleotide sequence to hybridize with the target sequence and direct sequence-specific binding of a CRISPR complex (comprising any one or combination of Cas proteins) to the target polynucleotide sequence. The terms "guide sequence" includes any one or pluirality of nucleic acid molecules consisting of an sgRNA, tracrRNA, crRNA, or tracr/crRNA duplex that hybridize with the target sequence and direct sequence-specific binding of a CRISPR complex to the target sequence. It is generally desirable to select a target sequence of DNA or RNA which is involved in the production of a protein whose synthesis is ultimately to be modulated, cut, altered or inhibited in its entirety by activity of a Cas9 enzyme or functional fragment thereof. The oligonucleotides of the disclosure are conveniently synthesized using solid phase synthesis of known methodology, and is designed at least at the nucleotide-binding domain to be complementary to or specifically hybridizable with the preselected nucleotide sequence of the target RNA or DNA. Nucleic acid synthesizers are commercially available and their use is understood by persons of ordinary skill in the art as being effective in generating any desired oligonucleotide of reasonable length. It is also possible to synthesize the sgRNA by use of T7 RNA polymerase and a DNA template added to a mixture with individual dNTPs at an appropriate concentrations so that each nucleotide (whether it be RNA nucleotide or a DNA nucleotide) of the sgRNA is polymerized sequentially by the T7 polymerase catalyzing a reaction linking each base. Methods of making the guide sequences disclosed herein are contemplated by this application in which such nucleotide sequences may be manufactured by solid phase synthesis, by recombinant expression of one or more nucleotides in an invitro culture, or a combination of both in which modifications may be introduced at one or more positions across the length of the sequences.

In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested, and a control guide sequence different from the test guide sequence, and comparing binding or rate of cleavage at the target sequence between the test and control guide sequence reactions. Other assays are possible, and will occur to those skilled in the art. In other experiments, a cell may be transfected with any one or combination of guide sequences without transfection of a nucleic acid encoding a Cas protein. The transfected cell may be engineered to already express a Cas protein.

A guide sequence may be selected to target any target sequence. In some embodiments, the target sequence is a sequence within a genome of a cell, either in vitro, ex vivo (such as in the generation of CAR T cells), or in vivo such as pharmaceutical compositions comprising any of the disclosed guide sequences being administered directly to a subject. In some embodiments, the compositions disclosed herein comprise a synthetic guide RNA comprising or consisting of any sequence selected to target any target sequence. Exemplary target sequences include those that are unique in the target genome. For example, for the *S. pyogenes* Cas9, a unique target sequence in a genome may include a Cas9 target site of the form MMMMMMMMNNNNNNNNNNNNXGG (SEQ ID NO: 20) where NNNNNNNNNNNNXGG (SEQ ID NO: 21) (N is A, G, T, or C; and X can be anything) has a single occurrence in the genome. A unique target sequence in a genome may include an *S. pyogenes* Cas9 target site of the form MMMMMMMMMNNNNNNNNNNNXGG (SEQ ID NO: 22) where NNNNNNNNNNNXGG (N is A, G, T, or C; and X can be anything) has a single occurrence in the genome. For the *S. thermophilus* CRISPR-Cas9, a unique target sequence in a genome may include a Cas9 target site of the form MMMMMMMMNNNNNNNNNNNNXX-AGAAW (SEQ ID NO: 23) where NNNNNNNNNNNNXXAGAAW (SEQ ID NO: 24) (N is A, G, T, or C; X can be anything; and W is A or T) has a single occurrence in the genome. A unique target sequence in a genome may include an *S. thermophilus* CRISPR1 Cas9 target site of the form MMMMMMMMMNNNNNNNNNNNXXAGAAW (SEQ ID NO: 25) where NNNNNNNNNNNXXAGAAW (SEQ ID NO: 26) (N is A, G, T, or C; X can be anything; and W is A or T) has a single occurrence in the genome. For the *S. pyogenes* Cas9, a unique target sequence in a genome may include a Cas9 target site of the form MMMMMMMMNNNNNNNNNNNNXGGXG (SEQ ID NO: 27) where NNNNNNNNNNNNXGGXG (SEQ ID NO: 28) (N is A, G, T, or C; and X can be anything) has a single occurrence in the genome. A unique target sequence in a genome may include an *S. pyogenes* Cas9 target site of the form MMMMMMMMMNNNNNNNNNNNXGGXG (SEQ ID NO: 29) where NNNNNNNNNNNXGGXG (SEQ ID NO: 30) (N is A, G, T, or C; and X can be anything) has a single occurrence in the genome. In each of these sequences "M" may be A, G, T, or C, and need not be considered in identifying a sequence as unique.

In some embodiments the disclosure relates to a composition comprising a guide sequence that is an RNA molecule that comprises a DNA-binding sequence that comprises at least one or a combination of the sgRNA sequences of Table 1. In some embodiments, the composition comprises any one or combination of one or a plurality of sgRNA sequences or tracrRNA/crRNA sequences disclosed here comprising at least one DNA-binding domain at least about 70%, about 75%, about 80%, about 85%, about 90%, about 91%, about 92%, about 93%, about 94%, about 95%, about 96%, about 97%, about 98%, about 99% homologous, or about 100% homologous to a nucleotide sequence of Table 1. In some embodiments, the composition comprises any one or combination of one or a plurality of sgRNA sequences or tracrRNA/crRNA sequences disclosed here comprising at least one DNA-binding domain at least about 70%, about 75%, about 80%, about 85%, about 90%, about 91%, about 92%, about 93%, about 94%, about 95%, about 96%, about 97%, about 98%, about 99% homologous, or about 100% homologous to a nucleotide sequence that is complementary to a nucleotide sequence of Table 1.

TABLE 1

Proposed DNA-binding sequences of sgRNAs

| Gene Name | Reference Sequence No. | Species | sgRNA target sequence (Spacer Sequence) | Sequence |
|---|---|---|---|---|
| PCSK9 | NM_153565.2. | Mouse | sgRNA-1 | GCACCCATACCTTGGAGCAA (SEQ ID NO: 85) |
| | | | sgRNA-2 | CCCATACCTTGGAGCAACGG (SEQ ID NO: 86) |
| | | | sgRNA-3 | GCTCGCCCTCCCGTCCCAGG (SEQ ID NO: 87) |
| PCSK9 | NM_174936.3. | Human | sgRNA-1 | GTTGGTCCCCAAAGTCCCCA (SEQ ID NO: 88) |
| | | | sgRNA-2 | GCTCCGGCAGCAGATGGCAA (SEQ ID NO: 89) |
| | | | sgRNA-3 | TCTTTGACTCTAAGGCCCAA (SEQ ID NO: 90) |
| FIX | NM_000133.3. | Human | sgRNA-1 | CATGTGGCCTGGTCAACAAG (SEQ ID NO: 91) |
| | | | sgRNA-2 | TGTGCTGGCTTCCATGAAGG (SEQ ID NO: 92) |
| | | | sgRNA-3 | TAGATCGAAGACATGTGGCT (SEQ ID NO: 93) |
| IL-10 | NM_000572.2. | Human | sgRNA-1 | TGAAAACAAGAGCAAGGCCG (SEQ ID NO: 94) |
| | | | sgRNA-2 | GCGCCGTAGCCTCAGCCTGA (SEQ ID NO: 95) |
| | | | sgRNA-3 | GGCGCATGTGAACTCCCTGG (SEQ ID NO: 96) |
| VEGFR1 | NM_002019.4 | Human | sgRNA-1 | GGTCAGCTACTGGGACACCG (SEQ ID NO: 97) |
| | | | sgRNA-2 | AGTGATGTTGAGGAAGAGGA (SEQ ID NO: 98) |
| | | | sgRNA-3 | GAGCTTCCTGAATTAAACTT (SEQ ID NO: 99) |

TABLE 1-continued

Proposed DNA-binding sequences of sgRNAs

| Gene Name | Reference Sequence No. | Species | sgRNA target sequence (Spacer Sequence) | Sequence |
|---|---|---|---|---|
| CTLA-4 | NM_005214.4 | Human | sgRNA-1 | CATAGACCCCTGTTGTAAGA (SEQ ID NO: 100) |
| | | | sgRNA-2 | AGGAAGTCAGAATCTGGGCA (SEQ ID NO: 101) |
| | | | sgRNA-3 | TGGCTTGCCTTGGATTTCAG (SEQ ID NO: 102) |
| cMyc | NM_002467 | Human | sgRNA-1 | GGTAGGGGAAGACCACCGAG (SEQ ID NO: 103) |
| | | | sgRNA-2 | GTATTTCTACTGCGACGAGG (SEQ ID NO: 104) |
| | | | sgRNA-3 | CTTCGGGGAGACAACGACGG (SEQ ID NO: 105) |
| Kras | NM_004985 | Human | sgRNA-1 | TCCCTTCTCAGGATTCCTAC (SEQ ID NO: 106) |
| | | | sgRNA-2 | AGATATTCACCATTATAGGT (SEQ ID NO: 107) |
| | | | sgRNA-3 | AATTACTACTTGCTTCCTGT (SEQ ID NO: 108) |
| Yap1 | NM_006106 | Human | sgRNA-1 | GGTCGGTCTCCGAGTCCCCG (SEQ ID NO: 109) |
| | | | sgRNA-2 | GATGATGTACCTCTGCCAGC (SEQ ID NO: 110) |
| | | | sgRNA-3 | TCAGATCGTGCACGTCCGCG (SEQ ID NO: 111) |

In some embodiments, the disclosure relates to compositions comprising a guide sequence, wherein the guide sequence comprises a nucleotide binding domain or a DNA-binding domain comprising at least one modified nucleotide. In some embodiments, the nucleotide binding domain or a DNA-binding domain consists of from about 15 to about 25 nucleotides; wherein the from 15 to about 25 nucleotides comprises a sequence similarity of about 90, 91, 92, 93, 94, 95, 96, 97, 98, 99%, or 100% sequence homology to any target sequences identified herein or in the table provided above. In some embodiments, the nucleotide binding domain or a DNA-binding domain consists of from about 15 to about 30 nucleotides; wherein the from 15 to about 25 nucleotides comprises a sequence similarity of about 90, 91, 92, 93, 94, 95, 96, 97, 98, 99%, or 100% sequence homology to any target sequence identified herein. In some embodiments, the nucleotide binding domain or a DNA-binding domain consists of from about 15 to about 40 nucleotides; wherein the from 15 to about 25 nucleotides comprises a sequence similarity of about 90, 91, 92, 93, 94, 95, 96, 97, 98, 99%, or 100% sequence homology to any target sequence identified herein. In some embodiments, the nucleotide binding domain or a DNA-binding domain consists of from about 15 to about 25 nucleotides; wherein the from 15 to about 25 nucleotides comprises a sequence similarity of about 90, 91, 92, 93, 94, 95, 96, 97, 98, 99%, or about 100% sequence homology to any target sequence identified herein. For instance, one of ordinary skill in art could identify other DNA-binding domains which may be structurally related to those sequences provided in Table 1 to be used in connection with a CRISPR complex utilizing a Cas enzyme. For instance, it is possible that for modulation of PCSK9 (GCACCCATACCTTGGAGCAA)(SEQ ID NO: 139), the sgRNA sequence used may have about 90, 91, 92, 93, 94, 95, 96, 97, 98, or 99% sequence homology to any of the sgRNA-1, 2, or 3 associated with the DNA-binding domain of PCSK9.

In some embodiments, any of the sequences disclosed herein may have a DNA-binding domain, a Cas-binding domain, a transcription termination domain and an RNA-binding domain. Any of the domains of the disclosed oligonucleotides may be in any order from 5' to 3' orientation and may be contiguous as to each other or any one or multiple domains or elements may be non-contiguous in relation to one or more of the other domains, such that a different element, amino acid sequence, nucleotide or set of modified nucleotides may precede the 5' and/or 3' area of any domain.

In some embodiments, for instance, any one or combination of domains or sequences disclosed herein may comprise a sequence of about 1, 2, 3, 4, 5, 6, 7, 8, 9, 10, 15, 20, 25, 30, 35, 40, 45, or 50 or more modified or unmodified nucleotides flanking the 3' or 5' end of each domain. In some embodiments, for instance, any one or combination of domains or sequences disclosed herein may comprise a sequence of about 1, 2, 3, 4, 5, 6, 7, 8, 9, 10, 15, 20, 25, 30, 35, 40, 45, or 50 or more modified or unmodified uracils flanking the 3' or 5' end of each domain. In some embodiments, the disclosed nucleic acid sequences has contiguous domains from the 5' to the 3' direction including a DNA-targeting domain, a Cas-binding domain, a transcription terminator domain, and, optionally a RNA-binding domain. In some embodiments, the disclosed nucleic acid sequences has contiguous domains from the 5' to the 3' direction including a DNA-targeting domain, a Cas-9 binding domain, a transcription terminator domain, and, optionally a RNA-binding domain. Each domain may comprise from about 10 to about 15, 20, 25, 30, 35, 40, 45, 50, 60, 65, 70, 75, 80, 85, 90, 95, 100, 110, 120, 130, 140, 150, 160, 170, 180, 190, 200, 210, 220, 230, 240, or 250 or more modified or unmodified nucleic acids of DNA or RNA. The disclosure relates, among other things, to the rationale design of sgRNA, tracr/crRNA duplexes, and, generally, guide sequences that activate and/or catalyze the reaction of a CRISPR enzyme with a target nucleic acid sequence. The disclosure relates to the discovery that guide sequences (whether in the form of sgRNA, tracr/crRNA duplexes, or tracr/crRNA single strands) can be heavily modified to enhance on-target enzymatic efficiency as long as certain nucleotides that bind to the CRISPR enzyme, variant or functional fragments thereof are conserved at certain positions and/or, in some cases, conserved in respect to certain substituents on each nucleotide that are capable of binding a Cas protein, variant or functional fragments thereof in the presence of such a the Cas protein, variant or functional fragments thereof. Certain positions of the guide sequence can be more heavily modified based upon their functional association to other components of the CRISPR complex. For instance, in some embodiments, the composition or pharmaceutical composition disclosed herein comprises one or a plurality of nucleic acid sequences on one or plurality of nucleic acid molecules wherein the nucleic acid sequences comprise contiguous domains in the 5' to 3' orientation: a DNA-targeting domain, a Cas-binding domain, and a transcription terminator domain.

In some embodiments, the composition or pharmaceutical composition disclosed herein comprise a guide sequence or pharmaceutically acceptable salt thereof, comprising the following domains in 5' to 3' orientation: a DNA-targeting domain, a Cas-9 binding domain, a transcription terminator domain; wherein position 1 of the guide sequence is considered the first nucleotide position in the DNA-binding domain and wherein the DNA-binding domain comprises positions 1 through 20, the Cas-9 binding domain comprises positions 21 through 62, and the transcription terminator domain comprises positions 63 through 102.

In some embodiments, the composition or pharmaceutical composition disclosed herein comprise a guide sequence or pharmaceutically acceptable salt thereof, comprise one or a plurality of contiguous domains, in the 5' to 3' orientation, selected from: a DNA-targeting domain, a Cas-binding domain, and a transcription terminator domain; wherein position 1 of the guide sequence is considered the first nucleotide in the DNA-binding domain and where the DNA-binding domain comprises positions 1 through 20, the Cas-binding domain comprises positions 21-62, and the transcription terminator domain comprises positions 63 through 102; wherein any modification disclosed herein is at any position within the guide sequence, except that any one or plurality of nucleotides that binds or associates with a Cas protein in any domain is unmodified. In some embodiments, the composition or pharmaceutical composition disclosed herein comprise a guide sequence or pharmaceutically acceptable salt thereof, comprise one or a plurality of contiguous domains, in the 5' to 3' orientation, selected from: a DNA-targeting domain, a Cas-binding domain, and a transcription terminator domain; wherein position 1 of the guide sequence is considered the first nucleotide in the DNA-binding domain and where the DNA-binding domain comprises positions 1 through 20, the Cas-binding domain comprises positions 21-62, and the transcription terminator domain comprises positions 63 through 102; wherein any modification disclosed herein is at any position within the guide sequence, except that any one or plurality of nucleotides that binds or associates with a Cas protein in any domain is unmodified at the 2' carbon position of the sugar moiety. In some embodiments, the guide sequence may have no more than 5%, 6%, 7%, 8%, 9%, 10%, 20%, 30%, 40%, 50%, 60%, 70%, 80%, 90%, 91%, 92%, 93%, 94%, 95%, 96%, 97%, 98%, or 99% modifications at any of the nucleotides in the guide sequence, except that any nucleotide that increases the stability between the guide sequence and a Cas protein (in a CRISPR complex or system) is left unmodified. In some embodiments, the guide sequence may have no more than 5%, 6%, 7%, 8%, 9%, 10%, 20%, 30%, 40%, 50%, 60%, 70%, 80%, 90%, 91%, 92%, 93%, 94%, 95%, 96%, 97%, 98%, or 99% modifications at any of the nucleotides in the guide sequence, except that any nucleotide that increases the stability between the guide sequence and a Cas protein (in a CRISPR complex or system) is left unmodified only at its 2' carbon position of the sugar moiety.

The disclosure also relates to compositions or pharmaceutical compositions comprising guide sequences (optionally with one or more pharmaceutically acceptable salts at such positions) comprising a conserved hydroxyl group at the 2' carbon of the ribose sugar or sugar moiety of one or a combination of the following positions of Table 2. In some embodiments, modifications to one or more of the positions in Table 2 may cause a decrease or abolishment of efficiency and/or efficacy of the sgRNA in which they are present.

TABLE 2

Conserved RNA Positions within a Guide Sequence for Enhanced CRISPR complex activity

| | Position | Nucleotide interaction at 2'OH | Source (FIG. 10e) |
|---|---|---|---|
| guide sequence | 1 | Varies | Cell |
| guide sequence | 12 | Varies | Science |
| guide sequence | 15 | Varies | Cell and Science |
| guide sequence | 16 | Varies | Cell and Science |
| guide sequence | 19 | Varies | Cell and Science |
| Fixed region | 22 | U | Cell and Science |
| Fixed region | 23 | U | Cell and Science |
| Fixed region | 24 | U | Cell and Science |
| Fixed region | 25 | U | Science |
| Fixed region | 26 | A | Science |
| Fixed region | 27 | G | Science |
| Fixed region | 43 | G | Cell and Science |
| Fixed region | 44 | U | Cell and Science |
| Fixed region | 45 | U | Cell and Science |
| Fixed region | 47 | A | Cell and Science |
| Fixed region | 49 | A | Science |
| Fixed region | 51 | A | Cell |
| Fixed region | 58 | G | Cell |
| Fixed region | 59 | U | Science |
| Fixed region | 62 | G | Cell and Science |
| Fixed region | 63 | U | Cell and Science |
| Fixed region | 64 | U | Cell and Science |
| Fixed region | 65 | A | Cell |
| Fixed region | 68 | A | Cell |
| Fixed region | 69 | A | Science |
| Fixed region | 82 | U | Science |

In some embodiments, the composition or pharmaceutical composition comprises a guide sequence, or one or more pharmaceutically acceptable salts thereof, comprising the following domains in 5' to 3' orientation: a DNA-binding domain, a Cas-binding domain, and a transcription terminator domain; wherein position 1 of the guide sequence corresponds to the first nucleotide position in the DNA-binding domain and wherein the DNA-binding domain comprises positions 1 through 20, the Cas-binding domain comprises positions 21 through 62, and the transcription terminator domain comprises positions 63 through 102. In some embodiments, position 1 is a uracil, thymine, adenine, or cytosine with a 2' hydroxyl group on the 2' carbon of the nucleotide of the sugar moiety and the guide sequence comprises any one or a plurality of modifications at positions 2-102. In some embodiments, position 12 is a uracil, thymine, adenine, or cytosine with a 2' hydroxyl group on the 2' carbon of the nucleotide of the sugar moiety and the guide sequence comprises any one or a plurality of modifications at positions 1-11 and 13-102. In some embodiments, position 15 is a uracil, thymine, adenine, or cytosine with a 2' hydroxyl group on the 2' carbon of the nucleotide of the sugar moiety and the guide sequence comprises any one or a plurality of modifications at positions 1-14 and 16-102. In some embodiments, position 16 is a uracil, thymine, adenine, or cytosine with a 2' hydroxyl group on the 2' carbon of the sugar moiety of the nucleotide and the guide sequence comprises any one or a plurality of modifications at positions 1-15 and 17-102. In some embodiments, position 19 is a uracil, thymine, adenine, or cytosine with a 2' hydroxyl group on the 2' carbon of the sugar moiety and the guide sequence comprises any one or a plurality of modifications at positions 1-18 and 20-102. In some embodiments, position 22 is a uracil, thymine, adenine, or cytosine with a 2' hydroxyl group on the 2' carbon of the sugar moiety and the guide sequence comprises any one or a plurality of modifications at positions 1-21 and 23-102. In some embodiments, position 23 is a uracil, thymine, adenine, or cytosine with a 2' hydroxyl group on the 2' carbon of the sugar moiety and the guide sequence comprises any one or a plurality of modifications at positions 1-22 and 24-102. In some embodiments, position 24 is a uracil, thymine, adenine, or cytosine with a 2' hydroxyl group on the 2' carbon of the sugar moiety and the guide sequence comprises any one or a plurality of modifications at positions 1-23 and 25-102. In some embodiments, position 25 is a uracil, thymine, adenine, or cytosine with a 2' hydroxyl group on the 2' carbon of the sugar moiety and the guide sequence comprises any one or a plurality of modifications at positions 1-24 and 26-102. In some embodiments, position 26 is a uracil, thymine, adenine, or cytosine with a 2' hydroxyl group on the 2' carbon of the sugar moiety and the guide sequence comprises any one or a plurality of modifications at positions 1-25 and 27-102. In some embodiments, position 27 is a uracil, thymine, adenine, or cytosine with a 2' hydroxyl group on the 2' carbon of the sugar moiety and the guide sequence comprises any one or a plurality of modifications at positions 1-26 and 28-102. In some embodiments, position 43 is a uracil, thymine, adenine, or cytosine with a 2' hydroxyl group on the 2' carbon of the sugar moiety and the guide sequence comprises any one or a plurality of modifications at positions 1-42 and 44-102. In some embodiments, position 44 is a uracil, thymine, adenine, or cytosine with a 2' hydroxyl group on the 2' carbon of the sugar moiety and the guide sequence comprises any one or a plurality of modifications at positions 1-43 and 45-102. In some embodiments, position 45 is a uracil, thymine, adenine, or cytosine with a 2' hydroxyl group on the 2' carbon of the sugar moiety and the guide sequence comprises any one or a plurality of modifications at positions 1-44 and 46-102. In some embodiments, position 47 is a uracil, thymine, adenine, or cytosine with a 2' hydroxyl group on the 2' carbon of the sugar moiety and the guide sequence comprises any one or a plurality of modifications at positions 1-46 and 48-102. In some embodiments, position 49 is a uracil, thymine, adenine, or cytosine with a 2' hydroxyl group on the 2' carbon of the sugar moiety and the guide sequence comprises any one or a plurality of modifications at positions 1-48 and 50-102. In some embodiments, position 51 is a uracil, thymine, adenine, or cytosine with a 2' hydroxyl group on the 2' carbon of the sugar moiety and the guide sequence comprises any one or a plurality of modifications at positions 1-50 and 52-102. In some embodiments, position 58 is a uracil, thymine, adenine, or cytosine with a 2' hydroxyl group on the 2' carbon of the sugar moiety and the guide sequence comprises any one or a plurality of modifications at positions 1-57 and 59-102. In some embodiments, position 59 is a uracil, thymine, adenine, or cytosine with a 2' hydroxyl group on the 2' carbon of the sugar moiety and the guide sequence comprises any one or a plurality of modifications at positions 1-58 and 60-102. In some embodiments, position 62 is a uracil, thymine, adenine, or cytosine with a 2' hydroxyl group on the 2' carbon of the sugar moiety and the guide sequence comprises any one or a plurality of modifications at positions 1-61 and 63-102. In some embodiments, position 63 is a uracil, thymine, adenine, or cytosine with a 2' hydroxyl group on the 2' carbon of the sugar moiety and the guide sequence comprises any one or a plurality of modifications at positions 1-62 and 64-102. In some embodiments, position 64 is a uracil, thymine, adenine, or cytosine with a 2' hydroxyl group on the 2' carbon of the sugar moiety and the guide sequence comprises any one or a plurality of modifications at positions 1-63 and 65-102. In some embodiments, position 65 is a uracil, thymine, adenine, or cytosine with a 2' hydroxyl group on the 2' carbon of the sugar moiety and the guide sequence comprises any one or a plurality of modifications at positions 1-64 and 66-102. In some embodiments, position 68 is a uracil, thymine, adenine, or cytosine with a 2' hydroxyl group on the 2' carbon of the sugar moiety and the guide sequence comprises any one or a plurality of modifications at positions 1-67 and 69-102. In some embodiments, position 69 is a uracil, thymine, adenine, or cytosine with a 2' hydroxyl group on the 2' carbon of the sugar moiety and the guide sequence comprises any one or a plurality of modifications at positions 1-68 and 70-102. In some embodiments, position 82 is a uracil, thymine, adenine, or cytosine with a 2' hydroxyl group on the 2' carbon of the sugar moiety and the guide sequence comprises any one or a plurality of modifications at positions 1-81 and 83-102.

In some embodiments, the composition or pharmaceutical composition comprises a guide sequence, or one or more pharmaceutically acceptable salts thereof, comprising the following domains in 5' to 3' orientation: a DNA-binding domain, a Cas-binding domain, and a transcription terminator domain; wherein position 1 of the guide sequence corresponds to the first nucleotide position in the DNA-binding domain and wherein the DNA-binding domain comprises positions 1 through 20, the Cas-binding domain comprises positions 21 through 62, and the transcription terminator domain comprises positions 63 through 102. In some embodiments, the guide sequence comprises any 1, 2, 3, 4, and/or 5 conserved hydroxyl groups on the 2' carbon of the sugar moiety at positions 1, 12, 15, 16, and/or 19 of the DNA-binding domain. In some embodiments, the guide sequence comprises any 1, 2, 3, 4, 5, 6, 7, 8, 9, 10, 11, 12, 13, 14, or 15 conserved hydroxyl groups on the 2' carbon of the sugar moiety at positions 22, 23, 24, 25, 26, 27, 43, 44, 45, 47, 49, 51, 58, 59, and/or 62 of the Cas-binding domain. In some embodiments, the guide sequence comprises any 1, 2, 3, 4, 5, and/or 6 conserved hydroxyl groups on the 2' carbon of the sugar moiety at positions 63, 64, 65, 68, 69, and/or 82 of the transcription terminator domain. In some embodiments, the guide sequence comprises any 1, 2, 3, 4, and/or 5 conserved hydroxyl groups on the 2' carbon of the sugar moiety at positions 1, 12, 15, 16, and/or 19 of the DNA-binding domain and any 1, 2, 3, 4, 5, 6, 7, 8, 9, 10, 11, 12, 13, 14, and/or 15 conserved hydroxyl groups on the 2' carbon of the sugar moiety at positions 22, 23, 24, 25, 26, 27, 43, 44, 45, 47, 49, 51, 58, 59, and/or 62 of the Cas-binding domain. In some embodiments, the guide sequence comprises any 1, 2, 3, 4, and/or 5 conserved hydroxyl groups on the 2' carbon of the sugar moiety at positions 1, 12, 15, 16, and/or 19 of the DNA-binding domain and any 1, 2, 3, 4, 5, and/or 6 conserved hydroxyl groups on the 2' carbon of the sugar moiety at positions 63, 64, 65, 68, 69, and/or 82 of the transcription terminator domain. In some embodiments, the guide sequence comprises any 1, 2, 3, 4, 5, 6, 7, 8, 9, 10, 11, 12, 13, 14, and/or 15 conserved hydroxyl groups on the 2' carbon of the sugar moiety at positions 22, 23, 24, 25, 26, 27, 43, 44, 45, 47, 49, 51, 58, 59, and/or 62 of the Cas-binding domain and any 1, 2, 3, 4, 5, and/or 6 conserved hydroxyl groups on the 2' carbon of the sugar moiety at positions 63, 64, 65, 68, 69, and/or 82 of the transcription terminator domain. In some embodiments, the guide sequence comprises any 1, 2, 3, 4, and/or 5 conserved hydroxyl groups on the 2' carbon of the sugar moiety at positions 1, 12, 15, 16, and/or 19 of the DNA-binding domain, any 1, 2, 3, 4, 5, 6, 7, 8, 9, 10, 11, 12, 13, 14, and/or 15 conserved hydroxyl groups on the 2' carbon of the sugar moiety at positions 22, 23, 24, 25, 26, 27, 43, 44, 45, 47, 49, 51, 58, 59, and/or 62 of the Cas-binding domain, and any 1, 2, 3, 4, 5, and/or 6 conserved hydroxyl groups on the 2' carbon of the sugar moiety at positions 63, 64, 65, 68, 69, and/or 82 of the transcription terminator domain.

In some embodiments, the guide sequence comprises any 1, 2, 3, 4, and/or 5 unmodified nucleic acid molecules at positions 1, 12, 15, 16, and/or 19 of the DNA-binding domain. In some embodiments, the guide sequence comprises any 1, 2, 3, 4, 5, 6, 7, 8, 9, 10, 11, 12, 13, 14, and/or 15 unmodified nucleic acid molecules at positions 22, 23, 24, 25, 26, 27, 43, 44, 45, 47, 49, 51, 58, 59, and/or 62 of the Cas-binding domain. In some embodiments, the guide sequence comprises any 1, 2, 3, 4, 5, and/or 6 unmodified nucleic acid molecules at positions 63, 64, 65, 68, 69, and/or 82 of the transcription terminator domain. In some embodiments, the guide sequence comprises any 1, 2, 3, 4, and/or 5 unmodified nucleic acid molecules at positions 1, 12, 15, 16, and/or 19 of the DNA-binding domain and any 1, 2, 3, 4, 5, 6, 7, 8, 9, 10, 11, 12, 13, 14, and/or 15 unmodified nucleic acid molecules at positions 22, 23, 24, 25, 26, 27, 43, 44, 45, 47, 49, 51, 58, 59, and/or 62 of the Cas-binding domain. In some embodiments, the guide sequence comprises any 1, 2, 3, 4, and/or 5 unmodified nucleic acid molecules at positions 1, 12, 15, 16, and/or 19 of the DNA-binding domain and any 1, 2, 3, 4, 5, and/or 6 unmodified nucleic acid molecules at positions 63, 64, 65, 68, 69, and/or 82 of the transcription terminator domain. In some embodiments, the guide sequence comprises any 1, 2, 3, 4, 5, 6, 7, 8, 9, 10, 11, 12, 13, 14, and/or 15 unmodified nucleic acid molecules at positions 22, 23, 24, 25, 26, 27, 43, 44, 45, 47, 49, 51, 58, 59, and/or 62 of the Cas-binding domain and any 1, 2, 3, 4, 5, and/or 6 unmodified nucleic acid molecules at positions 63, 64, 65, 68, 69, and/or 82 of the transcription terminator domain. In some embodiments, the guide sequence comprises any 1, 2, 3, 4, and/or 5 unmodified nucleic acid molecules at positions 1, 12, 15, 16, and/or 19 of the DNA-binding domain, any 1, 2, 3, 4, 5, 6, 7, 8, 9, 10, 11, 12, 13, 14, and/or 15 unmodified nucleic acid molecules at positions 22, 23, 24, 25, 26, 27, 43, 44, 45, 47, 49, 51, 58, 59, and/or 62 of the Cas-binding domain, and any 1, 2, 3, 4, 5, and/or 6 unmodified nucleic acid molecules at positions 63, 64, 65, 68, 69, and/or 82 of the transcription terminator domain. In some embodiments, the guide sequence is free of a modification at any one or combination of positions set forth in Table 2. In some embodiments, the guide sequence is free of any akyl modification at any one or combination of 2' carbons in the ribose at the positions set forth in Table 2. In some embodiments, the guide sequence is free of any O-methyl modification at any one or combination of positions set forth in Table 2.

The disclosure also relates to the discovery that certain domains within guide sequences (whether in the form of sgRNA, tracr/crRNA duplexes, or tracr/crRNA single strands) can be heavily modified to enhance on-target enzymatic efficiency as long as certain nucleotides that bind to the Cas protein, variant or functional fragments thereof are conserved at certain positions and/or conserved in respect to certain substituents on each nucleotide that interact with the Cas protein, variant or functional fragments thereof in the presence of such as the Cas protein, variant or functional fragments thereof. In some embodiments, the guide sequences described herein comprise modifications in the DNA-binding domain, or, in some embodiments, in the seed region of the DNA-binding domain. In some embodiments, their sugar moiety such that the 2' position of the sugar moiety is a hydroxyl group. In some embodiments, the disclosure relates to a composition or pharmaceutical composition comprising a nucleic acid comprising the following domains contiguously oriented in the 5' to 3' direction:

$X_1$ domain-DNA-binding domain-Cas binding domain-transcription terminator domain-$X_2$ domain;

wherein the $X_1$ domain is from about 0 to about 100 nucleotides in length, the DNA-binding domain is from about 1 to about 20 nucleotides in length, the Cas-binding domain is from about 30 to about 50 nucleotides in length, the transcription terminator domain is from about 30 to about 70 nucleotides in length, and wherein the $X_2$ domain is from about 0 to about 200 nucleotides in length, and wherein position 1 corresponds to the first nucleotide in the DNA-binding domain and each position thereafter is a successive positive integer; and each nucleotide in the $X_1$ domain, if not 0 nucleotides in length, is assigned a position of a negative integer beginning with the position −1 at the nucleotide adjacent to position 1 in the 5' direction. In some embodiments, the disclosure relates to a composition or pharmaceutical composition comprising a nucleic acid that comprises the following domains contiguously oriented in the 5' to 3' direction:

$X_1$ domain-DNA-binding domain-Cas binding domain-transcription terminator domain-$X_2$ domain; wherein the $X_1$ domain and the $X_2$ domain are 0 nucleotides in length, the DNA-binding domain is about 20 nucleotides in length, the Cas-binding domain is about 40 nucleotides in length, the transcription terminator domain is about 39 nucleotides in length.

In some embodiments, the disclosure relates to a composition or pharmaceutical composition comprising a nucleic acid comprises the following domains contiguously oriented in the 5' to 3' direction: $X_1$ domain-DNA-binding domain-Cas binding domain-transcription terminator domain-$X_2$ domain;

wherein the X1 domain and the X2 domain are 0 nucleotides in length, the DNA-binding domain is about 20 nucleotides in length, the Cas-binding domain is about 40 nucleotides in length, the transcription terminator domain is about 39 nucleotides in length; and wherein the nucleic acid sequence comprises one or a combination of ribonucleotides at the positions identified in Table 2. In some embodiments, the one or a combination of ribonucleotides at the positions identified in Table 2 comprise 2' hydroxyl groups within the sugar moieties of the nucleotide.

The disclosure also relates to the combination of one or a plurality of modifications in the guide sequence. Any modifications at any position of the guide sequence or sequences may be made. In some embodiments, however, the modification are free of 2'O-methyl mutations at one or more of the positions identified in this disclosure. In some embodiments, the the guide sequence or sequences are free of 2'O-alkyl mutations at one or more of the positions in the Cas-binding domain. In some embodiments, the modifications are free of 2'-fluoro mutations at one or more of the positions in the Cas-binding domain. In some embodiments, the guide sequence or sequences are free of phosphorothioate linkages at one or more of the positions in the Cas-binding domain. In some embodiments, the guide sequence or sequences are free of phosphorothioate linkages at one or more of the nucleotides capable of increasing the stability of the guide sequence association with a Cas protein in a CRISPR complex. In some embodiments, the guide sequence or sequences are free of phosphorothioate linkages at one or more of the nucleotides capable of increasing the stability of the guide sequence association with a Cas protein in a CRISPR complex. n some embodiments, the guide sequence or sequences are free of phosphorothioate linkages at one or more of the nucleotides capable of enhancing the enzymatic efficiency of the guide sequence association with a Cas protein in a CRISPR complex.

The disclosure relates to compositions and pharmaceutical compositions comprising one or a plurality of guide sequences disclosed herein, wherein the one or a plurality of guide sequences comprises from about 1% to about 99% modified nucleotides, wherein each modified nucleotide comprisesat least two modification disclosed herein. The disclosure also relates to compositions and pharmaceutical compositions comprising one or a plurality of guide sequences disclosed herein, wherein the one or a plurality of guide sequences comprises from about 1% to about 99% modified nucleotides, wherein each modified nucleotide comprises a 2' halogen at its 2' carbon of its sugar moiety and a phosphorothioate linkage between at least one of its adjacent nucleotides. In any embodiment, the one or plurality of guide sequences may comprise one or more nucelotides having Formula W, X, Y, and/or Z positioned in the sequence either contiguously or noncontiguously.

In some embodiments, the disclosure relates to compositions comprising a guide sequence, wherein the guide sequence comprises a transcription terminator domain comprising at least one modified nucleotide. In some embodiments, the disclosure relates to compositions comprising a guide sequence, wherein the guide sequence comprises a transcription terminator domain comprising at least one modified nucleotide comprising a modification at a 2' carbon in its sugar moiety. In some embodiments, the disclosure relates to compositions comprising a guide sequence, wherein the guide sequence comprises a transcription terminator domain comprising from about 1% to about 100% modified nucleotides. In some embodiments, the disclosure relates to compositions comprising a guide sequence, wherein the guide sequence comprises a transcription terminator domain comprising from about 10% to about 100% modified nucleotides. In some embodiments, the disclosure relates to compositions comprising a guide sequence, wherein the guide sequence comprises a transcription terminator domain comprising from about 20% to about 100% modified nucleotides. In some embodiments, the disclosure relates to compositions comprising a guide sequence, wherein the guide sequence comprises a transcription terminator domain comprising from about 30% to about 100% modified nucleotides. In some embodiments, the disclosure relates to compositions comprising a guide sequence, wherein the guide sequence comprises a transcription terminator domain comprising from about 40% to about 100% modified nucleotides. In some embodiments, the disclosure relates to compositions comprising a guide sequence, wherein the guide sequence comprises a transcription terminator domain comprising from about 50% to about 100% modified nucleotides. In some embodiments, the disclosure relates to compositions comprising a guide sequence, wherein the guide sequence comprises a transcription terminator domain comprising from about 60% to about 100% modified nucleotides. In some embodiments, the disclosure relates to compositions comprising a guide sequence, wherein the guide sequence comprises a transcription terminator domain comprising from about 70% to about 100% modified nucleotides. In some embodiments, the disclosure relates to compositions comprising a guide sequence, wherein the guide sequence comprises a transcription terminator domain comprising from about 80% to about 100% modified nucleotides. In some embodiments, the disclosure relates to compositions comprising a guide sequence, wherein the guide sequence comprises a transcription terminator domain comprising from about 90% to about 100% modified nucleotides. In some embodiments, the disclosure relates to compositions comprising a guide sequence, wherein the guide sequence comprises a transcription terminator domain comprising from about 95% to about 100% modified nucleotides.

The disclosure relates to compositions and pharmaceutical compositions comprising a guide sequence and/or a crRNA-tracrRNA duplex, wherein the guide sequence or crRNA-tracrRNA comprises a DNA-binding domain (the sequence complementary to a target sequence of choice) comprising at least one unmodified nucleotide. In some embodiments, the disclosure relates to compositions comprising a guide sequence and/or a crRNA-tracrRNA duplex, wherein the a guide sequence and/or a crRNA-tracrRNA duplex comprises a DNA-binding domain comprising at least one nucleotide comprising an unmodified hydroxyl or hydrogen substituent at its 2' carbon in its sugar moiety. In some embodiments, the disclosure relates to compositions comprising a guide sequence and/or a crRNA-tracrRNA duplex, wherein the a guide sequence and/or a crRNA-tracrRNA duplex comprises a DNA-binding domain comprising at least one nucleotide comprising an unmodified hydroxyl group at its 2' carbon in its sugar moiety. In some embodiments, the disclosure relates to compositions comprising a guide sequence and/or a crRNA-tracrRNA duplex, wherein the a guide sequence and/or a crRNA-tracrRNA duplex comprises a DNA-binding domain comprising one or a combination of unmodified hydroxyl group at its 2' carbon in its sugar moiety at positions identified in Table 2. In some embodiments, the disclosure relates to compositions comprising a guide sequence and/or a crRNA-tracrRNA duplex, wherein the a guide sequence and/or a crRNA-tracrRNA duplex comprises a DNA-binding domain comprising 1, 2, 3, 4, 5, 6, 7, 8, 9, 10, 11, 12, 13, 14, 15, 16, 17, 18, 19, 20, 21, 22, 23, 24, 25, 26, or 27 of the unmodified hydroxyl groups at the 2' carbon in its sugar moiety at positions identified in Table 2.

In some embodiments, the disclosure relates to compositions comprising a guide sequence and/or a crRNAtracrRNA duplex, wherein the guide sequence and/or a crRNA-tracrRNA duplex comprises a transcription terminator domain comprising from about 1% to about 100% modified nucleotides. In some embodiments, the disclosure relates to compositions comprising a guide sequence and/or a crRNA-tracrRNA duplex, wherein the guide sequence and/or a crRNA-tracrRNA duplex comprises a transcription terminator domain comprising from about 10% to about 100% modified nucleotides. In some embodiments, the disclosure relates to compositions comprising a guide sequence and/or a crRNA-tracrRNA duplex, wherein the guide sequence and/or a crRNA-tracrRNA duplex comprises a transcription terminator domain comprising from about 20% to about 100% modified nucleotides. In some embodiments, the disclosure relates to compositions comprising a guide sequence and/or a crRNA-tracrRNA duplex, wherein the guide sequence and/or a crRNA-tracrRNA duplex comprises a transcription terminator domain comprising from about 30% to about 100% modified nucleotides. In some embodiments, the disclosure relates to compositions comprising a guide sequence and/or a crRNA-tracrRNA duplex, wherein the guide sequence and/or a crRNA-tracrRNA duplex comprises a transcription terminator domain comprising from about 40% to about 100% modified nucleotides. In some embodiments, the disclosure relates to compositions comprising a guide sequence and/or a crRNA-tracrRNA duplex, wherein the guide sequence and/or a crRNA-tracrRNA duplex comprises a transcription terminator domain comprising from about 50% to about 100% modified nucleotides. In some embodiments, the disclosure relates to compositions comprising a guide sequence and/or a crRNA-tracrRNA duplex, wherein the guide sequence and/or a crRNA-tracrRNA duplex comprises a transcription terminator domain comprising from about 60% to about 100% modified nucleotides. In some embodiments, the disclosure relates to compositions comprising a guide sequence and/or a crRNA-tracrRNA duplex, wherein the guide sequence and/or a crRNA-tracrRNA duplex comprises a transcription terminator domain comprising from about 70% to about 100% modified nucleotides. In some embodiments, the disclosure relates to compositions comprising a guide sequence and/or a crRNA-tracrRNA duplex, wherein the guide sequence and/or a crRNA-tracrRNA duplex comprises a transcription terminator domain comprising from about 80% to about 100% modified nucleotides. In some embodiments, the disclosure relates to compositions comprising a guide sequence and/or a crRNA-tracrRNA duplex, wherein the guide sequence and/or a crRNA-tracrRNA duplex comprises a transcription terminator domain comprising from about 90% to about 100% modified nucleotides. In some embodiments, the disclosure relates to compositions comprising a guide sequence and/or a crRNA-tracrRNA duplex, wherein the guide sequence and/or a crRNA-tracrRNA duplex comprises a transcription terminator domain comprising from about 95% to about 100% modified nucleotides.

In some embodiments, the disclosure relates to compositions comprising a guide sequence and/or a crRNA-tracrRNA duplex, wherein the guide sequence and/or a crRNA-tracrRNA duplex comprises a nucleotide binding domain (such as a DNA-binding domain) comprising at least one modified nucleotide. In some embodiments, the disclosure relates to compositions comprising a guide sequence and/or a crRNA-tracrRNA duplex, wherein the guide sequence and/or a crRNA-tracrRNA duplex comprises a nucleotide binding domain comprising at least one modified nucleotide at its 2' carbon. In some embodiments, the disclosure relates to compositions comprising a guide sequence and/or a crRNA-tracrRNA duplex, wherein the guide sequence and/or a crRNA-tracrRNA duplex comprises a nucleotide binding domain comprising from about 1% to about 100% modified nucleotides. In some embodiments, the disclosure relates to compositions comprising a guide sequence and/or a crRNA-tracrRNA duplex, wherein the guide sequence and/or a crRNA-tracrRNA duplex comprises a nucleotide binding domain comprising from about 10% to about 100% modified nucleotides. In some embodiments, the disclosure relates to compositions comprising a guide sequence and/or a crRNA-tracrRNA duplex, wherein the guide sequence and/or a crRNA-tracrRNA duplex comprises a nucleotide binding domain comprising from about 20% to about 100% modified nucleotides. In some embodiments, the disclosure relates to compositions comprising a guide sequence and/or a crRNA-tracrRNA duplex, wherein the guide sequence and/or a crRNA-tracrRNA duplex comprises a nucleotide binding domain comprising from about 30% to about 100% modified nucleotides. In some embodiments, the disclosure relates to compositions comprising a guide sequence and/or a crRNA-tracrRNA duplex, wherein the guide sequence and/or a crRNA-tracrRNA duplex comprises a nucleotide binding domain comprising from about 40% to about 100% modified nucleotides. In some embodiments, the disclosure relates to compositions comprising a guide sequence and/or a crRNA-tracrRNA duplex, wherein the guide sequence and/or a crRNA-tracrRNA duplex comprises a nucleotide binding domain comprising from about 50% to about 100% modified nucleotides. In some embodiments, the disclosure relates to compositions comprising a guide sequence and/or a crRNA-tracrRNA duplex, wherein the guide sequence and/or a crRNA-tracrRNA duplex comprises a nucleotide binding domain comprising from about 60% to about 100% modified nucleotides. In some embodiments, the disclosure relates to compositions comprising a guide sequence and/or a crRNA-tracrRNA duplex, wherein the guide sequence and/or a crRNA-tracrRNA duplex comprises a nucleotide binding domain comprising from about 70% to about 100% modified nucleotides. In some embodiments, the disclosure relates to compositions comprising a guide sequence and/or a crRNA-tracrRNA duplex, wherein the guide sequence and/or a crRNA-tracrRNA duplex comprises a nucleotide binding domain comprising from about 80% to about 100% modified nucleotides. In some embodiments, the disclosure relates to compositions comprising a guide sequence and/or a crRNA-tracrRNA duplex, wherein the guide sequence and/or a crRNA-tracrRNA duplex comprises a nucleotide binding domain comprising from about 90% to about 100% modified nucleotides. In some embodiments, the disclosure relates to compositions comprising a guide sequence and/or a crRNA-tracrRNA duplex, wherein the guide sequence and/or a crRNA-tracrRNA duplex comprises a nucleotide binding domain comprising from about 95% to about 100% modified nucleotides. In some embodiments, the disclosure relates to compositions comprising a guide sequence and/or a crRNA-tracrRNA duplex, wherein the guide sequence and/or a crRNA-tracrRNA duplex comprises a nucleotide binding domain comprising from about 35% to about 75% modified nucleotides. In some embodiments, the disclosure relates to compositions comprising a guide sequence and/or a crRNA-tracrRNA duplex, wherein the guide sequence and/or a crRNA-tracrRNA duplex comprises a nucleotide binding domain comprising from about 40% to about 60% modified nucleotides.

In some embodiments, the disclosure relates to compositions comprising a guide sequence comprising, consisting essentially of, or consisting of a sequence that 70%, 75%, 80%, 85%, 90%, 91%, 92%, 93%, 94%, 95%, 96%, 97%, 98%, 99% to the RNA sequence:

(SEQ ID NO: 12)
UUAUCAACUUGAAAAAGUGGCACCGAGUCGGUGCUUUUUUU.

In some embodiments, the disclosure relates to compositions comprising a guide sequence comprising, consisting essentially of, or consisting of a sequence that 70%, 75%, 80%, 85%, 90%, 91%, 92%, 93%, 94%, 95%, 96%, 97%, 98%, 99% to SEQ ID NO:12, wherein the guide sequence comprises at one modified nucleotide. In some embodiments, the disclosure relates to compositions comprising a guide sequence comprising, consisting essentially of, or consisting of a sequence that 70%, 75%, 80%, 85%, 90%, 91%, 92%, 93%, 94%, 95%, 96%, 97%, 98%, 99% to SEQ ID NO:12, wherein the guide sequence comprises at least one modified nucleotide at its 2' carbon. In some embodiments, the disclosure relates to compositions comprising a guide sequence comprising, consisting essentially of, or consisting of a sequence that 70%, 75%, 80%, 85%, 90%, 91%, 92%, 93%, 94%, 95%, 96%, 97%, 98%, 99% to SEQ ID NO:12, wherein the guide sequence comprises from about 1% to about 100% modified nucleotides. In some embodiments, the disclosure relates to a composition comprising a guide sequence comprising, consisting essentially of, or consisting of a sequence that 70%, 75%, 80%, 85%, 90%, 91%, 92%, 93%, 94%, 95%, 96%, 97%, 98%, 99% to SEQ ID NO:12, wherein SEQ ID NO:12 comprises from about 1% to about 100% modified nucleotides. In some embodiments, the disclosure relates to a composition comprising a guide sequence comprising, consisting essentially of, or consisting of a sequence that 70%, 75%, 80%, 85%, 90%, 91%, 92%, 93%, 94%, 95%, 96%, 97%, 98%, 99% to SEQ ID NO:12, wherein SEQ ID NO:12 comprises from about 10% to about 100% modified nucleotides. In some embodiments, the disclosure relates to a composition comprising a guide sequence comprising, consisting essentially of, or consisting of a sequence that 70%, 75%, 80%, 85%, 90%, 91%, 92%, 93%, 94%, 95%, 96%, 97%, 98%, 99% to SEQ ID NO:12, wherein SEQ ID NO:12 comprises from about 20% to about 100% modified nucleotides. In some embodiments, the disclosure relates to a composition comprising a guide sequence comprising, consisting essentially of, or consisting of a sequence that 70%, 75%, 80%, 85%, 90%, 91%, 92%, 93%, 94%, 95%, 96%, 97%, 98%, 99% to SEQ ID NO:12, wherein SEQ ID NO:12 comprises from about 30% to about 100% modified nucleotides. In some embodiments, the disclosure relates to a composition comprising a guide sequence comprising, consisting essentially of, or consisting of a sequence that 70%, 75%, 80%, 85%, 90%, 91%, 92%, 93%, 94%, 95%, 96%, 97%, 98%, 99% to SEQ ID NO:12, wherein SEQ ID NO:12 comprises from about 40% to about 100% modified nucleotides. In some embodiments, the disclosure relates to a composition comprising a guide sequence comprising, consisting essentially of, or consisting of a sequence that 70%, 75%, 80%, 85%, 90%, 91%, 92%, 93%, 94%, 95%, 96%, 97%, 98%, 99% to SEQ ID NO:12, wherein SEQ ID NO:12 comprises from about 50% to about 100% modified nucleotides. In some embodiments, the disclosure relates to a composition comprising a guide sequence comprising, consisting essentially of, or consisting of a sequence that 70%, 75%, 80%, 85%, 90%, 91%, 92%, 93%, 94%, 95%, 96%, 97%, 98%, 99% to SEQ ID NO:12, wherein SEQ ID NO:12 comprises from about 60% to about 100% modified nucleotides. In some embodiments, the disclosure relates to a composition comprising a guide sequence comprising, consisting essentially of, or consisting of a sequence that 70%, 75%, 80%, 85%, 90%, 91%, 92%, 93%, 94%, 95%, 96%, 97%, 98%, 99% to SEQ ID NO:12, wherein SEQ ID NO:12 comprises from about 70% to about 100% modified nucleotides. In some embodiments, the disclosure relates to a composition comprising a guide sequence comprising, consisting essentially of, or consisting of a sequence that 70%, 75%, 80%, 85%, 90%, 91%, 92%, 93%, 94%, 95%, 96%, 97%, 98%, 99% to SEQ ID NO:12, wherein SEQ ID NO:12 comprises from about 80% to about 100% modified nucleotides. In some embodiments, the disclosure relates to a composition comprising a guide sequence comprising, consisting essentially of, or consisting of a sequence that 70%, 75%, 80%, 85%, 90%, 91%, 92%, 93%, 94%, 95%, 96%, 97%, 98%, 99% to SEQ ID NO:12, wherein SEQ ID NO:12 comprises from about 90% to about 100% modified nucleotides. In some embodiments, the disclosure relates to a composition comprising a guide sequence comprising, consisting essentially of, or consisting of a sequence that 70%, 75%, 80%, 85%, 90%, 91%, 92%, 93%, 94%, 95%, 96%, 97%, 98%, 99% to SEQ ID NO:12, wherein SEQ ID NO:12 comprises from about 95% to about 100% modified nucleotides.

In some embodiments, the disclosure relates to compositions comprising a guide sequence comprising, consisting essentially of, or consisting of a sequence that 70%, 75%, 80%, 85%, 90%, 91%, 92%, 93%, 94%, 95%, 96%, 97%, 98%, 99% to the RNA sequence: GGGCGAGGAGCUGUUCACCG (SEQ ID NO: 13). In some embodiments, the disclosure relates to compositions comprising a guide sequence comprising, consisting essentially of, or consisting of a sequence that 70%, 75%, 80%, 85%, 90%, 91%, 92%, 93%, 94%, 95%, 96%, 97%, 98%, 99% to SEQ ID NO:13, wherein the guide sequence comprises at one modified nucleotide. In some embodiments, the disclosure relates to compositions comprising a guide sequence comprising, consisting essentially of, or consisting of a sequence that 70%, 75%, 80%, 85%, 90%, 91%, 92%, 93%, 94%, 95%, 96%, 97%, 98%, 99% to SEQ ID NO:13, wherein the guide sequence comprises at least one modified nucleotide at its 2' carbon. In some embodiments, the disclosure relates to compositions comprising a guide sequence comprising, consisting essentially of, or consisting of a sequence that 70%, 75%, 80%, 85%, 90%, 91%, 92%, 93%, 94%, 95%, 96%, 97%, 98%, 99% to SEQ ID NO:13, wherein the guide sequence comprises from about 1% to about 100% modified nucleotides. In some embodiments, the disclosure relates to a composition comprising a guide sequence comprising, consisting essentially of, or consisting of a sequence that 70%, 75%, 80%, 85%, 90%, 91%, 92%, 93%, 94%, 95%, 96%, 97%, 98%, 99% to SEQ ID NO:13, wherein SEQ ID NO:13 comprises from about 1% to about 100% modified nucleotides. In some embodiments, the disclosure relates to a composition comprising a guide sequence comprising, consisting essentially of, or consisting of a sequence that 70%, 75%, 80%, 85%, 90%, 91%, 92%, 93%, 94%, 95%, 96%, 97%, 98%, 99% to SEQ ID NO:13, wherein SEQ ID NO:13 comprises from about 10% to about 100% modified nucleotides. In some embodiments, the disclosure relates to a composition comprising a guide sequence comprising, consisting essentially of, or consisting of a sequence that 70%, 75%, 80%, 85%, 90%, 91%, 92%, 93%, 94%, 95%, 96%, 97%, 98%, 99% to SEQ ID NO:13, wherein SEQ ID NO:13 comprises from about 20% to about 100% modified nucleotides. In some embodiments, the disclosure relates to a composition comprising a guide sequence comprising, consisting essentially of, or consisting of a sequence that 70%, 75%, 80%, 85%, 90%, 91%, 92%, 93%, 94%, 95%, 96%, 97%, 98%, 99% to SEQ ID NO:13, wherein SEQ ID NO:13 comprises from about 30% to about 100% modified nucleotides. In some embodiments, the disclosure relates to a composition comprising a guide sequence comprising, consisting essentially of, or consisting of a sequence that 70%, 75%, 80%, 85%, 90%, 91%, 92%, 93%, 94%, 95%, 96%, 97%, 98%, 99% to SEQ ID NO:13, wherein SEQ ID NO:13 comprises from about 40% to about 100% modified nucleotides. In some embodiments, the disclosure relates to a composition comprising a guide sequence comprising, consisting essentially of, or consisting of a sequence that 70%, 75%, 80%, 85%, 90%, 91%, 92%, 93%, 94%, 95%, 96%, 97%, 98%, 99% to SEQ ID NO:13, wherein SEQ ID NO:13 comprises from about 50% to about 100% modified nucleotides. In some embodiments, the disclosure relates to a composition comprising a guide sequence comprising, consisting essentially of, or consisting of a sequence that 70%, 75%, 80%, 85%, 90%, 91%, 92%, 93%, 94%, 95%, 96%, 97%, 98%, 99% to SEQ ID NO:13, wherein SEQ ID NO:13 comprises from about 60% to about 100% modified nucleotides. In some embodiments, the disclosure relates to a composition comprising a guide sequence comprising, consisting essentially of, or consisting of a sequence that 70%, 75%, 80%, 85%, 90%, 91%, 92%, 93%, 94%, 95%, 96%, 97%, 98%, 99% to SEQ ID NO:13, wherein SEQ ID NO:13 comprises from about 70% to about 100% modified nucleotides. In some embodiments, the disclosure relates to a composition comprising a guide sequence comprising, consisting essentially of, or consisting of a sequence that 70%, 75%, 80%, 85%, 90%, 91%, 92%, 93%, 94%, 95%, 96%, 97%, 98%, 99% to SEQ ID NO:13, wherein SEQ ID NO:13 comprises from about 80% to about 100% modified nucleotides. In some embodiments, the disclosure relates to a composition comprising a guide sequence comprising, consisting essentially of, or consisting of a sequence that 70%, 75%, 80%, 85%, 90%, 91%, 92%, 93%, 94%, 95%, 96%, 97%, 98%, 99% to SEQ ID NO:13, wherein SEQ ID NO:13 comprises from about 90% to about 100% modified nucleotides. In some embodiments, the disclosure relates to a composition comprising a guide sequence comprising, consisting essentially of, or consisting of a sequence that 70%, 75%, 80%, 85%, 90%, 91%, 92%, 93%, 94%, 95%, 96%, 97%, 98%, 99% to SEQ ID NO:13, wherein SEQ ID NO:13 comprises from about 95% to about 100% modified nucleotides.

In some embodiments, the disclosure relates to a composition comprising a guide sequence comprising, consisting essentially of, or consisting of a sequence that 70%, 75%, 80%, 85%, 90%, 91%, 92%, 93%, 94%, 95%, 96%, 97%, 98%, 99% to any nucleic acid or amino acid sequence disclosed herein.

In some embodiments, the disclosure relates to a compositions comprising a guide sequence comprising, consisting essentially of, or consisting of a sequence that is 70%, 75%, 80%, 85%, 90%, 91%, 92%, 93%, 94%, 95%, 96%, 97%, 98%, 99% or 100% homologous to any one or combination of SEQ ID NO: 1, SEQ ID NO: 2, SEQ ID NO: 3, SEQ ID NO: 4. In some embodiments, the disclosure relates to a compositions comprising a guide sequence comprising, consisting essentially of, or consisting of a sequence that is 70%, 75%, 80%, 85%, 90%, 91%, 92%, 93%, 94%, 95%, 96%, 97%, 98%, 99% or 100% homologous to SEQ ID NO: 1. In some embodiments, the disclosure relates to a compositions comprising a guide sequence comprising, consisting essentially of, or consisting of a sequence that is 70%, 75%, 80%, 85%, 90%, 91%, 92%, 93%, 94%, 95%, 96%, 97%, 98%, 99% or 100% homologous to SEQ ID NO: 2. In some embodiments, the disclosure relates to a compositions comprising a guide sequence comprising, consisting essentially of, or consisting of a sequence that is 70%, 75%, 80%, 85%, 90%, 91%, 92%, 93%, 94%, 95%, 96%, 97%, 98%, 99% or 100% homologous to SEQ ID NO: 3. In some embodiments, the disclosure relates to a compositions comprising a guide sequence comprising, consisting essentially of, or consisting of a sequence that is 70%, 75%, 80%, 85%, 90%, 91%, 92%, 93%, 94%, 95%, 96%, 97%, 98%, 99% or 100% homologous to SEQ ID NO: 4. In some embodiments, the disclosure relates to a compositions comprising a guide sequence comprising, consisting essentially of, or consisting of a sequence that is 70%, 75%, 80%, 85%, 90%, 91%, 92%, 93%, 94%, 95%, 96%, 97%, 98%, 99% or 100% homologous to SEQ ID NO: 5. In some embodiments, the disclosure relates to a compositions comprising a guide sequence comprising, consisting essentially of, or consisting of a sequence that is 70%, 75%, 80%, 85%, 90%, 91%, 92%, 93%, 94%, 95%, 96%, 97%, 98%, 99% or 100% homologous to SEQ ID NO: 6. In some embodiments, the disclosure relates to a compositions comprising a guide sequence comprising, consisting essentially of, or consisting of a sequence that is 70%, 75%, 80%, 85%, 90%, 91%, 92%, 93%, 94%, 95%, 96%, 97%, 98%, 99% or 100% homologous to SEQ ID NO: 7. In some embodiments, the disclosure relates to a compositions comprising a guide sequence comprising, consisting essentially of, or consisting of a sequence that is 70%, 75%, 80%, 85%, 90%, 91%, 92%, 93%, 94%, 95%, 96%, 97%, 98%, 99% or 100% homologous to SEQ ID NO: 8. In some embodiments, the disclosure relates to a compositions comprising a guide sequence comprising, consisting essentially of, or consisting of a sequence that is 70%, 75%, 80%, 85%, 90%, 91%, 92%, 93%, 94%, 95%, 96%, 97%, 98%, 99% or 100% homologous to SEQ ID NO: 9. In some embodiments, the disclosure relates to a compositions comprising a guide sequence comprising, consisting essentially of, or consisting of a sequence that is 70%, 75%, 80%, 85%, 90%, 91%, 92%, 93%, 94%, 95%, 96%, 97%, 98%, 99% or 100% homologous to SEQ ID NO: 10.

In some embodiments, the disclosure relates to a compositions comprising a guide sequence comprising, consisting essentially of, or consisting of a sequence that is 70%, 75%, 80%, 85%, 90%, 91%, 92%, 93%, 94%, 95%, 96%, 97%, 98%, 99% or 100% homologous to SEQ ID NO:43. In some embodiments, the disclosure relates to a compositions comprising a guide sequence comprising, consisting essentially of, or consisting of a sequence that is 70%, 75%, 80%, 85%, 90%, 91%, 92%, 93%, 94%, 95%, 96%, 97%, 98%, 99% or 100% homologous to SEQ ID NO:44. In some embodiments, the disclosure relates to a compositions comprising a guide sequence comprising, consisting essentially of, or consisting of a sequence that is 70%, 75%, 80%, 85%, 90%, 91%, 92%, 93%, 94%, 95%, 96%, 97%, 98%, 99% or 100% homologous to SEQ ID NO:45. In some embodiments, the disclosure relates to a compositions comprising a guide sequence comprising, consisting essentially of, or consisting of a sequence that is 70%, 75%, 80%, 85%, 90%, 91%, 92%, 93%, 94%, 95%, 96%, 97%, 98%, 99% or 100% homologous to SEQ ID NO:46. In some embodiments, the disclosure relates to a compositions comprising a guide sequence comprising, consisting essentially of, or consisting of a sequence that is 70%, 75%, 80%, 85%, 90%, 91%, 92%, 93%, 94%, 95%, 96%, 97%, 98%, 99% or 100% homologous to SEQ ID NO:47. In some embodiments, the disclosure relates to a compositions comprising a guide sequence comprising, consisting essentially of, or consisting of a sequence that is 70%, 75%, 80%, 85%, 90%, 91%, 92%, 93%, 94%, 95%, 96%, 97%, 98%, 99% or 100% homologous to SEQ ID NO:48. In some embodiments, the disclosure relates to a compositions comprising a guide sequence comprising, consisting essentially of, or consisting of a sequence that is 70%, 75%, 80%, 85%, 90%, 91%, 92%, 93%, 94%, 95%, 96%, 97%, 98%, 99% or 100% homologous to SEQ ID NO:49. In some embodiments, the disclosure relates to a compositions comprising a guide sequence comprising, consisting essentially of, or consisting of a sequence that is 70%, 75%, 80%, 85%, 90%, 91%, 92%, 93%, 94%, 95%, 96%, 97%, 98%, 99% or 100% homologous to SEQ ID NO:50. In some embodiments, the disclosure relates to a compositions comprising a guide sequence comprising, consisting essentially of, or consisting of a sequence that is 70%, 75%, 80%, 85%, 90%, 91%, 92%, 93%, 94%, 95%, 96%, 97%, 98%, 99% or 100% homologous to SEQ ID NO:51. In some embodiments, the disclosure relates to a compositions comprising a guide sequence comprising, consisting essentially of, or consisting of a sequence that is 70%, 75%, 80%, 85%, 90%, 91%, 92%, 93%, 94%, 95%, 96%, 97%, 98%, 99% or 100% homologous to SEQ ID NO:52. In some embodiments, the disclosure relates to a compositions comprising a guide sequence comprising, consisting essentially of, or consisting of a sequence that is 70%, 75%, 80%, 85%, 90%, 91%, 92%, 93%, 94%, 95%, 96%, 97%, 98%, 99% or 100% homologous to SEQ ID NO:53. In some embodiments, the disclosure relates to a compositions comprising a guide sequence comprising, consisting essentially of, or consisting of a sequence that is 70%, 75%, 80%, 85%, 90%, 91%, 92%, 93%, 94%, 95%, 96%, 97%, 98%, 99% or 100% homologous to SEQ ID NO:54. In some embodiments, the disclosure relates to a compositions comprising a guide sequence comprising, consisting essentially of, or consisting of a sequence that is 70%, 75%, 80%, 85%, 90%, 91%, 92%, 93%, 94%, 95%, 96%, 97%, 98%, 99% or 100% homologous to SEQ ID NO:55. In some embodiments, the disclosure relates to a compositions comprising a guide sequence comprising, consisting essentially of, or consisting of a sequence that is 70%, 75%, 80%, 85%, 90%, 91%, 92%, 93%, 94%, 95%, 96%, 97%, 98%, 99% or 100% homologous to SEQ ID NO:56. In some embodiments, the disclosure relates to a compositions comprising a guide sequence comprising, consisting essentially of, or consisting of a sequence that is 70%, 75%, 80%, 85%, 90%, 91%, 92%, 93%, 94%, 95%, 96%, 97%, 98%, 99% or 100% homologous to SEQ ID NO:57. In some embodiments, the disclosure relates to a compositions comprising a guide sequence comprising, consisting essentially of, or consisting of a sequence that is 70%, 75%, 80%, 85%, 90%, 91%, 92%, 93%, 94%, 95%, 96%, 97%, 98%, 99% or 100% homologous to SEQ ID NO:58. In some embodiments, the disclosure relates to a compositions comprising a guide sequence comprising, consisting essentially of, or consisting of a sequence that is 70%, 75%, 80%, 85%, 90%, 91%, 92%, 93%, 94%, 95%, 96%, 97%, 98%, 99% or 100% homologous to SEQ ID NO:59. In some embodiments, the disclosure relates to a compositions comprising a guide sequence comprising, consisting essentially of, or consisting of a sequence that is 70%, 75%, 80%, 85%, 90%, 91%, 92%, 93%, 94%, 95%, 96%, 97%, 98%, 99% or 100% homologous to SEQ ID NO:60. In some embodiments, the disclosure relates to a compositions comprising a guide sequence comprising, consisting essentially of, or consisting of a sequence that is 70%, 75%, 80%, 85%, 90%, 91%, 92%, 93%, 94%, 95%, 96%, 97%, 98%, 99% or 100% homologous to SEQ ID NO:61. In some embodiments, the disclosure relates to a compositions comprising a guide sequence comprising, consisting essentially of, or consisting of a sequence that is 70%, 75%, 80%, 85%, 90%, 91%, 92%, 93%, 94%, 95%, 96%, 97%, 98%, 99% or 100% homologous to SEQ ID NO:62. In some embodiments, the disclosure relates to a compositions comprising a guide sequence comprising, consisting essentially of, or consisting of a sequence that is 70%, 75%, 80%, 85%, 90%, 91%, 92%, 93%, 94%, 95%, 96%, 97%, 98%, 99% or 100% homologous to SEQ ID NO:63. In some embodiments, the disclosure relates to a compositions comprising a guide sequence comprising, consisting essentially of, or consisting of a sequence that is 70%, 75%, 80%, 85%, 90%, 91%, 92%, 93%, 94%, 95%, 96%, 97%, 98%, 99% or 100% homologous to SEQ ID NO:64. In some embodiments, the disclosure relates to a compositions comprising a guide sequence comprising, consisting essentially of, or consisting of a sequence that is 70%, 75%, 80%, 85%, 90%, 91%, 92%, 93%, 94%, 95%, 96%, 97%, 98%, 99% or 100% homologous to SEQ ID NO:65. In some embodiments, the disclosure relates to a compositions comprising a guide sequence comprising, consisting essentially of, or consisting of a sequence that is 70%, 75%, 80%, 85%, 90%, 91%, 92%, 93%, 94%, 95%, 96%, 97%, 98%, 99% or 100% homologous to SEQ ID NO:66. In some embodiments, the disclosure relates to a compositions comprising a guide sequence comprising, consisting essentially of, or consisting of a sequence that is 70%, 75%, 80%, 85%, 90%, 91%, 92%, 93%, 94%, 95%, 96%, 97%, 98%, 99% or 100% homologous to SEQ ID NO:67. In some embodiments, the disclosure relates to a compositions comprising a guide sequence comprising, consisting essentially of, or consisting of a sequence that is 70%, 75%, 80%, 85%, 90%, 91%, 92%, 93%, 94%, 95%, 96%, 97%, 98%, 99% or 100% homologous to SEQ ID NO:68. In some embodiments, the disclosure relates to a compositions comprising a guide sequence comprising, consisting essentially of, or consisting of a sequence that is 70%, 75%, 80%, 85%, 90%, 91%, 92%, 93%, 94%, 95%, 96%, 97%, 98%, 99% or 100% homologous to SEQ ID NO:69. In some embodiments, the disclosure relates to a compositions comprising a guide sequence comprising, consisting essentially of, or consisting of a sequence that is 70%, 75%, 80%, 85%, 90%, 91%, 92%, 93%, 94%, 95%, 96%, 97%, 98%, 99% or 100% homologous to SEQ ID NO:70. In some embodiments, the disclosure relates to a compositions comprising a guide sequence comprising, consisting essentially of, or consisting of a sequence that is 70%, 75%, 80%, 85%, 90%, 91%, 92%, 93%, 94%, 95%, 96%, 97%, 98%, 99% or 100% homologous to SEQ ID NO:71. In some embodiments, the disclosure relates to a compositions comprising a guide sequence comprising, consisting essentially of, or consisting of a sequence that is 70%, 75%, 80%, 85%, 90%, 91%, 92%, 93%, 94%, 95%, 96%, 97%, 98%, 99% or 100% homologous to SEQ ID NO:72. In some embodiments, the disclosure relates to a compositions comprising a guide sequence comprising, consisting essentially of, or consisting of a sequence that is 70%, 75%, 80%, 85%, 90%, 91%, 92%, 93%, 94%, 95%, 96%, 97%, 98%, 99% or 100% homologous to SEQ ID NO:73. In some embodiments, the disclosure relates to a compositions comprising a guide sequence comprising, consisting essentially of, or consisting of a sequence that is 70%, 75%, 80%, 85%, 90%, 91%, 92%, 93%, 94%, 95%, 96%, 97%, 98%, 99% or 100% homologous to SEQ ID NO:74.

In some embodiments, the disclosure relates to a compositions comprising a guide sequence comprising a Cas-binding domain comprising, consisting essentially of, or consisting of a sequence that is 70%, 75%, 80%, 85%, 90%, 91%, 92%, 93%, 94%, 95%, 96%, 97%, 98%, 99%, or 100% homologous to SEQ ID NO: 11. In some embodiments, the Cas-binding domain comprises a sequence 70%, 75%, 80%, 85%, 90%, 91%, 92%, 93%, 94%, 95%, 96%, 97%, 98%, or 99% homologous to SEQ ID NO:11 and comprises between about 42 nucleotides to about 150 nucleotides in length and comprises at least one or a combination of conserved nucleotides disclosed in Table 3 whereby the position number of 1 corresponds to position 1 of SEQ ID NO:11, and wherein, if the Cas-binding domain is more than 42 nucleotides long, position 43 an onward is contiguous with position 42 of SEQ ID NO:11 (such as SEQ ID NO:11-$N_{(1\text{-}110\ nt)}$), where $N_{(1\text{-}110\ nt)}$ can be any modified or unmodified nucleotide (A, U, C, G) in length from 1-110 or more nucleotides. In some embodiments, the $N_{(1\text{-}110\ nt)}$ can be any modified or unmodified nucleotide (A, U, C, G) in length capable of forming a modified or unmodified loop region as set forth in "Genome-scale transcriptional activation by an engineered CRISPR-Cas9 complex" *Nature* (Zhang, et al.); 517, 583-588 (29 Jan. 2015), which is herein incorporated by reference in its entirety. The additional nucleotides in the Cas-binding domain may bind other RNAs or proteins as desired while conserving cas-binding to the sgRNA in the Cas-binding domain.

In some embodiments, the disclosure relates to a compositions comprising a guide sequence comprising a Cas-binding domain comprising, consisting essentially of, or consisting of SEQ ID NO:11 or a domain sharing a disclosed percent homology with SEQ ID NO:11 optionally comprising from about 5, 10, 20, 30, 40, 50, 60, 70, 80, 90, 100, 110, 120, 130, 140, 150, 160, 170, 180, 190 or more nucleotides on the 3' end of SEQ ID NO:11. In some embodiments, the disclosure relates to a compositions comprising a guide sequence comprising a DNA-binding domain or nucleotide binding domain comprising, consisting essentially of, or consisting of GGGCGAGGAGCUGUUCACCG or a domain sharing a disclosed percent homology with GGGCGAGGAGCUGUUCACCG optionally comprising from 1, 2, 3, 4, 5, or more nucleotides on the 3' end of GGGCGAGGAGCUGUUCACCG. In some embodiments, the In some embodiments, the disclosure relates to a compositions comprising a guide sequence comprising a DNA-binding domain or nucleotide binding domain comprising, consisting essentially of, or consisting of GGCGAGGAGCUGUUCACCG, GCGAGGAGCUGUUCACCG CGAGGAGCUGUUCACCG, or GAGGAGCUGUUCACCG or any functional fragment thereof capable of binding a nucleotide sequence encoding a functional fragment of GFP. In some embodiments, the In some embodiments, the disclosure relates to a compositions comprising a guide sequence comprising a DNA-binding domain or nucleotide binding domain comprising, consisting essentially of, or consisting of the sequences set forth in Table 4 or disclosed herein.

In some embodiments, the disclosure relates to a compositions comprising a guide sequence comprising a Cas-binding domain comprising, consisting essentially of, or consisting of a sequence that is 70%, 75%, 80%, 85%, 90%, 91%, 92%, 93%, 94%, 95%, 96%, 97%, 98%, or 99%, homologous to SEQ ID NO:11 and comprising at least one or combination of conserved nucleotides identified in Table 3.

TABLE 3 sgRNA conserved nucleotides. sgRNA comprising one or a combination of the following nucleotides of the Cas9 binding domain and/or the transcription terminator region maintain or enhance Cas9 binding. sgRNA has been modified at 2O' position in one or a combination of the following nucleotides has reduced Cas9 binding.

| Cas9 binding domain # Based upon position of SEQ ID NO: 11 | nucleotide |
|---|---|
| 2 | U |
| 3 | U |
| 4 | U |
| 23 | G |
| 24 | U |
| 25 | U |
| 27 | A |
| 31 | A |
| 38 | G |
| 42 | G |
| **Terminator region # (based upon position number immediately downstream from the last nucleotide of the Cas-binding domain)** | **nucleotide** |
| 1 | U |
| 2 | U |
| 3 | A |
| 6 | A |

In some embodiments, the composition comprises a plurality of domains from a 5' to 3' orientation: a DNA-binding domain, a Cas-protein binding domain, and a transcription terminator domain, wherein the DNA-binding domain comprises from about 1% to about 99% modified ribonucleotides and/or the transcription terminator domain comprises from about 1% to about 99% modified ribonucleotides; and the Cas-protein binding domain comprises from about 42 to about 150 nucleotides comprising SEQ ID NO:11 or a nucleotide sequence in which position 2 of SEQ ID NO:11 is a uracil. In some embodiments, the composition comprises a plurality of domains from a 5' to 3' orientation: a DNA-binding domain, a Cas-protein binding domain, and a transcription terminator domain, wherein the DNA-binding domain comprises from about 1% to about 99% modified ribonucleotides and/or the transcription terminator domain comprises from about 1% to about 99% modified ribonucleotides; and the Cas-protein binding domain comprises from about 42 to about 150 nucleotides comprising SEQ ID NO:11 or a nucleotide sequence in which position 3 of SEQ ID NO:11 is a uracil. In some embodiments, the composition comprises a plurality of domains from a 5' to 3' orientation: a DNA-binding domain, a Cas-protein binding domain, and a transcription terminator domain, wherein the DNA-binding domain comprises from about 1% to about 99% modified ribonucleotides and/or the transcription terminator domain comprises from about 1% to about 99% modified ribonucleotides; and the Cas-protein binding domain comprises from about 42 to about 150 nucleotides comprising SEQ ID NO:11 or a nucleotide sequence in which position 4 of SEQ ID NO:11 is a uracil. In some embodiments, the composition comprises a plurality of domains from a 5' to 3' orientation: a DNA-binding domain, a Cas-protein binding domain, and a transcription terminator domain, wherein the DNA-binding domain comprises from about 1% to about 99% modified ribonucleotides and/or the transcription terminator domain comprises from about 1% to about 99% modified ribonucleotides; and the Cas-protein binding domain comprises from about 42 to about 150 nucleotides comprising SEQ ID NO:11 or a nucleotide sequence in which position 23 of SEQ ID NO:11 is a guanine. In some embodiments, the composition comprises a plurality of domains from a 5' to 3' orientation: a DNA-binding domain, a Cas-protein binding domain, and a transcription terminator domain, wherein the DNA-binding domain comprises from about 1% to about 99% modified ribonucleotides and/or the transcription terminator domain comprises from about 1% to about 99% modified ribonucleotides; and the Cas-protein binding domain comprises from about 42 to about 150 nucleotides comprising SEQ ID NO:11 or a nucleotide sequence in which position 24 of SEQ ID NO:11 is a uracil. In some embodiments, the composition comprises a plurality of domains from a 5' to 3' orientation: a DNA-binding domain, a Cas-protein binding domain, and a transcription terminator domain, wherein the DNA-binding domain comprises from about 1% to about 99% modified ribonucleotides and/or the transcription terminator domain comprises from about 1% to about 99% modified ribonucleotides; and the Cas-protein binding domain comprises from about 42 to about 150 nucleotides comprising SEQ ID NO:11 or a nucleotide sequence in which position 25 of SEQ ID NO:11 is a uracil. In some embodiments, the composition comprises a plurality of domains from a 5' to 3' orientation: a DNA-binding domain, a Cas-protein binding domain, and a transcription terminator domain, wherein the DNA-binding domain comprises from about 1% to about 99% modified ribonucleotides and/or the transcription terminator domain comprises from about 1% to about 99% modified ribonucleotides; and the Cas-protein binding domain comprises from about 42 to about 150 nucleotides comprising SEQ ID NO:11 or a nucleotide sequence in which position 27 of SEQ ID NO:11 is an adenine. In some embodiments, the composition comprises a plurality of domains from a 5' to 3' orientation: a DNA-binding domain, a Cas-protein binding domain, and a transcription terminator domain, wherein the DNA-binding domain comprises from about 1% to about 99% modified ribonucleotides and/or the transcription terminator domain comprises from about 1% to about 99% modified ribonucleotides or deoxyribonucleotides; and the Cas-protein binding domain comprises from about 42 to about 150 nucleotides comprising SEQ ID NO:11 or a nucleotide sequence in which position 31 of SEQ ID NO:11 is an adenine. In some embodiments, the composition comprises a plurality of domains from a 5' to 3' orientation: a DNA-binding domain, a Cas-protein binding domain, and a transcription terminator domain, wherein the DNA-binding domain comprises from about 1% to about 99% modified ribonucleotides and/or the transcription terminator domain comprises from about 1% to about 99% modified ribonucleotides; and the Cas-protein binding domain comprises from about 42 to about 150 nucleotides comprising SEQ ID NO:11 or a nucleotide sequence in which position 38 of SEQ ID NO:11 is a guanine. In some embodiments, the composition comprises a plurality of domains from a 5' to 3' orientation: a DNA-binding domain, a Cas-protein binding domain, and a transcription terminator domain, wherein the DNA-binding domain comprises from about 1% to about 99% ribonucleotides or deoxyribonucleotides and/or the transcription terminator domain comprises from about 1% to about 99% modified ribonucleotides or deoxyribonucleotides; and the Cas-protein binding domain comprises from about 42 to about 150 nucleotides comprising SEQ ID NO:11 or a nucleotide sequence in which position 42 of SEQ ID NO:11 is a guanine.

In some embodiments, the composition comprises any sgRNA or tracr/mate sequences disclosed herein, wherein the sgRNA or tracr/mate sequence comprises a plurality of contiguous domains from a 5' to 3' orientation: a DNA-binding domain, a Cas-protein binding domain, and a transcription terminator domain; wherein the DNA binding comprises a sequence at least 60, 70, 80, 90 or 100% complementary to a target sequence and is from about 15 to about 30 nucleotides long; wherein the Cas-protein binding domain comprises a nucleotide sequence that has 75, 80, 85, 90, 95, 96, 97, 98, 99, or 100% sequence homology to SEQ ID NO:11 and is from about 42 to about 200 nucleotides long; and wherein the transcription terminator domain comprises a sequence at least 60, 70, 80, 90 or 100% complementary to SEQ ID NO:12 and is from about 35 to about 200 nucleotides long. In some embodiments, the composition comprises any sgRNA disclosed herein, wherein the sgRNA comprises a plurality of contiguous domains from a 5' to 3' orientation: a DNA-binding domain, a Cas-protein binding domain, and a transcription terminator domain; wherein the DNA binding comprises a sequence at least 60, 70, 80, 90 or 100% complementary to a target sequence and is from about 25 to about 30 nucleotides long; wherein the Cas-protein binding domain comprises a nucleotide sequence that has 75, 80, 85, 90, 95, 96, 97, 98, 99, or 100% sequence homology to SEQ ID NO:11 and is from about 42 to about 200 nucleotides long; and wherein the transcription terminator domain comprises a sequence at least 60, 70, 80, 90 or 100% complementary to SEQ ID NO:12 and is from about 35 to about 200 nucleotides long.

In some embodiments, the composition comprises a plurality of domains from a 5' to 3' orientation: a DNA-binding domain, a Cas-protein binding domain, and a transcription terminator domain, wherein the DNA-binding domain comprises from about 1% to about 99% modified ribonucleotides and/or the Cas-protein binding domain comprises from about 1% to about 99% modified ribonucleotides; and the transcription terminator domain comprises from about 35 to about 200 or more nucleotides comprising SEQ ID NO:12 or a nucleotide sequence in which position 1 of SEQ ID NO:12 is a uracil. In some embodiments, the composition comprises a plurality of domains from a 5' to 3' orientation: a DNA-binding domain, a Cas-protein binding domain, and a transcription terminator domain, wherein the DNA-binding domain comprises from about 1% to about 99% modified ribonucleotides and/or the Cas-protein binding domain comprises from about 1% to about 99% modified ribonucleotides; and the transcription terminator domain comprises from about 35 to about 200 or more nucleotides comprising SEQ ID NO:12 or a nucleotide sequence in which position 2 of SEQ ID NO:12 is a uracil. In some embodiments, the composition comprises a plurality of domains from a 5' to 3' orientation: a DNA-binding domain, a Cas-protein binding domain, and a transcription terminator domain, wherein the DNA-binding domain comprises from about 1% to about 99% modified ribonucleotides and/or the Cas-protein binding domain comprises from about 1% to about 99% modified ribonucleotides; and the transcription terminator domain comprises from about 35 to about 200 or more nucleotides comprising SEQ ID NO:12 or a nucleotide sequence in which position 3 of SEQ ID NO:12 is an adenine. In some embodiments, the composition comprises a plurality of domains from a 5' to 3' orientation: a DNA-binding domain, a Cas-protein binding domain, and a transcription terminator domain, wherein the DNA-binding domain comprises from about 1% to about 99% modified ribonucleotides and/or the Cas-protein binding domain comprises from about 1% to about 99% modified ribonucleotides; and the transcription terminator domain comprises from about 35 to about 200 or more nucleotides comprising SEQ ID NO:12 or a nucleotide sequence in which position 6 of SEQ ID NO:12 is an adenine.

In some embodiments, the disclosure relates to a compositions comprising a guide sequence comprising, consisting essentially of, or consisting of a sequence that is 70%, 75%, 80%, 85%, 90%, 91%, 92%, 93%, 94%, 95%, 96%, 97%, 98%, 99% homologous to any one or combination of sequences disclosed herein, wherein the guide sequence comprises a fragment or variant of the sequences disclosed herein but possesses the same or substantially the same function as the full-length sequence disclosed herein. For example, in the case of a fragment or variant of a guide RNA disclosed herein that comprises modified nucleotides in the DNA-binding domain, in some embodiments, the variant or fragment would be functional insomuch as it would exceed or retain some or all of its capacity to bind DNA at that domain as compared to the full-length sequence.

In some embodiments, the DNA-binding domain is free of modifications in any one of its first 2, 3, 4, 5 or more nucleotides on its 5' end. In some embodiments the transcription terminator domain is free of modifications on any of its last 2, 3, 4, 5 or more nucleotides on its 3' end.

The disclosure relates to a nucleic acid sequence comprising at least one or a combination of domains from a 5' to 3' orientation: a DNA-binding domain, a Cas protein-binding domain, and a transcription terminator domain, wherein the DNA-binding domain comprises from about 1% to about 99% modified nucleotides and/or the transcription terminator domain comprises from about 1% to about 99% modified nucleotides. The disclosure relates to a nucleic acid sequence consisting of a series of contiguous domains from a 5' to 3' orientation: a DNA-binding domain, a Cas protein-binding domain, and a transcription terminator domain, wherein the DNA-binding domain comprises from about 1% to about 99% modified nucleotides and/or the transcription terminator domain comprises from about 1% to about 99% modified nucleotides; and wherein the Cas protein-binding domain comprises from about 1% to about 99% modified nucleotides comprising one or a combination of the nucleotides in Table 3.

Any of the disclosed nucleic acid sequences may comprise any one or combination or set of modifications disclosed herein. In some embodiments, the guide nucleic acid, crRNA and/or tracer comprises RNA, DNA, or combinations of both RNA and DNA. In some embodiments, the either as a part of a modified nucleobase or a modified sugar.

Modifications to nucleotides are known in the art but include any of the disclosed modifications disclosed in the present application. Oligonucleotides particularly suited for the practice of one or more embodiments of the present disclosure comprise 2'-sugar modified oligonucleotides wherein one or more of the 2'-deoxy ribofuranosyl moieties of the nucleoside is modified with a halo, alkoxy, aminoalkoxy, alkyl, azido, or amino group. For example, the substitutions which may be independently selected from F, CN, $CF_3$, $OCF_3$, OCN, O-alkyl, 5-alkyl, SMe, $SO_2Me$, $ONO_2$, $NO_2$, $NH_3$, $NH_2$, NH-alkyl, $OCH_3{=}CH_2$ and OCCH. In each of these, alkyl is a straight or branched chain of $C_1$ to $C_{20}$, having unsaturation within the carbon chain. A preferred alkyl group is $C_1$-$C_9$ alkyl. A further preferred alkyl group is $C_5$-$C_{20}$ alkyl.

A first group of substituents include 2'-deoxy-2'-fluoro substituents. A further preferred group of substituents include $C_1$ through $C_{20}$ alkoxyl substituents. An additional group of substituents include cyano, fluoromethyl, thioalkoxyl, fluoroalkoxyl, alkylsulfinyl, alkylsulfonyl, allyloxy or alkeneoxy substituents.

In further embodiments of the present disclosure, the individual nucleotides of the oligonucleotides of the disclosure are connected via phosphorus linkages. Phosphorus linkages include phosphodiester, phosphorothioate and phosphorodithioate linkages. In one preferred embodiment of this disclosure, nuclease resistance is conferred on the oligonucleotides by utilizing phosphorothioate internucleoside linkages.

In further embodiments of the disclosure, nucleosides can be joined via linkages that substitute for the internucleoside phosphate linkage. Macromolecules of this type have been identified as oligonucleosides. The term "oligonucleoside" thus refers to a plurality of nucleoside units joined by non-phosphorus linkages. In such oligonucleosides the linkages include an O—$CH_2$—$CH_2$—O— linkage (i.e., an ethylene glycol linkage) as well as other novel linkages disclosed in U.S. Pat. No. 5,223,618, issued Jun. 29, 1993, U.S. Pat. No. 5,378,825, issued Jan. 3, 1995 and U.S. patent application Ser. No. 08/395,168, filed Feb. 27, 1995. Other modifications can be made to the sugar, to the base, or to the phosphate group of the nucleotide. Representative modifications are disclosed in International Publication Numbers WO 91/10671, published Jul. 25, 1991, WO 92/02258, published Feb. 20, 1992, WO 92/03568, published Mar. 5, 1992, and U.S. Pat. No. 5,138,045, issued Aug. 11, 1992, all of which are herein incorporated by reference in their entireties.

In some embodiments, a guide sequence is selected to reduce the degree of secondary structure within the guide sequence. Secondary structure may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g. A. R. Gruber et al., 2008, Cell 106(1): 23-24; and PA Carr and GM Church, 2009, Nature Biotechnology 27(12): 1151-62). Further algorithms may be found in U.S. application Ser. No. 61/836,080 filed Jun. 17, 2013; incorporated herein by reference.

In some embodiments, the disclosure relates to modifications of the guide sequence that include positions of the sequences disclosed herein replaced by modified nucleotides or guide sequences that include additions of long non-coding RNAs (lncRNAs).

lncRNA has attracted much attention due to their large number and biological significance. Many lncRNAs have been identified as mapping to regulatory elements including gene promoters and enhancers, ultraconserved regions and intergenic regions of protein-coding genes. Yet, the biological function and molecular mechanisms of lncRNA in human diseases in Data from the literature suggest that lncRNA, often via interaction with proteins, functions in specific genomic loci or use their own transcription loci for regulatory activity. In some embodiments, the guide sequence of the disclosure comprises a length of contiguous lncRNA from about 150 nucleotides to about 250, 300, 350, 400, 450, or 500 nucleotides. In some embodiments, the guide sequence comprises a nucleotide domain that is at least 70%, 75%, 80%, 85%, 90%, 95%, 96%, 97%, 98%, 99% complementary to a known lncRNA sequence. The guide sequence may comprise an RNA binding domain that comprises such a complementary sequence or may comprise one or a plurality of RNA binding domains that comprises a at least 70%, 75%, 80%, 85%, 90%, 95%, 96%, 97%, 98%, 99% complementary to a known lncRNA sequence.

In another embodiment, the disclosure provides a cell or a vector comprising one of the sgRNAs of the disclosure or functional fragments thereof. The cell may be an animal cell or a plant cell. In some embodiments, the cell is a mammalian cell, such as a human cell.

In one aspect, the disclosure provides a vector system comprising one or more vectors. In some embodiments, the system comprises: (a) a synthetic guide sequence comprising at least one of the nucleic acid sequences disclosed herein, wherein the guide sequence directs sequence-specific binding of a CRISPR complex to a target sequence in a eukaryotic cell, wherein the CRISPR complex comprises a CRISPR enzyme complexed with (1) the guide sequence that is hybridized to the target sequence, and, optionally (2) a tracr mate sequence that is hybridized to a tracr sequence; and (b) a first regulatory element operably linked to an enzyme-coding sequence encoding said CRISPR enzyme comprising a nuclear localization sequence; wherein expressible components (the enzyme-coding sequence and the tracr sequences) are located on the same or different vectors of the system. In some embodiments, component (a) further comprises the tracr sequence downstream of the tracr mate sequence under the control of a tracr regulatory element. In some embodiments, component (a) further comprises one or more additional guide sequences operably linked to the tracr regulatory element, wherein when expressed, each the additional guide sequences direct sequence specific binding of a CRISPR complex to a different target sequence in a eukaryotic cell. In some embodiments, the system comprises the tracr sequence under the control of its own, second regulatory element, such as a polymerase III promoter. In some embodiments, the tracr sequence exhibits at least 50%, 60%, 70%, 80%, 90%, 95%, or 99% of sequence complementarity along the length of the tracr mate sequence when optimally aligned. Determining optimal alignment is within the purview of one of skill in the art. For example, there are publically and commercially available alignment algorithms and programs such as, but not limited to, ClustalW, Smith-Waterman in matlab, Bowtie, Geneious, Biopython and SeqMan. In some embodiments, the CRISPR complex comprises one or more nuclear localization sequences of sufficient strength to drive accumulation of said CRISPR complex in a detectable amount in the nucleus of a eukaryotic cell. Without wishing to be bound by theory, it is believed that a nuclear localization sequence is not necessary for CRISPR complex activity in eukaryotes, but that including such sequences enhances activity of the system, especially as to targeting nucleic acid molecules in the nucleus. In some embodiments, the CRISPR enzyme is a type II CRISPR system enzyme. In some embodiments, the CRISPR enzyme is a Cas9 enzyme. In some embodiments, the Cas9 enzyme is *S. pneumoniae, S. pyogenes*, or *S. thermophilus* Cas9, and may include mutated Cas9 derived from these organisms. The enzyme may be a Cas9 homolog or ortholog. In some embodiments, the CRISPR enzyme is codon-optimized for expression in a eukaryotic cell. In some embodiments, the CRISPR enzyme directs cleavage of one or two strands at the location of the target sequence. In some embodiments, the CRISPR enzyme lacks DNA strand cleavage activity. In some embodiments, the first regulatory element is a polymerase III promoter. In some embodiments, the second regulatory element is a polymerase II promoter.

In general, and throughout this specification, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Another aspect of the disclosure relates to a composition comprising a nucleic acid disclosed herein and one or a plurality of recombinant expression vectors. Generally, the disclosure relates to composition comprising a synthetic guide sequence and one or a plurality of recombinant expression vectors. Recombinant expression vectors can comprise a nucleic acid of the disclosure in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell).

The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g. 1, 2, 3, 4, 5, or more pol III promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) (see, e.g., Boshart et al, Cell, 41:521-530 (1985)), the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-1 (Mol. Cell. Biol., Vol. 8(1), p. 466-472, 1988); SV40 enhancer; and the intron sequence between exons 2 and 3 of rabbit 3-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. One or more nucleic acid sequences and one or more vectors can be introduced into host cells to thereby form complexes with other cellular or non-natural compounds, produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.).

The disclosure also relates to pharmaceutical compositions comprising: (i) one or guide sequences disclosed herein or one or more pharmaceutically acceptable salts thereof; and (ii) a pharmaceutically acceptable carrier. The term "pharmaceutically acceptable salts" refers to physiologically and pharmaceutically acceptable salts of the nucleic acid sequences of the disclosure: i. e., salts that retain the desired biological activity of the nucleic acid sequences and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," J. of Pharnut Sci., 1977, 66:1). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present disclosure. As used herein, a "pharmaceutical addition salt" includes a pharmaceutically acceptable salt of an acid form of one of the components of the compositions of the disclosure. These include organic or inorganic acid salts of the amines. In some embodiments, a pharmaceutically acceptable salt is selected from one or a combination of hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids; for example acetic acid, propionic acid, glycolic acid, succinic acid, malefic acid, hydroxymaleic acid, methylmaleic acid, fiunaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, malefic acid, fumaric acid, glucoruc acid, citric acid, malic acid, ascorbic acid, benzoic acid, tannic acid, palimitic acid, alginic acid, polyglutamic acid, naphthalenesulfonic acid, methanesulfonic acid, p-toluenesulfonic acid, naphthalenedisulfonic acid, polygaiacturonic acid, and the like; and (d) salts formed from elemental anions such as chlorine, bromine, and iodine.

The practice of the present disclosure employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)), all of which are incorporated by reference in their entireties.

The term radioactive moiety means a substituent or component of a compound that comprises at least one radioisotope. Any radioisotope may be used. In some embodiments, the radioisotope is selected from Table 4. In some embodiments, the substituent or component of a compound of the present invention may incorporate any one, two, three, or more radioisotopes disclosed in Table 4.

TABLE 4

| Radioisotopes that may be incorporated into pharmaceutical compositions |
| --- |
| $^{2}H$, $^{3}H$, $^{13}C$, $^{14}C$, $^{15}N$, $^{16}O$, $^{17}O$, $^{31}P$, $^{32}P$, $^{35}S$, $^{18}F$, $^{36}Cl$, $^{225}Ac$, $^{227}Ac$, $^{212}Bi$, $^{213}Bi$, $^{109}Cd$, $^{60}Co$, $^{64}Cu$, $^{67}Cu$, $^{166}Dy$, $^{169}Er$, $^{152}Eu$, $^{154}Eu$, $^{153}Gd$, $^{198}Au$, $^{166}Ho$, $^{125}I$, $^{131}I$, $^{192}Ir$, $^{177}Lu$, $^{99}Mo$, $^{194}Os$, $^{103}Pd$, $^{195m}Pt$, $^{32}P$, $^{33}P$, $^{223}Ra$, $^{186}Re$, $^{188}Re$, $^{105}Rh$, $^{145}Sm$, $^{153}Sm$, $^{47}Sc$, $^{75}Se$, $^{85}Sr$, $^{89}Sr$, $^{99m}TC$, $^{228}Th$, $^{229}Th$, $^{170}Tm$, $^{117m}Sn$, $^{188}W$, $^{127}Xe$, $^{175}Yb$, $^{90}Y$, $^{91}Y$ |

TABLE 5

| Table of Chemotherapeutic Agents |
| --- |
| Alkylating agents |
| Cyclophosphamide |
| Mechlorethamine |
| Chlorambucil |
| Melphalan |
| Anthracyclines |
| Daunorubicin |
| Doxorubicin |
| Epirubicin |
| Idarubicin |
| Mitoxantrone |
| Valrubicin |
| Cytoskeletal disruptors (Taxanes) |
| Paclitaxel |
| Docetaxel |
| Epothilones |
| Histone Deacetylase Inhibitors |
| Vorinostat |
| Romidepsin |
| Inhibitors of Topoisomerase I |
| Irinotecan |
| Topotecan |
| Inhibitors of Topoisomerase II |
| Etoposide |
| Teniposide |
| Tafluposide |
| Kinase inhibitors |
| Bortezomib |
| Erlotinib |
| Gefitinib |
| Imatinib |
| Vemurafenib |
| Vismodegib |
| Monoclonal antibodies |
| Bevacizumab |
| Cetuximab |
| Ipilimumab |
| Ofatumumab |
| Ocrelizumab |
| Panitumab |
| Rituximab |
| Nucleotide analogs and precursor analogs |
| Azacitidine |
| Azathioprine |
| Capecitabine |
| Cytarabine |
| Doxifluridine |
| Fluorouracil |
| Gemcitabine |
| Hydroxyurea |
| Mercaptopurine |
| Methotrexate |
| Tioguanine (formerly Thioguanine) |
| Peptide antibiotics |
| Bleomycin |
| Actinomycin |
| Platinum-based agents |
| Carboplatin |
| Cisplatin |
| Oxaliplatin |
| Retinoids |
| Tretinoin |
| Alitretinoin |
| Bexarotene |
| Vinca alkaloids and derivatives |
| Vinblastine |
| Vincristine |
| Vindesine |
| Vinorelbine |
| Actinomycin |
| All-trans retinoic acid |
| Azacitidine |
| Azathioprine |
| Bleomycin |
| Bortezomib |
| Carboplatin |
| Capecitabine |
| Cisplatin |
| Chlorambucil |
| Cyclophosphamide |
| Cytarabine |
| Daunorubicin |
| Docetaxel |
| Doxifluridine |
| Doxorubicin |
| Epirubicin |
| Epothilone |
| Etoposide |
| Fluorouracil |
| Gemcitabine |
| Hydroxyurea |
| Idarubicin |
| Imatinib |
| Irinotecan |
| Mechlorethamine |
| Mercaptopurine |
| Methotrexate |
| Mitoxantrone |
| Oxaliplatin |
| Paclitaxel |
| Pemetrexed |
| Teniposide |
| Tioguanine |
| Topotecan |
| Valrubicin |
| Vinblastine |
| Vincristine |
| Vindesine |
| Vinorelbine |

Compositions of the disclosure include pharmaceutical compositions comprising: a particle comprising any of the guides sequences or nucleic acid sequences disclosed herein, or pharmaceutically acceptable salts thereof: and a pharmaceutically acceptable carrier.

As used herein, a "particle" refers to any entity having a diameter of less than 100 microns (µm). Typically, particles have a longest dimension (e.g. diameter) of 1000 nm or less. In some embodiments, particles have a diameter of 300 nm or less. In some embodiments, nanoparticles have a diameter of 200 nm or less. In some embodiments, nanoparticles have a diameter of 100 nm or less. In general, particles are greater in size than the renal excretion limit, but are small enough to avoid accumulation in the liver. In some embodiments, a population of particles may be relatively uniform in terms of size, shape, and/or composition. In general, inventive particles are biodegradable and/or biocompatible. Inventive particles can be solid or hollow and can comprise one or more layers. In some embodiments, particles are spheres, spheroids, flat, plate-shaped, cubes, cuboids, ovals, ellipses, cylinders, cones, or pyramids. In some embodiments, particles can be a matrix of polymers. In some embodiments, the matrix is cross-linked. In some embodiments, formation of the matrix involves a cross-linking step. In some embodiments, the matrix is not substantially cross-linked. In some embodiments, formation of the matrix does not involve a cross-linking step. In some embodiments, particles can be a non-polymeric particle (e.g. a metal particle, quantum dot, ceramic, inorganic material, bone, etc.). Components of the pharmaceutical compositions disclosed herein may comprise particles or may be microparticles, nanoparticles, liposomes, and/or micelles comprising one ore more disclosed nucleic acid seqeunces. As used herein, the term "nanoparticle" refers to any particle having a diameter of less than 1000 nm. Examples of nanoparticles are disclosed in *Nature Biotechnology* 31, 638-646, which is herein incorporated by reference in its entirety.

Pharmaceutical "carrier" or "excipient", as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. *Remington's The Science and Practice of Pharmacy,* 21st Edition, A. R. Gennaro, (Lippincott, Williams & Wilkins, Baltimore, Md., 2006) discloses various excipients used in formulating pharmaceutical compositions and known techniques for the preparation thereof. Except insofar as any conventional excipient is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, the pharmaceutically acceptable excipient or carrier is at least 95%, 96%, 97%, 98%, 99%, or 100% pure. In some embodiments, the excipient is approved for use in humans and for veterinary use. In some embodiments, the excipient is approved by United States Food and Drug Administration. In some embodiments, the excipient is pharmaceutical grade. In some embodiments, the excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in the inventive formulations. Excipients such as cocoa butter and suppository waxes, coloring agents, coating agents, sweetening, flavoring, and perfuming agents can be present in the composition, according to the judgment of the formulator.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite[aluminum silicate] and Veegum[magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include, but are not limited to, starch (e.g. cornstarch and starch paste); gelatin; sugars (e.g. sucrose, glucose, dextrose, dextrin, molasses, lactose, lactitol, mannitol); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan); alginates; polyethylene oxide; polyethylene glycol; inorganic calcium salts; silicic acid; polymethacrylates; waxes; water; alcohol; etc.; and combinations thereof.

Methods of Making Compositions and Modifications

Modified oligonucleotides and guide sequence of the disclosure may be made with automated, solid phase synthesis methods known in the art. During solid phase synthesis, phosphoramidite monomers are sequentially coupled to a nucleoside that is covalently linked to a solid support. This nucleoside is the 3' terminal nucleoside of the modified oligonucleotide. Typically, the coupling cycle comprises four steps: detritylation (removal of a 5'-hydroxyl protecting group with acid), coupling (attachment of an activated phosphoroamidite to the support bound nucleoside or oligonucleotide), oxidation or sulfurization (conversion of a newly formed phosphite trimester with an oxidizing or sulfurizing agent), and capping (acetylation of unreacted 5'-hydroxy 1 groups). After the final coupling cycle, the solid support-bound oligonucleotide is subjected to a detritylation step, followed by a cleavage and deprotection step that simultaneously releases the oligonucleotide from the solid support and removes the protecting groups from the bases. The solid support is removed by filtration, the filtrate is concentrated and the resulting solution is tested for identity and purity. The oligonucleotide is then purified, for example using a column packed with anion-exchange resin.

This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference in its entirety.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts. Any of the olignucelotide backbone modifications here may replace any one of the internucleotide linkages set forth in Formula W, X, Y, and/or Z.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference in its entirety.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

Some embodiments of the disclosure are oligonucleotides with phosphorothioate backbones and oligonucleosides with heteroatom backbones, and in particular —CH2-NH—O—CH2-, CH2-N(CH3)-O—CH2- [known as a methylene(methylimino) or MMI backbone], —CH2-O—N(CH3)-CH2-, —CH2-N(CH3)-N(CH3)-CH2- and —O—N(CH3)-CH2-CH2-[wherein the native phosphodiester backbone is represented as —O—P—O—CH2-] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. In some embodiments, oligonucleotides of the disclosure comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)nO]mCH_3$, $O(CH_2)nOCH_3$, $O(CH_2)nNH_2$, $O(CH_2)nCH_3$, $O(CH_2)nONH_2$, and $O(CH_2)nON[(CH_2)nCH_3)]_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, acetamide, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—CH2CH2OCH3, also known as 2'-O-(2-methoxyethyl) or 2'-MOE) (Martin et al., Helv. Chim. Acta, 1995, 78, 486-504) i.e., an alkoxyalkoxy group. Another modification includes 2'-dimethylaminooxyethoxy, i.e., a $O(CH_2)_2ON(CH_3)_2$ group, also known as 2'-DMAOE, and 2'-dimethylamino-ethoxyethoxy (2'-DMAEOE), i.e., 2'-O—$CH_2$—O—CH2-$N(CH_2)_2$.

Other modifications include 2'-methoxy (2'-O—$CH_3$), 2'-aminopropoxy (2'-$OCH_2CH_2CH_2NH_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

Oligonucleotides may also include a modified thioester group on the 2', 3' and/or 5' nucleoside. Such modifications in the 5' carbon of the ribose sugar also for formation of single 5'-S-thioester linkages between nucleotides in a synthetic nucleotide sequence. In any 3' or 5' linkage between nucleotides any one or both positions may create a series of linkages between nucleotides in one or a plurality of synthetic guide nucleic acids disclosed herein. The linkages at the 2' or 3' can create thioester bond, phosphorothioriate linkages between two or a plurality of nucleosides in the oligonucleotide. In some embodiments, the guide nucleic acid comprises at least two contiguous nucleosides linked by a phosphate containing group as shown in the following formula:

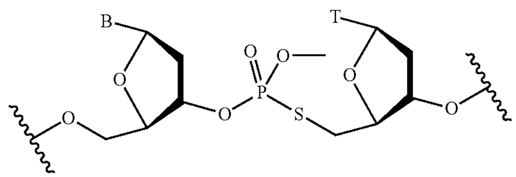

wherein B and T are independently selected as any natural or non-natural (modified) nucleobase, O is oxygen, P is phosphorous, and S is sulphur. In some embodiments, the naturally occurring 3' and/or 2' linkage in the nucleotide is replaced or supplemented with one or a plurality of linkers atoms. Such linkages are disclosed in US Publication WO/2002/061110, which is incorporated by reference in its entirety, but any chemical linker to bridge a 3' or 2' bond between two nucleotides is contemplated herein. Strategically placed sulfur atoms in the backbone of nucleic acids have found widespread utility in probing of specific interactions of proteins, enzymes and metals. Sulfur replacement for oxygen may be carried out at the 2'-position of RNA and in the 3'-5'-positions of RNA and of DNA. Polyribonucleotide containing phosphorothioate linkages were obtained as early as 1967 by Eckstein et al. using DNA-dependent RNA polymerase from *E. coli* (57). DNA-dependent RNA polymerase is a complex enzyme whose essential function is to transcribe the base sequence in a segment of DNA into a complementary base sequence of a messenger RNA molecule. Nucleoside triphosphates are the substrates that serve as the nucleotide units in RNA. In the polymerization of triphosphates, the enzyme requires a DNA segment that serves as a template for the base sequence in the newly synthesized RNA. In the original procedure, Uridine 5'-O-(1-thiotriphosphate), adenosine 5'-O-triphosphate, and only d (AT) as a template was used. As a result, an alternating copolymer is obtained, in which every other phosphate is replaced by a phosphorothioate group. Using the same approach and uridine 5'-O-(1-thiotriphosphate) and adenosine 5'-O-(1-thiotriphosphate), polyribonucleotide containing an all phosphorothioate backbone can also synthesized. In both cases, nucleoside 5'-O-(1-thiotriphosphates) as a mixture of two diastereomers can be used. In some embodiments, alternating phosphorothioate groups link a DNA or RNA or hybrid sequence of predominantly RNA to form alternating phosphorothioate backbones. Optionally, linkers of any cyclic or acyclic hydrocarbon chains of varying length may be incorporated into the guide nucleic acid. In some embodiments, linkers of the disclosure comprise one or a plurality of: branched or non-branched alkyl, hydroakyl, hydroxyl, halogen, metal, nitrogen, or other atoms.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are particularly useful for increasing the binding affinity of the oligomeric compounds of the disclosure. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., Antisense Research and Applications, CRC Press, Boca Raton, 1993, pp. 276-278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941, and 5,750,692, each of which is herein incorporated by reference in its entirety.

Another modification of the oligonucleotides of the disclosure involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), palmityl moiety (Mishra et al., Biochim. Biophys. Acta, 995, 1264, 229-237), or an octadecylamine or hexylamino-carbonyl-oxycholesterol moiety (Crooke et al., J. Pharmacol. Exp. Ther., 1996, 277, 923-937).

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference in its entirety.

It is not necessary for all positions in a given compound to be uniformly modified, and in fact more than one of the aforementioned modifications may be incorporated in a single sequence or compound or even at a single nucleoside or functional group within one or a plurality of positions within a nucleoside or an oligonucleotide.

Oligonucleotides of the present disclosure also relate to guide sequences comprising a one or a combination of: a DNA-binding domain, a Cas protein-binding domain, and a transcription terminator domain, and one or more targeting domains. As used herein "targeting domains" may be oligonucleotides, amino acid sequences, sugar moieties, lipid moieties or hybrids of any of the foregoing that are responsible for directing transformation or transfection or anchoring of the guide sequence disclosed herein into a cell of choice that comprises a target sequence. Creation of such chimeric molecules can be synthetically manufacture by known chemical arts.

For example, GalNAc-conjugated modification are known to direct oligonucleotides to liver cells. Modifications, such as GalNAc-conjugated modification, may be made to any one or combination of oligonucleotides disclosed herein with automated solid phase synthesis, similar to the solid phase synthesis that produced unconjugated oligonucleotides. During the synthesis of GalNAc-conjugated oligonucleotides, the phosphoramidite monomers are sequentially coupled to a GalNAc conjugate which is covalently linked to a solid support. The synthesis of GalNAc conjugates and GalNAc conjugate solid support is described, for example in U.S. Pat. No. 8,106,022, which is herein incorporated by reference in its entirety for the description of the synthesis of carbohydrate-containing conjugates, including conjugates comprising one or more GalNAc moieties, and of the synthesis of conjugate covalently linked to solid support.

The disclosure also relates to synthesizing one or a plurality of oligonucleotides, such as sgRNA molecules. 2'-deoxy-2'-modified nucleosides of adenine, guanine, cytosine, thymidine and certain analogs of these nucleobases may be prepared and incorporated into oligonucleotides via solid phase nucleic acid synthesis. Novel oligonucleotides can be assayed for their hybridization properties and their ability to resist degradation by nucleases compared to the unmodified oligonucleotides. Initially, small electronegative atoms or groups can be selected because they would not be expected to sterically interfere with required Watson-Crick base pair hydrogen bonding (hybridization). However, electronic changes due to the electronegativity of the atom or group in the 2'-position may profoundly affect the sugar conformation.

2'-Substituted oligonucleotides can be synthesized by standard solid phase nucleic acid synthesis using an automated synthesizer such as Model 380B (Perkin-Elmer/Applied Biosystems) or MilliGen/Biosearch 7500 or 8800. Triester, phosphoramidite, or hydrogen phosphonate coupling chemistries [Oligonucleotides. Antisense Inhibitors of Gene Expression. M. Caruthers, p. 7, J. S. Cohen (Ed.), CRC Press, Boca Raton, Fla., 1989] are used with these synthesizers to provide the desired oligonucleotides. The Beaucage reagent [J. Amer. Chem. Soc., 112, 1253 (1990)] or elemental sulfur [Beaucage et al., Tet. Lett., 22, 1859 (1981)] is used with phosphoramidite or hydrogen phosphonate chemistries to provide 2'-substituted phosphorothioate oligonucleotides.

2'-substituted nucleosides (A, G, C, T(U), and other modified nucleobases) may be prepared by modification of several literature procedures as described below.

Procedure 1. Nucleophilic Displacement of 2'-Leaving Group in Arabino Purine Nucleosides. Nucleophilic displacement of a leaving group in the 2'-up position (2'-deoxy-2'-(leaving group)arabino sugar) of adenine or guanine or their analog nucleosides. General synthetic procedures of this type have been described by Ikehara et al., Tetrahedron, 34, 1133 (1978); ibid., 31, 1369 (1975); Chemistry and Pharmaceutical Bulletin, 26, 2449 (1978); ibid., 26, 240 (1978); Ikehara, Accounts of Chemical Research, 2, 47 (1969); and Ranganathan, Tetrahedron Letters, 15, 1291 (1977).

Procedure 2. Nucleophilic Displacement of 2,2'-Anhydro Pyrimidines. Nucleosides thymine, uracil, cytosine or their analogs are converted to 2'-substituted nucleosides by the intermediacy of 2,2'-cycloanhydro nucleoside as described by Fox et al., Journal of Organic Chemistry, 29, 558 (1964).

Procedure 3. 2'-Coupling Reactions. Appropriately 3',5'-sugar and base protected purine and pyrimidine nucleosides having a unprotected 2'-hydroxyl group are coupled with electrophilic reagents such as methyl iodide and diazomethane to provide the mixed sequences containing a 2'-OMe group H. Inoue et al., Nucleic Acids Research, 15, 6131.

Procedure 4. 2-Deoxy-2-substituted Ribosylations. 2-Substituted-2-deoxyribosylation of the appropriately protected nucleic acid bases and nucleic acids base analogs has been reported by Jarvi et al., Nucleosides & Nucleotides, 8, 1111-1114 (1989) and Hertel et al., Journal of Organic Chemistry, 53, 2406 (1988).

Procedure 5. Enzymatic Synthesis of 2'-Deoxy-2'-Substituted Nucleosides. The 2-Deoxy-2-substituted glycosyl transfer from one nucleoside to another with the aid of pyrimidine and purine ribo or deoxyribo phosphorolyses has been described by Rideout and Krenitsky, U.S. Pat. No. 4,381,344 (1983).

Procedure 6. Conversion of 2'-Substituents Into New Substituents. 2'-Substituted-2'-deoxynucleosides are converted into new substituents via standard chemical manipulations. For example, Chladek et al. [Journal of Carbohydrates, Nucleosides & Nucleotides, 7, 63 (1980)] describes the conversion of 2'-deoxy-2'-azidoadenosine, prepared from arabinofuranosyladenine, into 2'-deoxy-2'-aminoadenosine.

Procedure 7. Free Radical Reactions. Conversions of halogen substituted nucleosides into 2'-deoxy-2'-substituted nucleosides via free radical reactions has been described by Parkes and Taylor [Tetrahedron Letters, 29, 2995 (1988)].

Procedure 8. Conversion of Ribonucleosides to 2'-Deoxy-2'-Substituted Nucleoside. Appropriately 3',5'-sugar and base protected purine and pyrimidine nucleosides having a unprotected 2'-hydroxyl group are converted to 2'-deoxy-2'-substituted nucleosides by the process of oxidation to the 2'-keto group, reaction with nucleophilic reagents, and finally 2'-deoxygenation. Procedures of this type have been described by De las Heras, et al. [Tetrahedron Letters, 29, 941 (1988)].

Procedure 9. In one process of the disclosure, 2'-deoxy substituted guanosine compounds are prepared via an (arabinofuranosyl)guanine intermediate obtained via an oxidation-reduction reaction. A leaving group at the 2' position of the arabinofuranosyl sugar moiety of the intermediate arabino compound is displaced via an SN2 reaction with an appropriate nucleophile. This procedure thus incorporates principles of both Procedure 1 and Procedure 8 above. 2'-Deoxy-2'-fluoroguanosine is preferably prepared via this procedure. The intermediate arabino compound was obtained utilizing a variation of the oxidation-reduction procedure of Hansske et al. [Tetrahedron, 40, 125 (1984)]. According to this disclosure, the reduction was effected starting at −78° C. and allowing the reduction reaction to exothermically warm to about −2° C. This results in a high yield of the intermediate arabino compound.

In conjunction with use of a low temperature reduction, utilization of a tetraisopropyldisiloxane blocking group (a "TPDS" group) for the 3' and 5' positions of the starting guanosine compound contributes to an improved ratio of intermediate arabino compound to the ribo compound following oxidation and reduction. Following oxidation and reduction, the N2 guanine amino nitrogen and the 2'-hydroxyl moieties of the intermediate arabino compound are blocked with isobutyryl protecting groups ("Ibu" groups). The tetraisopropyldisiloxane blocking group is removed and the 3' and 5' hydroxy groups are further protected with a second blocking group, a tetrahydropyranyl blocking group ("THP" group). The isobutyryl group is selectively removed from 2'-hydroxyl group followed by derivation of the 2' position with a triflate leaving group. The triflate group was then displaced with inversion about the 2' position to yield the desired 2'-deoxy-2'-fluoroguanosine compound.

In addition to the triflate leaving group, other leaving groups include, but are not limited to, alkylsulfonyl, substituted alkylsulfonyl, arylsulfonyl, substituted arylsulfonyl, heterocyclosulfonyl or trichloroacetimidate. Representative examples include p-(2,4-dinitroanilino)benzenesulfonyl, benzenesulfonyl, methylsulfonyl, p-methylbenzenesulfonyl, p-bromobenzenesulfonyl, trichloroacetimidate, acyloxy, 2,2,2-trifluoroethanesulfonyl, imidazolesulfonyl and 2,4,6-trichlorophenyl.

The isobutyryl group remaining on the N2 heterocyclic amino moiety of the guanine ring can be removed to yield a completely deblocked nucleoside. However, preferably, for incorporation of the 2'-deoxy-2'-substituted compound into an oligonucleotide, deblocking of the 2 isobutyryl protecting group is deferred until after oligonucleotide synthesis is complete. Normally for use in automated nucleic acid synthesizers, blocking of the N2 guanine moiety with an isobutyryl group is preferred. Thus, advantageously, the N2-isobutyryl-blocked 2'-deoxy-2'-substituted guanosine compounds resulting from the method of the disclosure can be directly used for oligonucleotide synthesis on automated nucleic acid synthesizers.

Methods

The disclosure relates to a method of reducing off-target enzyme activity of a Cas protein or functional fragment thereof comprising exposing the Cas protein or functional fragment thereof to a chemically modified nucleic acid sequence disclosed herein comprising at least one fluorinated nucleotide.

The disclosure relates to a method of enhancing enzyme activity of a Cas protein or functional fragment thereof comprising exposing the Cas protein or functional fragment thereof to a chemically modified nucleic acid sequence disclosed herein comprising at least one unmodified nucleotide at one or more positions that bind to or interact with to the Cas protein or functional fragment thereof in an enzymatically active CRISPR complex.

The disclosure also relates to a method of altering expression of at least one gene product in a cell comprising introducing into a cell an engineered, non-naturally occurring CRISPR associated (Cas) (CRISPR-Cas) system comprising: (a) a vector comprising a nucleotide sequence encoding any CRISPR enzyme disclosed herein, any mutated CRISPR enzyme having at least 70%, 75%, 80%, 85%, 90%, 91%, 92%, 93%, 94%, 95%, 9%, 97%, 98%, or 99% sequence homology to any CRISPR enzyme disclosed herein (such as Table E), or functional fragment thereof; and (b) a nucleic acid sequence disclosed herein, wherein components (a) and (b) are located on same or different vectors of the system; wherein the cell contains and expresses a DNA molecule having a target sequence and encoding the gene product; and wherein the guide RNA targets and hybridizes with a DNA target sequence, the CRISPR enzyme or functional fragment thereof cleaves the DNA molecule, whereby expression of the at least one gene product is altered.

The disclosure also relates to a method of altering expression of at least one gene product in a cell comprising introducing into a cell an engineered, non-naturally occurring CRISPR associated (Cas) (CRISPR-Cas) system comprising: (a) a vector comprising a nucleotide sequence encoding a Type I, Type-II, or Type III Cas9 protein or functional fragment thereof; and (b) a nucleic acid sequence disclosed herein, wherein components (a) and (b) are located on same or different vectors of the system; wherein the cell contains and expresses a DNA molecule having a target sequence and encoding the gene product; and wherein the guide RNA targets and hybridizes with a DNA target sequence and the Cas9 protein or functional fragment thereof cleaves the DNA molecule, whereby expression of the at least one gene product is altered.

The disclosure also relates to a method of improving the enzymatic efficiency of a Cas protein or functional fragment thereof comprising: exposing the Cas protein or functional fragment thereof to a chemically a modified nucleic acid sequence disclosed herein. In some embodiments, the modified nucleic acid sequence is a guide sequence comprising ribonucleotides and at least one fluorinated nucleotide in at least one or plurality of any domain disclosed herein. In some embodiments, the step of exposing the Cas protein or functional fragment thereof to a chemically a modified nucleic acid sequence disclosed herein. In some embodiments the enzymatic efficiency is increased by no less than from about 5% to about 10%. In some embodiments the enzymatic efficiency is increased by no less than from about 5% to about 15%. In some embodiments the enzymatic efficiency is increased by no less than from about 5% to about 20%. In some embodiments the enzymatic efficiency is increased by no less than from about 5% to about 25%. In some embodiments the enzymatic efficiency is increased by no less than from about 1% to about 25%. In some embodiments the enzymatic efficiency is increased by no less than from about 1% to about 20%. In some embodiments the enzymatic efficiency is increased by no less than from about 1% to about 15%. In some embodiments the enzymatic efficiency is increased by no less than from about 1% to about 10%. In some embodiments the enzymatic efficiency is increased by no less than from about 2 times to about 10 times the efficiency of the same Cas protein exposed to a unmodified guide sequence.

The disclosure also relates to a method of increasing the sensitivity of a cancer cell to one or more chemotherapeutic agents, the method comprising contacting a cancer cell with one or more pharmaceutical compositions disclosed herein.

The disclosure also relates to a method of increasing the sensitivity of a cancer in a subject in need thereof to one or more chemotherapeutic agents, the method comprising administering to a subject diagnosed with cancer or suspected of having cancer one or more pharmaceutical compositions disclosed herein. In some embodiments, the cancer in the subject is not responsive to chemotherapeutic agents.

The disclosure also relates to a method of destroying a cancer stem cell, the method comprising contacting a cancer stem cell with one or more pharmaceutical compositions disclosed herein. The disclosure also relates to a method of making a chimeric antigen receptor (CAR) positive T cell by exposing one or more T cells, isolated from a subject. to one or a plurality of guide seqeunces disclosed herein.

The disclosure also relates to a method of treating or preventing growth and/or proliferation of a cancer stem cell in a subject diagnosed with or suspected of having cancer, the method comprising administering to a subject diagnosed with cancer or suspected of cancer one or more pharmaceutical compositions disclosed herein.

The disclosure also relates to a method of treating or preventing liver disease in a subject diagnosed with or suspected of having liver disease, the method comprising administering to a subject diagnosed with liver disease one or more pharmaceutical compositions disclosed herein.

The disclosure also relates to a method of treating or preventing cardiovascular disease in a subject diagnosed with or suspected of having cardiovascular disease, the method comprising administering to a subject diagnosed with cardiovascular disease one or more pharmaceutical compositions disclosed herein, wherein the composition comprises a concentration of one or plurality of sgRNA molecules comprising a DNA-binding domain capable of binding PSCK9 (such as disclosed in Table 1) sufficient to activate a Cas enzyme in the subject.

According to one aspect of the present disclosure, a eukaryotic cell is transfected with a two component system including one or a plurality of guide sequences complementary to genomic DNA and an enzyme that interacts with the guide sequence when it is duplexed with the target sequence of genomic DNA. The one or a plurality of guide sequences and the enzyme are expressed by the cell. The RNA of the RNA/enzyme complex then binds to complementary genomic DNA. The enzyme then performs a function, such as cleavage of the genomic DNA. In some embodiments, the one or a plurality of guide sequences include from about 10 nucleotides to about 250 nucleotides. In some embodiments, the one or a plurality of guide sequences include from about 20 nucleotides to about 100 nucleotides. According to certain aspects, the enzyme may perform any desired function in a site specific manner for which the enzyme has been engineered. According to one aspect, the eukaryotic cell is a yeast cell, plant cell or mammalian cell. According to one aspect, the enzyme cleaves genomic sequences targeted by one or a plurality of guide sequences, thereby creating a genomically altered eukaryotic cell. According to one aspect, the present disclosure provides a method of genetically altering a human cell by including: (i) one or a plurality of synthetic guide sequence; and (ii) one or a plurality of nucleic acids encoding an RNA complementary to genomic DNA into the genome of the cell; and (iii) a nucleic acid encoding an enzyme that performs a desired function on genomic DNA into the genome of the cell. According to one aspect, the RNA and the enzyme are expressed, and the RNA hybridizes with complementary genomic DNA. According to one aspect, the enzyme is activated to perform a desired function, such as cleavage or nicking, in a site-specific manner when the RNA is hybridized to the complementary genomic DNA. According to one aspect, the RNA and the enzyme are components of a bacterial Type I, Type II, or Type III CRISPR system.

According to one aspect, the disclosure relates to a method of altering a eukaryotic cell comprising: transfecting the eukaryotic cell with a nucleic acid disclosed herein complementary to genomic DNA of the eukaryotic cell, transfecting the eukaryotic cell with a nucleic acid encoding an enzyme that interacts with the RNA and cleaves the genomic DNA in a site-specific manner, wherein the cell expresses the RNA and the enzyme, the RNA binds to complementary genomic DNA and the enzyme cleaves the genomic DNA in a site specific manner. According to one aspect, the enzyme is Cas9 or modified Cas9 or a homolog of Cas9. According to one aspect, the eukaryotic cell is a yeast cell, a plant cell or a mammalian cell. According to one aspect, the a nucleic acid disclosed herein comprises from about 10 to about 250 nucleotides. According to one aspect, the nucleic acid disclosed herein comprises from about 20 to about 100 nucleotides.

According to one aspect, a method of altering a human cell is provided including transfecting the human cell with a nucleic acid encoding RNA complementary to genomic DNA of the eukaryotic cell, transfecting the human cell with a nucleic acid encoding an enzyme that interacts with the RNA and cleaves the genomic DNA in a site specific manner, wherein the human cell expresses the RNA and the enzyme, the RNA binds to complementary genomic DNA and the enzyme cleaves the genomic DNA in a site specific manner. According to one aspect, the enzyme is Cas9 or modified Cas9 or a homolog of Cas9. Modified cas9 proteins or homologs of Cas9 are for instance disclosed in U.S. Pat. No. 9,074,199, which is incorporated herein by reference. According to one aspect, the RNA includes between about 10 to about 250 nucleotides. According to one aspect, the RNA includes between about 20 to about 100 nucleotides. The step of transfecting a nucleic acid encoding an RNA may be added to any method disclosed herein so that there is sequential or concurrent transfection of not only synthetic guide sequences such as those disclosed herein but also one or a plurality of vectors comprising According to one aspect, the disclosure relates to a method of altering a eukaryotic cell at a plurality of genomic DNA sites comprising: transfecting the eukaryotic cell with one or a plurality of nucleic acids complementary to different sites on genomic DNA of the eukaryotic cell, transfecting the eukaryotic cell with a nucleic acid encoding an enzyme that interacts with the nucleic acid complementary to different sites on genomic DNA of the eukaryotic cell, such that the enzyme cleaves the genomic DNA in a site-specific manner, wherein the cell expresses the enzyme, the nucleic acids complementary to different sites on genomic DNA of the eukaryotic cell bind to complementary genomic DNA and the enzyme cleaves the genomic DNA in a site specific manner. According to one aspect, the enzyme is Cas9. According to one aspect, the eukaryotic cell is a yeast cell, a plant cell or a mammalian cell. According to one aspect, the a nucleic acid disclosed herein comprises from about 10 to about 250 nucleotides. According to one aspect, the nucleic acid disclosed herein comprises from about 20 to about 100 nucleotides.

The disclosure relates to a composition comprising a cell with any one or combination of nucleic acid sequences disclosed herein. In some embodiments, the cell is a plant, insect or mammalian cell. In some embodiments, the cell is a eukaryotic cell or a prokaryotic cell. the cell may be isolated from the body, a component of a culture system, or part of an organism. In general, the system and methods described herein include at least two components: (1) the RNAs or DNA/RNA hybrid (guide nucleic acid, a crRNA, tracrRNA, and/or a single cr/tracrRNA hybrid) targeted to a particular sequence in a cell (e.g., either genomic DNA, or in an extrachromosomal plasmid, such as a reporter); and (2) a Cas protein disclosed herein. In some cases, a system also can include a nucleic acid containing a donor sequence targeted to a sequence in the cell. The donor sequence and the guide sequence may be on one or a plurality of nucleic acid molecules. The Cas protein disclosed herein can create targeted DNA double-strand breaks at the desired locus (or loci), and the host cell can repair the double-strand break using the provide donor DNA sequence, thereby incorporating the modification stably into the host genome.

The construct(s) containing the guide RNA or RNA/DNA hybrid molecules, crRNA, tracrRNA, cr/tracrRNA hybrid, Cas protein disclosed herein coding sequence, and, where applicable, donor sequence, can be delivered to a cell using, for example, biolistic bombardment, electrostatic potential or through transformation permeability reagents (reagents known to increase the permeability of the cell wall or cell membrane). Alternatively, the system components can be delivered using *Agrobacterium*-mediated transformation, insect vectors, grafting, or DNA abrasion, according to methods that are standard in the art, including those described herein. In some embodiments, the system components can be delivered in a viral vector (e.g., a vector from a DNA virus such as, without limitation, geminivirus, AAV, adenovirus, lentiviral strains attenuated for human use, bean yellow dwarf virus, wheat dwarf virus, tomato leaf curl virus, maize streak virus, tobacco leaf curl virus, tomato golden mosaic virus, or Faba bean necrotic yellow virus, or a vector from an RNA virus such as, without limitation, a tobravirus (e.g., tobacco rattle virus, tobacco mosaic virus), potato virus X, or barley stripe mosaic virus.

After an organism is infected, administered or transfected with a sequence encoding a Cas protein disclosed herein or a functional fragment thereof, a crRNA, a trRNA, a crRNA and a tracrRNA, a cr/tracrRNA hybrid, and/or a synthetic guide nucleic acid (and, in some cases, a donor sequence), any suitable method can be used to determine whether targeted mutagenesis has occurred at the target site. In some embodiments, a phenotypic change can indicate that a donor sequence has been integrated into the target site. Such is the case for transgenic plants encoding a defective GUS:NPTII reporter gene, for example. PCR-based methods also can be used to ascertain whether a genomic target site contains targeted mutations or donor sequence, and/or whether precise recombination has occurred at the 5' and 3' ends of the donor.

Kits

In some embodiments, kits in accordance with the present disclosure may be used to mutate endogenous genetic material in cell types of interest. In some embodiments, kits for mutating cells comprise the nucleic acids, compositions, or pharmaceutical compositions described herein and, optionally, cell growth medium and a cell type of interest. Any nucleic acid, composition, or component thereof disclosed may be arranged in a kit either individually or in combination with any other Any nucleic acid, composition, or component thereof. The disclosure provides a kit to perform any of the methods described herein. In some embodiments, the kit comprises at least one container comprising one or a plurality of oligonucleotides comprising a DNA-binding domain sequence complementary to genomic DNA inside of a cell. In some embodiments, the kit comprises at least one container comprising any of the polypeptides or functional fragments described herein. In some embodiments, the polypeptides are in solution (such as a buffer with adequate pH and/or other necessary additive to minimize degradation of the polypeptides during prolonged storage). In some embodiments, the polypeptides or oligonucleotides are lyophilized for the purposes of resuspension after prolonged storage. In some embodiments, the kit comprises: at least one container comprising one or a plurality of polypeptides comprising or functional fragments disclosed herein and/or oligonucleotides disclosed herein; and a solid support upon which genomic DNA of a cell may be mutated. In some embodiments, the kit optionally comprises instructions to perform any or all steps of any method described herein.

The kit may contain two or more containers, packs, or dispensers together with instructions for preparation of an array. In some embodiments, the kit comprises at least one container comprising the oligonucleotides described herein and a second container comprising a means for maintenance, use, and/or storage of the oligonucleotides such as storage buffer. In some embodiments, the kit comprises a composition comprising any polypeptide disclosed herein in solution or lyophilized or dried and accompanied by a rehydration mixture. In some embodiments, the polypeptides and rehydration mixture may be in one or more additional containers.

The compositions included in the kit may be supplied in containers of any sort such that the shelf-life of the different components are preserved, and are not adsorbed or altered by the materials of the container. For example, suitable containers include simple bottles that may be fabricated from glass, organic polymers, such as polycarbonate, polystyrene, polypropylene, polyethylene, ceramic, metal or any other material typically employed to hold reagents or food; envelopes, that may consist of foil-lined interiors, such as aluminum or an alloy. Other containers include test tubes, vials, flasks, and syringes. The containers may have two compartments that are separated by a readily removable membrane that upon removal permits the components of the compositions to mix. Removable membranes may be glass, plastic, rubber, or other inert material.

Kits may also be supplied with instructional materials. Instructions may be printed on paper or other substrates, and/or may be supplied as an electronic-readable medium, such as a floppy disc, CD-ROM, DVD-ROM, zip disc, videotape, audio tape, or other readable memory storage device. Detailed instructions may not be physically associated with the kit; instead, a user may be directed to an internet web site specified by the manufacturer or distributor of the kit, or supplied as electronic mail.

The disclosure also provides a kit comprising: an guide sequence disclosed herein; and a vector comprising a nucleic acid sequence encoding a Cas protein or CRISPR enzyme operably linked to a regulatory element active in a eukaryotic cell. In some embodiments, the kit further comprises at least one of the following: one or a plurality of eukaryotic cells comprising regulatory protein capable of trans-activation of the regulatory element, cell growth media, a volume of fluorescent stain or dye, and a set of instructions, optionally accessible remotely through an electronic medium.

Any and all journal articles, patent applications, issued patents, or other cited references disclosed herein are incorporated by reference in their respective entireties.

1. U.S. Pat. No. 8,697,359
2. WO/2015/048690, 60, 72
3. 201410067479
4. Nature Biotechnology 32, 1262-1267
5. Nature Biotech, 2014 March; 32(3) 279-84 (K. Juong—MGH).
6. US Patent Publication 2010/0076057
7. US Patent Publication 2011/0189776
8. US Patent Publication 2011/0223638
9. US Patent Publication 2013/0130248
10. Makarova et al., "Evolution and classification of the CRISPR-Cas systems" 9(6) Nature
11. Reviews Microbiology 467-477 (1-23) (June 2011).
12. Wiedenheft et al., "RNA-guided genetic silencing systems in bacteria and archaea" 482
13. Nature 331-338 (Feb. 16, 2012).
14. Jinek et al., "A Programmable Dual-RNA-Guided DNA Endonuclease in Adaptive Bacterial Immunity" 337 Science 816-821 (Aug. 17, 2012).

Carroll, "A CRISPR Approach to Gene Targeting" 20(9) Molecular Therapy 1658-1660 (September 2012).

Background

Al-Attar et al., Clustered Regularly Interspaced Short Palindromic Repeats (CRISPRs): The Hallmark of an Ingenious Antiviral Defense Mechanism in Prokaryotes, Biol Chem. (2011) vol. 392, Issue 4, pp. 277-289.

Hale et al., Essential Features and Rational Design of CRISPR RNAs That Function With the Cas RAMP Module Complex to Cleave RNAs, Molecular Cell, (2012) vol. 45, Issue 3, 292-302. Erik Sontheimer, Project 7: Establishing RNA-Directed DNA Targeting in Eukaryotic Cells; Project dates: Nov. 16, 2011 to Dec. 31, 2012 (Feb. 4, 2012).

Gasiunas et al., "Cas9-crRNA ribonucleoprotein complex mediates specific DNA cleavage for adaptive immunity in bacteria" 109(39) Proceedings of the National Academy of Sciences USA E2579-E2586 (Sep. 4, 2012).

U.S. Pat. Nos. 7,919,277, 8,282,920, 8,361,725, 8,501,405,
U.S. Pat. Nos. 8,546,553, 8,557,561, 8,586,709, 8,592,556,
U.S. Pat. Nos. 8,609,421, 8,673,568, 8,758,764, 8,771,766,
U.S. Pat. Nos. 8,771,945, 8,795,965, 8,809,026, 8,841,260,
U.S. Pat. Nos. 8,846,329, 8,846,354, 8,865,406, 8,871,445,
U.S. Pat. Nos. 8,889,356, 8,889,418, 8,895,308, 8,906,616,
U.S. Pat. Nos. 8,932,814, 8,940,507, 8,945,839, 8,993,233,
U.S. Pat. Nos. 8,999,641, 9,023,649, 9,057,071, 9,068,179,
U.S. Pat. Nos. 9,074,199, 9,101,100, 9,102,936

EXAMPLES

Example 1 Rationale for sgRNA Modifications

The chemical modifications of oligonucleotides (ON) have been used for oligo therapy, e.g. antisense ONs (AONs), small interfering RNAs (siRNAs), and microRNA-targeting ONs (anti-miRNAs). Proper chemical modifications hold the potential to optimize biological activity and therapeutic application. The CRISPR system tool consists of the Cas9 nuclease, and a single guide RNA (sgRNA) or alternative (tracrRNA/crRNA) for efficient gene editing. Current studies do not indicate whether the sgRNA (or the tracrRNA/crRNA) can be chemically modified. If the sgRNA can be modified, there is no information indicating whether chemically modification of sgRNA could benefit CRISPR mediated gene editing.

We hypothesized that sgRNA can tolerate certain levels of chemical modification, and some modifications may enhance sgRNA activity. To test our hypothesis and as the first proof-of-concept experiment, we first substituted native RNA with 2'-Fluoro modified RNA. It has been shown that in short oligos (antisense ONs, small interfering RNAs and microRNA-targeting ONs), 2'-Fluoro modified RNA increase their biological activity through better stability in serum[1]. To explore which part of sgRNA can be modified, we split sgRNA into three function regions: the 20-25-nt-long base-pairing region for specific DNA binding, a 42-nt-long dCas9 handle hairpin for Cas9 protein binding and a 40-nt-long transcription terminator hairpin derived from *S. pyogenes* (FIG. 1). We applied a solid phase synthesis method[2] to synthesize multiple sgRNAs. We first synthesized sgRNAs containing sequence targeting in the base-pairing region to target GFP protein: sgRNA 1 is without any chemical modification as a native strand (GFP-1); sgRNA 2 (GFP-2) substitutes most U and C in the transcription terminator region with 2'-Fluoro modified RNA; and sgRNA 3 (GFP-3) substitutes eight RNA nucleotides with 2'-Fluoro modified RNA out of twenty RNA nucleotides in base-pairing region (FIG. 2).

Figure 3:
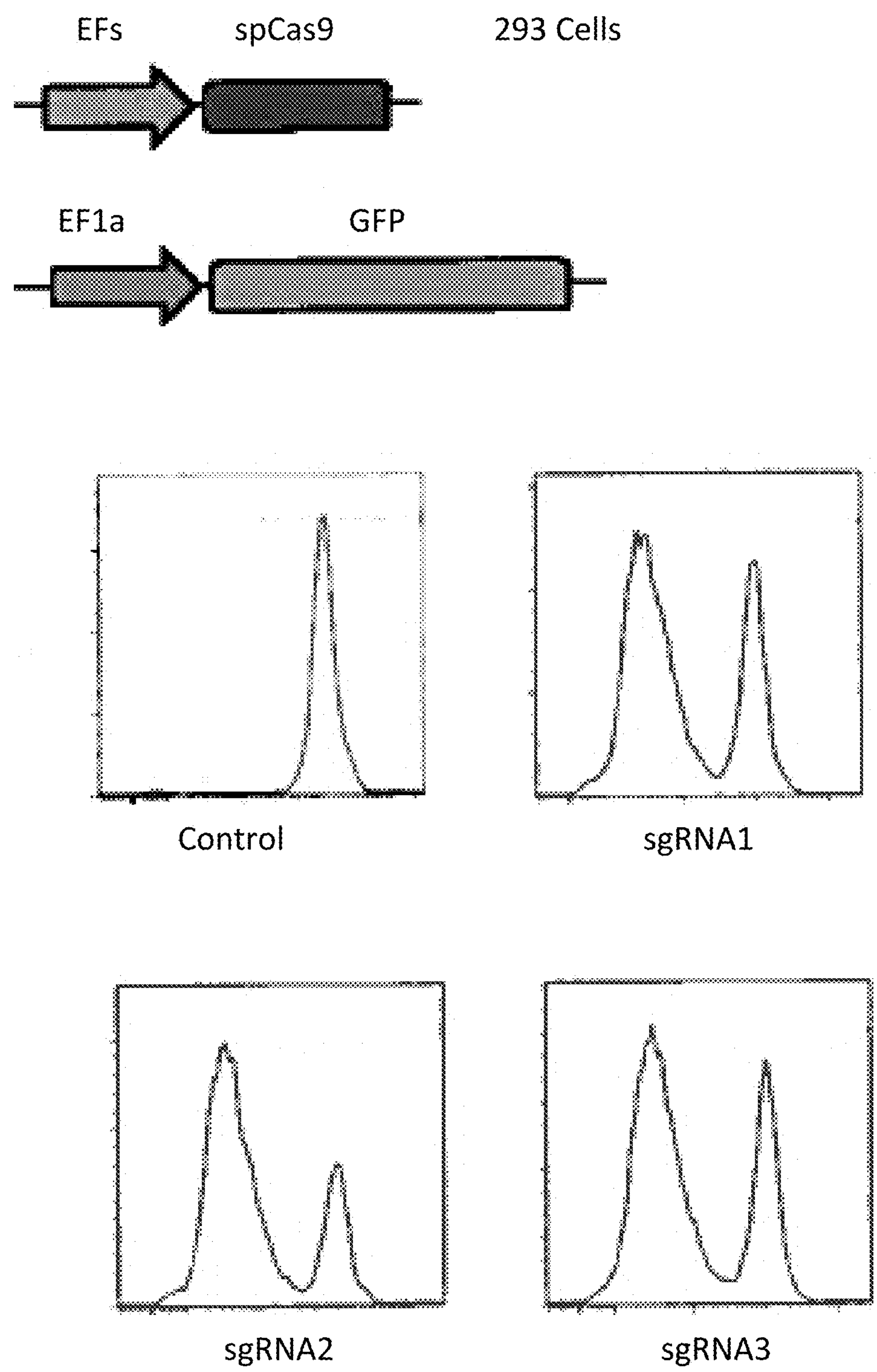
FIG. 3 depicts the results of genome editing with modified sgRNAs. 293 cells were engineered to express EGFP and spCas9, sgRNA1, sgRNA2, and sgRNA3 were introduced to cells via transfection and FACS was performed 5 days after transfection. As compared to the control group, all 3 sgRNAs can efficiently perform gene editing, sgRNA2, with chemical modifications at the 40-nt-long transcription terminator hairpin region, has the highest efficiency.
Figure 4A:
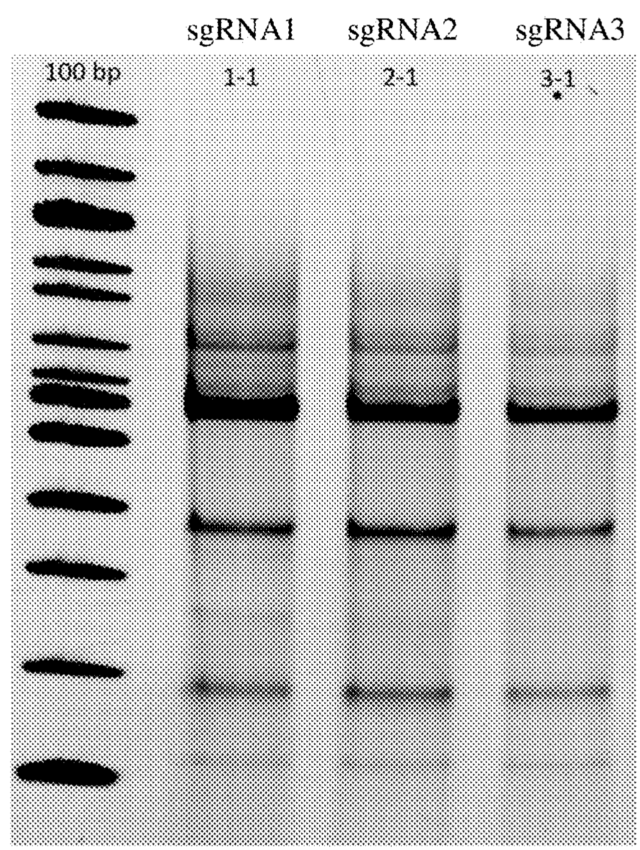
FIGS. 4A, 4B, 4C, 4D, and 4E depict the DNA editing effect of sgRNAs at different concentrations.
Figure 4B:
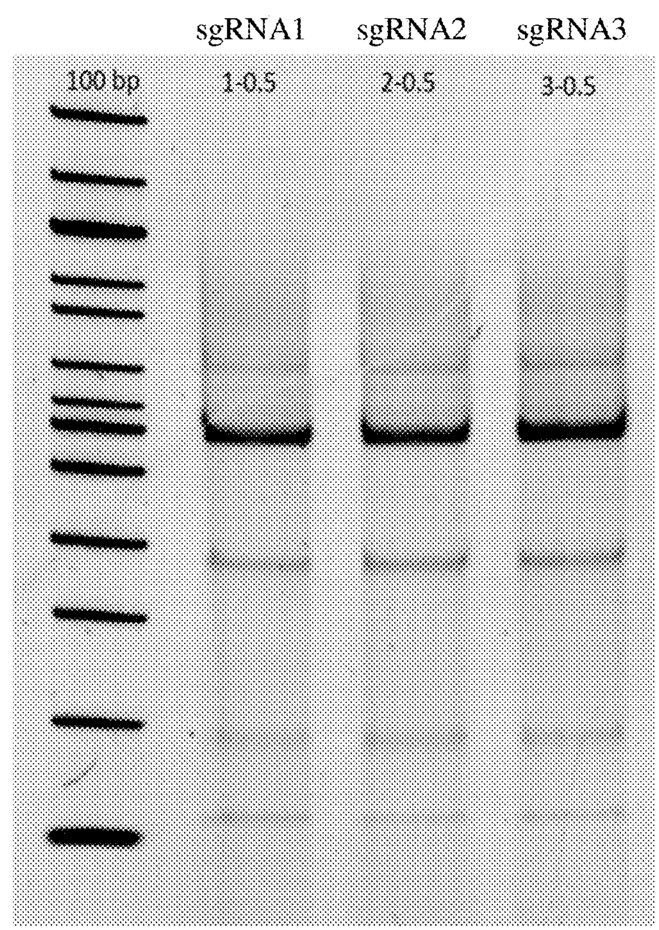
Figure 4C:
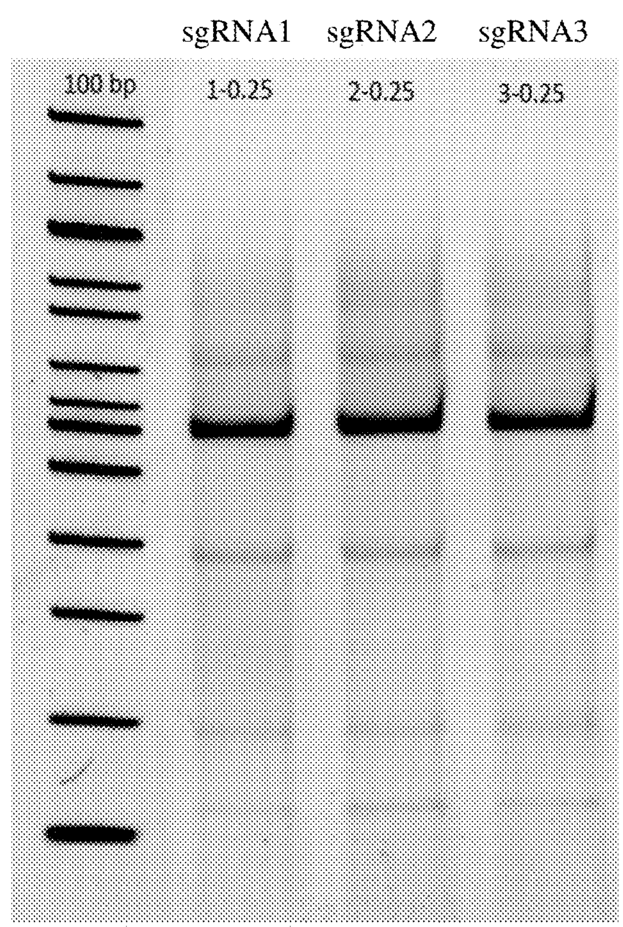
Figure 4D:
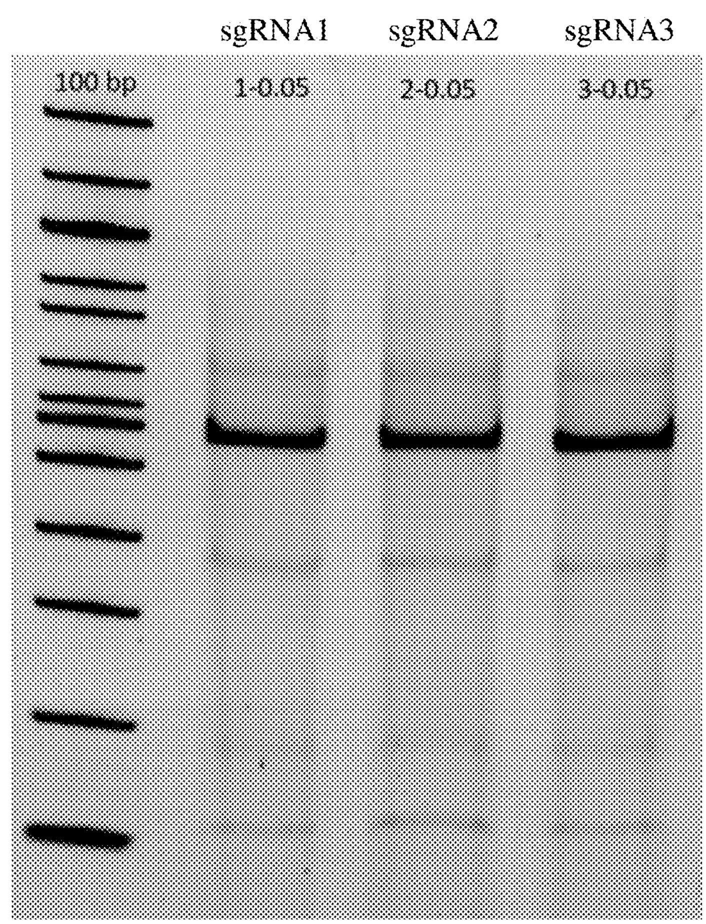
Figure 4E:
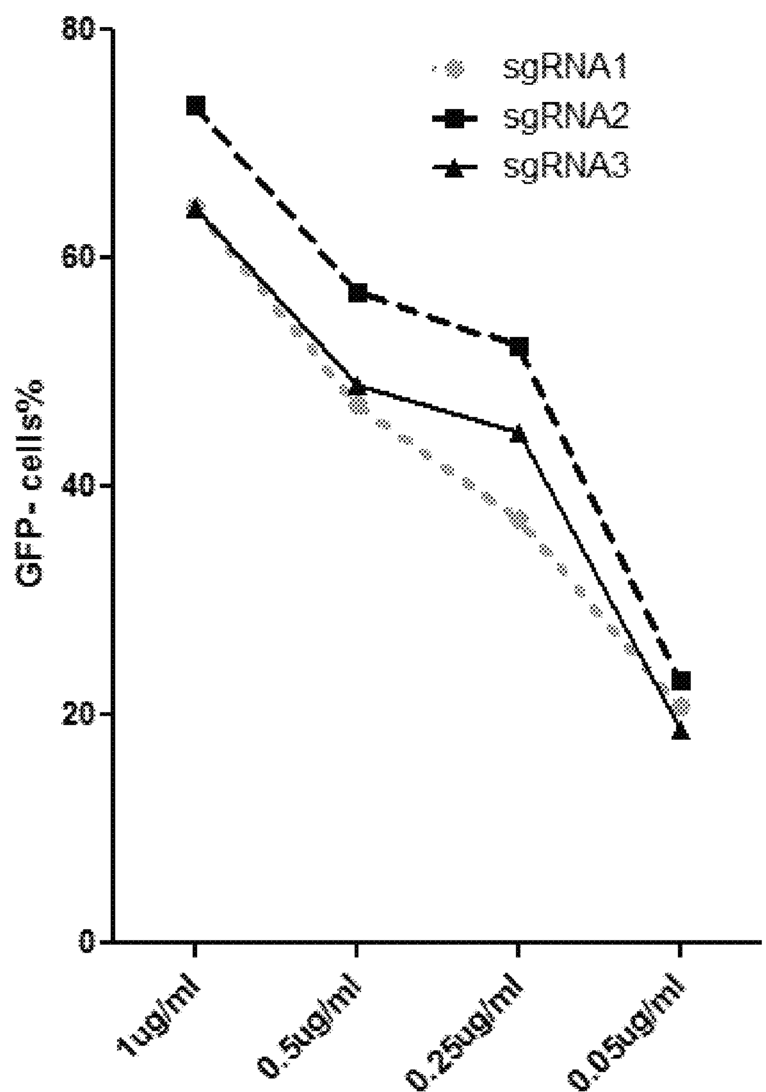

We engineered HEK293 cells to express EGFP and spCas9 (FIG. 3). A sgRNA that targets EGFP in cells would guide spCas9 to target EGFP and perform gene editing. It leads to indel formation at EGFP site and disrupts EGFP expression. We transfected GFP-1 or 2 or 3 into those cells, and performed flow cytometry analysis 5 days after. We found that GFP-1 treated cells can perform gene editing, reducing GFP positive cells from 98% to 34%. It is obvious and consistent that GFP-2 (with chemical modification at 40-nt-long transcription terminator hairpin region) has higher efficiency than GFP-1, by reducing GFP positive cells to about 25%. GFP-3 has modification at DNA binding region, and reached the same efficiency of GFP-1. It indicates that DNA binding region is tolerated with chemical modifications. Thus it is reasonable to propose to enhance target specificity of CRISPR system by chemically modifying DNA binding region of sgRNAs.

To confirm our data, we also performed a Surveyor assay to detect indel formations at predicted genomic sites. The results are consistent with flow cytometry that GFP-2 is more potent than GFP-1, and GFP-3 is with similar potency as GFP-1. To further testing the potency of sgRNAs, we did a dose titration of GFP-1-3 and test gene editing efficiency. In both flow cytometry and surveyor assay we found that at various concentrations (1 ug/ml, 0.5 ug/ml, 0.25 ug/ml and 0.05 ug/ml) of sgRNAs, GFP-2 is consistently more potent than GFP-1, and GFP-3 holds similar potency of GFP-1. It indicates that chemical modifications improve efficiency of sgRNA.

Figure 5A:
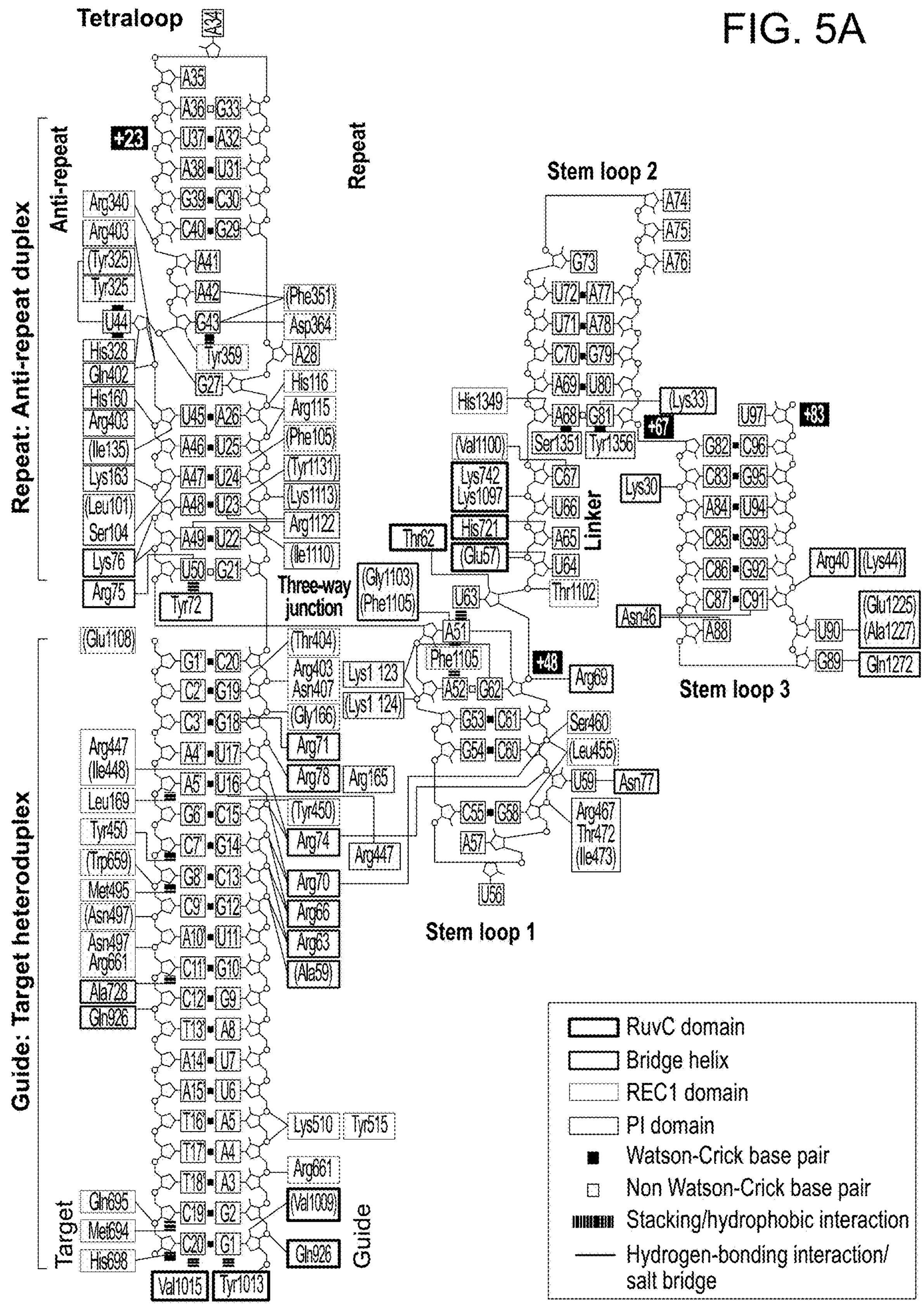
Figure 6A:
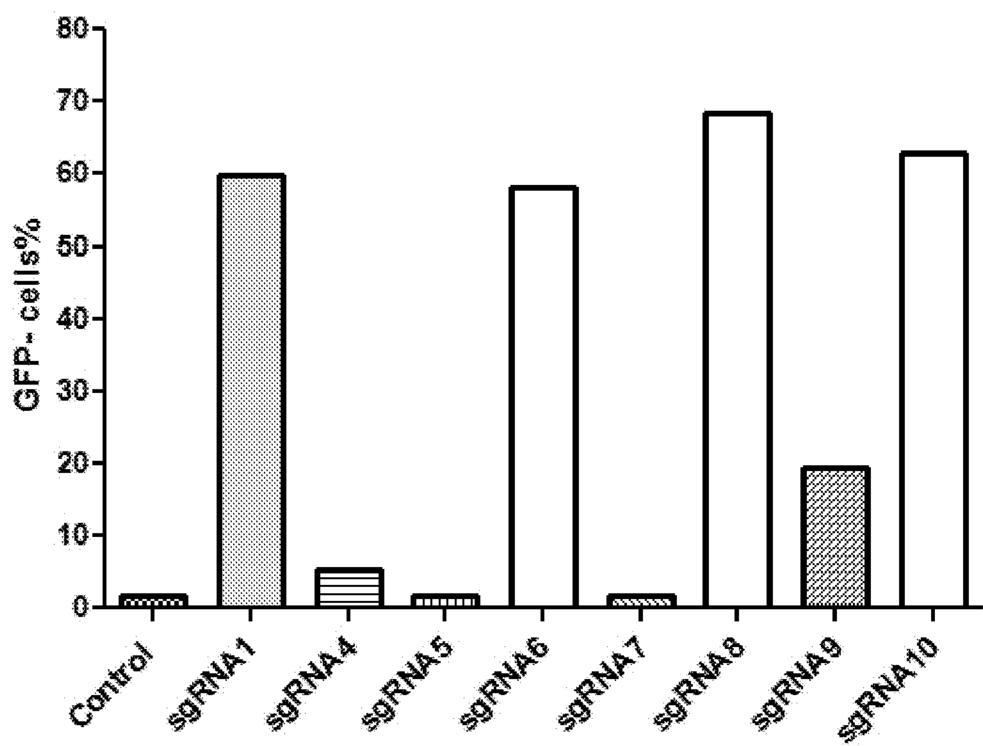
FIGS. 6A, 6B, and 6C depict the results of Cas9 interaction of various sgRNAs.
Figure 6B:
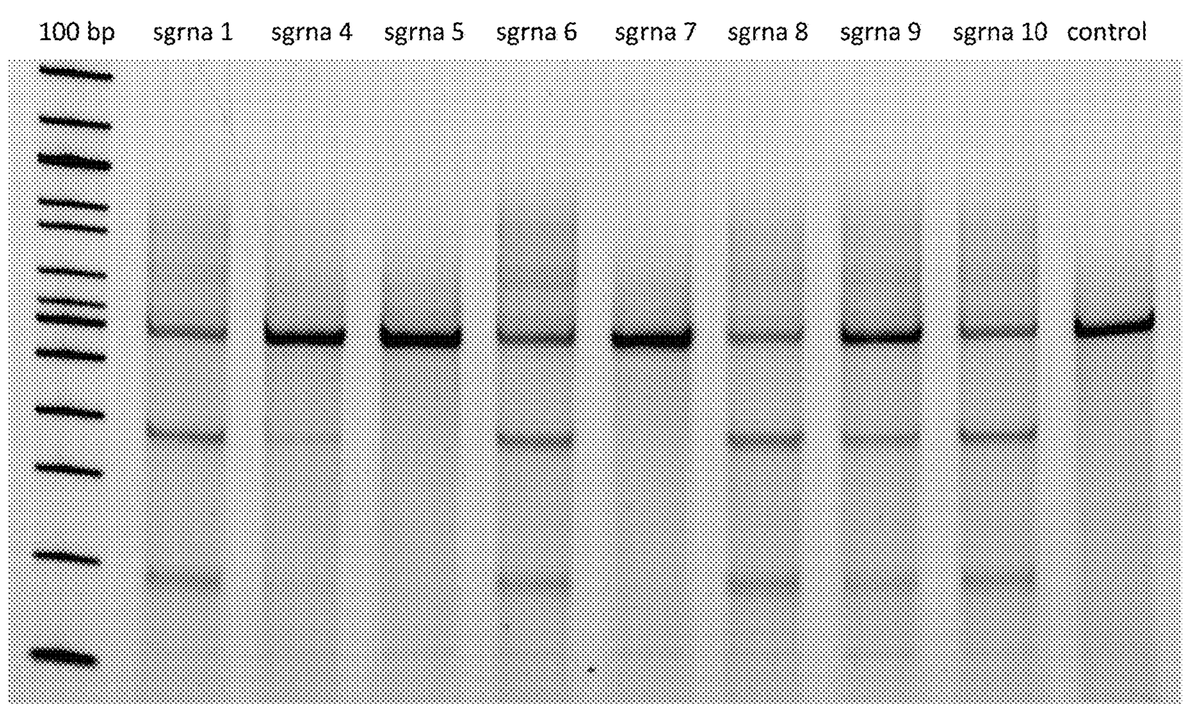
Figure 6C:
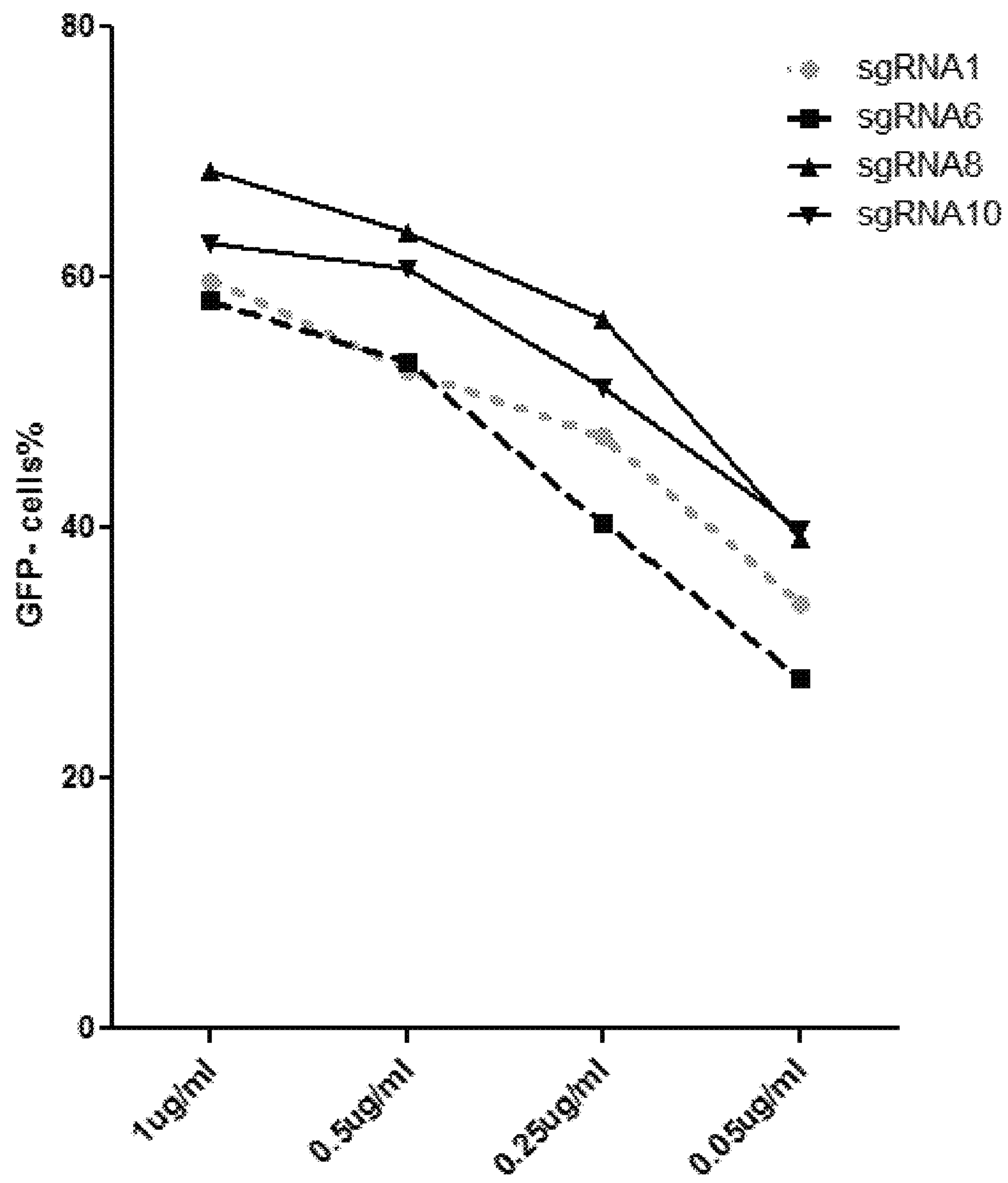

With our initial experiments as proof-of-concept that sgRNA can be chemically modified, and chemical modification can increase potency of sgRNAs, we explored which positions of sgRNA were sensitive to chemically modifications. We researched sgRNA/Cas9 structure[3] (FIG. 5A), and found that multiple RNA nucleotides interact with Cas9 protein. In particular, nucleotides 1, 12, 15, 16, and 19 of the specific DNA binding region; 2, 3, 4, 23, 24, 25, 27, 31, 38, and 42 of the Cas9 binding domain; and 1, 2, 3, and 6 of the transcription terminator region hold 2' position of RNA to interact with Cas9 protein. We hypothesized that substituting one or multiple of those nucleotides at 2' position will affect the activity of sgRNAs. To test our hypothesis, we designed additional seven sgRNAs (GFP 4-10; FIG. 5B). Among them, GFP-4 contains five 2'-Fluoro modified RNA, GFP-5 contains seven and GFP-7 contains eleven at those nucleotides interacting with 2' positions. Among those nucleotides, only four nucleotides in GFP-7 are in DNA binding regions. Those modifications abolish most activity of GFP-4, and totally abolish activity of GFP-5 and GFP-7 (FIGS. 6A and 6B). This data indicates that modifications of 2' of those interacting nucleotides at regions other than DNA binding are highly sensitive. In contrast, GFP-6 and GFP-8 has four 2'-Fluoro modified RNA of those nucleotides interacting with 2' positions in the DNA binding region. It appears that modifications in this region, even at 2' position of Cas9 interacting nucleotides, will not affect potency of sgRNA, as evidenced by full or enhanced activity of GFP-6 and GFP-8. GFP-8 is more potent than GFP-1, which indicates that substituting 2'-Fluoro modified RNA at proper nucleotides enhances its activity (FIGS. 6A-6C). This data suggests that modifications at those 2' positions, which interact with Cas9 protein in the DNA binding region, may not decrease CRISPR activity.

To test whether other 2' modifications at those nucleotides interacting Cas9 with 2' are tolerated, we substituted native RNA with 2' O-Methyl RNA at those positions in GFP-9. We found that with two nucleotides substitution of those interacting nucleotides significantly decrease its activity. It indicates 2' sensitivity is not restricted to 2'-Fluoro modification. Further, we substituted multiple native RNA with 2' O-Methyl RNA without modifying those interacting nucleotides in GFP-10. GFP-10 works more potent than unmodified one GFP-1, as evidenced by flow cytometry at various dose of sgRNAs (FIG. 6C). It indicates that sgRNA modification can be reached by various chemical modifications alone, or with their combinations.

Example 2 Ex Vivo Approach to Target CCR5 and/or CXCR4 at Hematopoietic Stem Progenitor Cells, Hematopoietic Stem Cells or T Cells [PROPHETIC]

We selected CCR5, which encodes a co-receptor for HIV entry. Its disruption increases the survival of CD4 T cells; persons homozygous for a 32-bp deletion (delta32/delta32) in CCR5 are resistant to HIV infection. In vitro, CD4 T cells from such persons are highly resistant to infection with CCR5-using strains of HIV, which are the dominant strains in vivo. Moreover, persons who are heterozygous for CCR5 delta32 and who have HIV infection have a slower progression to the acquired immunodeficiency syndrome. Furthermore, the effectiveness of blocking or inhibiting CCR5 with the use of small-molecule inhibitors has been shown in humans. Finally, one person who underwent allogeneic transplantation with progenitor cells homozygous for the CCR5-delta32 deletion has remained off antiviral therapy for more than 4 years, with undetectable HIV RNA and proviral DNA in the blood, bone marrow, and rectal mucosa. Thus, report the partial induction of acquired genetic resistance to HIV infection after targeted gene disruption[4].

X-CCR5 refers to autologous CD4+ enriched T cells that have been transduced ex vivo with X-CCR5, which are CRISPR in mRNA, DNA or protein format and chemically modified sgRNA targeting human gene CCR5, resulting in modification of the CCR5 gene. CRISPR target sequence found specifically in the region encoding the first transmembrane domain of the CCR5 gene, just upstream from the naturally occurring CCR5-Δ32 mutation. Expression of the CCR5-specific CRISPR induces a double stranded break in the cell's DNA which is repaired by cellular machinery leading to random sequence insertions or deletions in most of transduced cells. These insertions and deletions disrupt the CCR5 coding sequence leading to frameshift mutation and termination of protein expression. Patients will undergo a 10 liter leukapheresis to collect $>10^9$ white blood cells. The leukapheresis product will be enriched for CD4+ cells by depleting monocytes via counter flow centrifugal elutriation, and by magnetically depleting CD8+ T-cells, both employing a single-use closed-system disposable set. The resulting enriched CD4+ T-cells will be activated with anti-CD3/anti-CD28 mAb coated paramagnetic beads and transduced with Cas9/chemically modified sgRNA. Cells will then expanded and cultured. T-cell expansion will continue after transfer to a WAVE Bioreactor for additional expansion under perfusion conditions. At the end of the culture period, cells are depleted of magnetic beads, washed, concentrated, and cryopreserved. Patients will be infused with X-CCR5, consisting of autologous CD4-enriched T cells that have been modified at the CCR5 gene locus by CRISPR/chemically modified sgRNA.

It is expected that chemically modified sgRNA exerts higher potency, less off-target effect, less unwanted immune-stimulatory effect. It will lead to higher yield and more viable of T cells. It is expected that chemically modified sgRNA can be introduced into T cells via non-viral methods, including lipid and polymer transfection, electroporation, cell-penetrating peptides, Cell Squeeze (SQZ Biotech), or through nanoparticle exposure to T-cells ex vivo. The methods described herein, disclosing sgRNA delivery with Cas9 delivery in various formats, (either viral or nonviral methods), create superior potency and minimized off-target effect.

CD4+ T cells modified by CCR5-targeted CRISPR will provide a feasible approach to treat HIV. However, disruption of CCR5 in human CD34+ hematopoietic stem/progenitor cells (HSPCs) is likely to provide a more durable anti-viral effect and to give rise to CCR5−/− cells in both the lymphoid and myeloid compartments that HIV-1 can infect[5]. To evaluate this approach, we will optimize the delivery of CCR5-specific Cas9/chemically modified sgRNA to human CD34+ HSPCs, and transplant the modified cells into patients, as described above. It will have better efficiency than unmodified sgRNAs. It may enable long-term control of HIV-1 in infected individuals.

Generally, CCR5 serves as the predominant co-receptor for HIV entry during initial transmission and through the early stages of infection. However, once HIV-1 infection is established, it is able to choose CXCR4 as an alternative co-receptor. With the emergence of CXCR4 tropic viruses, CCR5 disruption will no longer be able to protect against the spread of HIV-1. For this reason, targeted CXCR4 disruption is also being considered as an additional strategy for inhibiting HIV-1 infection. Delivery of Cas9/chemically modified sgRNAs to target CXCR4 alone or Cas9/chemically modified sgRNAs to target both CCR5 and CXCR4 in either T cells or HSPCs may provide long-term control of HIV-1 in infected individuals.

Example 3 Ex Vivo Approach for Immunotherapy: Generate CAR T Cells; Editing the Genome of T-Cells [PROPHETIC]

Artificial T cell receptors (also known as chimeric T cell receptors, chimeric immunoreceptors, chimeric antigen receptors (CARs)) are engineered receptors, which graft an arbitrary specificity onto an immune effector cell. Typically, these receptors are used to graft the specificity of a monoclonal antibody onto a T cell; with transfer of their coding sequence facilitated by retroviral vectors. Artificial T cell receptors are under investigation as a therapy for cancer, using a technique called adoptive cell transfer. T cells are removed from a patient and modified so that they express receptors specific to the particular form of cancer. The T cells, which can then recognize and kill the cancer cells, are reintroduced into the patient. Phase I clinical studies of this approach have shown efficacy. The selection and modification of CAR T cells are described in U.S. Pat. No. 9,102,761 that is incorporated by reference in its entirety. T cells that are isolated from a patient may be transfected with any of the compositions disclosed herein by any of the disclosed methods.

Combining the adoptive transfer of tumor-specific T-cells with therapies that increase their anti-tumor capacity is viewed as a promising strategy to improve treatment outcome. The ex vivo genetic engineering step that underlies T-cell re-direction offers a unique angle to combine antigen receptor delivery with the targeting of cell-intrinsic pathways that restrict T-cell effector functions. A CRISPR complex can disrupt gene expression in T-cells in order to enhance effector functions or to bypass tumor immune suppression. This approach would avoid the systemic administration of compounds that disrupt immune homeostasis, potentially avoiding autoimmune adverse effects, and could improve the efficacy of T-cell based adoptive therapies[6]. CAR T cells therapy rely on the infusion in a patient's circulation of ex vivo expanded tumor-infiltrating lymphocytes (TILs) or peripheral blood T-cells transduced with viral vectors expressing a tumor-specific antigen receptor. This engineering step offers the opportunity to transfer additional genetic material conferring T-cells with enhanced anti-tumor activity. Targeted genome editing relying on viral gene transfer could readily be combined with the delivery of antigen receptors at little additional cost in one unique therapeutic entity. Cell-intrinsic disruption of immune checkpoints in tumor-specific T-cells is likely to display a better safety profile than the systemic administration of blocking agents. The co-inhibitory receptor PD-1 will be expressed on activated T-cells and its engagement by its two known ligands PD-L1 and PD-L2 will inhibit proximal signaling events triggered by TCR stimulation through recruitment of the phosphatase SHP-2. Several other co-inhibitory receptors expressed by T-cells qualify as targets for gene editing coupled with antigen receptor delivery. For instance, several co-inhibitory receptors use the tyrosine phosphatases SHP-1 and/or SHP-2 to inhibit T-cell activation. Inhibition of SHP-1/2 expression may therefore confer resistance to several checkpoint pathways used by tumors. All those genetic modification in T cells can be reached with high efficiency and less off-target effect by using chemically modified sgRNA and Cas9. Moreover, CRISPR-mediated homology directed repair (HDR) by chemically modified sgRNA in human immune cells could allow therapeutic editing of disease mutations in patient cells and introduction of specific sequences, including chimeric T cell receptors, into targeted locus.

So far Car-T cells only work as an autologous treatment, where the T cells are isolated from the patient, engineered ad hoc, grown to great numbers, and reintroduced to that same patient. Otherwise, if the T cells came directly from another patient, they would likely turn against the body, inducing graft versus host disease (GVHD). The cost of such operation is extremely high. It is feasible to develop an off-the-shelf, or allogeneic, CAR T-cell product that would not cause GHVD but uses T-cells expanded from non-autologous donors or sources. To do this, we will engineer cells so that they don't attack the cells in the body and vice versa by exposing the cells to a CRISPR complex that eliminate T-cell markers that identify the T cells as foreign, namely, human leukocyte antigen (HLA) proteins using chemically modified sgRNA and Cas9. It is feasible to delete expression of the entire class of HLA type II molecules and/or part of HLA type I proteins by exposing the cells with one or more modified sgRNAs targeting the HLA type II and/or HLA type I protein.

Example 4 Ex Vivo Approach for Correction of Diseases Mediated by Hematological Stem Cells (HSCs) [PROPHETIC]

HSC-mediated diseases include sickle-cell disease (SCD), beta thalassemia etc[7]. Disorders of β-globin such as β-thalassemia and SCD are among the most common monogenic defects in the world. About 275,000 babies with SCD and 56,000 babies with β-thalassemia are born each year. In β-thalassemia, mutations affecting every step in β-globin expression have been reported, from initiation of transcription to posttranslational modification. These defects either result in decreased β-globin production (β+) or an absence of β-globin production (β0). The decreased β-globin synthesis in β-thalassemia results in excess of alpha globin, leading to intracellular precipitation of excess unbound alpha globin chains in erythroid precursors. This condition results in red cell membrane damage, early cell death, and ineffective erythropoiesis. Despite aggressive iron chelation, iron overload leading to tissue damage and organ toxicity is the leading cause of morbidity and mortality in these patients. Inadequate transfusions lead to massive erythroid hyperplasia, extramedullary hematopoiesis, splenomegaly, and failure to thrive. SCD is caused by a point mutation (A-T) in the sixth codon of the β-globin gene. This genetic defect results in defective β-globin, which polymerizes in the deoxygenated state leading to change in shape of an otherwise round, doughnut-shaped, flexible red blood cell (RBC) into a hook/sickle-shaped, inflexible RBC that obstructs micro-vessels and has reduced survival from repeated cycles of sickling and unsickling. SCD is characterized clinically by varying degree of anemia, and episodic vaso-occulsive crisis leading to multiorgan damage and premature death. Despite improvement in the supportive care, the estimated life expectancy for patients with SCD is significantly foreshortened; the median age at death was 42 years for men and 48 years for women with SCD. At present, allogeneic hematopoietic stem cell transplant (HCT) is the only established definitive curative option for patients with β-thalassemia and SCD. In both these diseases, the overall survival following matched sibling donor (MSD) HCT is excellent in children, with disease-free survival rates greater than 80%, and a graft failure rate of about 10%. However, most patients do not have a human leucocyte antigen (HLA)-matched sibling. In SCD, it is estimated that less than 14% have a matched sibling and, in the United States. Delivery of chemically modified sgRNA with Cas9 or any other peptide with Cas9-like function into hematological stem cells or iPSC to correct those SCD and beta thalassemia disease genes can cure those patients without a human leucocyte antigen (HLA)-matched sibling.

Example 5 Nanoparticle Delivery and Conjugate Delivery of Chemically Modified sgRNAs to Hepatocytes In Vivo for Treating Liver Related Diseases [PROPHETIC]

Nanoparticles were formulated using controlled microfluidic mixing systems with chemically modified sgRNA to reduce TLR (Toll-like receptor) responses, increase its stability and potency in vivo and reduce off-target effect. It can be co-delivered with Cas9 mRNA nanoparticles. It will efficiently target any gene in hepatocytes. We take PCSK9 as an example here. Proprotein convertase subtilisin/kexin type 9 (PCSK9) has emerged as a promising therapeutic target for the prevention of coronary heart disease (CHD). A gene specifically expressed in and secreted from the liver and believed to function primarily as an antagonist to the LDL receptor (LDLR), PCSK9 was originally identified as the cause of autosomal dominant hypercholesterolemia in some families, with gain-of-function mutations in the gene driving highly elevated LDL-C levels and premature CHD[8]. In subsequent studies, individuals with single loss-of-function mutations in PCSK9 were found to experience a significant reduction of both LDL-C levels (≈30-40%) as well as CHD risk (88%). Notably, even individuals with 2 loss-of-function mutations in PCSK9—resulting in ≈80% reduction in LDL-C levels—seem to suffer no adverse clinical consequences. This observation suggests that therapies directed against PCSK9 would offer cardiovascular benefit without any accompanying undesirable effects. Just 10 years after the discovery of PCSK9, PCSK9-targeting monoclonal antibodies are being evaluated in clinical trials. Yet even if these antibody-based drugs prove effective, their effects on LDL-C are short-lived, and patients will have to receive injections of drugs every few weeks, which will limit their use as preventative therapy.

As a proof-of-concept experiment for targeting PCSK9 using chemically modified sgRNAs, we designed sgRNAs again PCSK9 (mus) using following guide sequences: 5' GCACCCATACCTTGGAGCAA 3'; 5' CCCATACCTTGGAGCAACGG 3', 5' GCTCGCCCTCCCGTCCCAGG 3'. We chemically modified 3 sgRNAs containing those guide sequences, formulate with polymer or lipid nanoparticles (such as C12-200 particles) and injected with Cas9 mRNA particles. Those particles will deliver chemically modified sgRNA and mRNA into hepatocytes, disrupt PCSK9 genes and reduce LDL-C levels. Moreover, a range of metabolic liver diseases and hemophilia can also be treated using chemically modified sgRNAs. A DNA donor can be delivery via viral or non-viral method with sgRNA and Cas9 mRNA particles. It will reach higher efficiency of gene editing than delivery of unmodified sgRNA, avoid immune response and decrease off-target effect.

Dynamic PolyConjugates (DPCs) and triantennary N-acetylgalactosamine (GalNAc) conjugates and cholesterol conjugate can delivery small interfering RNA (siRNA). The chemically stabilized siRNA is conjugated at the 3 terminus of the passenger strand. It allows delivery of siRNA with high efficiency to hepatocytes. We will conjugate chemically modified sgRNAs at 5 or 3 terminus or any position within the sgRNAs, e.g. several loops region outside Cas9 binding pocket, as DPCs PolyConjugates, GalNAc and cholesterol conjugates. Those conjugates are stable in serum, efficiently deliver sgRNAs into hepatocytes, and minimized immune response. The Cas9 complex including modified sgRNA can be delivered in mRNA, DNA or protein format as viral delivery or non-viral delivery including nanoparticles and conjugate, etc.

Example 6 Nanoparticle Delivery and Conjugate Delivery of Chemically Modified sgRNAs In Vivo for Treating Cancer and Diseases Outside Liver [PROPHETIC]

Chemically modified sgRNAs will allow efficiently genome editing at in vivo level. Combining with a potent Cas9 delivery system, it will lead to high efficiency gene editing at tissue of interest, such as tumor. In particular, it could lead to knock out one more multiple mutated cancer driver genes in tumor tissue, e.g. cMyc, Kras, Yap1, etc. It will provide a feasible and novel way for cancer therapy. Moreover, it is feasible to target other targets in tumor, such as molecules involved in angiogenesis and tumor immunosuppression environment, including genes of IL-10, VEGFR, CTL4, etc. Conjugated or nanoparticle encapsulated chemically modified sgRNA will execute much higher potency than unmodified sgRNAs into tumor tissues.

Conjugate delivery of sgRNA using cholesterol conjugate will allow delivery of sgRNAs into tissues outside liver, e.g. muscles. It will allow gene editing at skeletal muscles, and provide cures for muscle related diseases, including Duchenne muscular dystrophy, Becker muscular dystrophy, Congenital muscular dystrophy, Emery-Dreifuss muscular dystrophy, Facioscapulohumeral muscular dystrophy, Limb-girdle muscular dystrophy, Myotonic muscular dystrophy, Oculopharyngeal muscular dystrophy, etc.

Gene name

*Homo sapiens* dystrophin (DMD)

RefSeq

NM_000109

SgRNA sequences for modification of the DMD gene in human cells

```
                                  (SEQ ID NO: 140)
GCAAACTTGATGGCAAACCG

                                  (SEQ ID NO: 141)
GCACCTGAAGAGTATCACAG

                                  (SEQ ID NO: 142)
TGTCTTGTAAAAGAACCCAG
```

All those above applications can be applied by also using chemically modified tracrRNA/crRNA duplex in place of a single sgRNA.

Example 7: sgRNA Chemical Modification for Efficient Gene Editing

We disclose methods for replacing ribonucleic acid (RNA) with deoxyribonucleic acid (DNA) of crRNA and single guide RNA (sgRNA) of CRISPR system. We designed and chemical synthesized crRNA containing deoxyribonucleic acid (DNA) at 20-nucleotide (nt) target region of the crRNA. We showed that partially replacing RNA in sgRNA with DNA allows efficient genome editing. The CRISPR/Cas9 system is described as RNA-guided nucleases. Here we show as a proof-of-concept that we can engineer crRNA to realize DNA/RNA guided nucleases by Cas9 or peptides with Cas9-like function. Due to the lower binding affinity of DNA/DNA than RNA/DNA, incorporate DNA into target region of crRNA allows lower binding affinity of crRNA to genomic DNA sequences, thus it tolerate mismatches less and significantly decreases off-target effect of CRISPR. This method is highly clinically relevant.

The type II bacterial clustered, regularly interspaced, palindromic repeats (CRISPR)-associated (Cas) system has been engineered into a powerful genome editing tool consisting of the Cas9 nuclease or other peptide with nuclease-like activity and a single guide RNA (sgRNA). The sgRNA targets *S. pyogenes* Cas9 (spCas9) or similar functional peptides to genomic regions that are complementary to the 20-nucleotide (nt) target region of the sgRNA and that contain a 5'-NGG-3' protospacer-adjacent motif (PAM). Double-stranded DNA breaks generated by Cas9 or similarly functioning peptides at target loci are repaired by non-homologous end-joining or homology-directed repair (HDR). The efficient delivery of the CRISPR-Cas complex is a key challenge for its therapeutic application. The clinical use of CRISPR-Cas9 requires the discovery and development of safer and more effective delivery systems. Toward this end, we now develop methods of RNA/DNA of crRNA to allow applications for different type of in vitro and ex vivo applications, and for embryo injections, as well as for in vivo delivery applications. Such modifications of crRNA can be used for different CRISPR system, such as *Staphylococcus aureus* (saCas9), *Streptococcus* thermophiles Cas9 (stCas9) or different Cas systems which recognize sgRNAs (such as, for example, Cas1 through Cas9). Such chemical modifications may also be applied to sgRNA system too.

The crRNA use 20-nucleotide (nt) target region in RNA format to target genomic DNA. It duplexes with tracrRNA, and binds to Cas9 protein or similar functioning peptides to perform genome editing when exposed to the genome DNA at a concentration sufficient to edit or mutate the genome DNA. A sgRNA is a crRNA-tracrRNA chimera with a nucleic acid sequence on a single nucleic acid molecule (FIG. 7). Several crRNA modifications were made (FIG. 8): cRNA-GFP-1 is a chemically synthesized crRNA targeting EGFP protein. It is in native RNA format. TracrRNA is chemically synthesized to allow co-delivery with different crRNAs. crRNA-GFP-3 replaces all 20 RNA nucleotide in crRNA target region with DNA. crRNA-GFP-7, 8, 9, 10, 4, 11, 12, 13, 14 replaces 18, 16, 14, 12, 10, 8, 6, 4 and 2 ribonucleotides in crRNA genomic target region with deoxyribonucleotides, respectively, starting at 5' end.

To test the effectiveness of these modifications, HEK 293 cells were engineered to express EGFP and spCas9 (FIG. 9). tracrRNA and various crRNA were introduced to cells via transfection protocols and FACS was performed 5 days after transfection. sgRNA1, which is chemically synthesized full length single guide RNA, is served as a positive control. Replacing up to 12 out of 20 RNA molecules with DNA nucleotides allows efficient genome editing. However, replacing 14 or more of ribonucleotide with deoxyribonucleotides abolishes its effect.

We can reach high efficiency gene editing using DNA/RNA guided Cas9 rather than RNA guided Cas9 RNAs. Such strategy can be used for other genome editing systems of CRISPR. It is possible to decrease off-target effect of such system due to lower binding affinity of DNA/DNA than RNA/DNA. DNA is more stable than RNA, thus it is possible to increase stability of "guide nucleotide" via RNA/DNA design.

REFERENCES

1. Deleavey, G. F. & Damha, M. J. Designing chemically modified oligonucleotides for targeted gene silencing. *Chem Biol* 19, 937-954 (2012).
2. Marshall, W. S. & Kaiser, R. J. Recent advances in the high-speed solid phase synthesis of RNA. *Current opinion in chemical biology* 8, 222-229 (2004).
3. Anders, C., Niewoehner, O., Duerst, A. & Jinek, M. Structural basis of PAM-dependent target DNA recognition by the Cas9 endonuclease. *Nature* 513, 569-573 (2014).
4. Tebas, P. et al. Gene editing of CCR5 in autologous CD4 T cells of persons infected with HIV. *N Engl J Med* 370, 901-910 (2014).
5. Holt, N. et al. Human hematopoietic stem/progenitor cells modified by zinc-finger nucleases targeted to CCR5 control HIV-1 in vivo. *Nat Biotechnol* 28, 839-847 (2010).
6. Lloyd, A., Vickery, O. N. & Laugel, B. Beyond the antigen receptor: editing the genome of T-cells for cancer adoptive cellular therapies. *Frontiers in immunology* 4, 221 (2013).

7. Chandrakasan, S. & Malik, P. Gene therapy for hemoglobinopathies: the state of the field and the future. *Hematology/oncology clinics of North America* 28, 199-216 (2014).

8. Ding, Q. et al. Permanent alteration of PCSK9 with in vivo CRISPR-Cas9 genome editing. *Circ Res* 115, 488-492 (2014).

Example 8: Chemical Modifications of the Fixed Region of sgRNA (the Cas-Binding Domain and the Transcription Terminator Domain)

To further understand the rules involved in the chemical modifications of sgRNA, we separated the sgRNA into a variable region and a fixed region. The variable region is the DNA-binding domain, and can vary to target different regions in the genome. The fixed region is 21nt to 101nt, including the Cas protein binding sequences (21nt-62nt) and the tail region (63nt-101nt) (FIG. 10*a*).

Figure 10C:
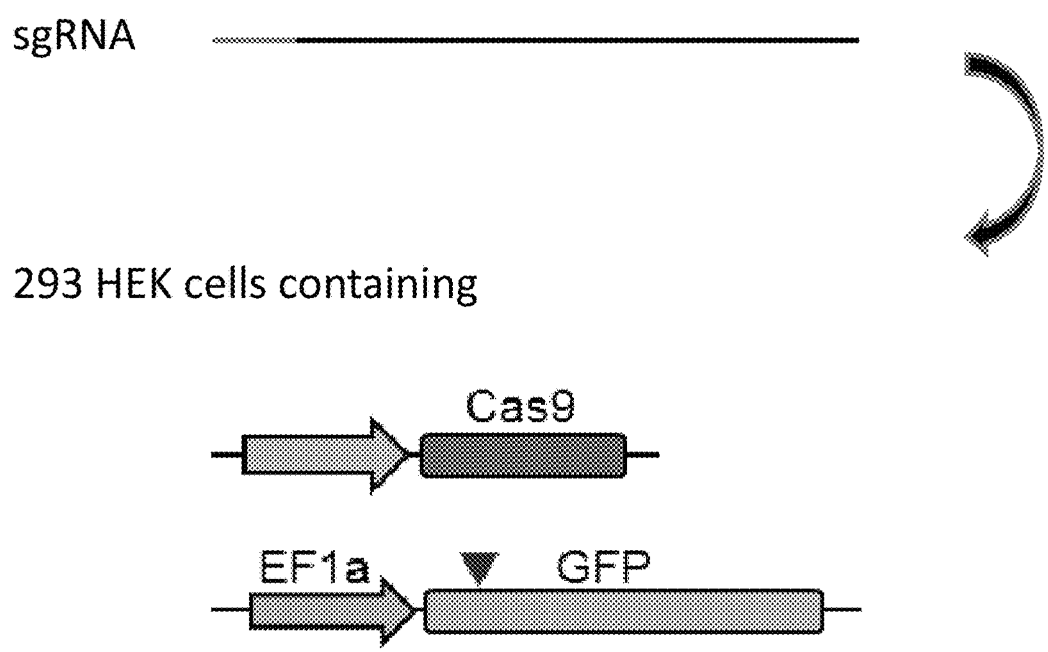
Figure 10D:
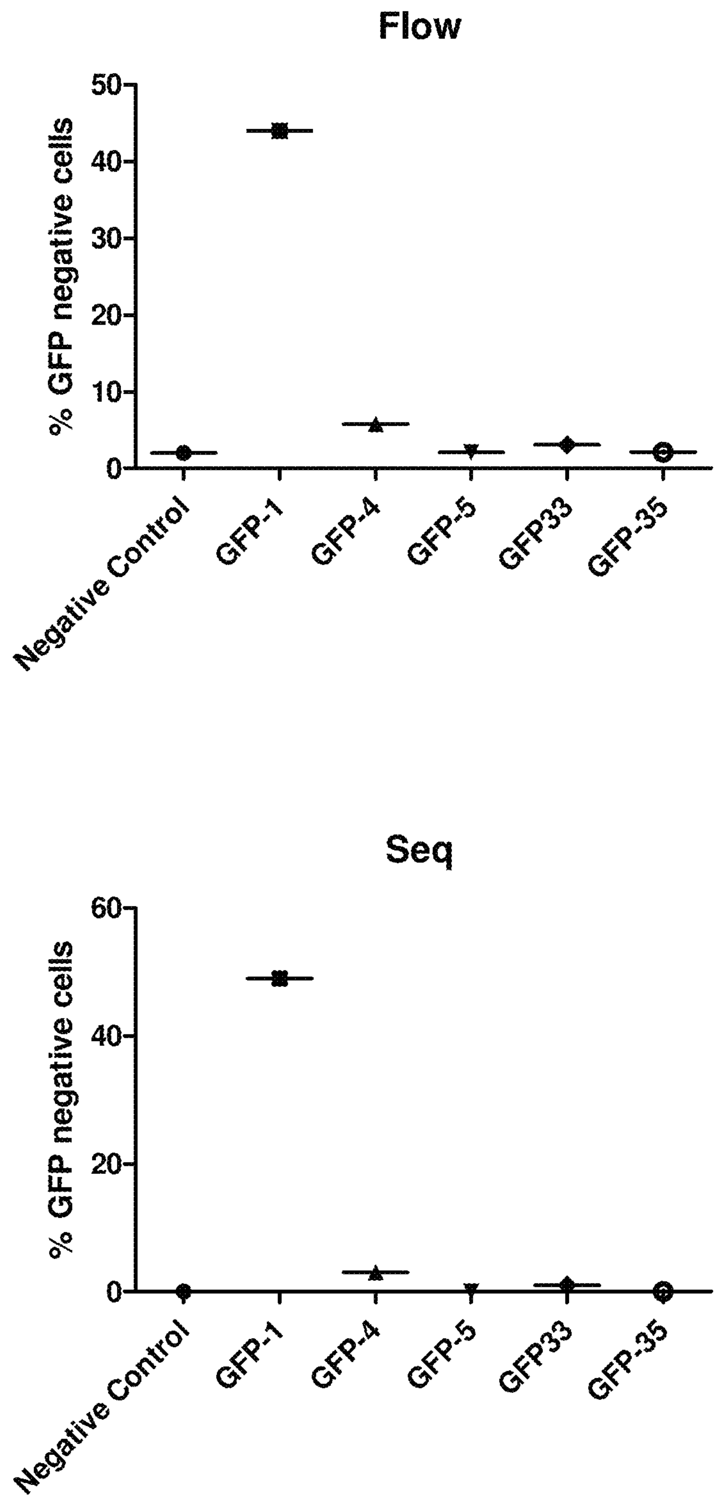

We first synthesized sgRNAs containing a guide sequence targeting GFP. The sgRNA 1 is without any chemically modification as defined as an unmodified, native strand (GFP-1; SEQ ID NO:1). As illustrated by FIG. 10*b*, sgRNA 4 (GFP-4; SEQ ID NO:4) substitutes all U and C in the Cas binding region with 2'-Fluoro modified RNA. We used a cell reporter system to test the efficiency of sgRNAs. We engineered HEK293 cells to express EGFP and spCas9 (FIG. 10*c*). Introducing an effective sgRNA into the cells induces indel formations at the GFP site, causing frame shifting of coding region and destruction expression of the GFP in cells (FIG. 10*c*). As showed in FIG. 1*d*, while GFP-1 was able to effectively generate GFP in negative (−) cells, the "U" and "C" modification on Cas9 binding region nearly abolished the effect of GFP-4. Further, when we substituted all U and C in the Cas9 binding region and the tail region (GFP-5, FIG. 10*b*), the efficiency of this sgRNA was diminished (FIG. 10*d*). To test whether the fixed region could tolerate other commonly used modifications, we introduced 2' O-Methyl RNA modifications (GFP-35, FIG. 10*b*) or phosphorothioate RNA modifications (GFP-33, FIG. 10*b*) at all nucleotides in the fixed region. We found that these two full-length modification strategies totally abolish the effect of these sgRNAs (FIG. 10*d*). These data indicate that the fixed region of sgRNA does not tolerate random modification. The flow cytometry results were confirmed by sequence analysis. (FIG. 10*d*).

Figure 10E:
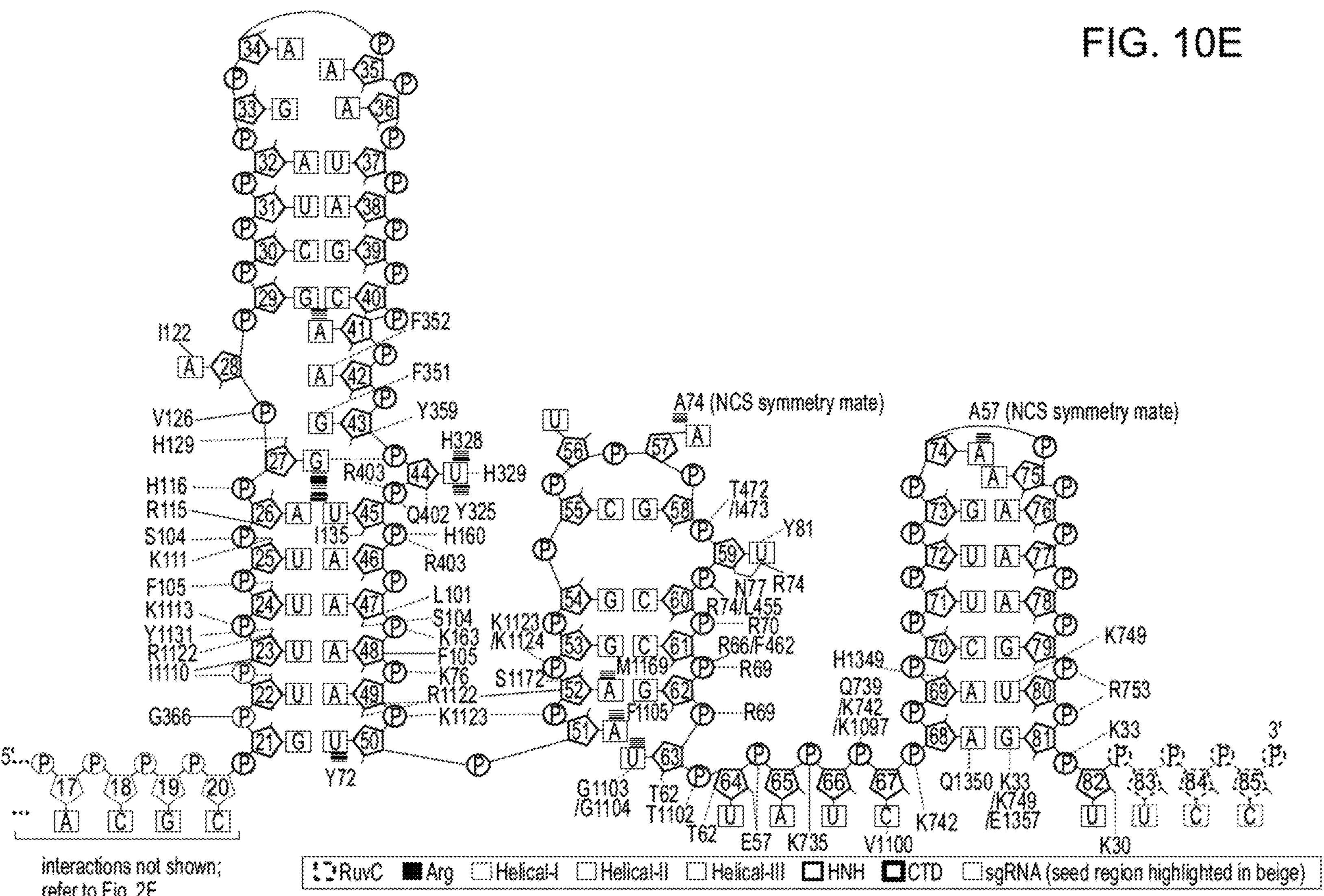
Figure 10E:
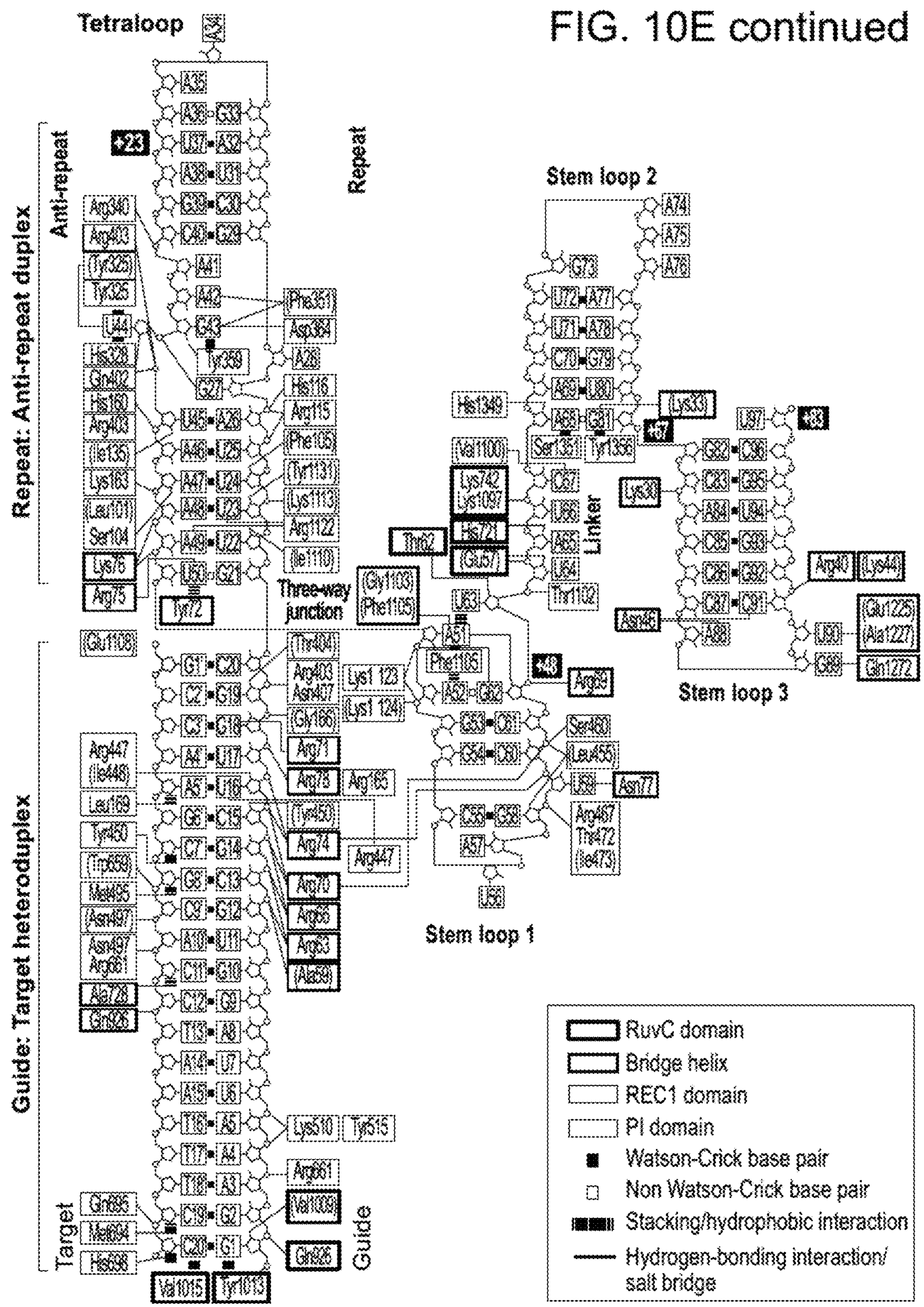
Figure 10F:
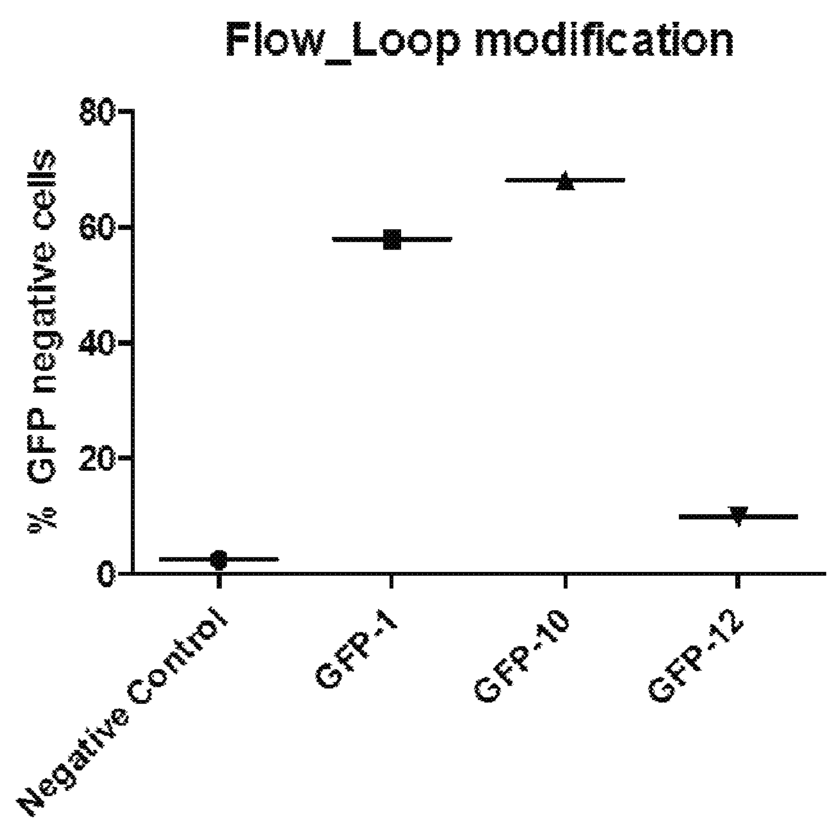

To explore the rules of modification, we introduced the concept of structure-guided design for sgRNA (FIG. 10*e*). According to the structure, we found that two major loops of sgRNAs (tetraloop and stem loop2) were outside of Cas-binding domain and with minimal Cas protein interactions. We hypothesized that these loops might tolerate chemical modifications. Indeed, modifying these two loops with 2' O-Methyl RNA is well tolerated. As a result, we observed a moderate increase of potency (FIG. 10*f*; GFP-10), likely due to such modification increase the stability of sgRNA. In a parallel design, we incorporated 2'-Fluoro modified RNA into these two loops. Surprisingly, the 2'-Fluoro modified RNA in loops abolished the effect of sgRNA (FIG. 10*f* GFP-12). It is possible that the heavy 2'-Fluoro modifications in the loop affects their secondary structures. Thus, we decided to use 2' O-Methyl modification for the following studies in fixed region.

Figure 10G:
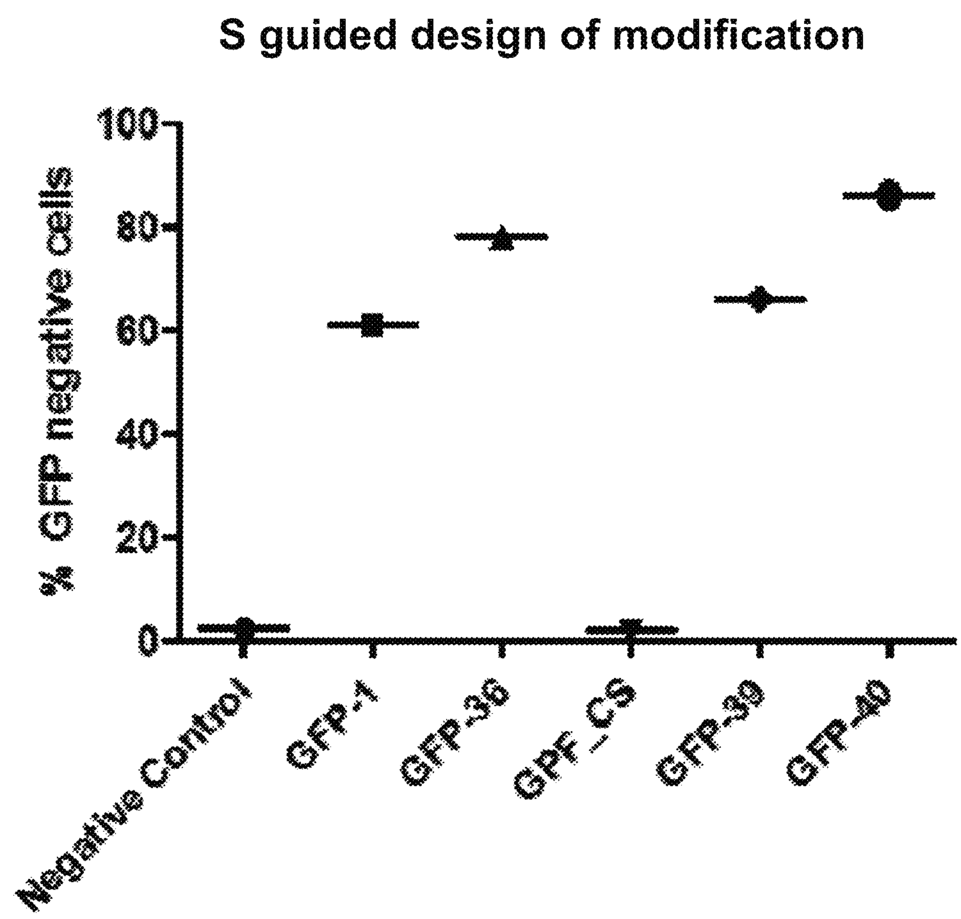

We closely looked into the structures of Cas9/sgRNA complex, and identified that multiple nucleotides in sgRNA interacted with Cas9 protein at the 2' hydroxyl (OH) group presenting in RNA (Table 2). We hypothesized that if we avoided the modification of 2' OH group in these sites but modified the remaining nucleotides, this heavily modified sgRNA could retain its activity. Indeed, the comprehensive, heavily modified sgRNA (GFP-36, FIG. 10*b*), in which 60 out of 81 nucleotides have been modified with 2' O-Methyl modification, significantly increases its genome editing activity in HEK293 cells (FIG. 10*g*). In contrast, a selective 2' O-Methyl modification at those nucleotides with 2' OH group interacting with Cas9 (GPF_CS, defined as "cautious sites" or "conserved sites") or previously full-length modification abolished their genome editing effect (FIG. 10*g*). This data demonstrates for the first time the importance of structure guided design for sgRNA.

Next, we sought to combine two different chemical modifications, the 2' O-Methyl and the phosphorothioate modifications. We found the fully phosphorothioate modification abolished the activity of sgRNA (FIG. 10*d*), and selectively modification at hypothetically Cas9-interacting sites (Table 6) at the fixed region decreases its activity. As a result, we decided to modify a partial tail region of sgRNA with phosphorothioate, which has minimal interaction with Cas9. Indeed, this tail phosphorothioate modified sgRNA maintains its activity with a moderate increase, likely due to enhance of stability (GFP-39). Thus, we decided to combine the phosphorothioate modification of GFP-39 and 2' O-Methyl modification of GFP-36 to generate GFP-40. We found that the combined modification was well tolerated and with a significant increase of efficiency of gene editing (FIG. 10*g*). We performed in vitro cleavage assay, and identified that in vitro cleavage activity is consistent with activity in 293 cells (FIG. 10*h*).

TABLE 6

Cas9 interacts with sgRNA at phosphodiester bond interaction:
Numbers below correspond to nucleotide number within the nucleotide sequence assuming a guide sequence of at least 92 contiguous nucleotides in a molecule comprising the following contiguous nucleotide domains in a 5' to 3' orientation: a DNA-Binding Domain, a Cas-Binding Domain, and Transcription Terminator Domain. Nucleotides numbers below indicate which nucleoside positions flank a phosphorothioate bond that interacts with a Cas protein or peptide with Cas-like activity. For purposes of the disclosure, a nucleotide position comprises a modification if the 3'Carbon of the sugar is bound to the next contiguous nucleoside downstream by a bond other than a natural phosphodiester bond. For example, "1 = 2" is a modification of position 1 of the nucleic acid sequence disclosed below, whereas position 2 is considered unmodified because there is a phosphodiester bond between the nucleosides at positions 2 and 3.

| Within the DNA-binding domain: | | | | | | | | | | | | |
|---|---|---|---|---|---|---|---|---|---|---|---|---|
| 1 = 2 | 3 = 4 | 4 = 5 | 5 = 6 | 11 = 12 | 12 = 13 | 13 = 14 | 14 = 15 | 15 = 16 | 16 = 17 | 17 = 18 | 18 = 19 | 19 = 20 |

TABLE 6-continued

Cas9 interacts with sgRNA at phosphodiester bond interaction:
Numbers below correspond to nucleotide number within the nucleotide sequence assuming a guide sequence of at least 92 contiguous nucleotides in a molecule comprising the following contiguous nucleotide domains in a 5' to 3' orientation: a DNA-Binding Domain, a Cas-Binding Domain, and Transcription Terminator Domain. Nucleotides numbers below indicate which nucleoside positions flank a phosphorothioate bond that interacts with a Cas protein or peptide with Cas-like activity. For purposes of the disclosure, a nucleotide position comprises a modification if the 3'Carbon of the sugar is bound to the next contiguous nucleoside downstream by a bond other than a natural phosphodiester bond. For example, "1 = 2" is a modification of position 1 of the nucleic acid sequence disclosed below, whereas position 2 is considered unmodified because there is a phosphodiester bond between the nucleosides at positions 2 and 3.

| Within the Fixed Region (the Cas-binding Domain and the Transcription Terminator Domain) | | | | | |
|---|---|---|---|---|---|
| 21 = 22 | 23 = 24 | 25 = 26 | 26 = 27 | 27 = 28 | 40 = 41 |
| G = U | U = U | U = A | A = G | G = A | C = A |
| 43 = 44 | 44 = 45 | 45 = 46 | 47 = 48 | 48 = 49 | 49 = 50 |
| G = U | U = U | U = A | A = A | A = A | A = U |
| 51 = 52 | 52 = 53 | 58 = 59 | 59 = 60 | 60 = 61 | 61 = 62 |
| A = A | A = G | G = U | U = C | C = C | C = G |
| 62 = 63 | 63 = 64 | 64 = 65 | 65 = 66 | 66 = 67 | 67 = 68 |
| G = U | U = U | U = A | A = U | U = C | C = A |
| 79 = 80 | 80 = 81 | 81 = 82 | 83 = 84 | 91 = 92 | |
| G = U | U = G | G = U | C = A | C = G | |

Example 9: Chemical Modifications of the Variable Region of sgRNA (the DNA-Binding Domain)

Figure 11B:
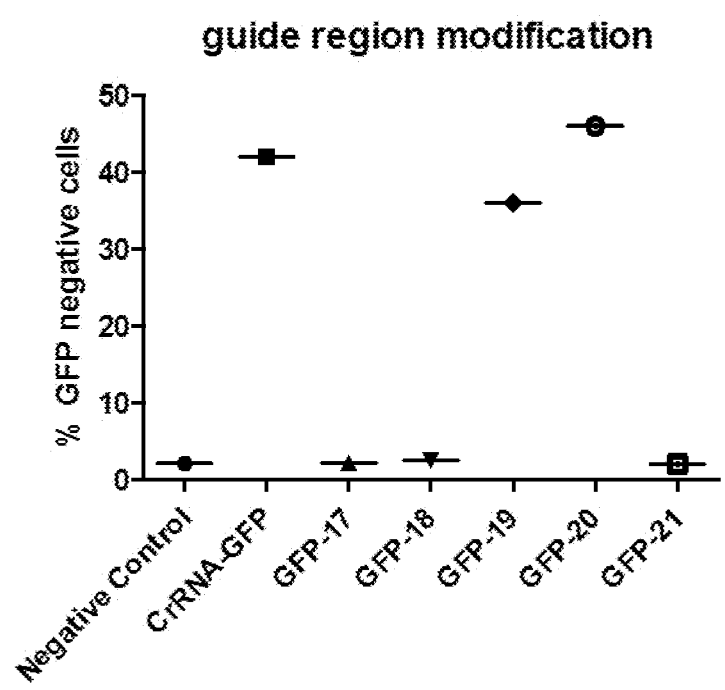

To explore the rules of chemical modification at the variable region (the guide sequences within the DNA bindiong domain), we decided to use crRNA/tracrRNA system to save the cost of synthesis (FIG. 11*a*). We first tested the efficiency of the full-length modification in guide region with 2' 0-Methyl modification (1-20 nt). We found that full-length modification with 2' O-Methyl abolished its effect (GFP-17, FIG. 11*b*). We sought to identify which part of modification caused such diminishment of enzymatic activity. We decided to execute a "half modification" strategy. We modified 1-10nt (as tail region, GFP-19) or 11-20 nt (as the seed region, GFP-18) (FIG. 11*a*). Not surprisingly, we found modification at the seed region abolished the gene editing activity (FIG. 11*b*). Interestingly, the modification at the tail region also decreased its editing efficiency (FIG. 11*b*). We decided to research on the structure of sgRNA/Cas9 at guide sequences. We identified five interaction sites (as "cautious sites") with Cas9 at the 2' hydroxyl (OH) group. Among them, four sites are located at seed region and one at tail region (Table 2). We designed and synthesized two crRNA, both with 5 nucleotides modification at the seed region and 5 at the tail region. The design of GFP-20 avoided modifying the five cautious (or conserved/unmodified) sites. In contrast, GFP-21 intentionally modified all five cautious sites (FIG. 11*a*). We found that GFF-20 fully maintains its activity with a slight increase, but modification on GFP-21 totally abolishes its effect (FIG. 11*b*). This data indicates that the strategy of structure-guided design is also critical for the modification of guide sequences. Importantly, a previous study indicated seed region of guide sequence cannot be modified; in contrast, here we showed the first time the seed region could be heavily modified (5 out 10 nucleotides at seed region were modified; 2 out of 5 nucleotides, which were immediately next to the protospacer adjacent motif (PAM) sequence, were modified).

Figure 11C:
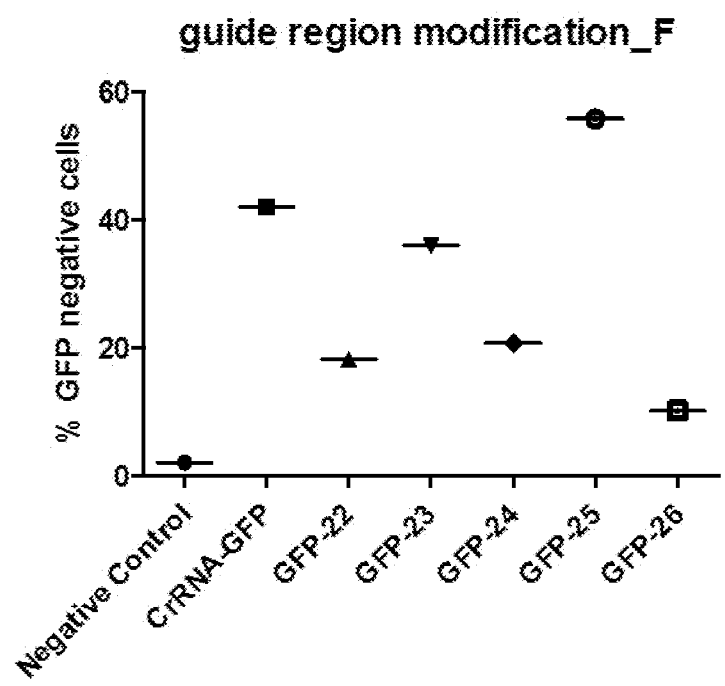

To explore whether other modifications on 2' OH group of nucleotide-binding domain follows the same pattern, we followed the same design pattern but replaced 2' O-Methyl with 2'-Fluoro. We found that the 2'-Fluoro modification on the nucleotide-binding domain followed exact the same pattern of 2' O-Methyl(FIG. 11C). Interestingly, the full-length modification of 2'-Fluoro or "half modification" on seed region significantly decreased but not abolished its activity as in the case of 2' O-Methyl. This observation can be explained by the fact that the size of 2'-Fluoro is smaller than 2' O-Methyl, thus it is possible that modification by 2'-Fluoro introduces fewer disturbances than 2' O-Methyl.

Figure 11D:
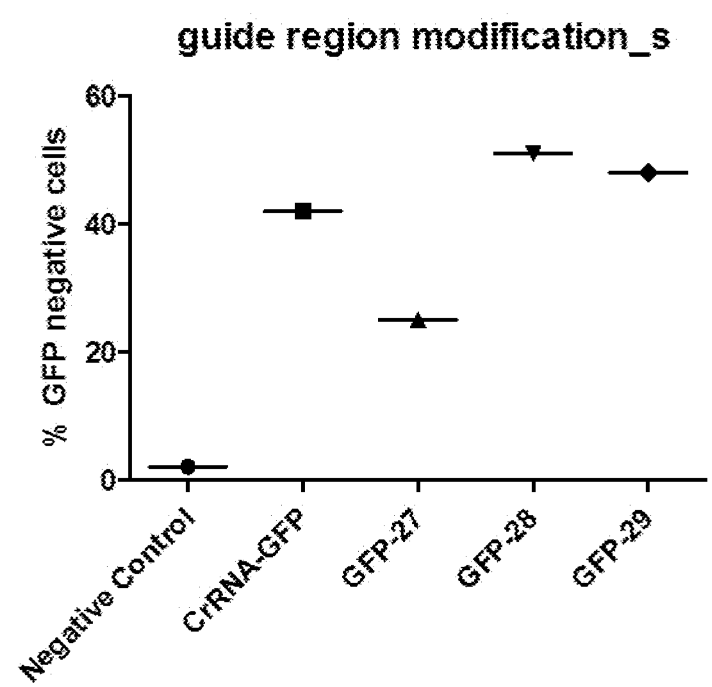
Figure 11E:
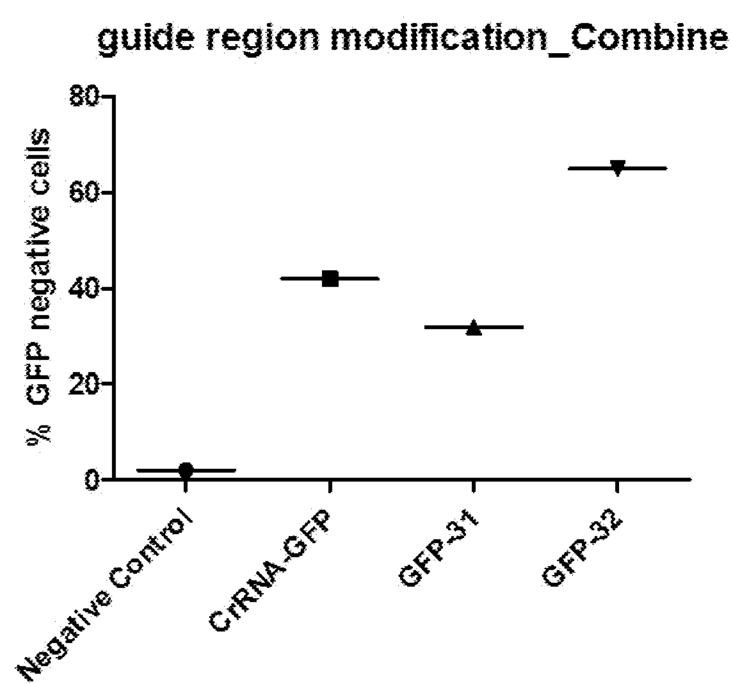

To identify whether we could combine two modifications at the guide sequence, we modified guide sequence with phosphorothioate. We found that full-length modification with phosphorothioate decreases the activity of crRNA (FIG. 11*d*), and "half modification" strategy has minimal impact on its on-target effect. Thus, we decided to add phosphorothioate modification on guide region but to avoid all potential interaction sites with Cas9 (Table 6), and to combine it with 2' O-Methyl or 2'-Fluoro (FIG. 11*e*). The combination of the 2'-Fluoro and phosphorothioate significantly increased its on-target effect, while the combination of the 2' 0-Methyl and phosphorothioate seemed to have less effect. As a result, we decided to carry on combination of the 2'-Fluoro and phosphorothioate on the guide sequences for further studies.

Figure 11F:
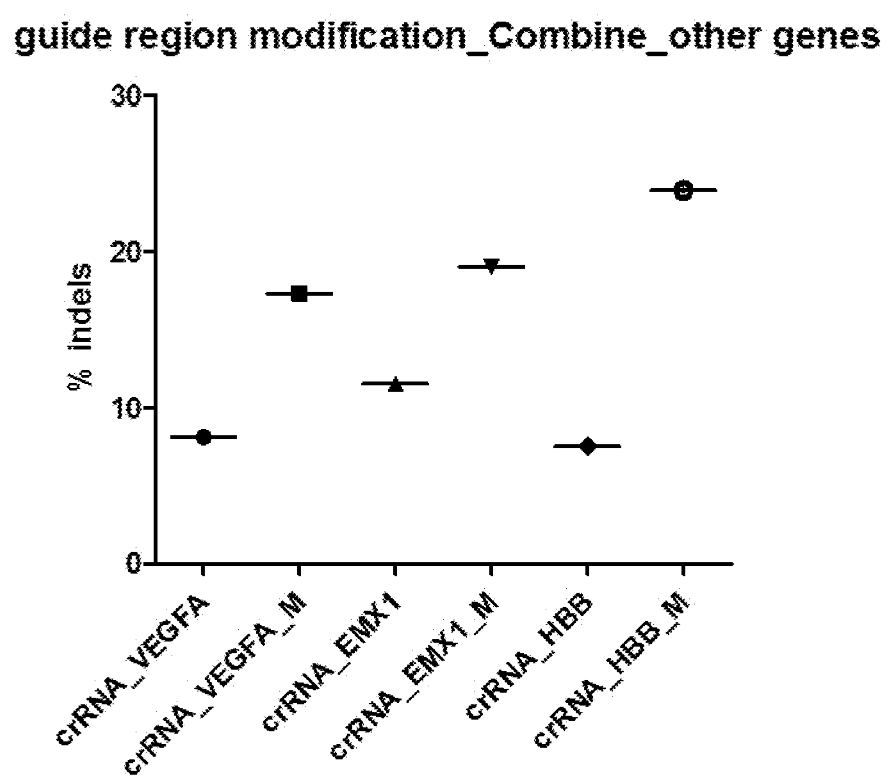

To explore whether such pattern of modification could be applied to various sequences, we synthesized additional crRNA sequences, targeting human gene VEGF-A (Vascular Endothelial Growth Factor A), HBB (hemoglobin subunit beta) and EXM1 (empty spiracles homeobox 1) (FIG. 11*f*). We found that our patterned modification at guide sequence significantly enhanced the gene editing efficiency of all three structurally divergent crRNAs (FIG. 11*f*).

Figure 12B:
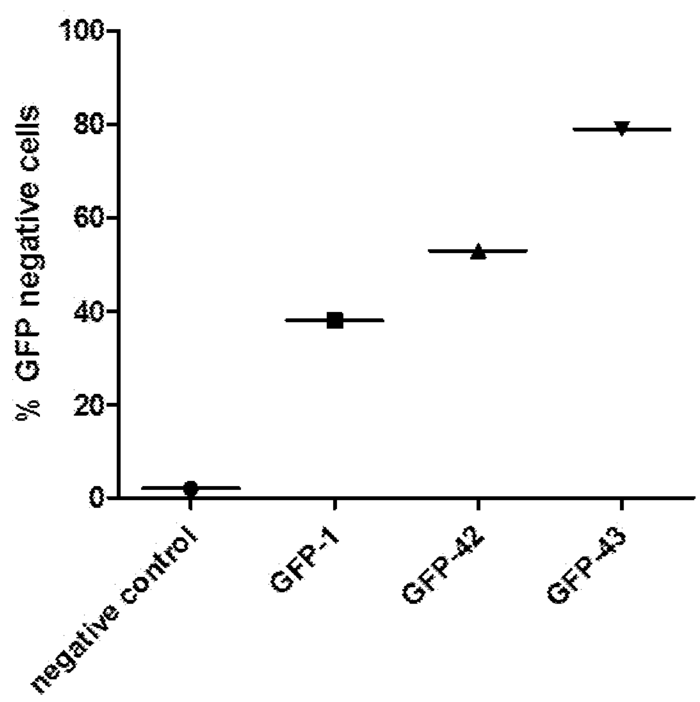
Figure 12C:
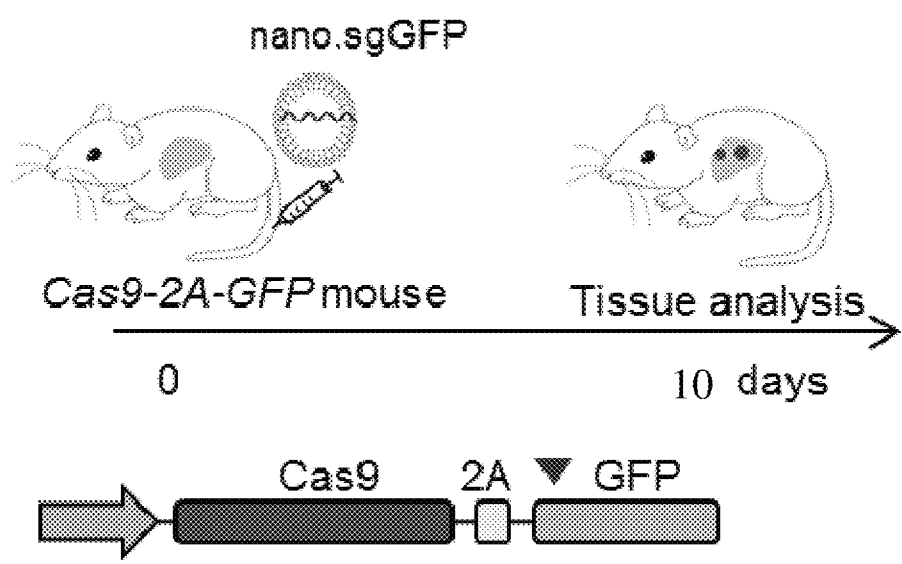
Figure 12E:
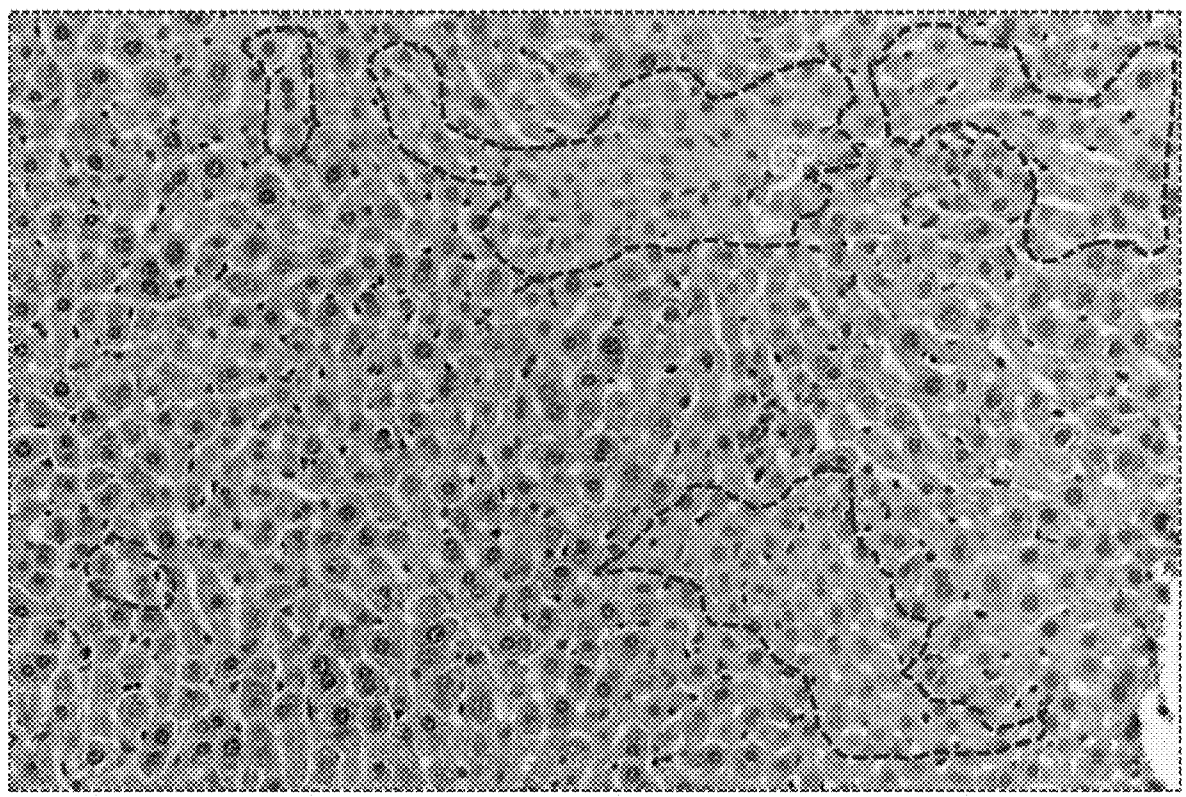
Figure 13:
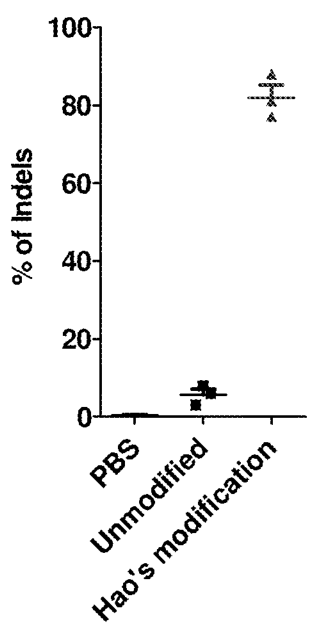
FIG. 13 depicts an experiment in which Cas9 mice were given 3 doses of unmodified (GFP-1) or modified sgRNA (GFP-43), at 1 mg/kg each time over a 3-day period. Indel formation in the liver was determined by deep seq analysis after 10 days.

Example 10: Combinations of Chemical Modifications of sgRNA and In Vivo Potency Next, we sought to combine the modifications at the variable and the fixed region (FIG. 12*a*). We compared the efficiency of unmodified sgRNA targeting GFP (GFP-42=GFP-1), previous published "light modification" of sequence (GFP-42, with 2' O-Methyl and phosphorothioate modifications at 3 nucleotides at the 5' end and 3' end, respectively) and our modifications (GFP-43). We co-delivered Cas9 mRNA and one of these three sgRNA to HEK293-GFP cells. We found our modified sgRNA is more potent than unmodified and light modified sgRNA (FIG. 12*b*). This result could be applied to many therapeutic applications using ex vivo approaches. To explore the in vivo application of our modified sgRNA, we performed in vivo delivery of our modified RNA by C12-200 based lipid nanoparticles (LNP) formulation (FIG. 12*c*). We compared the delivery efficiency of unmodified sgRNA (GFP-42) and our modified sgRNA (GFP-43). We found with a single injection of unmodified LNP-sgRNA into Cas9-expression mice at the dose of 1 mg/kg, the unmodified sgRNA induced <1% of indels in the liver (FIG. 12*d*). In contrast, our modification induced about 10% of indels. We explored the possibility of repeated injections and accumulated effect in vivo, which is not likely to reach by viral delivery. We found that two injections of LNP-sgRNA with our modification induced 38% indel formations; in contrast, unmodified sgRNA remained about 3.5% (FIG. 12*d*). We performed immunohistochemistry staining of GFP in liver. We identified a large portion of GFP-cells in the liver after two doses of LNP-modified sgRNA treatment (as circulated by dash lines), indicating a strong gene editing effect in a preclinical animal model (FIG. 12*e*).

Example 11

Figure 14:
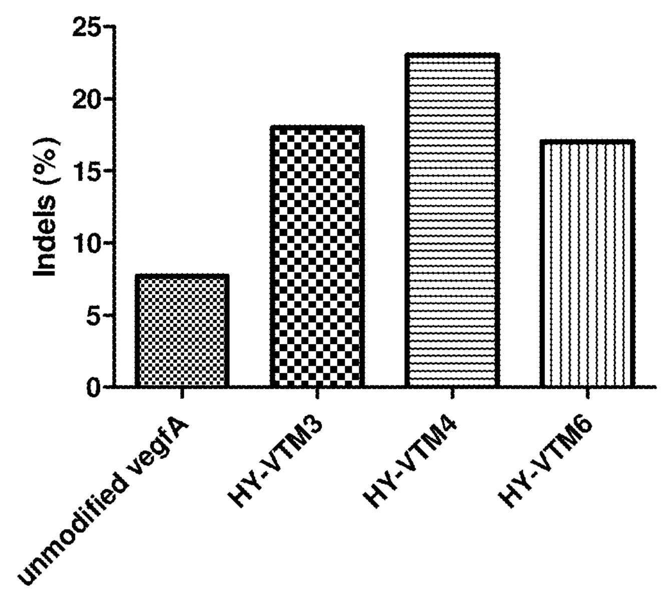
FIG. 14 depicts chemical modifications of guide sequences for human gene VEGFA (Vascular Endothelial Growth Factor A). HY-VTM3, HY-VTM4 and HY-VTM6 induce indel formation in 293HEK T cells after transfection. This data indicate more examples of structure guided chemical modifications of crRNA and the guide sequence.

The following crRNAsequences were used in the experiments depicted in FIG. 14 whereby modified crRNA sequences were transfected with with a tracrRNA of:

AAACAGCAUAGCAAGUUAAAAUAAGGCUAGUCCGUUAUCAACUUGAAAAA GUGGCACCGAGUCGGUGCUUUUUUU

HY-VTM3
(SEQ ID NO: 116)
GsAfsCfsCCCsCsUfsCfsCfsAfCCfCfCGCfCfUCGUUUUAGAGCUA UGCUGUUUUG

HY-VTM4
(SEQ ID NO: 117)
GfsAfsCfsCCCsCsUfsCfsCfsAfCCfCfCGCfCfUCGUUUUAGAGCU AUGCUGUUUUG

HY-VTM6
(SEQ ID NO: 118)
GsAfsCfsCsCsCsCsUfsCfsCfsAfCCfCfCGCfCfUCGUUUUAGAGC UAUGCUGUUUUG

Example 12

Figure 15:
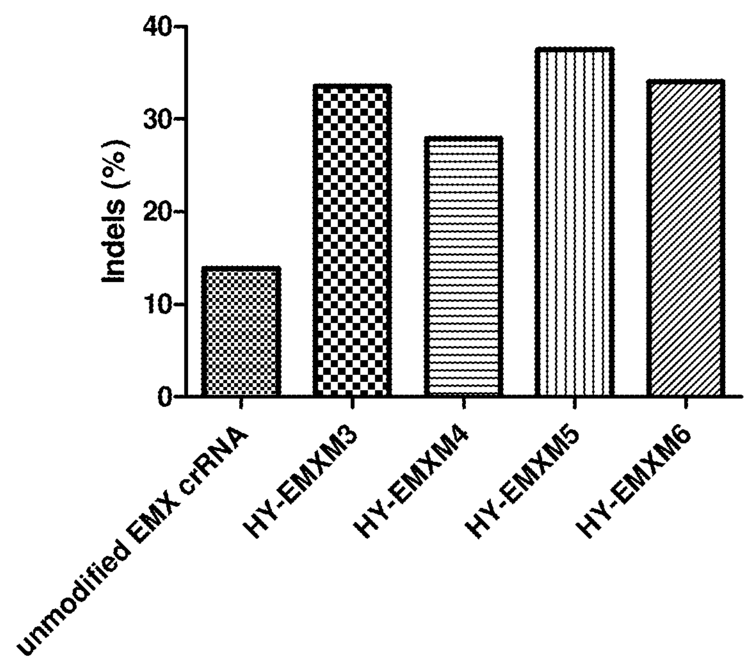
FIG. 15 depicts chemical modifications of guide sequences for human gene Homeobox protein EMX1 (EMX) (HY-EMXM3, HY-EMXM4 HY-EMX5, HY-EMXM6) induce indel formation at Homeobox protein EMX1 (EMX) site in 293HEK T cells. This data indicate more examples of sequences generated as structure guided chemical modifications of crRNA and such modifications can work for genome editing for DNA-binding domains homologous to structurally divergent genes.

The following sequences were used in the experiments depicted in FIG. 15 whereby modified crRNA sequences below were transfected with with a tracrRNA of:

AAACAGCAUAGCAAGUUAAAAUAAGGCUAGUCCGUUAUCAACUUGAAAAA GUGGCACCGAGUCGGUGCUUUUUUU

HY-EMXM3
(SEQ ID NO: 119)
GsAfsGfsUCCsGsAfsGfsCfsAfGAfAfGAAfGfAAGUUUUAGAGCUA UGCUGUUUUG

HY-EMXM4
(SEQ ID NO: 120)
GfsAfsGfsUCCsGsAfsGfsCfsAfGAfAfGAAfGfAAGUUUUAGAGCU AUGCUGUUUUG

-continued

HY-EMXM5
(SEQ ID NO: 121)
gsasgsUCCsGsAfsGfsCfsAfGAfAfGAAfGfAAGUUUUAGAGCUAUG CUGUUUUG HY-EMXM6
(SEQ ID NO: 122)
GsAfsGfsUsCsCsGsAfsGfsCfsAfGAfAfGAAfGfAAGUUUUAGAGC UAUGCUGUUUUG Example 13

Figure 16:
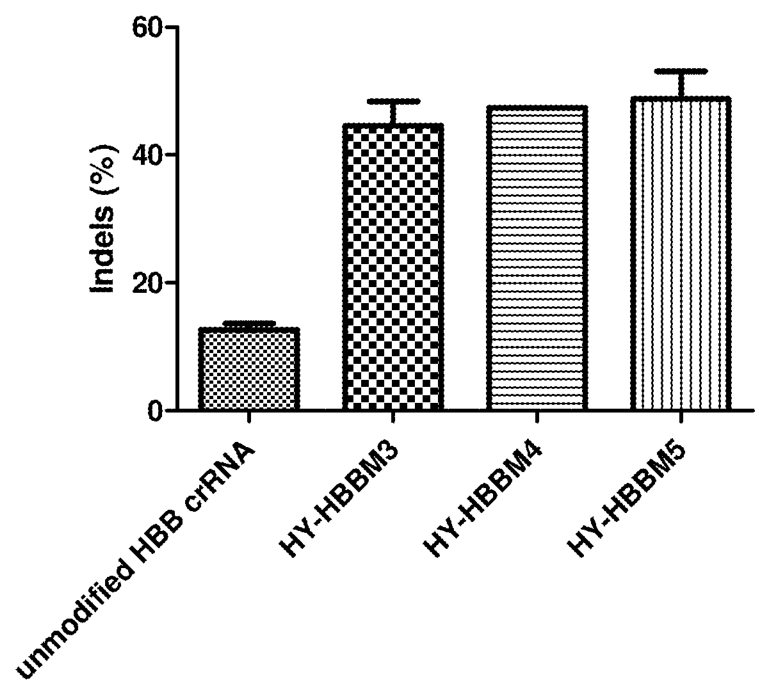
FIG. 16 depicts chemical modifications of guide sequences for human gene HBB (Hemoglobin Subunit Beta) (HY-HBBM3, HY-HBBM4 HY-HBBM5) induce indel formation at HBB site in 293HEK T cells. This data indicate more examples of sequences generated as structure guided chemical modifications of crRNA and such modifications can work for genome editing for various structurally divergent genes.

The following sequences were used in the experiments depicted in FIG. 16 whereby modified crRNA sequences below were transfected with with a tracrRNA of:

AAACAGCAUAGCAAGUUAAAAUAAGGCUAGUCCGUUAUCAACUUGAAAAA GUGGCACCGAGUCGGUGCUUUUUUU

HY-HBBM3
(SEQ ID NO: 123)
CsUfsUfsGCCsCsCfsAfsCfsAfGGfGfCAGfUfAAGUUUUAGAGCUA UGCUGUUUUG

HY-HBBM4
(SEQ ID NO: 124)
CfsUfsUfsGCCsCsCfsAfsCfsAfGGfGfCAGfUfAAGUUUUAGAGCU AUGCUGUUUUG

HY-HBBM5
(SEQ ID NO: 125)
csusUsGCCsCsCfsAfsCfsAfGGfGfCAGfUfAAGUUUUAGAGCUAUG CUGUUUUG Example 14

Figure 17:
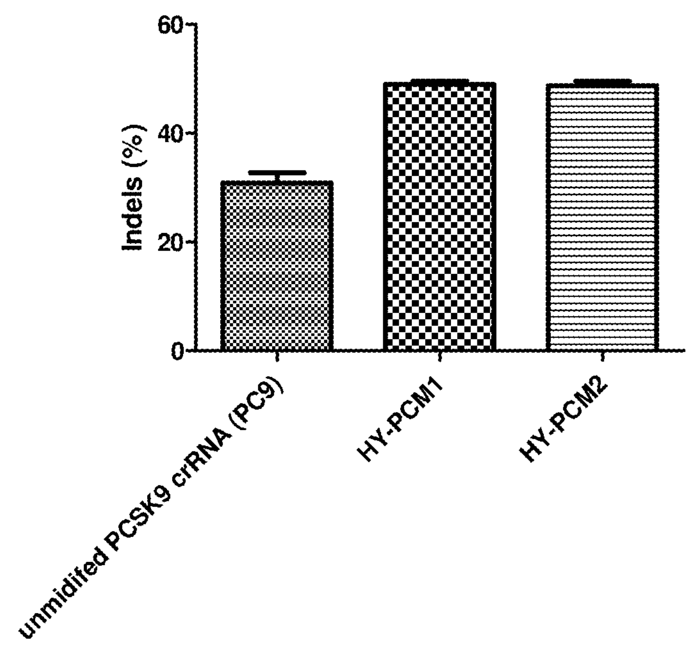
FIG. 17 depicts chemical modifications of guide sequences for mouse gene Pcsk9 (proprotein convertase subtilisin/kexin type 9) (HY-PCM1, HY-PCM2) induce indel formation at PCSK9 site in mouse cell line AML12. This data indicate more examples of sequences generated as structure guided chemical modifications of crRNA and such modifications can work in different species and different cells.

The following sequences were used in the experiments depicted in FIG. 17 whereby modified crRNA sequences below were transfected into 293HEK cells cultured to confluence with a tracrRNA of:

AAACAGCAUAGCAAGUUAAAAUAAGGCUAGUCCGUUAUCAACUUGAAAAA GUGGCACCGAGUCGGUGCUUUUUUU

HY-PC9
(SEQ ID NO: 126)
GGCUGAUGAGGCCGCACAUGGUUUUAGAGCUAUGCUGUUUUG

HY-PC9M1
(SEQ ID NO: 127)
GGfsCfUGAsUsGfsAfsGfsGfCCfGfCACfAfUGGUUUUAGAGCUAUG CUGUUUUG

HY-PC9M2
(SEQ ID NO: 128)
GsGfsCfsUGAUGfAfGfGfCCfGfCACfAfUGGUUUUAGAGCUAUGCUG UUUUG

Example 15

Figure 18A:
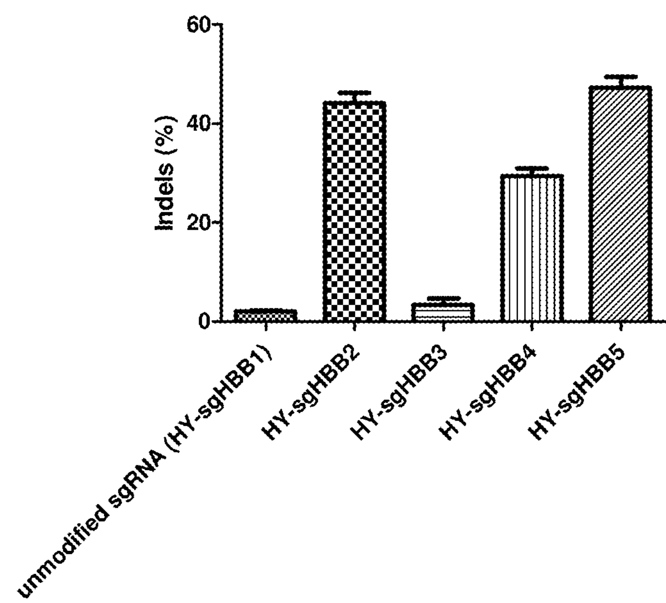
FIGS. 18A-18C depict a combined pattern of structure-guided chemical modifications of guide sequence and the sgRNA structure sequences for sgRNA and target site other than GFP. We use HBB as an example. One of the sgRNA and Cas9 mRNA were co-delivered by electroporation. Structure guided chemical modifications of HBB sgRNA induce indel formation at HBB site in human primary CD34+ Hematopoietic stem cells (HSCs), K562 cells and 293T cells. Underlined sequences in Example Section corresponding to FIGS. 18A-18C are the Cas9 binding domains. The sequence 3' downstream of the cas-9 binding domain is the transcription terminator domain.
Figure 18B:
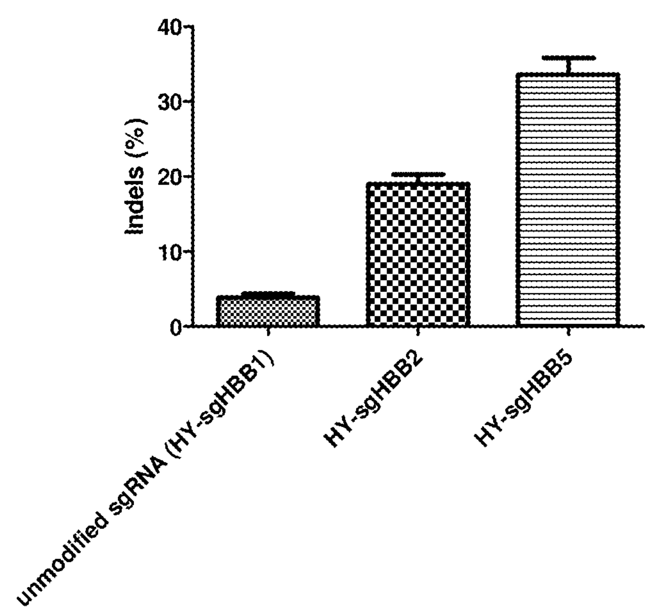
Figure 18C:
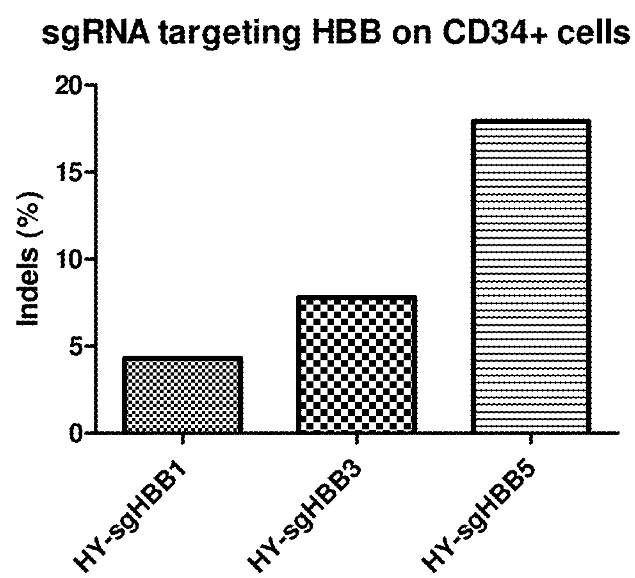

The following sgRNA sequences were used in the experiments depicted in FIG. 18A through 18C whereby modified sgRNA sequences below were transfected into 3 types of cells in vitro: K652 cells (FIG. 18A), 293HEK cells (FIG. 18B), and CD34+ cells (FIG. 18C), respectively.

```
HY-sgHBB1 (N: RNA residues: RNA)
                                        (SEQ ID NO: 129)
CUUGCCCCACAGGGCAGUAAGUUUUAGAGCUAGAAAUAGCAAGUUAAAAU

AAGGCUAGUCCGUUAUCAACUUGAAAAAGUGGCACCGAGUCGGUGCUUUU

HY-sgHBB2 (s: phosphorothioate; Nf: 2 F
modification RNA; N: RNA residues: RNA; n: 2'-O-
methyl modification RNA; lower case residues (n) =
DNA nucleoside)
                                        (SEQ ID NO: 130)
CUfsUfGCCsCsCfsAfsCfsAfGGfGfCAGfUfAAgUUUUAGagcuaga

aauagcaaGUUaAaAuAaggcuaGUccGUUAucAAcsususgsasasasa

sasgugGscascscsgsasgsuscgsgsusgscsususususu

HY-sgHBB3 (s: phosphorothioate; N: RNA residues:
RNA; n: 2'-O-methyl modification RNA)
                                        (SEQ ID NO: 131)
csususGCCCCACAGGGCAGUAAGUUUUAGAGCUAGAAAUAGCAAGUUAA

AAUAAGGCUAGUCCGUUAUCAACUUGAAAAAGUGGCACCGAGUCGGUGCU

Usususu

HY-sgHBB4
                                        (SEQ ID NO: 132)
CsUfsUfsGCCsCsCfsAfsCfsAfGGfGfCAGfUfAAgUUUUAGagcua

gaaauagcaaGUUaAaAuAaggcuaGUccGUUAucAAcsususgsasasa

sasasgugGscascscsgsasgsuscgsgsusgscsususususu

HY-sgHBB5
                                        (SEQ ID NO: 133)
CfsUfsUfsGsCsCsCsCfsAfsCfsAfGGfGfCAGfUfAAgUUUUAGag

cuagaaauagcaaGUUaAaAuAaggcuaGUccGUUAucAAcsususgsas

asasasasgugGscascscsgsasgsuscgsgsusgscsususususu
```

Example 16

DNA-RNA hybrid on guide sequence decreases off-target effect

```
HYVT1 (all)
                                        (SEQ ID NO: 134)
rGrArCrCrCrCrCrUrCrCrArCrCrCrCrGrCrCrUrCrGrUrUrUrU

rArGrArGrCrUrArUrGrCrUrGrUrUrUrUrG

HYVT2 (10 + 10)
                                        (SEQ ID NO: 135)
GACCCCCTCCrArCrCrCrCrGrCrCrUrCrGrUrUrUrUrArGrArGrC

rUrArUrGrCrUrGrUrUrUrUrG
```

Figure 9:
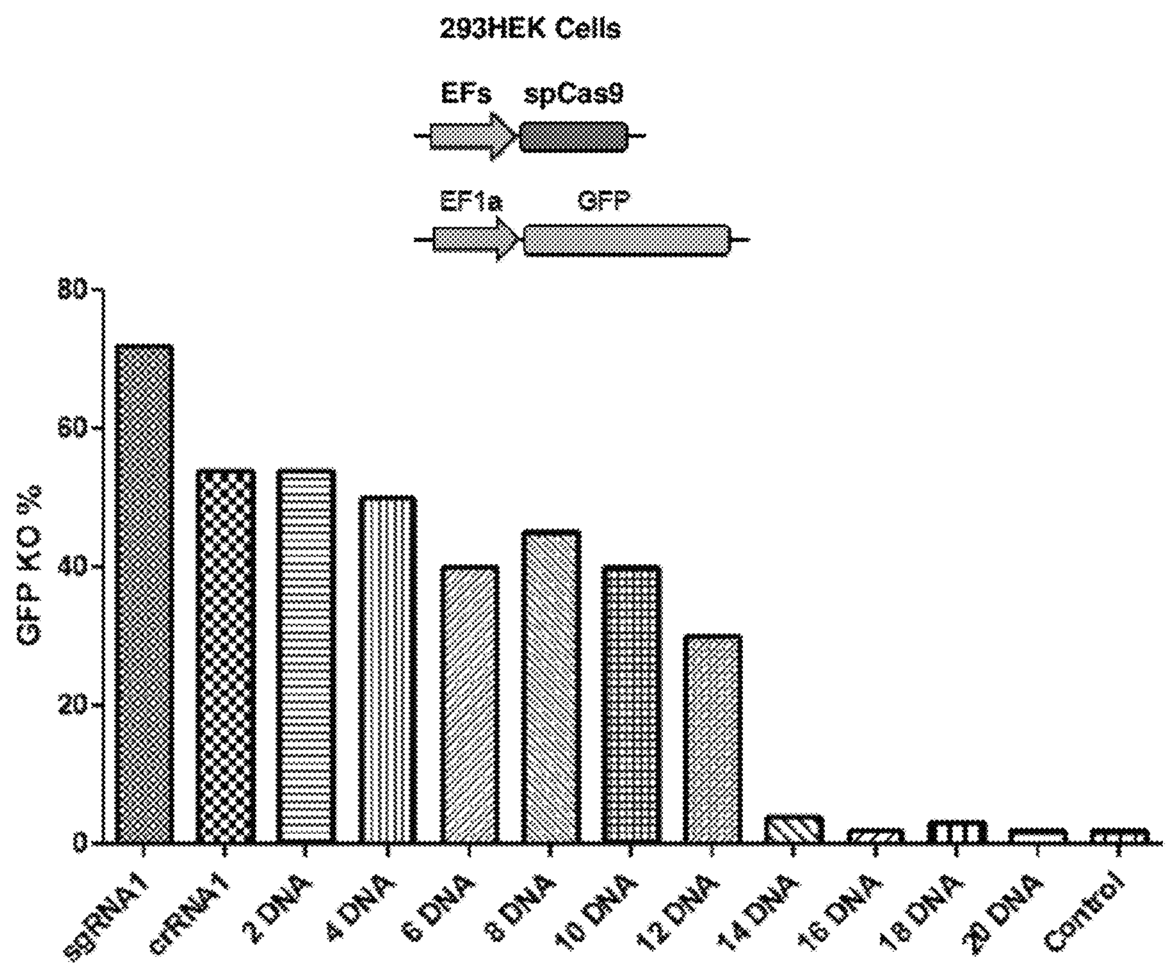
FIG. 9 depicts the percentage of genome editing with modified crRNA: HEK 293 cells were engineered to express EGFP and spCas9. tracrRNA and various crRNA were introduced to cells via transfection and FACS was performed 5 days after transfection. sgRNA1, which is chemically synthesized full length single guide RNA, is served as a positive control. Replacing up to 12 out of 20 RNA molecules with DNA allows efficient genome editing. However, replacing 14 or more of ribonucleotide with deoxyribonucleotides abolishes its effect.

In our previous example, we showed in FIG. 9 and FIG. 11 that replacement of 1-20 RNA monomer with DNA and showed such DNA/RNA hybrid crRNA perform effective genome editing in 293 cells. We propose such pattern of modification can decrease off-target effect. Here we followed the same protocol decribed in Example 7 to show that using a well established high frequency guide sequence targeting VEGFA (Vascular Endothelial Growth Factor A), the replacement of DNA in the guide sequence (HYVT2) significantly decreases off-target effect by showing less indel formation at multiple off-target sites (OT) sites, and maintains its on-target effect (On-target) (FIG. 19).

Figure 19:
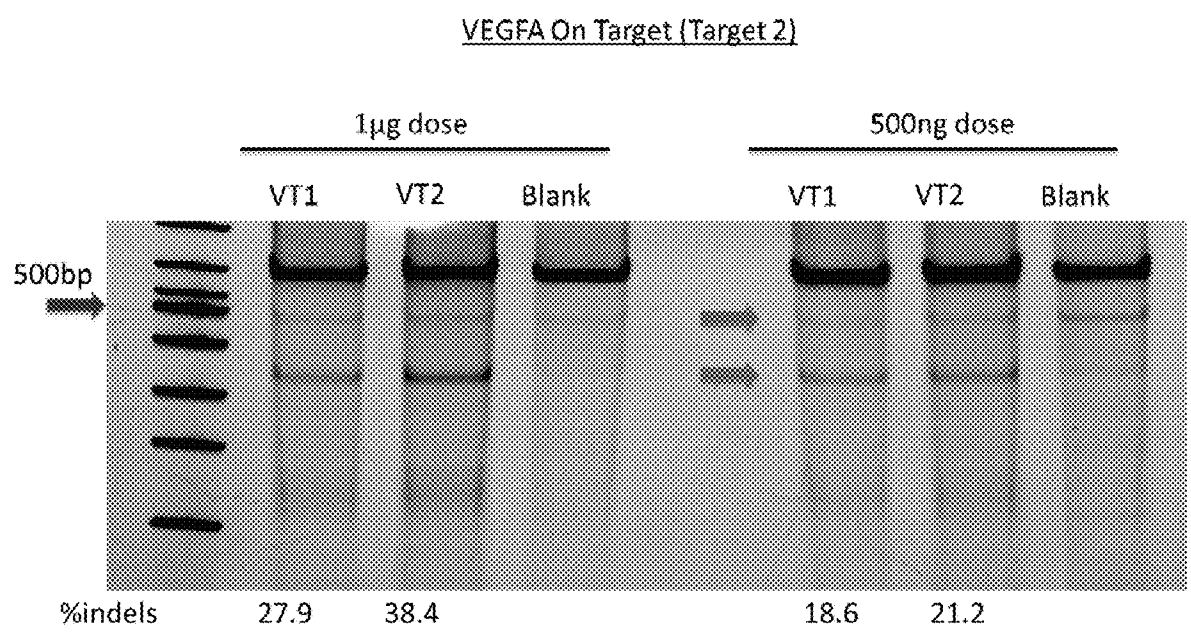
FIG. 19, FIG. 20, and FIG. 21 depict the DNA isolated from confluent 293HEK cells and exposed to and transfected with the amount of crRNA: tracrRNA duplex using the protocols described in Examples 7-9. The amount of genomic DNA loaded onto each agarose gel is depicted on the top of the Figure. The results indicate that modified crRNA sequences decrease off target efficiency as compared to unmodified sequences. The relative off-trget efficiency measured by correlating the percentage of indel formation in the genomic DNA (such percentage appearing on the bottom of each lane).
Figure 20:
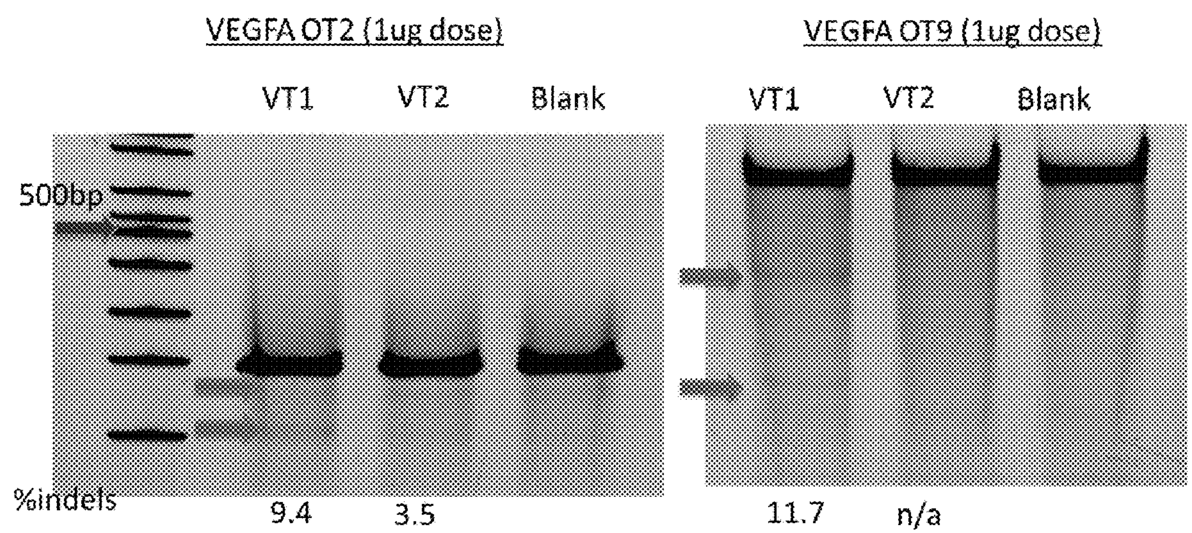
Figure 21:
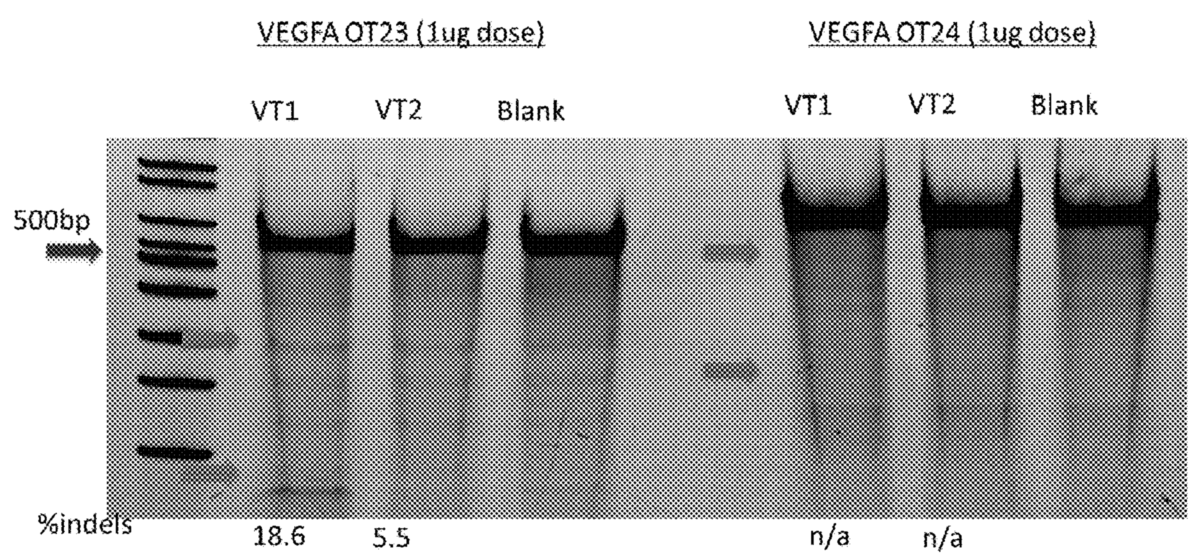

The experiments depicted in FIGS. 19-21 used T7 assay to detect indel formation in genomic DNA exposed to modified and unmodified crRNA sequences. T7 Endonuclease I recognizes and cleaves non-perfectly matched DNA. Therefore increased modifications catalyzed by the guide sequence in the DNA-binding domain was correlated to the a number corresponding to the percent of total genomic DNA with indel formation. This protocol describes how to determine genome targeting efficiency by digesting annealed PCR products with T7 Endonuclease I. In the first step, PCR products are produced from the genomic DNA of cells whose genomes were targeted using known primers for Cas9, TALEN, ZFN etc. In the second step, the PCR products are annealed and digested with T7 Endonuclease I. Fragments are analyzed to determine the efficiency of genome targeting.

CRISPR is an RNA-guided endonuclease, the specificity of which relies on the guide RNA sequence (20 nt). The mismatch of sgRNA and genomic DNA sequence can be tolerated, which indicate off-target sites gene editing. Our approach can decrease such off-target gene editing as shown. Pickup off-target site: The loci we assessed included all genomic sites that differ by one or two nucleotides as well as subsets of genomic sites that differ by three to six nucleotides and with a bias toward those that had one or more of these mismatches in the 5' half of the sgRNA targeting sequence (FIGS. 20 and 21).

Example 17

In some embodiments, sgRNA or crRNA:tracrRNA duplexes disclosed herein comprise Cas-binding domains and transcription terminator domains that are capable of binding one or more peptides with Cas9-like activity when exposed to a gene editing enzyme and a target DNA at a concentration sufficient to catalyze the reaction between the geneediting enzyme and the target DNA sequence. Below is a representative sample of amino acid sequences corresponding to gene editing enzymes which may be components in the disclosed CRISPR complexes. Vectors comprising nucleic acid sequences encoding such editing amino acid sequences are also contemplated by the disclosure.

An example of a crRNA sequence that may bind a peptide with Cas9-like activity at a biophysically acceptable concentration is crRNA sequence:

AAUUUCUACUGUUGUAGAUGAGAGAUUUAGGAGAGAAUGAC

Underline: CFP1 binding region no underline: DNA binding region

This sequence should be bound to a type V CRISPR-associated protein Cpf1 [Acidaminococcus sp. BV3L6] NCBI Reference Sequence: WP 021736722.1. FnCpf1 locus sequences (permanent sequence links)

Other DNA-binding domains can be found at:

pFnCpfl (pY001) benchling.com/s/Yz 1hC8BN/edit pFnCpfl_min (pY002) benchling.com/s/UZ2wCOF2/edit pFnCpfl_Δcas (pY003) benchling.com/s/ctaThKG6/edit which are incorporated by reference in their entireties.

- type II CRISPR RNA-guided endonuclease Cas9 [*Staphylococcus aureus*] NCBI Reference Sequence: WP_001573634.1
- type II CRISPR RNA-guided endonuclease Cas9 [*Streptococcus pyogenes*] GenBank: AMA70685.1
- The C2c2 CRISPR locus was amplified from DNA from *Leptotrichia shahii* DSM 19757
- *Francisella novicida* (FnCas9) type II-B CRISPR-associated RNA-guided endonuclease Cas9/Csx12 [*Francisella tularensis*] NCBI Reference Sequence: WP_032729892.1
- Cas 3 CRISPR-associated helicase Cas3 [*Escherichia coli*] GenBank: CCQ30152.2

TABLE E

| Accession Numbers of Cas proteins (or those related with Cas-like function) and Nucleic Acids encoding the same. All amino acid and nucleic acid sequences associated with the Accession Numbers below as of Jun. 29, 2016, are incorporated by reference in their entireties. Any mutants or variants that are at least 70, 75, 80, 85, 90, 95, 96, 97, 98, 99% homologous to the encoded nucleic acids or amino acids set forth in the Accession Numbers below are also incorporated by reference in their entireties. |
| --- |
| NC_014644.1; NC_002967.9; NC_007929.1; NC_000913.3; NC_004547.2; NC_009380.1; NC_011661.1; NC_010175.1; NC_010175.1; NC_010175.1; NC_003413.1; NC_000917.1; NC_002939.5; NC_018227.2; NC_004829.2; NC_021921.1; NC_014160.1; NC_011766.1; NC_007681.1; NC_021592.1; NC_021592.1; NC_021169.1; NC_020517.1; NC_018656.1; NC_018015.1; NC_018015.1; NC_017946.1; NC_017576.1; NC_017576.1; NC_015865.1; NC_015865.1; NC_015680.1; NC_015680.1; NC_015474.1; NC_015435.1; NC_013790.1; NC_013790.1; NC_012883.1; NC_012470.1; NC_016051.1; NC_010610.1; NC_009515.1; NC_008942.1; NC_007181.1; NC_007181.1; NC_006624.1; NC_006448.1; NC_002935.2; NC_002935.2; NC_002950.2; NC_002950.2; NC_002663.1; NC_002663.1; NC_004557.1; NC_004557.1; NC_019943.1; NC_019943.1; NC_019943.1; NC_017459.1; NC_017459.1; NC_015518.1; NC_015460.1; NC_015416.1; NC_014933.1; NC_013961.1; NC_013202.1; NC_013158.1; NC_009464.1; NC_008508.1; NC_007426.1; NC_000917.1; NC_003901.1; NC_003901.1; NC_003106.2; NC_009434.1; NC_005085.1; NC_005085.1; NC_020247.1; NC_020247.1; NC_020246.1; NC_020246.1; NC_018224.1; NC_015943.1; NC_011138.3; NC_009778.1; NC_006834.1; NC_014228.1; NC_010002.1; NC_013892.1; NC_010296.1; NC_009615.1; NC_012632.1; NC_012632.1; NC_012588.1; NC_012588.1; NC_007643.1; NC_002939.5; NC_011296.1; NC_011296.1; NC_018609.1; NC_021355.1; NC_021355.1; NC_020800.1; NC_019942.1; NC_019792.1; NC_015958.1; NC_015678.1; NC_015636.1; NC_015562.1; NC_014222.1; NC_014222.1; NC_014002.1; NC_013887.1; NC_013156.1; NC_011832.1; NC_009953.1; NC_009635.1; NC_009634.1; NC_008618.1; NC_007955.1; NC_007955.1; NC_007955.1; NC_007955.1; NC_007955.1; NC_007796.1; NC_002754.1; NC_002754.1; NC_011835.1; NC_013198.1; NC_000962.3; NC_002163.1; NC_017034.1; NC_009089.1; NC_008698.1; NC_020419.1; NC_020419.1; NC_020419.1; NC_015847.1; NC_014374.1; NC_013520.1; NC_010482.1; NC_009776.1; NC_009776.1; NC_009033.1; NC_000916.1; NC_018015.1; NC_015518.1; NC_014537.1; NC_009440.1; NC_007644.1; NC_007644.1; NC_022246.1; NC_019943.1; NC_016023.1; NC_016023.1; NC_015416.1; NC_013722.1; NC_013722.1; NC_009464.1; NC_007643.1; NC_007643.1; NC_007643.1; NC_003106.2; NC_004342.2; NC_018658.1; NC_017276.1; NC_017275.1; NC_016112.1; NC_016112.1; NC_003552.1; NC_003197.1; NC_003198.1; NC_012726.1; NC_012623.1; NC_015964.1; NC_023069.1; NC_023044.1; NC_022777.1; NC_022777.1; NC_022777.1; NC_013769.1; NC_013769.1; NC_011832.1; NC_011296.1; NC_009712.1; NC_009634.1; NC_009439.1; NC_009135.1; NC_008599.1; NC_007796.1; NC_007796.1; NC_007796.1; NC_007355.1; NC_021082.1; NC_018001.1; NC_009785.1; NC_022084.1; NC_018092.1; NC_014804.1; NC_014147.1; NC_009053.1; NC_000961.1; NC_000961.1; NC_021058.1; NC_018876.1; NC_018876.1; NC_018081.1; NC_011567.1; NC_016901.1; NC_014500.1; NC_013715.1; NC_019977.1; NC_019042.1; NC_017274.1; NC_015954.1; NC_015676.1; NC_015320.1; NC_014122.1; NC_014122.1; NC_013407.1; NC_014961.1; NC_013926.1; NC_013926.1; NC_021353.1; NC_008818.1; NC_021058.1; NC_015151.1; NC_013849.1; NC_009051.1; NC_018876.1; NC_018876.1; NC_014507.1; NC_015574.1; NC_014500.1; NC_012622.1; NC_012589.1; NC_009515.1; NC_017275.1; NC_000913.3; NC_017527.1; NC_018227.2; NC_007355.1; NC_014106.1; NC_010610.1; NC_008054.1; NC_007164.1; NC_015760.1; NC_009953.1; NC_010572.1; NC_009613.3; NC_014334.1; NC_008526.1; NC_026150.1; NC_015776.1; NC_007116.6; NC_012779.2; NC_003901.1; NC_020892.1; NC_011832.1; NC_003143.1; NC_003143.1; NC_008800.1; NC_011308.1; NC_008942.1; NC_007297.1; NC_005877.1; NC_005877.1; NC_002689.2; NC_006085.1; NC_004116.1; NC_010397.1; NC_009917.1; NC_012490.1; NC_006067.1; NW_004197518.1; NC_022777.1; NC_019042.1; NC_004547.2; NC_002695.1; NC_017634.1; NC_003143.1; NC_002737.2; NC_002737.2; NC_000918.1; NC_020913.1; NC_006448.1; NC_022093.1; NC_022093.1; NC_015680.1; NC_007297.1; NC_004350.2; NC_004350.2; NC_004350.2; NC_004350.2; NC_003454.1; NC_000853.1; NC_018876.1; NC_009440.1; NC_009009.1; NC_009009.1; NC_002932.3; NC_002932.3; NC_026150.1; NC_003552.1; NC_025263.1; NC_016112.1; NC_011098.1; NC_007643.1; NC_007643.1; NC_007643.1; NC_006347.1; NC_005140.1; NC_004342.2; NC_002945.3; NW_007382731.1; NW_007381138.1; NC_024320.1; NW_005756335.1; NW_003384463.1; NC_019977.1; NC_011296.1; NC_007929.1; NC_000913.3; NC_003413.1; NC_002754.1; NC_010175.1; NC_010175.1; NC_010175.1; NC_011661.1; NC_014537.1; NC_012470.1; NC_004829.2; NC_015516.1; NC_014374.1; NC_009033.1; NC_007681.1; NC_002689.2; NC_006085.1; NC_021592.1; NC_021592.1; NC_021169.1; NC_020517.1; NC_018015.1; NC_018015.1; NC_018015.1; NC_017946.1; NC_017946.1; NC_017576.1; NC_017576.1; NC_015865.1; NC_015865.1; NC_015847.1; NC_015680.1; NC_015680.1; NC_015474.1; NC_015435.1; NC_014106.1; NC_013790.1; NC_012883.1; NC_012804.1; NC_016051.1; NC_011529.1; NC_010482.1; NC_009515.1; NC_009440.1; NC_008942.1; NC_008054.1; NC_007181.1; NC_006624.1; NC_006448.1; NC_006448.1; NC_002935.2; NC_002935.2; NC_002950.2; NC_002663.1; NC_019943.1; NC_019943.1; NC_017459.1; NC_017459.1; NC_016023.1; NC_015518.1; NC_015460.1; NC_015460.1; NC_015416.1; NC_014933.1; NC_013202.1; NC_013158.1; NC_009464.1; NC_008508.1; NC_003901.1; NC_009434.1; NC_005085.1; NC_020247.1; NC_020246.1; NC_018224.1; NC_015943.1; NC_009380.1; NC_006834.1; NC_003552.1; NC_017276.1; NC_017275.1; NC_010296.1; NC_009615.1; NC_012632.1; NC_012632.1; NC_012623.1; NC_012588.1; NC_012588.1; NC_007181.1; NC_002939.5; NC_020247.1; NC_020246.1; NC_011296.1; NC_011296.1; NC_011296.1; NC_018609.1; NC_015964.1; NC_021355.1; NC_020800.1; NC_019942.1; NC_019792.1; NC_015958.1; NC_015760.1; NC_015678.1; NC_015636.1; NC_015562.1; NC_014222.1; NC_014222.1; NC_013887.1; NC_013769.1; NC_013156.1; NC_009953.1; NC_009635.1; NC_009634.1; NC_009135.1; NC_008618.1; NC_008599.1; NC_007955.1; NC_007796.1; NC_007355.1; NC_002754.1; NC_010572.1; NC_015151.1; NC_000962.3; NC_021921.1; NC_002163.1; NC_017034.1; NC_009089.1; NC_008698.1; NC_020419.1; NC_020419.1; NC_020419.1; NC_014160.1; NC_011766.1; NC_007681.1; NC_000916.1; NC_017527.1; NC_013790.1; NC_013790.1; NC_000917.1; NC_000917.1; NC_004557.1; NC_004557.1; NC_022246.1; NC_017384.1; NC_013722.1; NC_007643.1; NC_007643.1; NC_007643.1; NC_007643.1; NC_007643.1; NC_002967.9; NC_004342.2; NC_016112.1; NC_016112.1; NC_005140.1; NC_005140.1; NC_012726.1; NC_023069.1; NC_023044.1; NC_022777.1; NC_022777.1; NC_011296.1; NC_021355.1; NC_009634.1; NC_007796.1; NC_007355.1; NC_021082.1; NC_013926.1; NC_020913.1; NC_014961.1; NC_014658.1; NC_013198.1; NC_005877.1; NC_009785.1; NC_022084.1; NC_018092.1; NC_014804.1; NC_000961.1; NC_021058.1; NC_018081.1; NC_013849.1; NC_011567.1; NC_015574.1; NC_014500.1; NC_012622.1; NC_012589.1; NC_012589.1; |

TABLE E-continued

Accession Numbers of Cas proteins (or those related with Cas-like function) and Nucleic Acids encoding the same. All amino acid and nucleic acid sequences associated with the Accession Numbers below as of Jun. 29, 2016, are incorporated by reference in their entireties. Any mutants or variants that are at least 70, 75, 80, 85, 90, 95, 96, 97, 98, 99% homologous to the encoded nucleic acids or amino acids set forth in the Accession Numbers below are also incorporated by reference in their entireties.

NC_019977.1; NC_019042.1; NC_017274.1; NC_017274.1; NC_015954.1; NC_015676.1; NC_015320.1;
NC_014122.1; NC_014122.1; NC_013407.1; NC_011835.1; NC_021353.1; NC_018001.1; NC_008818.1;
NC_000961.1; NC_015931.1; NC_019042.1; NC_013961.1; NC_011138.3; NC_009778.1; NC_014228.1;
NC_013892.1; NC_011832.1; NC_009439.1; NC_007955.1; NC_007796.1; NC_013520.1; NC_016070.1;
NC_007426.1; NC_003106.2; NC_003106.2; NC_018227.2; NC_000913.3; NC_005085.1; NC_009613.3;
NC_014334.1; NW_006726754.1; NC_002663.1; NC_003143.1; NC_003076.8; NC_015666.1;
NC_014644.1; NC_004116.1; NC_003454.1; NC_011567.1; NC_024905.1; NC_003295.1; NC_008526.1;
NC_012871.1; NC_012871.1; NC_010682.1; NC_002737.2; NC_002737.2; NC_017954.1; NC_009515.1;
NC_007297.1; NC_007297.1; NC_004350.2; NC_004350.2; NC_000853.1; NC_009009.1; NC_007644.1;
NC_007644.1; NC_002967.9; NC_002932.3; NC_002932.3; NC_007643.1; NC_007606.1; NC_006347.1;
NC_002945.3; NW_006804726.1; NW_006383769.1; NC_013769.1; NC_014644.1; NC_000913.3;
NC_019943.1; NC_019943.1; NC_011661.1; NC_010175.1; NC_002950.2; NC_004547.2; NC_013887.1;
NC_013156.1; NC_007426.1; NC_002939.5; NC_021169.1; NC_020517.1; NC_018015.1; NC_017946.1;
NC_015865.1; NC_015680.1; NC_009515.1; NC_004557.1; NC_005085.1; NC_006834.1; NC_011296.1;
NC_010175.1; NC_020800.1; NC_015958.1; NC_009635.1; NC_008618.1; NC_007355.1; NC_009089.1;
NC_020419.1; NC_021592.1; NC_021592.1; NC_015847.1; NC_013790.1; NC_016051.1; NC_007644.1;
NC_007644.1; NC_017459.1; NC_015416.1; NC_013722.1; NC_007643.1; NC_007643.1; NC_007643.1;
NC_009434.1; NC_005085.1; NC_003552.1; NC_014318.1; NC_021355.1; NC_014222.1; NC_014222.1;
NC_011832.1; NC_009634.1; NC_009135.1; NC_021082.1; NC_000961.1; NC_015574.1; NC_014228.1;
NC_014122.1; NC_009439.1; NC_017459.1; NC_015460.1; NC_011138.3; NC_009380.1; NC_017275.1;
NC_013892.1; NC_021353.1; NC_015676.1; NC_011296.1; NC_007955.1; NC_009953.1; NC_009953.1;
NC_021921.1; NC_014160.1; NC_010482.1; NC_009776.1; NC_009033.1; NC_016070.1; NC_016070.1;
NC_015435.1; NC_009440.1; NC_017384.1; NC_013722.1; NC_016112.1; NC_012726.1; NC_022777.1;
NC_008698.1; NC_008599.1; NC_007955.1; NC_007355.1; NC_014147.1; NC_021058.1; NC_021058.1;
NC_016901.1; NC_014500.1; NC_014500.1; NC_014961.1; NC_018001.1; NC_015931.1; NC_015151.1;
NC_013849.1; NC_013715.1; NC_011766.1; NC_018001.1; NC_014644.1; NC_017034.1; NC_009033.1;
NC_002754.1; NC_009089.1; NC_002939.5; NC_014106.1; NC_010610.1; NC_008054.1; NC_003413.1;
NC_009464.1; NC_008526.1; NC_015474.1; NC_012804.1; NC_015518.1; NC_017276.1; NC_017275.1;
NC_012632.1; NC_012623.1; NC_012588.1; NC_015636.1; NC_015562.1; NC_013769.1; NC_002754.1;
NC_017634.1; NC_014160.1; NC_011766.1; NC_016070.1; NC_015435.1; NC_009440.1; NC_009440.1;
NC_012726.1; NC_012632.1; NC_012588.1; NC_013887.1; NC_013156.1; NC_011296.1; NC_002754.1;
NC_011835.1; NC_018092.1; NC_021058.1; NC_012622.1; NC_012589.1; NC_015954.1; NC_013407.1;
NC_018001.1; NC_013849.1; NC_017274.1; NC_000913.3; NC_003413.1; NC_018092.1; NC_000961.1;
NC_000918.1; NC_007796.1; NC_000868.1; NC_022084.1; NC_018015.1; NC_015865.1; NC_015680.1;
NC_015474.1; NC_014804.1; NC_012470.1; NC_006624.1; NC_002663.1; NC_016023.1; NC_013202.1;
NC_013158.1; NC_008508.1; NC_000917.1; NC_015943.1; NC_019792.1; NC_019042.1; NC_015760.1;
NC_015678.1; NC_014122.1; NC_004119.1; NC_007681.1; NC_007681.1; NC_007297.1; NC_002935.2;
NC_002932.3; NC_003454.1; NC_014933.1; NC_011567.1; NC_004342.2; NC_016112.1; NC_003197.1;
NC_022777.1; NC_015320.1; NC_002695.1; NC_003143.1; NC_002737.2; NC_012883.1; NC_010610.1;
NC_000916.1; NC_004350.2; NC_000853.1; NC_000917.1; NC_006347.1; NC_018658.1; NC_015870.2;
NC_011751.1; NC_013961.1; NC_009778.1; NC_020990.1; NC_016112.1; NC_000868.1; NC_003413.1;
NC_022084.1; NC_018092.1; NC_017946.1; NC_015680.1; NC_015680.1; NC_015474.1; NC_014106.1;
NC_012804.1; NC_009053.1; NC_008054.1; NC_006624.1; NC_000961.1; NC_021058.1; NC_015518.1;
NC_018224.1; NC_017276.1; NC_017276.1; NC_017275.1; NC_017275.1; NC_010296.1; NC_010296.1;
NC_009615.1; NC_012632.1; NC_012632.1; NC_012632.1; NC_012623.1; NC_012623.1; NC_012622.1;
NC_012622.1; NC_012589.1; NC_012589.1; NC_012588.1; NC_012588.1; NC_012588.1; NC_020892.1;
NC_019792.1; NC_017970.1; NC_017274.1; NC_017274.1; NC_016159.1; NC_013887.1; NC_013769.1;
NC_013156.1; NC_002754.1; NC_002754.1; NC_002754.1; NC_003687.1; NC_006814.3; NC_006814.3;
NC_014418.1; NC_010152.1; NC_017946.1; NC_017954.1; NC_009776.1; NC_008818.1; NC_008818.1;
NC_000961.1; NC_000918.1; NC_015931.1; NC_015931.1; NC_014537.1; NC_007181.1; NC_006624.1;
NC_003106.2; NC_004342.2; NC_020247.1; NC_020246.1; NC_018472.1; NC_012623.1; NC_012589.1;
NC_006045.2; NC_023069.1; NC_022777.1; NC_019942.1; NC_017274.1; NC_013769.1; NC_009953.1;
NC_008698.1; NC_007493.2; NC_002754.1; NC_002754.1; NC_005125.1; NC_021347.1; NC_022093.1;
NC_022093.1; NC_015931.1; NC_007164.1; NC_015416.1; NC_015151.1; NC_000917.1; NC_003106.2;
NC_002932.3; NC_014500.1; NC_004337.2; NC_007087.3; NC_012726.1; NC_024314.1;
NW_003120284.1; NW_003120529.1; NW_003126883.1; NW_003384275.1; NC_023069.1;
NC_016567.1; NC_009954.1; NC_000913.3; NC_000913.3; NC_000913.3; NC_000913.3; NC_027204.1;
NC_002754.1; NC_010175.1; NC_016070.1; NC_000868.1; NC_003413.1; NC_017527.1; NC_002939.5;
NC_018227.2; NC_007355.1; NC_014205.1; NC_014160.1; NC_009033.1; NC_007681.1; NC_020517.1;
NC_018015.1; NC_016070.1; NC_015865.1; NC_015847.1; NC_015680.1; NC_015474.1; NC_015315.1;
NC_013790.1; NC_012883.1; NC_012470.1; NC_016051.1; NC_011529.1; NC_010610.1; NC_009515.1;
NC_009440.1; NC_007181.1; NC_006624.1; NC_019943.1; NC_019943.1; NC_017459.1; NC_015518.1;
NC_014933.1; NC_007426.1; NC_003901.1; NC_003106.2; NC_003106.2; NC_009434.1; NC_005085.1;
NC_020247.1; NC_020246.1; NC_006834.1; NC_017276.1; NC_017276.1; NC_017276.1; NC_017275.1;
NC_017275.1; NC_010296.1; NC_009615.1; NC_012632.1; NC_012632.1; NC_012623.1; NC_012623.1;
NC_012588.1; NC_012588.1; NC_007643.1; NC_021355.1; NC_020800.1; NC_015958.1; NC_015678.1;
NC_014222.1; NC_013769.1; NC_013769.1; NC_009635.1; NC_009634.1; NC_009135.1; NC_008618.1;
NC_007796.1; NC_002754.1; NC_002754.1; NC_017034.1; NC_019413.1; NC_020419.1; NC_017946.1;
NC_014374.1; NC_014374.1; NC_011766.1; NC_011766.1; NC_010482.1; NC_009776.1; NC_009776.1;
NC_009033.1; NC_008942.1; NC_021169.1; NC_015518.1; NC_014537.1; NC_012804.1; NC_007644.1;
NC_015416.1; NC_013722.1; NC_007643.1; NC_016112.1; NC_016112.1; NC_012726.1; NC_012726.1;
NC_023069.1; NC_023069.1; NC_021355.1; NC_019942.1; NC_014002.1; NC_021082.1; NC_005830.1;
NC_018001.1; NC_017954.1; NC_014961.1; NC_022084.1; NC_018092.1; NC_014804.1; NC_021058.1;

TABLE E-continued

Accession Numbers of Cas proteins (or those related with Cas-like function) and Nucleic Acids encoding the same. All amino acid and nucleic acid sequences associated with the Accession Numbers below as of Jun. 29, 2016, are incorporated by reference in their entireties. Any mutants or variants that are at least 70, 75, 80, 85, 90, 95, 96, 97, 98, 99% homologous to the encoded nucleic acids or amino acids set forth in the Accession Numbers below are also incorporated by reference in their entireties.

NC_021058.1; NC_021058.1; NC_015574.1; NC_015216.1; NC_014500.1; NC_012622.1; NC_012622.1;
NC_012589.1; NC_012589.1; NC_012589.1; NC_005265.1; NC_011661.1; NC_019977.1; NC_017274.1;
NC_017274.1; NC_017274.1; NC_015954.1; NC_008701.1; NC_009965.1; NC_014961.1; NC_013926.1;
NC_018001.1; NC_013741.1; NC_013741.1; NC_008818.1; NC_000961.1; NC_015931.1; NC_015931.1;
NC_015151.1; NC_015151.1; NC_013849.1; NC_015320.1; NC_014122.1; NC_000913.3; NC_011217.1;
NC_003413.1; NC_005360.1; NC_005361.1; NC_009986.1; NC_021921.1; NC_007681.1; NC_021169.1;
NC_017946.1; NC_015865.1; NC_015680.1; NC_015474.1; NC_012804.1; NC_002950.2; NC_004557.1;
NC_017459.1; NC_016023.1; NC_013202.1; NC_013158.1; NC_018224.1; NC_015943.1; NC_003552.1;
NC_012632.1; NC_012588.1; NC_011296.1; NC_011296.1; NC_021355.1; NC_019942.1; NC_019792.1;
NC_015958.1; NC_007955.1; NC_009089.1; NC_018015.1; NC_018015.1; NC_007644.1; NC_004557.1;
NC_022777.1; NC_022777.1; NC_015562.1; NC_008599.1; NC_007355.1; NC_018092.1; NC_000961.1;
NC_011567.1; NC_013926.1; NC_021353.1; NC_022084.1; NC_015574.1; NC_003106.2; NC_015320.1;
NC_016070.1; NC_013588.1; NC_011835.1; NC_011766.1; NC_009776.1; NC_009033.1; NC_010482.1;
NC_009440.1; NC_015518.1; NC_003106.2; NC_017276.1; NC_017275.1; NC_012632.1; NC_012623.1;
NC_012588.1; NC_013769.1; NC_002754.1; NC_017034.1; NC_014374.1; NC_015416.1; NC_003106.2;
NC_012726.1; NC_013715.1; NC_025439.1; NC_017954.1; NC_014961.1; NC_013849.1; NC_012622.1;
NC_012589.1; NC_017274.1; NC_018001.1; NC_015931.1; NC_009380.1; NC_000010.11; NC_006477.3;
AC_000185.1; NC_013907.1; NC_025687.1; NC_012021.3; NC_023046.1; NC_023650.1;
NW_006159565.1; NC_018160.1; NC_027878.1; NC_024803.1; NW_007540324.1; NC_020497.1;
NC_026657.1; NC_003280.10; NC_004354.4; NC_001140.6; NC_003070.9; NT_078265.2;
NW_006890056.1; NW_003613826.1; NC_026506.1; NC_023616.1; NC_025973.2; NC_024333.1;
NW_006717075.1; NW_006438113.1; NW_006399752.1; NW_005785394.1; NC_019873.1;
NC_019482.1; NC_018902.1; NC_022199.1; NC_008801.1; NC_026145.1; NC_015446.2; NC_026940.1;
NC_025695.1; NC_025207.1; NW_006749282.1; NC_015438.2; NC_016093.1; NC_007418.2;
NC_000076.6; NC_003423.3; NC_003423.3; NC_001134.8; NC_015474.1; NC_005104.4; NC_007126.6;
NC_007124.6; NC_006093.3; NC_024464.1; NC_007124.6; NC_008397.2; NC_010572.1; NC_010572.1;
NC_017301.1; NC_017941.2; NC_016407.2; NC_016410.2; NC_012026.1; NC_021921.1; NC_018092.1;
NC_017946.1; NC_015865.1; NC_015680.1; NC_015435.1; NC_012804.1; NC_016051.1; NC_011529.1;
NC_009515.1; NC_009515.1; NC_009440.1; NC_007164.1; NC_006624.1; NC_002935.2; NC_000916.1;
NC_017459.1; NC_015151.1; NC_014933.1; NC_014729.1; NC_014537.1; NC_013209.1; NC_013202.1;
NC_013158.1; NC_011567.1; NC_010364.1; NC_008212.1; NC_007426.1; NC_002607.1; NC_003366.1;
NC_023013.1; NC_018224.1; NC_016946.1; NC_016946.1; NC_015948.1; NC_015666.1; NC_014297.1;
NC_013967.1; NC_013922.1; NC_013743.1; NC_009783.1; NC_009380.1; NC_005786.2; NC_005785.6;
NC_006396.1; NC_002944.2; NC_010002.1; NC_020990.1; NC_009615.1; NC_009614.1; NC_008313.1;
NC_013929.1; NC_017765.1; NC_017844.1; NC_014323.1; NC_007973.1; NC_019962.1; NC_019792.1;
NC_019042.1; NC_016114.1; NC_016114.1; NC_015954.1; NC_011753.2; NC_010505.1; NC_009953.1;
NC_009953.1; NC_008268.1; NC_007866.1; NC_008596.1; NC_008596.1; NC_000868.1; NC_004668.1;
NC_009760.1; NC_006820.1; NC_003888.3; NC_025463.1; NC_021921.1; NC_021921.1; NC_006883.2;
NC_017034.1; NC_014423.1; NC_017941.2; NC_004603.1; NC_007088.5; NC_008367.1; NC_021776.1;
NT_078267.5; NC_002656.1; NC_022774.1; NC_011091.1; NC_005881.2; NC_011183.1; NC_015937.1;
NC_008584.1; NC_024122.1; NC_022768.1; NC_022772.1; NC_013085.1; NC_010154.1; NC_010152.1;
NC_010155.1; NC_009804.1; NC_009803.1; NC_005342.2; NC_004333.2; NC_023735.1; NC_023694.1;
NC_027364.1; NC_019526.1; NC_023607.1; NC_021353.1; NC_021592.1; NC_012039.1; NC_008942.1;
NC_002936.3; NC_005877.1; NC_021169.1; NC_021058.1; NC_020517.1; NC_020388.1; NC_020388.1;
NC_018656.1; NC_015435.1; NC_014804.1; NC_013790.1; NC_013790.1; NC_009440.1; NC_009051.1;
NC_007929.1; NC_007929.1; NC_005042.1; NC_003454.1; NC_003238.2; NC_021313.1; NC_019943.1;
NC_019943.1; NC_017459.1; NC_017384.1; NC_015288.1; NC_015287.1; NC_015284.1; NC_015281.1;
NC_015280.1; NC_014334.1; NC_014297.1; NC_013967.1; NC_013202.1; NC_011129.1; NC_007426.1;
NC_007426.1; NC_003901.1; NC_003901.1; NC_004342.2; NC_014622.2; NC_023731.1; NC_023729.1;
NC_023716.1; NC_017275.1; NC_015574.1; NC_015216.1; NC_015216.1; NC_013922.1; NC_013922.1;
NC_013743.1; NC_012966.1; NC_012966.1; NC_011913.1; NC_010397.1; NC_010296.1; NC_009380.1;
NC_006396.1; NC_006347.1; NC_002944.2; NC_003552.1; NC_004663.1; NW_006890135.1;
NC_026750.1; NC_021285.1; NC_017765.1; NC_014942.1; NC_014435.1; NC_014318.1; NC_008526.1;
NC_007197.1; NC_006687.1; NC_022543.1; NC_022528.1; NC_022528.1; NC_012623.1; NC_012622.1;
NC_012589.1; NC_023617.1; NC_006049.2; NC_006048.2; NC_013486.1; NC_006071.1; NC_006038.1;
NC_006037.1; NC_012878.1; NC_012875.1; NC_008480.2; NC_011089.1; NW_007907148.1;
NW_008246060.1; NW_007726404.1; NW_007677829.1; NW_007620716.1; NC_024318.1;
NC_024311.1; NW_007578198.1; NW_007370681.1; NW_007249782.1; NC_023643.1;
NW_006921657.1; NW_006799972.1; NW_006804151.1; NW_006784004.1; NW_006532274.1;
NW_006725466.1; NW_006712311.1; NW_006610005.1; NW_006501061.1; NW_006399824.1;
NW_006408538.1; NW_006288853.1; NW_006383157.1; NW_006224511.1; NW_005882862.1;
NW_006210709.1; NW_006159730.1; NW_005859001.1; NW_005855688.1; NW_005871110.1;
NW_005843034.1; NW_005819063.1; NW_005815230.1; NW_005395486.1; NW_005369027.1;
NC_022320.1; NC_022280.1; NC_022028.1; NW_007359849.1; NW_007359875.1; NC_021678.1;
NW_004454176.1; NW_004205048.1; NC_019861.1; NC_018434.1; NC_018733.2; NC_018893.1;
NC_016133.1; NC_016135.1; NC_016098.1; NC_010459.4; NC_022211.1; NC_015018.2; NC_013686.1;
NC_011470.1; NC_009144.2; NC_007796.1; NC_018609.1; NC_027340.1; NC_027218.1; NC_027132.1;
NC_026928.1; NC_026583.1; NC_026440.1; NC_025422.1; NC_025447.1; NC_023862.1; NC_023553.1;
NC_023587.1; NC_023564.1; NC_022973.1; NC_022984.1; NC_022086.1; NC_021307.1; NC_021321.1;
NC_021335.1; NC_021320.1; NC_020159.1; NC_019974.1; NC_019974.1; NC_019974.1; NC_019974.1;
NC_019962.1; NC_019962.1; NC_019942.1; NC_018283.1; NC_018227.2; NC_016653.1; NC_016570.1;
NC_013600.1; NC_015954.1; NC_015958.1; NC_015676.1; NC_015274.1; NC_015296.1; NC_014371.1;
NC_014253.1; NC_013769.1; NC_013084.1; NC_013081.1; NC_013079.1; NC_012865.1; NC_012029.1;

TABLE E-continued

Accession Numbers of Cas proteins (or those related with Cas-like function) and Nucleic Acids encoding the same.
All amino acid and nucleic acid sequences associated with the Accession Numbers below as of Jun. 29, 2016, are incorporated by reference in their entireties. Any mutants or variants that are at least 70, 75, 80, 85, 90, 95, 96, 97, 98, 99% homologous to the encoded nucleic acids or amino acids set forth in the Accession Numbers below are also incorporated by reference in their entireties.

NC_011023.1; NC_011019.1; NC_010537.1; NC_009954.1; NC_007796.1; NC_007493.2; NC_007355.1; NC_002946.2; NC_002946.2; NC_002519.1; NC_006089.3; NC_006089.3; NC_003214.2; NC_010356.1; NC_004463.1; NC_007797.1; NC_002737.2; NC_025375.1; NC_005125.1; NC_027120.1; NC_018280.1; NC_016566.1; NC_007077.3; NC_019419.2; NC_012223.2; NC_021783.1; NC_021342.2; NC_021315.1; NC_020204.1; NC_025443.1; NC_023549.1; NC_019924.1; NC_019550.1; NC_019549.1; NC_014457.1; NC_023566.1; NC_004927.1; NC_003345.1; NC_014322.1; NC_027119.1; NC_019452.1; NC_010153.1; NC_021780.1; NC_021775.1; NC_020419.1; NC_020419.1; NC_013926.1; NC_005364.2; NC_017954.1; NC_012039.1; NC_000918.1; NC_013790.1; NC_022093.1; NC_022093.1; NC_022093.1; NC_022093.1; NC_021592.1; NC_021169.1; NC_018015.1; NC_015931.1; NC_015435.1; NC_014408.1; NC_013790.1; NC_012883.1; NC_008818.1; NC_008818.1; NC_008818.1; NC_008818.1; NC_007297.1; NC_006570.2; NC_000916.1; NC_004350.2; NC_003454.1; NC_000853.1; NC_018876.1; NC_017527.1; NC_021313.1; NC_020388.1; NC_015518.1; NC_015416.1; NC_015416.1; NC_015151.1; NC_015151.1; NC_014537.1; NC_014537.1; NC_014537.1; NC_014537.1; NC_014507.1; NC_013849.1; NC_013849.1; NC_009464.1; NC_000917.1; NC_000917.1; NC_000917.1; NC_000917.1; NC_002932.3; NC_026153.1; NC_020177.2; NC_027207.1; NC_025260.1; NC_018224.1; NC_016449.1; NC_016453.1; NC_015574.1; NC_007643.1; NC_007643.1; NC_026756.1; NC_026492.1; NC_026490.1; NC_021366.1; NC_014946.1; NC_014950.1; NC_009667.1; NC_009048.1; NC_006682.1; NW_001820527.3; NC_018213.1; NC_009364.1; NC_026477.1; NC_017844.1; NC_016494.1; NC_016492.1; NC_016457.1; NC_016475.1; NC_016507.1; NC_016502.1; NC_012726.1; NC_011672.1; NC_011687.1; NC_006036.2; NC_006032.2; NC_026933.1; NC_026006.1; NC_026003.1; NC_015018.2; NC_025820.1; NC_025701.1; NC_024796.1; NC_024460.1; NW_007378989.1; NW_007377463.1; NW_007546349.1; NW_007546273.1; NC_024245.1; NC_024241.1; NC_024130.1; NC_024126.1; NW_006921822.1; NW_006534794.1; NW_006749448.1; NW_006601119.1; NW_003140815.1; NW_006272001.1; NW_006280498.1; NC_023166.1; NC_023167.1; NC_023200.1; NC_023183.1; NW_006263308.1; NC_016107.1; NC_023053.1; NW_006238943.1; NW_006239104.1; NW_006235748.1; NW_006190770.1; NW_006188714.1; NW_005871025.1; NW_005872046.1; NW_005841850.1; NW_005372290.1; NC_010456.4; NC_021165.1; NC_021163.1; NC_020492.1; NC_020496.1; NC_015448.2; NC_026660.1; NW_003803976.1; NC_019833.1; NC_012601.1; NW_003139842.1; NC_012012.3; NW_003384299.1; NW_001760161.1; NC_008802.1; NC_027383.1; NC_023044.1; NC_026591.1; NC_025446.1; NC_025442.1; NC_025428.1; NC_024783.1; NC_023856.1; NC_023755.1; NC_023753.1; NC_023751.1; NC_023749.1; NC_023749.1; NC_020853.1; NC_020851.1; NC_020845.1; NC_020844.1; NC_020837.1; NC_020082.1; NC_019977.1; NC_019942.1; NC_019791.1; NC_019724.1; NC_019530.1; NC_019524.1; NC_019519.1; NC_019518.1; NC_019457.1; NC_019417.1; NC_019401.1; NC_018396.1; NC_016520.1; NC_016531.1; NC_016073.1; NC_015676.1; NC_015569.1; NC_015466.1; NC_015320.1; NC_012995.1; NC_012992.1; NC_012867.1; NC_011832.1; NC_010175.1; NC_009954.1; NC_009712.1; NC_007710.1; NC_009189.1; NC_009181.1; NC_008698.1; NC_008698.1; NC_007955.1; NC_007796.1; NC_012589.1; NC_012588.1; NC_004086.1; NC_004342.2; NC_022096.1; NC_014644.1; NC_011661.1; NC_010175.1; NC_002754.1; NC_002754.1; NC_003413.1; NC_021921.1; NC_002754.1; NC_018015.1; NC_018015.1; NC_015865.1; NC_015847.1; NC_015680.1; NC_015680.1; NC_015680.1; NC_015474.1; NC_015474.1; NC_015435.1; NC_012804.1; NC_012470.1; NC_009515.1; NC_009440.1; NC_006624.1; NC_006624.1; NC_004557.1; NC_004557.1; NC_016023.1; NC_015518.1; NC_013202.1; NC_013158.1; NC_003106.2; NC_003106.2; NC_015943.1; NC_011138.3; NC_009778.1; NC_009380.1; NC_003552.1; NC_014228.1; NC_017276.1; NC_017275.1; NC_013892.1; NC_012632.1; NC_012632.1; NC_012623.1; NC_012588.1; NC_012588.1; NC_011296.1; NC_011296.1; NC_019792.1; NC_015678.1; NC_014222.1; NC_013887.1; NC_013887.1; NC_013769.1; NC_013156.1; NC_013156.1; NC_011832.1; NC_009953.1; NC_009635.1; NC_009634.1; NC_009439.1; NC_008618.1; NC_007955.1; NC_007355.1; NC_010572.1; NC_016070.1; NC_000868.1; NC_009089.1; NC_020419.1; NC_021592.1; NC_017946.1; NC_017946.1; NC_011766.1; NC_010482.1; NC_009776.1; NC_009033.1; NC_021169.1; NC_014537.1; NC_013790.1; NC_016051.1; NC_000917.1; NC_003454.1; NC_018224.1; NC_017459.1; NC_015416.1; NC_014933.1; NC_016112.1; NC_003198.1; NC_012726.1; NC_014222.1; NC_009135.1; NC_023069.1; NC_023044.1; NC_022777.1; NC_021355.1; NC_019942.1; NC_015958.1; NC_015760.1; NC_009953.1; NC_008599.1; NC_022084.1; NC_018092.1; NC_018092.1; NC_000961.1; NC_021058.1; NC_011567.1; NC_015574.1; NC_012622.1; NC_012589.1; NC_002950.2; NC_000913.3; NC_017274.1; NC_015676.1; NC_015320.1; NC_014122.1; NC_014122.1; NC_017301.1; NC_021353.1; NC_018001.1; NC_018001.1; NC_000961.1; NC_000961.1; NC_015931.1; NC_015931.1; NC_013849.1; NC_002950.2; NC_002663.1; NC_015460.1; NC_005085.1; NC_010002.1; NC_013722.1; NC_003106.2; NC_007796.1; NC_014147.1; NC_009053.1; NC_016901.1; NC_014500.1; NC_003413.1; NC_016070.1; NC_022777.1; NC_015516.1; NC_020517.1; NC_014106.1; NC_010610.1; NC_008942.1; NC_008054.1; NC_007164.1; NC_002935.2; NC_013961.1; NC_009434.1; NC_006834.1; NC_020990.1; NC_009615.1; NC_020800.1; NC_021082.1; NC_009089.1; NC_014160.1; NC_007644.1; NC_019943.1; NC_017384.1; NC_013722.1; NC_007643.1; NC_007643.1; NC_007643.1; NC_002939.5; NC_004342.2; NC_005085.1; NC_008526.1; NC_014500.1; NC_009515.1; NC_003280.10; NC_008508.1; NC_008508.1; NC_004342.2; NC_010296.1; NC_003197.1; NC_007090.3; NW_006623966.1; NC_015020.2; NC_019042.1; NC_011273.1; NC_002695.1; NC_002737.2; NC_007581.1; NC_017954.1; NC_014961.1; NC_014658.1; NC_007681.1; NC_007681.1; NC_000918.1; NC_000916.1; NC_022093.1; NC_021592.1; NC_015865.1; NC_014804.1; NC_012883.1; NC_010610.1; NC_008818.1; NC_007297.1; NC_004350.2; NC_000853.1; NC_015151.1; NC_007644.1; NC_000917.1; NC_004113.1; NC_002932.3; NC_002932.3; NC_022239.1; NC_016112.1; NC_016112.1; NC_003901.1; NC_018658.1; NC_014431.1; NC_014318.1; NC_011751.1; NC_009359.1; NC_026939.1; NC_024803.1; NC_024313.1; NW_005890115.1; NC_026659.1; NC_023752.1; NC_009954.1; NC_007955.1; NC_007796.1; NC_025443.1; NC_025687.1; NC_009698.1; NC_022777.1; NC_002754.1; NC_000961.1; NC_011661.1; NC_000868.1; NC_000868.1; NC_003413.1; NC_003413.1; NC_021921.1; NC_000916.1; NC_021169.1; NC_018015.1; NC_018015.1; NC_018015.1; NC_017946.1; NC_017946.1; NC_015865.1; NC_015865.1; NC_015865.1; NC_015680.1; NC_015680.1; NC_015680.1; NC_015474.1; NC_015474.1;

TABLE E-continued

Accession Numbers of Cas proteins (or those related with Cas-like function) and Nucleic Acids encoding the same. All amino acid and nucleic acid sequences associated with the Accession Numbers below as of Jun. 29, 2016, are incorporated by reference in their entireties. Any mutants or variants that are at least 70, 75, 80, 85, 90, 95, 96, 97, 98, 99% homologous to the encoded nucleic acids or amino acids set forth in the Accession Numbers below are also incorporated by reference in their entireties.

NC_012883.1; NC_012804.1; NC_012804.1; NC_016051.1; NC_016051.1; NC_011529.1; NC_011529.1;
NC_007181.1; NC_006624.1; NC_006624.1; NC_006624.1; NC_006448.1; NC_004557.1; NC_004557.1;
NC_017459.1; NC_015518.1; NC_015518.1; NC_015460.1; NC_013202.1; NC_013158.1; NC_000917.1;
NC_020247.1; NC_020246.1; NC_003552.1; NC_017275.1; NC_010296.1; NC_012632.1; NC_012632.1;
NC_012588.1; NC_012588.1; NC_011296.1; NC_011296.1; NC_021355.1; NC_019792.1; NC_015958.1;
NC_015636.1; NC_015562.1; NC_013887.1; NC_013156.1; NC_007955.1; NC_007355.1; NC_002754.1;
NC_002754.1; NC_009778.1; NC_000962.3; NC_009089.1; NC_021592.1; NC_017946.1; NC_015680.1;
NC_018015.1; NC_014537.1; NC_014537.1; NC_012883.1; NC_012804.1; NC_018224.1; NC_017459.1;
NC_016023.1; NC_015943.1; NC_023069.1; NC_023044.1; NC_019942.1; NC_014222.1; NC_008599.1;
NC_002754.1; NC_022084.1; NC_022084.1; NC_022084.1; NC_018092.1; NC_014804.1; NC_014804.1;
NC_021058.1; NC_017274.1; NC_015320.1; NC_014122.1; NC_013407.1; NC_014658.1; NC_000961.1;
NC_000961.1; NC_018092.1; NC_015151.1; NC_013849.1; NC_011567.1; NC_013926.1; NC_002754.1;
NC_013520.1; NC_013520.1; NC_007181.1; NC_007426.1; NC_003106.2; NC_020247.1; NC_020246.1;
NC_017276.1; NC_017275.1; NC_012632.1; NC_012623.1; NC_012588.1; NC_011296.1; NC_011296.1;
NC_013769.1; NC_013769.1; NC_012726.1; NC_021058.1; NC_012622.1; NC_012589.1; NC_015151.1;
NC_015954.1; NC_004547.2; NC_000913.3; NC_010175.1; NC_016070.1; NC_002950.2; NC_009380.1;
NC_009089.1; NC_009495.1; NC_022777.1; NC_007796.1; NC_014106.1; NC_008054.1; NC_002663.1;
NC_013961.1; NC_011138.3; NC_014228.1; NC_020990.1; NC_013892.1; NC_015760.1; NC_009953.1;
NC_009953.1; NC_009439.1; NC_010572.1; NC_002971.3; NC_021353.1; NC_014644.1; NC_010610.1;
NC_002935.2; NC_013722.1; NC_009464.1; NC_007643.1; NC_002939.5; NC_010002.1; NC_003198.1;
NC_014318.1; NC_008526.1; NC_011832.1; NC_008701.1; NC_007955.1; NC_007796.1; NC_014147.1;
NC_009053.1; NC_014500.1; NC_016901.1; NC_015676.1; NC_020418.1; NW_003613864.1;
NC_000011.10; NW_006800487.1; NC_006603.3; NW_003614246.1; NC_012602.1; NC_013790.1;
NC_009515.1; NC_015574.1; NC_007871.1; NC_006478.3; NC_004347.2; NC_009006.2; NT_078266.2;
NC_003454.1; NW_006212882.1; NC_011913.1; NC_009917.1; NW_007675828.1; NW_007370782.1;
NW_007248774.1; NC_023642.1; NW_006775074.1; NW_006730123.1; NW_006718075.1;
NW_006711808.1; NW_006400147.1; NW_006408681.1; NW_006384369.1; NW_005882764.1;
NW_006200097.1; NC_022285.1; NW_004209914.1; NC_018435.1; NC_018732.2; NC_018165.1;
NC_027879.1; NC_019830.1; NC_013906.1; NC_009150.2; NC_000964.3; NC_002696.2; NC_017034.1;
NC_007581.1; NC_018001.1; NC_017954.1; NC_014961.1; NC_014961.1; NC_011766.1; NC_009776.1;
NC_007681.1; NC_007681.1; NC_005877.1; NC_005877.1; NC_005877.1; NC_002689.2; NC_000918.1;
NC_000918.1; NC_021592.1; NC_015931.1; NC_015931.1; NC_010482.1; NC_009033.1; NC_000853.1;
NC_015518.1; NC_015416.1; NC_013849.1; NC_009440.1; NC_009440.1; NC_009009.1; NC_007644.1;
NC_000917.1; NC_003106.2; NC_011916.1; NC_007643.1; NC_006347.1; NC_004342.2; NC_002945.3;
NC_012589.1; NC_012623.1; NC_011672.1; NC_016131.1; NW_004454187.1; NC_019862.1;
NC_010451.3; NC_015768.1; NC_020173.2; NC_017972.1; NC_015320.1; NC_011832.1; NC_010175.1;
NC_010175.1; NC_008599.1; NC_006461.1; NC_015637.1; NC_009784.1; NC_016114.1; NC_001493.2;
NC_008508.1; NC_003197.1; NC_017844.1; NW_006399893.1; NC_002695.1; NC_017634.1;
NC_003143.1; NC_017941.2; NC_004605.1; NC_004605.1; NC_019411.1; NC_007164.1; NC_002932.3;
NC_005085.1; NC_027207.1; NC_016452.1; NC_016112.1; NC_009784.1; NC_007606.1; NC_002506.1;
NC_018658.1; NC_011751.1; NC_016497.1; NC_011678.1; NC_006035.2; NC_026147.1; NC_013913.1;
NC_024132.1; NC_006461.1; NC_000913.3; NC_014106.1; NC_008054.1; NC_013961.1; NC_011138.3;
NC_009778.1; NC_014228.1; NC_020990.1; NC_013892.1; NC_015760.1; NC_009953.1; NC_009953.1;
NC_009439.1; NC_010572.1; NC_014644.1; NC_010610.1; NC_002935.2; NC_009464.1; NC_007643.1;
NC_002939.5; NC_003198.1; NC_014318.1; NC_008526.1; NC_011832.1; NC_007955.1; NC_007796.1;
NC_015676.1; NC_015637.1; NC_009784.1; NC_016114.1; NC_001493.2; NC_008508.1; NC_003197.1;
NC_017844.1; NC_002695.1; NC_017941.2; NC_004605.1; NC_007164.1; NC_002932.3; NC_016452.1;
NC_016112.1; NC_007606.1; NC_002506.1; NC_018658.1; NC_011751.1; NC_026147.1; NC_024132.1;
NC_006461.1; NC_004547.2; NC_002663.1; NC_002971.3; NC_013722.1; NC_010002.1; NC_014147.1;
NC_009053.1; NC_014500.1; NC_016901.1; NC_020418.1; NW_006399893.1; NC_017634.1;
NC_003143.1; NC_004605.1; NC_019411.1; NC_005085.1; NC_027207.1; NC_009784.1; NC_016497.1;
NC_011678.1; NC_006035.2; NC_013913.1; NC_000913.3; NC_002950.2; NC_019943.1; NC_021355.1;
NC_019942.1; NC_021058.1; NC_017576.1; NC_009785.1; NC_019943.1; NC_010175.1; NC_002754.1;
NC_016070.1; NC_003413.1; NC_003413.1; NC_021921.1; NC_015516.1; NC_007681.1; NC_021169.1;
NC_020517.1; NC_018015.1; NC_017946.1; NC_017946.1; NC_015865.1; NC_015847.1; NC_015680.1;
NC_015680.1; NC_015680.1; NC_015474.1; NC_015435.1; NC_014106.1; NC_013790.1; NC_012470.1;
NC_010610.1; NC_010610.1; NC_010482.1; NC_009515.1; NC_009440.1; NC_008942.1; NC_008054.1;
NC_006624.1; NC_017459.1; NC_015518.1; NC_014933.1; NC_013961.1; NC_013202.1; NC_013158.1;
NC_000917.1; NC_003901.1; NC_003106.2; NC_009434.1; NC_005085.1; NC_018224.1; NC_015943.1;
NC_009380.1; NC_006834.1; NC_003552.1; NC_020990.1; NC_017276.1; NC_017275.1; NC_009615.1;
NC_012632.1; NC_012632.1; NC_012623.1; NC_012588.1; NC_012588.1; NC_020800.1; NC_019792.1;
NC_015760.1; NC_015678.1; NC_014222.1; NC_013887.1; NC_013887.1; NC_013156.1; NC_013156.1;
NC_009953.1; NC_009634.1; NC_008618.1; NC_008599.1; NC_007355.1; NC_002754.1; NC_002754.1;
NC_021082.1; NC_000868.1; NC_009089.1; NC_009089.1; NC_020419.1; NC_021592.1; NC_014644.1;
NC_000916.1; NC_015474.1; NC_014537.1; NC_012804.1; NC_016051.1; NC_007644.1; NC_006624.1;
NC_004557.1; NC_004557.1; NC_017384.1; NC_016023.1; NC_013722.1; NC_007643.1; NC_007643.1;
NC_016112.1; NC_016112.1; NC_014318.1; NC_008526.1; NC_012726.1; NC_023044.1; NC_022777.1;
NC_014222.1; NC_011296.1; NC_009953.1; NC_018001.1; NC_017954.1; NC_022084.1; NC_018092.1;
NC_018092.1; NC_018015.1; NC_000961.1; NC_011567.1; NC_000917.1; NC_015574.1; NC_014500.1;
NC_012622.1; NC_012589.1; NC_017274.1; NC_015320.1; NC_014122.1; NC_021353.1; NC_000916.1;
NC_000961.1; NC_000961.1; NC_015931.1; NC_013849.1; NC_011296.1; NC_002754.1; NC_022084.1;
NC_006590.3; NW_003613770.1; NW_006770037.1; NW_005882719.1; NW_006717982.1;
NW_003159449.1; NW_007676006.1; NW_004454173.1; NC_009167.2; NC_021161.1; NC_007131.6;

TABLE E-continued

Accession Numbers of Cas proteins (or those related with Cas-like function) and Nucleic Acids encoding the same.
All amino acid and nucleic acid sequences associated with the Accession Numbers below as of Jun. 29, 2016, are incorporated by reference in their entireties. Any mutants or variants that are at least 70, 75, 80, 85, 90, 95, 96, 97, 98, 99% homologous to the encoded nucleic acids or amino acids set forth in the Accession Numbers below are also incorporated by reference in their entireties.

NC_010443.4; NC_013929.1; NC_016114.1; NC_020416.1; NC_014160.1; NC_004342.2; NC_021366.1; NC_014430.1; NW_007727498.1; NW_006777583.1; NW_006732012.1; NW_006399890.1; NW_005882776.1; NC_019874.1; NC_013918.1; NC_026607.2; NC_022777.1; NC_019042.1; NC_011421.1; NC_009784.1; NC_002695.1; NC_002737.2; NC_021315.1; NC_007581.1; NC_022761.1; NC_000918.1; NC_012883.1; NC_007297.1; NC_004350.2; NC_003454.1; NC_000853.1; NC_009464.1; NC_002932.3; NC_002932.3; NC_016112.1; NC_006347.1; NC_004342.2; NC_018658.1; NC_010397.1; NC_002678.2; NC_011751.1; NC_011695.1; NC_025697.1; NC_025205.1; NW_006239047.1; NW_005372402.1; NC_020494.1; NW_003804572.1; NC_016132.1; NC_027344.1; NC_025442.1; NC_015320.1; NC_014923.1; NC_013046.1; NC_011167.1; NC_007955.1; NC_002754.1; NC_008818.1; NC_000918.1; NC_014222.1; NC_011661.1; NC_003413.1; NC_010175.1; NC_015474.1; NC_013202.1; NC_018224.1; NC_003552.1; NC_009635.1; NC_007355.1; NC_009089.1; NC_021592.1; NC_015847.1; NC_009515.1; NC_018015.1; NC_006624.1; NC_019943.1; NC_017459.1; NC_015943.1; NC_015416.1; NC_022777.1; NC_022777.1; NC_014222.1; NC_011296.1; NC_009634.1; NC_022084.1; NC_018092.1; NC_000961.1; NC_011567.1; NC_015574.1; NC_014122.1; NC_021353.1; NC_015320.1; NC_014122.1; NC_019471.1; NC_026149.1; NW_006711753.1; NC_025697.1; NW_007540505.1; NW_006749413.1; NC_008809.1; NT_033779.5; NC_000961.1; NC_015562.1; NC_011645.1; NC_017034.1; NC_019912.1; NC_011318.1; NT_167064.1; NC_002939.5; NC_011904.1; NC_008314.1; NC_024342.1; NW_007370677.1; NW_006804181.1; NW_006711988.1; NW_006399752.1; NW_006299715.1; NW_005785016.1; NW_005805521.1; NC_018726.2; NC_018726.2; NC_008801.1; NC_013081.1; NC_006840.2; NC_023007.1; NC_014649.1; NC_007681.1; NC_007681.1; NC_007681.1; NC_000918.1; NC_021592.1; NC_013790.1; NC_003454.1; NC_000853.1; NC_004557.1; NC_007644.1; NW_007544598.1; NC_027207.1; NC_003901.1; NC_009908.2; NC_016506.1; NC_006041.1; NC_006029.1; NC_025997.1; NW_007733735.1; NW_006799945.1; NW_006749276.1; NC_016088.1; NW_005871062.1; NW_005369870.1; NW_005372669.1; NW_004204575.1; NC_021355.1; NC_014222.1; NC_009135.1; NC_000868.1; NC_003413.1; NC_017946.1; NC_015680.1; NC_015474.1; NC_012804.1; NC_006624.1; NC_016070.1; NC_013887.1; NC_013156.1; NC_022084.1; NC_018092.1; NC_018001.1; NC_000961.1; NC_013849.1; NC_016091.1; NC_013929.1; NC_018734.2; NC_018609.1; NC_003413.1; NC_014961.1; NC_018092.1; NC_021313.1; NC_013488.1; NC_023186.1; NC_022777.1; NC_021921.1; NC_013158.1; NC_019792.1; NC_004557.1; NC_019943.1; NC_015516.1; NC_012470.1; NC_016023.1; NC_009434.1; NC_005085.1; NC_006834.1; NC_015678.1; NC_020419.1; NC_020517.1; NC_007644.1; NC_017384.1; NC_014933.1; NC_013722.1; NC_007643.1; NC_016112.1; NC_009615.1; NC_002950.2; NC_021082.1; NC_014500.1; NC_008804.1; NC_007873.1; NC_004342.2; NC_018015.1; NC_016901.1; NC_007796.1; NC_008195.1; NC_013158.1; NC_014371.1; NC_019042.1; NC_011044.1; NC_002946.2; NC_002946.2; NC_002737.2; NC_018859.1; NC_026932.1; NC_010610.1; NC_008942.1; NC_007297.1; NC_004350.2; NC_004350.2; NC_002932.3; NC_016112.1; NC_015574.1; NC_004342.2; NC_014942.1; NC_026148.1; NC_025703.1; NW_007680270.1; NC_020493.1; NC_023554.1; NC_022327.1; NC_022331.1; NC_022328.1; NC_016522.1; NC_002663.1; NC_018609.1; NC_006448.1; NC_017576.1; NC_015964.1; NC_002163.1; NC_002967.9; NC_009785.1; NC_004829.2; NC_017576.1; NC_002935.2; NC_013198.1; NC_020419.1; NC_009613.3; NC_022246.1; NC_007643.1; NC_018081.1; NC_007117.6; NC_023622.1; NC_007297.1; NC_024462.1; NC_003076.8; NC_019042.1; NC_002737.2; NC_004350.2; NC_004116.1; NC_017946.1; NC_000961.1; NT_167064.1; NC_002967.9; NC_012963.1; NC_023658.1; NW_006725355.1; NW_006400033.1; NW_006385373.1; NW_005815240.1; NW_004197941.1; NC_009094.1; NC_019516.1; NC_008599.1; NC_004740.1; NC_007929.1; NC_006570.2; NC_014429.1; NC_026477.1; NC_016462.1; NC_025688.1; NC_025693.1; NC_024800.1; NW_006399825.1; NC_019403.1; NC_016524.1; NC_007709.1; NC_000007.14; NC_000962.3; NC_021058.1; NC_021058.1; NC_002754.1; NC_017946.1; NC_015680.1; NC_011529.1; NC_017276.1; NC_012622.1; NC_012622.1; NC_000961.1; NC_013520.1; NC_006448.1; NC_002950.2; NC_017276.1; NC_017275.1; NC_012632.1; NC_012588.1; NC_015636.1; NC_013887.1; NC_013769.1; NC_013156.1; NC_009635.1; NC_015680.1; NC_010482.1; NC_009698.1; NC_012726.1; NC_015562.1; NC_011296.1; NC_011296.1; NC_009634.1; NC_012589.1; NC_012589.1; NC_013407.1; NC_013926.1; NC_012622.1; NC_013156.1; NC_011296.1; NC_013790.1; NC_009033.1; NC_016070.1; NC_013849.1; NC_019977.1; NC_013407.1; NC_015869.2; NC_011661.1; NC_000853.1; NC_000917.1; NC_002945.3; NC_002754.1; NC_007114.6; NC_019473.1; NC_023623.1; NW_007577872.1; NC_013900.1; NW_003155240.1; NC_000005.10; NC_002689.2; NC_009009.1; NC_014222.1; NC_003413.1; NC_014374.1; NC_011766.1; NC_000918.1; NC_022093.1; NC_018092.1; NC_000853.1; NC_017527.1; NC_015151.1; NC_009495.1; NC_015562.1; NC_014222.1; NC_015460.1; NC_015460.1; NC_015460.1; NC_009440.1; NC_007643.1; NC_003552.1; NW_006263392.1; AC_000177.1; NC_004316.3; NC_016411.2; NC_012225.1; NC_005788.4; NC_014323.1; NC_008818.1; NC_017960.1; NW_006436284.1; NW_006211808.1; NC_013743.1; NC_009380.1; NW_005393620.1; NC_011089.1; NW_007727769.1; NW_007673341.1; NC_024350.1; NW_006921745.1; NW_006533007.1; NW_006532497.1; NW_006712293.1; NW_006501110.1; NW_006400054.1; NW_006408600.1; NW_005882775.1; NW_005785850.1; NW_005812630.1; NC_022312.1; NW_004454213.1; NC_018441.1; NC_018723.2; NC_016133.1; NC_010446.4; NC_009164.2; NC_003047.1; NC_007088.5; NC_009776.1; NC_015931.1; NC_000916.1; NC_015518.1; NC_007643.1; NC_003901.1; NC_016491.1; NC_026938.1; NW_007379404.1; NW_007377898.1; NC_008809.1; NC_016103.1; NC_016099.1; NW_005372401.1; NW_003140313.1; NW_003383754.1; NC_008599.1; NC_016522.1; NC_014122.1; NC_011167.1; NC_010175.1; NC_008698.1; NC_007355.1; NC_005877.1; NC_003106.2; NC_012623.1; NC_012589.1; NC_023069.1; NC_008701.1; NC_018015.1; NC_007181.1; NC_020247.1; NW_004218575.1; NC_022973.1; NC_022984.1; NC_017459.1; NC_007426.1; NC_002663.1; NC_016023.1; NW_006433950.1; NW_006383296.1; NC_015636.1; NC_015562.1; NC_015562.1; NC_015954.1; NC_011832.1; NC_007796.1; NC_004547.2; NC_002663.1; NC_010002.1; NC_015460.1; NC_013722.1; NC_014147.1; NC_009053.1; NC_016901.1; NC_014500.1; NC_020418.1; NW_006890166.1; NC_012019.3; NC_017634.1; NC_003143.1; NC_002971.3; NC_016477.1; NC_025693.1; NC_004547.2; NC_002663.1;

TABLE E-continued

Accession Numbers of Cas proteins (or those related with Cas-like function) and Nucleic Acids encoding the same. All amino acid and nucleic acid sequences associated with the Accession Numbers below as of Jun. 29, 2016, are incorporated by reference in their entireties. Any mutants or variants that are at least 70, 75, 80, 85, 90, 95, 96, 97, 98, 99% homologous to the encoded nucleic acids or amino acids set forth in the Accession Numbers below are also incorporated by reference in their entireties.

NC_005085.1; NC_010002.1; NC_015460.1; NC_020418.1; NC_013722.1; NC_014147.1; NC_009053.1; NC_016901.1; NC_014500.1; NC_000919.1; NC_009784.1; NW_006804308.1; NC_017634.1; NC_003143.1; NC_004605.1; NC_007284.2; NC_019472.1; NC_004547.2; NC_009784.1; NC_020418.1; NC_002663.1; NC_015460.1; NC_005085.1; NC_010002.1; NC_002971.3; NC_013722.1; NC_014147.1; NC_009053.1; NC_016901.1; NC_014500.1; NC_017634.1; NC_003143.1; NC_004605.1; NC_016457.1; NW_007546277.1; NC_014644.1; NC_002939.5; NC_000913.3; NC_011138.3; NC_014228.1; NC_013892.1; NC_009953.1; NC_003198.1; NC_014106.1; NC_007643.1; NC_007643.1; NC_016112.1; NC_014318.1; NC_011832.1; NC_009953.1; NC_009439.1; NC_007955.1; NC_014500.1; NC_015676.1; NC_014106.1; NC_010610.1; NC_009440.1; NC_008054.1; NC_007164.1; NC_015518.1; NC_017276.1; NC_017275.1; NC_012632.1; NC_012623.1; NC_012588.1; NC_015760.1; NC_013769.1; NC_009953.1; NC_002754.1; NC_010572.1; NC_012622.1; NC_012589.1; NC_017274.1; NC_008054.1; NC_020990.1; NC_015760.1; NC_009778.1; NC_008526.1; NC_008481.2; AC_000180.1; NW_005842445.1; NC_026935.1; NW_005784896.1; NW_007359860.1; NC_013961.1; NC_010610.1; NC_009440.1; NC_007164.1; NC_008508.1; NC_010296.1; NC_003197.1; NW_008237220.1; NW_005882971.1; NW_005853887.1; NW_005394383.1; NC_018890.1; NC_018390.1; NC_013051.1; NC_002695.1; NC_002677.1; NC_009464.1; NC_002932.3; NC_018658.1; NC_011751.1; NC_026504.1; NC_013486.1; NW_005372181.1; NC_007796.1; NC_014644.1; NC_002939.5; NC_000913.3; NC_011138.3; NC_020990.1; NC_011832.1; NC_009953.1; NC_009439.1; NC_014106.1; NC_007643.1; NC_016112.1; NC_003198.1; NC_014318.1; NC_015676.1; NC_007955.1; NC_013961.1; NC_015760.1; NC_002935.2; NC_008526.1; NC_014644.1; NW_005819431.1; NC_016105.1; NC_009778.1; NC_008508.1; NC_003197.1; NC_014228.1; NC_013892.1; NW_005785758.1; NC_002695.1; NC_010572.1; NC_010610.1; NC_007164.1; NC_009464.1; NC_002932.3; NC_007643.1; NC_018658.1; NC_011751.1; NC_025998.1; NC_009953.1; NC_007796.1; NC_017459.1; NC_007426.1; NC_010296.1; NC_015562.1; NC_021058.1; NC_013407.1; NC_007181.1; NC_020247.1; NC_020246.1; NC_013769.1; NC_011832.1; NC_007796.1; NC_015954.1; NC_005877.1; NW_007377947.1; NC_008698.1; NC_017459.1; NC_007426.1; NC_010296.1; NC_015636.1; NC_015562.1; NC_011832.1; NC_007796.1; NC_021058.1; NC_015954.1; NC_013407.1; NC_011832.1; NC_007796.1; NC_007181.1; NC_020247.1; NC_020246.1; NC_017275.1; NC_013769.1; NC_000016.10; NC_005877.1; NC_008698.1; NC_011296.1; NC_002754.1; NC_009033.1; NC_017946.1; NC_015680.1; NC_015518.1; NC_003106.2; NC_017276.1; NC_017275.1; NC_012632.1; NC_012588.1; NC_013887.1; NC_013769.1; NC_013156.1; NC_002754.1; NC_015435.1; NC_009440.1; NC_006624.1; NC_012726.1; NC_012623.1; NC_022084.1; NC_021058.1; NC_012622.1; NC_012589.1; NC_000961.1; NC_011766.1; NC_010482.1; NC_000917.1; NC_011913.1; NW_006715916.1; NC_021792.1; NC_009776.1; NC_022093.1; NC_015931.1; NC_008818.1; NC_026477.1; NC_023069.1; NC_024142.1; NC_017576.1; NC_007929.1; NC_002967.9; NC_018081.1; NC_017576.1; NC_013198.1; NC_009785.1; NC_022279.1; NC_000003.12; NC_025981.2; NC_018153.1; NC_006448.1; NC_008482.2; NC_007865.1; NW_006890062.1; NC_012871.1; NC_008476.2; NW_006204462.1; NW_005819170.1; NC_019042.1; NC_002737.2; NC_007297.1; NC_004350.2; NC_004116.1; NC_014334.1; NC_022246.1; NC_011661.1; NC_010175.1; NC_015680.1; NC_013520.1; NC_011529.1; NC_006448.1; NC_015460.1; NC_011296.1; NC_011296.1; NC_013887.1; NC_009635.1; NC_000962.3; NC_017946.1; NC_018015.1; NC_013790.1; NC_015562.1; NC_013156.1; NC_013407.1; NC_013926.1; NC_013407.1; NC_015518.1; NC_015636.1; NC_015562.1; NC_009387.2; NC_007268.2; NC_007244.2; NC_000916.1; NC_021058.1; NC_017276.1; NC_017275.1; NC_018229.1; NC_012632.1; NC_012623.1; NC_012622.1; NC_012589.1; NC_012588.1; NC_013769.1; NC_002754.1; NC_005027.1; NC_005877.1; NC_000961.1; NC_000853.1; NC_014537.1; NC_009009.1; NC_003552.1; NC_002945.3; NC_012726.1; NW_007547664.1; NC_010175.1; NC_010175.1; NC_000962.3; NC_011296.1; NC_000961.1; NC_011661.1; NC_017946.1; NC_016070.1; NC_015680.1; NC_013520.1; NC_011529.1; NC_014537.1; NC_011296.1; NC_015636.1; NC_015562.1; NC_013887.1; NC_009635.1; NC_008698.1; NC_008698.1; NC_014205.1; NC_009033.1; NC_018015.1; NC_013790.1; NC_015562.1; NC_013156.1; NC_015151.1; NC_013407.1; NC_013407.1; NC_013926.1; NC_008701.1; NC_003106.2; NC_003106.2; NC_012589.1; NC_000916.1; NC_003552.1; NC_002754.1; NC_002754.1; NC_002689.2; NC_000853.1; NC_002945.3; NC_001140.6; NC_011296.1; NC_000962.3; NC_011661.1; NC_010175.1; NC_000961.1; NC_015680.1; NC_013520.1; NC_011529.1; NC_006448.1; NC_015460.1; NC_015636.1; NC_013156.1; NC_009635.1; NC_017946.1; NC_015562.1; NC_013887.1; NC_011296.1; NC_013407.1; NC_013926.1; NC_013407.1; NC_002689.2; NC_000916.1; NC_000853.1; NC_003552.1; NC_002945.3; NC_000962.3; NC_000961.1; NC_011661.1; NC_010175.1; NC_017946.1; NC_015680.1; NC_013520.1; NC_011529.1; NC_006448.1; NC_011296.1; NC_011296.1; NC_015636.1; NC_015562.1; NC_013887.1; NC_013156.1; NC_009635.1; NC_014205.1; NC_009033.1; NC_014537.1; NC_013790.1; NC_015562.1; NC_008698.1; NC_013407.1; NC_013926.1; NC_013407.1; NC_008701.1; NC_002689.2; NC_000853.1; NC_003552.1; NC_002945.3; NC_000962.3; NC_003106.2; NC_017276.1; NC_017275.1; NC_012632.1; NC_012588.1; NC_002754.1; NC_016070.1; NC_014537.1; NC_014537.1; NC_012726.1; NC_009954.1; NC_009954.1; NC_017274.1; NC_021058.1; NC_015151.1; NC_015151.1; NC_009135.1; NC_009785.1; NC_009615.1; NC_015678.1; NC_002737.2; NT_078268.4; NC_012470.1; NC_007297.1; NC_021058.1; NC_017576.1; NC_022246.1; NC_022246.1; NC_009668.1; NW_006921704.1; NC_012004.1; NC_019042.1; NC_025414.1; NC_014374.1; NC_008818.1; NC_022093.1; NC_012804.1; NC_004350.2; NC_004116.1; NC_009009.1; NC_009009.1; NC_002662.1; NC_022239.1; NC_016112.1; NC_002945.3; NC_025689.1; NC_024243.1; NC_018227.2; NC_002754.1; NC_012589.1; NC_017276.1; NC_012726.1; NC_002754.1; NC_012622.1; NC_012622.1; NC_017274.1; NC_012632.1; NC_012588.1; NC_010482.1; NC_017527.1; NC_017275.1; NC_011296.1; NC_012622.1; NC_012589.1; NC_021058.1; NC_013849.1; NC_019977.1; NC_013156.1; NC_021058.1; NC_013407.1; NC_003413.1; NC_003413.1; NC_000918.1; NC_018092.1; NC_018092.1; NC_015680.1; NC_000916.1; NC_000853.1; NC_000917.1; NC_003106.2; NC_003901.1; NC_013769.1; NC_007355.1; NC_001134.8; NC_009698.1; NC_002950.2; NC_003106.2; NC_017276.1; NC_002754.1; NC_015680.1; NC_017527.1; NC_009634.1; NC_012622.1; NC_017276.1; NC_017275.1; NC_012632.1; NC_012588.1; NC_013769.1; NC_014222.1; NC_021058.1; NC_012622.1; NC_012589.1;

TABLE E-continued

| Accession Numbers of Cas proteins (or those related with Cas-like function) and Nucleic Acids encoding the same. All amino acid and nucleic acid sequences associated with the Accession Numbers below as of Jun. 29, 2016, are incorporated by reference in their entireties. Any mutants or variants that are at least 70, 75, 80, 85, 90, 95, 96, 97, 98, 99% homologous to the encoded nucleic acids or amino acids set forth in the Accession Numbers below are also incorporated by reference in their entireties. |
|---|
| NC_021058.1; NC_012622.1; NC_012589.1; NC_003413.1; NC_000918.1; NC_018092.1; NC_000853.1; NC_000917.1; NC_002754.1; NC_009698.1; NC_011296.1; NC_015680.1; NC_002950.2; NC_000917.1; NC_003106.2; NC_002754.1; NC_000916.1; NC_002754.1; NC_017274.1; NC_006448.1; NC_017527.1; NC_017276.1; NC_012632.1; NC_012588.1; NC_014374.1; NC_010482.1; NC_009776.1; NC_009776.1; NC_017276.1; NC_012726.1; NC_013769.1; NC_012622.1; NC_012622.1; NC_012622.1; NC_012589.1; NC_012589.1; NC_021058.1; NC_021058.1; NC_015931.1; NC_013849.1; NC_017275.1; NC_003413.1; NC_008818.1; NC_000918.1; NC_000918.1; NC_018092.1; NC_000853.1; NC_014222.1; NC_002754.1; NC_000917.1; NC_002754.1; NC_015680.1; NC_003106.2; NC_017276.1; NC_017276.1; NC_012632.1; NC_012588.1; NC_002754.1; NC_017527.1; NC_009634.1; NC_013769.1; NC_008698.1; NC_021058.1; NC_012622.1; NC_012622.1; NC_012622.1; NC_012589.1; NC_012589.1; NC_017274.1; NC_021058.1; NC_002950.2; NC_009698.1; NC_017275.1; NC_010482.1; NC_003413.1; NC_011766.1; NC_000918.1; NC_022093.1; NC_018092.1; NC_008818.1; NC_014537.1; NC_009698.1; NC_009495.1; NC_012726.1; NC_014222.1; NC_014222.1; NC_009954.1; NC_002754.1; NC_002754.1; NC_015680.1; NC_017274.1; NC_002754.1; NC_017527.1; NC_014537.1; NC_017276.1; NC_017276.1; NC_017275.1; NC_012632.1; NC_012588.1; NC_009954.1; NC_014374.1; NC_010482.1; NC_012726.1; NC_013769.1; NC_009634.1; NC_021058.1; NC_015151.1; NC_012622.1; NC_012622.1; NC_012622.1; NC_012589.1; NC_021058.1; NC_012589.1; NC_003106.2; NC_002950.2; NC_003413.1; NC_000918.1; NC_018092.1; NC_000853.1; NC_000917.1; NC_002939.5; NC_011835.1; NC_018227.2; NC_013715.1; NC_016091.1; NC_016102.1; NC_012594.1; NC_009953.1; NC_007355.1; NC_002939.5; NC_023646.1; NC_006111.3; NC_025815.1; NC_010449.4; NC_024467.1; NC_024459.1; NC_016114.1; NC_006113.3; NC_013172.1; NW_006921737.1; NW_006159630.1; NW_005785086.1; NC_013715.1; NC_009953.1; NC_007425.2; NC_017527.1; NC_007643.1; NC_007643.1; NC_025202.1; NC_024803.1; NC_023179.1; NC_022205.1; NC_018227.2; NC_007355.1; NC_009668.1; NC_013715.1; NW_005876445.1; NC_005115.4; NC_000080.6; NW_003614076.1; NC_022058.1; NC_024797.1; NW_003805272.1; NC_018227.2; NC_009135.1; NC_007355.1; NC_002939.5; NW_007359863.1; NC_012875.1; NC_010175.1; NC_010175.1; NC_015460.1; NC_005140.1; NC_005140.1; NC_000916.1; NC_015518.1; NC_021058.1; NC_017276.1; NC_017275.1; NC_012632.1; NC_012623.1; NC_012588.1; NC_013769.1; NC_002754.1; NC_002754.1; NC_012622.1; NC_012589.1; NC_002935.2; NC_015435.1; NC_009440.1; NC_012726.1; NW_003383698.1; NC_011661.1; NC_017527.1; NC_013849.1; NC_010175.1; NC_015680.1; NC_018015.1; NC_000917.1; NC_000918.1; NC_011296.1; NC_011661.1; NC_015518.1; NC_011661.1; NC_010175.1; NC_016070.1; NC_015680.1; NC_015435.1; NC_011529.1; NC_003106.2; NC_013887.1; NC_013887.1; NC_013156.1; NC_002754.1; NC_015680.1; NC_017946.1; NC_014205.1; NC_011766.1; NC_009033.1; NC_016070.1; NC_015518.1; NC_015460.1; NC_015435.1; NC_014537.1; NC_013790.1; NC_013790.1; NC_009440.1; NC_012623.1; NC_013156.1; NC_015562.1; NC_014222.1; NC_011296.1; NC_011296.1; NC_008698.1; NC_007796.1; NC_007796.1; NC_007796.1; NC_002754.1; NC_014147.1; NC_013407.1; NC_013407.1; NC_008701.1; NC_013926.1; NC_015151.1; NC_015151.1; NC_017274.1; NC_017274.1; NC_013407.1; NC_011753.2; NW_006494614.1; AC_000171.1; NW_005785783.1; NW_007546298.1; NC_026658.1; NC_013926.1; NC_007624.1; NC_011910.1; NC_009668.1; NC_009914.1; NC_026504.1; NC_015320.1; NC_007859.1; NC_006584.3; NC_003413.1; NC_002754.1; NC_013520.1; NC_013520.1; NC_008818.1; NC_022084.1; NC_021058.1; NC_021058.1; NC_021058.1; NC_018015.1; NC_018015.1; NC_015865.1; NC_015518.1; NC_015435.1; NC_014804.1; NC_012883.1; NC_011529.1; NC_007181.1; NC_014729.1; NC_013158.1; NC_010575.1; NC_009464.1; NC_005085.1; NC_020247.1; NC_020246.1; NC_017276.1; NC_017276.1; NC_017276.1; NC_017275.1; NC_017275.1; NC_016901.1; NC_012724.2; NC_010296.1; NC_007952.1; NC_004663.1; NC_013929.1; NC_012632.1; NC_012632.1; NC_012623.1; NC_012623.1; NC_012622.1; NC_012589.1; NC_012589.1; NC_012588.1; NC_012588.1; NW_007907215.1; NW_007729274.1; NW_006713510.1; NW_006384629.1; NW_005819424.1; NW_005395962.1; NC_022273.1; NC_019466.1; NC_018739.2; NC_016132.1; NC_012593.1; NC_026744.1; NC_026585.1; NC_026584.1; NC_022067.1; NC_017274.1; NC_017274.1; NC_017274.1; NC_016563.1; NC_015562.1; NC_013769.1; NC_013769.1; NC_010175.1; NC_002754.1; NC_002754.1; NC_009089.1; NC_014374.1; NC_009776.1; NC_005877.1; NC_005877.1; NC_005877.1; NC_002689.2; NC_002689.2; NC_002689.2; NC_000918.1; NC_022093.1; NC_022093.1; NC_022093.1; NC_018092.1; NC_015931.1; NC_015931.1; NC_015931.1; NC_015865.1; NC_010482.1; NC_010482.1; NC_000916.1; NC_000961.1; NC_000961.1; NC_000853.1; NC_000853.1; NC_021313.1; NC_020388.1; NC_018876.1; NC_015151.1; NC_013849.1; NC_009440.1; NC_007426.1; NC_007181.1; NC_007181.1; NC_007181.1; NC_003106.2; NC_027207.1; NC_027206.1; NC_020247.1; NC_020247.1; NC_020247.1; NC_020246.1; NC_020246.1; NC_020246.1; NC_006347.1; NC_005140.1; NC_013486.1; NC_013486.1; NC_012726.1; NC_012632.1; NC_012589.1; NC_012588.1; NC_006038.1; NC_012012.3; NW_007540743.1; NW_007546279.1; NC_024240.1; NC_024325.1; NC_024128.1; NC_024128.1; NW_001814964.1; NW_006739654.1; NW_006272017.1; NW_006272029.1; NC_006586.3; NC_015562.1; NC_015562.1; NC_023069.1; NC_023069.1; NC_023069.1; NC_023069.1; NC_023752.1; NC_019792.1; NC_017274.1; NC_015636.1; NC_013887.1; NC_011296.1; NC_010175.1; NC_010175.1; NC_010175.1; NC_009954.1; NC_009635.1; NC_008698.1; NC_007796.1; NC_007796.1; NC_002754.1; NC_002754.1; NC_007422.4; NC_010175.1. |

The invention claimed is:

1. A composition comprising a nucleic acid molecule comprising from a 5' to 3' orientation: a Cas protein-binding domain and a transcription terminator domain wherein:

a) the Cas-protein binding domain comprises a nucleotide sequence having at least 95% sequence identity to SEQ ID NO: 11;

b) one or more nucleotides in the Cas-protein binding domain has a 2'-O-methyl modification and the nucleotides at positions 2, 3, 4, 23, 24, 25, 27, 31, 38 and 42 of SEQ ID NO: 11 are not chemically modified;

c) the transcription terminator domain comprises a nucleotide sequence having at least 95% sequence identity to SEQ ID NO: 114; and d) the transcription terminator domain comprises at least one phosphorothioate modification and the nucleotides at positions 1, 2, 3, and 6 of SEQ ID NO: 114 are not chemically modified.

2. The composition of claim 1, wherein the Cas protein-binding domain is from about 30 to about 55 nucleotides in length and the transcription terminator domain is from about 17 to about 45 nucleotides in length.

3. The composition of claim 1, wherein the Cas-protein binding domain comprises at least one 2' O-fluoro modified nucleotide.

4. The composition of claim 1, wherein the transcription terminator domain comprises at least one 2' O-fluoro modified nucleotide, and a conserved nucleotide at position 1, 2, 3 and/or 6 of SEQ ID NO:114.

5. The composition of claim 1, wherein the Cas protein-binding domain consists of from 38 to 42 contiguous ribonucleotides; and wherein the transcription terminator domain consists of from 38 to 42 contiguous ribonucleotides.

6. The composition of claim 1, wherein the nucleic acid molecule is at least 70% homologous to SEQ ID NO:2.

7. The composition of claim 1, wherein the nucleic acid molecule is at least 70% homologous to SEQ ID NO:4.

8. The composition of claim 1 further comprising:

a nucleic acid comprising a regulatory element operable in a eukaryotic cell operably linked to at least one nucleic acid encoding a Cas protein or functional fragment thereof.

9. The composition of claim 8 further comprising a lipid or polymer that encapsulates the nucleic acid molecule.

10. The composition of claim 1, wherein the nucleic acid molecule consists of from 80 to 101 nucleotides.

11. The composition of claim 1, wherein the Cas-protein binding domain comprises the nucleic acid sequence of SEQ ID NO: 11.

12. The composition of claim 1, wherein the nucleotides at positions 2, 3, 4, 23, 24, 25, 27, 31, 38 and 42 of SEQ ID NO: 11 are conserved.

13. The composition of claim 1, wherein the transcription terminator domain comprises at least one 2'-O-methyl modified nucleotide.

14. The composition of claim 1, wherein the transcription terminator domain comprises three phosphorothioate modifications.

15. A pharmaceutical composition comprising the composition of claim 1 and a pharmaceutically acceptable carrier.

16. A kit comprising: (a) one or more vectors comprising: a first regulatory element operable in a eukaryotic cell operably linked to a nucleotide sequence encoding a Cas protein or a functional fragment thereof and (b) the composition of claim 1.

17. A composition comprising a first nucleic acid molecule and a second nucleic acid molecule, wherein the first nucleic acid molecule and the second nucleic acid molecule are sufficiently complementary to form a duplex and in combination comprise a series of contiguous domains from a 5' to 3' orientation: a Cas protein-binding domain and a transcription terminator domain, and wherein:

a) the Cas-protein binding domain comprises a nucleotide sequence having at least 95% sequence identity to SEQ ID NO: 11;

b) one or more nucleotides in the Cas-protein binding domain has a 2'-O-methyl modification and the nucleotides at positions 2, 3, 4, 23, 24, 25, 27, 31, 38 and 42 of SEQ ID NO: 11 are not chemically modified;

c) the transcription terminator domain comprises a nucleotide sequence having at least 95% sequence identity to SEQ ID NO: 114; and d) the transcription terminator domain comprises at least one phosphorothioate modification, and the nucleotides at positions 1, 2, 3, and 6 of SEQ ID NO: 114 are not chemically modified.

18. The composition of claim 17, wherein the composition further comprises a nucleic acid comprising a regulatory element operable in a eukaryotic cell operably linked to at least one nucleic acid encoding a Cas protein or functional fragment thereof.

19. The composition of claim 18, wherein the composition further comprises a lipid or polymer that encapsulates the nucleic acid molecule.

20. A pharmaceutical composition comprising the composition of claim 17 and a pharmaceutically acceptable carrier.

* * * * *

SEQUENCE LISTING

<160> NUMBER OF SEQ ID NOS: 142

<210> SEQ ID NO 1
<211> LENGTH: 101
<212> TYPE: RNA
<213> ORGANISM: Artificial Sequence
<220> FEATURE:
<223> OTHER INFORMATION: sgRNA1 GFP-1

<400> SEQUENCE: 1
gggcgaggag cuguucaccg guuuuagagc uagaaauagc aaguuaaaau aaggcuaguc 60
cguuaucaac uugaaaaagu ggcaccgagu cggugcuuuu u 101

<210> SEQ ID NO 2
<211> LENGTH: 101
<212> TYPE: RNA
<213> ORGANISM: Artificial Sequence
<220> FEATURE:
<223> OTHER INFORMATION: sgRNA2 GFP-2
<220> FEATURE:
<221> NAME/KEY: misc_feature
<222> LOCATION: (66)..(67)
<223> OTHER INFORMATION: fluorinated base
<220> FEATURE:
<221> NAME/KEY: misc_feature
<222> LOCATION: (70)..(72)
<223> OTHER INFORMATION: fluorinated base
<220> FEATURE:
<221> NAME/KEY: misc_feature
<222> LOCATION: (80)..(80)
<223> OTHER INFORMATION: fluorinated base
<220> FEATURE:
<221> NAME/KEY: misc_feature
<222> LOCATION: (83)..(83)
<223> OTHER INFORMATION: fluorinated base
<220> FEATURE:
<221> NAME/KEY: misc_feature
<222> LOCATION: (85)..(86)
<223> OTHER INFORMATION: fluorinated base
<220> FEATURE:
<221> NAME/KEY: misc_feature
<222> LOCATION: (90)..(91)
<223> OTHER INFORMATION: fluorinated base
<220> FEATURE:
<221> NAME/KEY: misc_feature
<222> LOCATION: (94)..(94)
<223> OTHER INFORMATION: fluorinated base
<220> FEATURE:
<221> NAME/KEY: misc_feature
<222> LOCATION: (96)..(101)
<223> OTHER INFORMATION: fluorinated base

<400> SEQUENCE: 2
gggcgaggag cuguucaccg guuuuagagc uagaaauagc aaguuaaaau aaggcuaguc 60
cguuaucaac uugaaaaagu ggcaccgagu cggugcuuuu u 101

<210> SEQ ID NO 3
<211> LENGTH: 101
<212> TYPE: RNA
<213> ORGANISM: Artificial Sequence
<220> FEATURE:
<223> OTHER INFORMATION: sgRNA3 GFP-3
<220> FEATURE:
<221> NAME/KEY: misc_feature
<222> LOCATION: (1)..(5)
<223> OTHER INFORMATION: fluorinated base
<220> FEATURE:
<221> NAME/KEY: misc_feature
<222> LOCATION: (11)..(12)
<223> OTHER INFORMATION: fluorinated base
<220> FEATURE:
<221> NAME/KEY: misc_feature
<222> LOCATION: (14)..(15)
<223> OTHER INFORMATION: fluorinated base

<400> SEQUENCE: 3
gggcgaggag cuguucaccg guuuuagagc uagaaauagc aaguuaaaau aaggcuaguc 60
cguuaucaac uugaaaaagu ggcaccgagu cggugcuuuu u 101

<210> SEQ ID NO 4
<211> LENGTH: 101
<212> TYPE: RNA
<213> ORGANISM: Artificial Sequence
<220> FEATURE:
<223> OTHER INFORMATION: 2F GPF-4
<220> FEATURE:
<221> NAME/KEY: misc_feature
<222> LOCATION: (22)..(25)
<223> OTHER INFORMATION: fluorinated base
<220> FEATURE:
<221> NAME/KEY: misc_feature
<222> LOCATION: (30)..(31)
<223> OTHER INFORMATION: fluorinated base
<220> FEATURE:
<221> NAME/KEY: misc_feature
<222> LOCATION: (37)..(37)
<223> OTHER INFORMATION: fluorinated base
<220> FEATURE:
<221> NAME/KEY: misc_feature
<222> LOCATION: (40)..(42)
<223> OTHER INFORMATION: fluorinated base
<220> FEATURE:
<221> NAME/KEY: misc_feature
<222> LOCATION: (44)..(45)
<223> OTHER INFORMATION: fluorinated base
<220> FEATURE:
<221> NAME/KEY: misc_feature
<222> LOCATION: (50)..(50)
<223> OTHER INFORMATION: fluorinated base
<220> FEATURE:
<221> NAME/KEY: misc_feature
<222> LOCATION: (55)..(56)
<223> OTHER INFORMATION: fluorinated base
<220> FEATURE:
<221> NAME/KEY: misc_feature
<222> LOCATION: (59)..(61)
<223> OTHER INFORMATION: fluorinated base

<400> SEQUENCE: 4
gggcgaggag cuguucaccg guuuuagagc uagaaauagc aaguuaaaau aaggcuaguc 60
cguuaucaac uugaaaaagu ggcaccgagu cggugcuuuu u 101

<210> SEQ ID NO 5
<211> LENGTH: 101
<212> TYPE: RNA
<213> ORGANISM: Artificial Sequence
<220> FEATURE:
<223> OTHER INFORMATION: 2F GFP-5
<220> FEATURE:
<221> NAME/KEY: misc_feature
<222> LOCATION: (22)..(25)
<223> OTHER INFORMATION: fluorinated base
<220> FEATURE:
<221> NAME/KEY: misc_feature
<222> LOCATION: (30)..(31)
<223> OTHER INFORMATION: fluorinated base
<220> FEATURE:
<221> NAME/KEY: misc_feature
<222> LOCATION: (37)..(37)
<223> OTHER INFORMATION: fluorinated base
<220> FEATURE:
<221> NAME/KEY: misc_feature
<222> LOCATION: (40)..(40)
<223> OTHER INFORMATION: fluorinated base
<220> FEATURE:

<221> NAME/KEY: misc_feature
<222> LOCATION: (44)..(45)
<223> OTHER INFORMATION: fluorinated base
<220> FEATURE:
<221> NAME/KEY: misc_feature
<222> LOCATION: (50)..(50)
<223> OTHER INFORMATION: fluorinated base
<220> FEATURE:
<221> NAME/KEY: misc_feature
<222> LOCATION: (55)..(56)
<223> OTHER INFORMATION: fluorinated base
<220> FEATURE:
<221> NAME/KEY: misc_feature
<222> LOCATION: (59)..(61)
<223> OTHER INFORMATION: fluorinated base
<220> FEATURE:
<221> NAME/KEY: misc_feature
<222> LOCATION: (63)..(64)
<223> OTHER INFORMATION: fluorinated base
<220> FEATURE:
<221> NAME/KEY: misc_feature
<222> LOCATION: (66)..(67)
<223> OTHER INFORMATION: fluorinated base
<220> FEATURE:
<221> NAME/KEY: misc_feature
<222> LOCATION: (70)..(72)
<223> OTHER INFORMATION: fluorinated base
<220> FEATURE:
<221> NAME/KEY: misc_feature
<222> LOCATION: (80)..(80)
<223> OTHER INFORMATION: fluorinated base
<220> FEATURE:
<221> NAME/KEY: misc_feature
<222> LOCATION: (83)..(83)
<223> OTHER INFORMATION: fluorinated base
<220> FEATURE:
<221> NAME/KEY: misc_feature
<222> LOCATION: (85)..(86)
<223> OTHER INFORMATION: fluorinated base
<220> FEATURE:
<221> NAME/KEY: misc_feature
<222> LOCATION: (90)..(91)
<223> OTHER INFORMATION: fluorinated base
<220> FEATURE:
<221> NAME/KEY: misc_feature
<222> LOCATION: (94)..(94)
<223> OTHER INFORMATION: fluorinated base
<220> FEATURE:
<221> NAME/KEY: misc_feature
<222> LOCATION: (96)..(101)
<223> OTHER INFORMATION: fluorinated base

<400> SEQUENCE: 5
gggcgaggag cuguucaccg guuuuagagc uagaaauagc aaguuaaaau aaggcuaguc 60
cguuaucaac uugaaaaagu ggcaccgagu cggugcuuuu u 101

<210> SEQ ID NO 6
<211> LENGTH: 101
<212> TYPE: RNA
<213> ORGANISM: Artificial Sequence
<220> FEATURE:
<223> OTHER INFORMATION: 2F GFP-6
<220> FEATURE:
<221> NAME/KEY: misc_feature
<222> LOCATION: (1)..(4)
<223> OTHER INFORMATION: fluorinated base
<220> FEATURE:
<221> NAME/KEY: misc_feature
<222> LOCATION: (11)..(12)
<223> OTHER INFORMATION: fluorinated base
<220> FEATURE:
<221> NAME/KEY: misc_feature
<222> LOCATION: (14)..(16)
<223> OTHER INFORMATION: fluorinated base
<220> FEATURE:
<221> NAME/KEY: misc_feature
<222> LOCATION: (18)..(19)
<223> OTHER INFORMATION: fluorinated base

<400> SEQUENCE: 6
gggcgaggag cuguucaccg guuuuagagc uagaaauagc aaguuaaaau aaggcuaguc 60
cguuaucaac uugaaaaagu ggcaccgagu cggugcuuuu u 101

<210> SEQ ID NO 7
<211> LENGTH: 101
<212> TYPE: RNA
<213> ORGANISM: Artificial Sequence
<220> FEATURE:
<223> OTHER INFORMATION: 2F GFP-7
<220> FEATURE:
<221> NAME/KEY: misc_feature
<222> LOCATION: (1)..(4)
<223> OTHER INFORMATION: fluorinated base
<220> FEATURE:
<221> NAME/KEY: misc_feature
<222> LOCATION: (11)..(12)
<223> OTHER INFORMATION: fluorinated base
<220> FEATURE:
<221> NAME/KEY: misc_feature
<222> LOCATION: (14)..(16)
<223> OTHER INFORMATION: fluorinated base
<220> FEATURE:
<221> NAME/KEY: misc_feature
<222> LOCATION: (18)..(19)
<223> OTHER INFORMATION: fluorinated base
<220> FEATURE:
<221> NAME/KEY: misc_feature
<222> LOCATION: (22)..(25)
<223> OTHER INFORMATION: fluorinated base
<220> FEATURE:
<221> NAME/KEY: misc_feature
<222> LOCATION: (30)..(31)
<223> OTHER INFORMATION: fluorinated base
<220> FEATURE:
<221> NAME/KEY: misc_feature
<222> LOCATION: (37)..(37)
<223> OTHER INFORMATION: fluorinated base
<220> FEATURE:
<221> NAME/KEY: misc_feature
<222> LOCATION: (40)..(40)
<223> OTHER INFORMATION: fluorinated base
<220> FEATURE:
<221> NAME/KEY: misc_feature
<222> LOCATION: (44)..(45)
<223> OTHER INFORMATION: fluorinated base
<220> FEATURE:
<221> NAME/KEY: misc_feature
<222> LOCATION: (50)..(50)
<223> OTHER INFORMATION: fluorinated base
<220> FEATURE:
<221> NAME/KEY: misc_feature
<222> LOCATION: (55)..(56)
<223> OTHER INFORMATION: fluorinated base
<220> FEATURE:
<221> NAME/KEY: misc_feature
<222> LOCATION: (59)..(61)
<223> OTHER INFORMATION: fluorinated base
<220> FEATURE:
<221> NAME/KEY: misc_feature
<222> LOCATION: (63)..(64)
<223> OTHER INFORMATION: fluorinated base
<220> FEATURE:
<221> NAME/KEY: misc_feature
<222> LOCATION: (66)..(67)
<223> OTHER INFORMATION: fluorinated base
<220> FEATURE:
<221> NAME/KEY: misc_feature
<222> LOCATION: (70)..(72)
<223> OTHER INFORMATION: fluorinated base
<220> FEATURE:
<221> NAME/KEY: misc_feature
<222> LOCATION: (80)..(80)

<223> OTHER INFORMATION: fluorinated base
<220> FEATURE:
<221> NAME/KEY: misc_feature
<222> LOCATION: (83)..(83)
<223> OTHER INFORMATION: fluorinated base
<220> FEATURE:
<221> NAME/KEY: misc_feature
<222> LOCATION: (85)..(86)
<223> OTHER INFORMATION: fluorinated base
<220> FEATURE:
<221> NAME/KEY: misc_feature
<222> LOCATION: (90)..(91)
<223> OTHER INFORMATION: fluorinated base
<220> FEATURE:
<221> NAME/KEY: misc_feature
<222> LOCATION: (94)..(94)
<223> OTHER INFORMATION: fluorinated base
<220> FEATURE:
<221> NAME/KEY: misc_feature
<222> LOCATION: (96)..(101)
<223> OTHER INFORMATION: fluorinated base

<400> SEQUENCE: 7
gggcgaggag cuguucaccg guuuuagagc uagaaauagc aaguuaaaau aaggcuaguc 60
cguuaucaac uugaaaaagu ggcaccgagu cggugcuuuu u 101

<210> SEQ ID NO 8
<211> LENGTH: 101
<212> TYPE: RNA
<213> ORGANISM: Artificial Sequence
<220> FEATURE:
<223> OTHER INFORMATION: 2F GFP-8
<220> FEATURE:
<221> NAME/KEY: misc_feature
<222> LOCATION: (1)..(4)
<223> OTHER INFORMATION: fluorinated base
<220> FEATURE:
<221> NAME/KEY: misc_feature
<222> LOCATION: (11)..(12)
<223> OTHER INFORMATION: fluorinated base
<220> FEATURE:
<221> NAME/KEY: misc_feature
<222> LOCATION: (14)..(15)
<223> OTHER INFORMATION: fluorinated base
<220> FEATURE:
<221> NAME/KEY: misc_feature
<222> LOCATION: (66)..(67)
<223> OTHER INFORMATION: fluorinated base
<220> FEATURE:
<221> NAME/KEY: misc_feature
<222> LOCATION: (70)..(70)
<223> OTHER INFORMATION: fluorinated base
<220> FEATURE:
<221> NAME/KEY: misc_feature
<222> LOCATION: (72)..(72)
<223> OTHER INFORMATION: fluorinated base
<220> FEATURE:
<221> NAME/KEY: misc_feature
<222> LOCATION: (80)..(80)
<223> OTHER INFORMATION: fluorinated base
<220> FEATURE:
<221> NAME/KEY: misc_feature
<222> LOCATION: (83)..(83)
<223> OTHER INFORMATION: fluorinated base
<220> FEATURE:
<221> NAME/KEY: misc_feature
<222> LOCATION: (85)..(86)
<223> OTHER INFORMATION: fluorinated base
<220> FEATURE:
<221> NAME/KEY: misc_feature
<222> LOCATION: (90)..(91)
<223> OTHER INFORMATION: fluorinated base
<220> FEATURE:
<221> NAME/KEY: misc_feature
<222> LOCATION: (94)..(94)
<223> OTHER INFORMATION: fluorinated base
<220> FEATURE:
<221> NAME/KEY: misc_feature
<222> LOCATION: (96)..(101)
<223> OTHER INFORMATION: fluorinated base

<400> SEQUENCE: 8
gggcgaggag cuguucaccg guuuuagagc uagaaauagc aaguuaaaau aaggcuaguc 60
cguuaucaac uugaaaaagu ggcaccgagu cggugcuuuu u 101

<210> SEQ ID NO 9
<211> LENGTH: 101
<212> TYPE: RNA
<213> ORGANISM: Artificial Sequence
<220> FEATURE:
<223> OTHER INFORMATION: u and c GFP-9
<220> FEATURE:
<221> NAME/KEY: misc_feature
<222> LOCATION: (62)..(66)
<223> OTHER INFORMATION: methylated base
<220> FEATURE:
<221> NAME/KEY: misc_feature
<222> LOCATION: (72)..(72)
<223> OTHER INFORMATION: methylated base
<220> FEATURE:
<221> NAME/KEY: misc_feature
<222> LOCATION: (74)..(76)
<223> OTHER INFORMATION: methylated base
<220> FEATURE:
<221> NAME/KEY: misc_feature
<222> LOCATION: (78)..(81)
<223> OTHER INFORMATION: methylated base

<400> SEQUENCE: 9
gggcgaggag cuguucaccg guuuuagagc uagaaauagc aaguuaaaau aaggcuaguc 60
cguuaucaac uugaaaaagu ggcaccgagu cggugcuuuu u 101

<210> SEQ ID NO 10
<211> LENGTH: 101
<212> TYPE: RNA
<213> ORGANISM: Artificial Sequence
<220> FEATURE:
<223> OTHER INFORMATION: u and c GFP-10
<220> FEATURE:
<221> NAME/KEY: misc_feature
<222> LOCATION: (29)..(32)
<223> OTHER INFORMATION: methylated base
<220> FEATURE:
<221> NAME/KEY: misc_feature
<222> LOCATION: (60)..(61)
<223> OTHER INFORMATION: methylated base

<400> SEQUENCE: 10
gggcgaggag cuguucaccg guuuuagagc uagaaauagc aaguuaaaau aaggcuaguc 60
cguuaucaac uugaaaaagu ggcaccgagu cggugcuuuu u 101

<210> SEQ ID NO 11
<211> LENGTH: 42
<212> TYPE: RNA
<213> ORGANISM: Artificial Sequence
<220> FEATURE:
<223> OTHER INFORMATION: sgRNA11

<400> SEQUENCE: 11
guuuuagagc uagaaauagc aaguuaaaau aaggcuaguc cg 42

<210> SEQ ID NO 12
<211> LENGTH: 41
<212> TYPE: RNA

```
<213> ORGANISM: Artificial Sequence
<220> FEATURE:
<223> OTHER INFORMATION: RNA12

<400> SEQUENCE: 12

uuaucaacuu gaaaaagugg caccgagucg gugcuuuuuu u                          41


<210> SEQ ID NO 13
<211> LENGTH: 20
<212> TYPE: RNA
<213> ORGANISM: Artificial Sequence
<220> FEATURE:
<223> OTHER INFORMATION: RNA13

<400> SEQUENCE: 13

gggcgaggag cuguucaccg                                                  20


<210> SEQ ID NO 14
<211> LENGTH: 5
<212> TYPE: PRT
<213> ORGANISM: Artificial Sequence
<220> FEATURE:
<223> OTHER INFORMATION: c-abl IV

<400> SEQUENCE: 14

Asp Arg Leu Arg Arg
1               5


<210> SEQ ID NO 15
<211> LENGTH: 7
<212> TYPE: PRT
<213> ORGANISM: Artificial Sequence
<220> FEATURE:
<223> OTHER INFORMATION: NS1 15

<400> SEQUENCE: 15

Pro Lys Gln Lys Lys Arg Lys
1               5


<210> SEQ ID NO 16
<211> LENGTH: 10
<212> TYPE: PRT
<213> ORGANISM: Artificial Sequence
<220> FEATURE:
<223> OTHER INFORMATION: Hepatitis virus delta antigen16

<400> SEQUENCE: 16

Arg Lys Leu Lys Lys Lys Ile Lys Lys Leu
1               5                   10


<210> SEQ ID NO 17
<211> LENGTH: 10
<212> TYPE: PRT
<213> ORGANISM: Artificial Sequence
<220> FEATURE:
<223> OTHER INFORMATION: Mx protein17

<400> SEQUENCE: 17

Arg Glu Lys Lys Lys Phe Leu Lys Arg Arg
1               5                   10


<210> SEQ ID NO 18
<211> LENGTH: 20
<212> TYPE: PRT
<213> ORGANISM: Artificial Sequence
<220> FEATURE:
<223> OTHER INFORMATION: ADP-ribose18
```

<400> SEQUENCE: 18

```
Lys Arg Lys Gly Asp Glu Val Asp Gly Val Asp Glu Val Ala Lys Lys
1               5                   10                  15

Lys Ser Lys Lys
            20
```

<210> SEQ ID NO 19
<211> LENGTH: 17
<212> TYPE: PRT
<213> ORGANISM: Artificial Sequence
<220> FEATURE:
<223> OTHER INFORMATION: glucocorticoid19

<400> SEQUENCE: 19

```
Arg Lys Cys Leu Gln Ala Gly Met Asn Leu Glu Ala Arg Lys Thr Lys
1               5                   10                  15

Lys
```

<210> SEQ ID NO 20
<211> LENGTH: 23
<212> TYPE: DNA
<213> ORGANISM: Artificial Sequence
<220> FEATURE:
<223> OTHER INFORMATION: Cas9 20
<220> FEATURE:
<221> NAME/KEY: misc_feature
<222> LOCATION: (9)..(21)
<223> OTHER INFORMATION: n is a, c, g, or t

<400> SEQUENCE: 20

```
mmmmmmmmnn nnnnnnnnnn ngg                                              23
```

<210> SEQ ID NO 21
<211> LENGTH: 15
<212> TYPE: DNA
<213> ORGANISM: Artificial Sequence
<220> FEATURE:
<223> OTHER INFORMATION: Cas9 21
<220> FEATURE:
<221> NAME/KEY: misc_feature
<222> LOCATION: (1)..(13)
<223> OTHER INFORMATION: n is a, c, g, or t

<400> SEQUENCE: 21

```
nnnnnnnnnn nnngg                                                       15
```

<210> SEQ ID NO 22
<211> LENGTH: 23
<212> TYPE: DNA
<213> ORGANISM: Artificial Sequence
<220> FEATURE:
<223> OTHER INFORMATION: S. pyogenes Cas9 22
<220> FEATURE:
<221> NAME/KEY: misc_feature
<222> LOCATION: (10)..(21)
<223> OTHER INFORMATION: n is a, c, g, or t

<400> SEQUENCE: 22

```
mmmmmmmmmn nnnnnnnnnn ngg                                              23
```

<210> SEQ ID NO 23
<211> LENGTH: 27
<212> TYPE: DNA
<213> ORGANISM: Artificial Sequence
<220> FEATURE:
<223> OTHER INFORMATION: Cas9 23

<220> FEATURE:
<221> NAME/KEY: misc_feature
<222> LOCATION: (9)..(22)
<223> OTHER INFORMATION: n is a, c, g, or t

<400> SEQUENCE: 23
mmmmmmmmnn nnnnnnnnnn nnagaaw 27

<210> SEQ ID NO 24
<211> LENGTH: 19
<212> TYPE: DNA
<213> ORGANISM: Artificial Sequence
<220> FEATURE:
<223> OTHER INFORMATION: Cas9 24
<220> FEATURE:
<221> NAME/KEY: misc_feature
<222> LOCATION: (1)..(14)
<223> OTHER INFORMATION: n is a, c, g, or t

<400> SEQUENCE: 24
nnnnnnnnnn nnnnagaaw 19

<210> SEQ ID NO 25
<211> LENGTH: 27
<212> TYPE: DNA
<213> ORGANISM: Artificial Sequence
<220> FEATURE:
<223> OTHER INFORMATION: S. thermophilus CRISPR1 Cas9 25
<220> FEATURE:
<221> NAME/KEY: misc_feature
<222> LOCATION: (10)..(22)
<223> OTHER INFORMATION: n is a, c, g, or t

<400> SEQUENCE: 25
mmmmmmmmmn nnnnnnnnnn nnagaaw 27

<210> SEQ ID NO 26
<211> LENGTH: 18
<212> TYPE: DNA
<213> ORGANISM: Artificial Sequence
<220> FEATURE:
<223> OTHER INFORMATION: S. thermophilus CRISPR1 Cas9 26
<220> FEATURE:
<221> NAME/KEY: misc_feature
<222> LOCATION: (1)..(13)
<223> OTHER INFORMATION: n is a, c, g, or t

<400> SEQUENCE: 26
nnnnnnnnnn nnnagaaw 18

<210> SEQ ID NO 27
<211> LENGTH: 25
<212> TYPE: DNA
<213> ORGANISM: Artificial Sequence
<220> FEATURE:
<223> OTHER INFORMATION: Cas9 27
<220> FEATURE:
<221> NAME/KEY: misc_feature
<222> LOCATION: (9)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 27
mmmmmmmmnn nnnnnnnnnn nggng 25

<210> SEQ ID NO 28

<211> LENGTH: 17
<212> TYPE: DNA
<213> ORGANISM: Artificial Sequence
<220> FEATURE:
<223> OTHER INFORMATION: Cas9 28
<220> FEATURE:
<221> NAME/KEY: misc_feature
<222> LOCATION: (1)..(13)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t

<400> SEQUENCE: 28
nnnnnnnnnn nnnggng 17

<210> SEQ ID NO 29
<211> LENGTH: 25
<212> TYPE: DNA
<213> ORGANISM: Artificial Sequence
<220> FEATURE:
<223> OTHER INFORMATION: S. pyogenes Cas9 29
<220> FEATURE:
<221> NAME/KEY: misc_feature
<222> LOCATION: (10)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 29
mmmmmmmmmn nnnnnnnnnn nggng 25

<210> SEQ ID NO 30
<211> LENGTH: 16
<212> TYPE: DNA
<213> ORGANISM: Artificial Sequence
<220> FEATURE:
<223> OTHER INFORMATION: S. pyogenes Cas9 30
<220> FEATURE:
<221> NAME/KEY: misc_feature
<222> LOCATION: (1)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 30
nnnnnnnnnn nnggng 16

<210> SEQ ID NO 31
<211> LENGTH: 42
<212> TYPE: RNA
<213> ORGANISM: Artificial Sequence
<220> FEATURE:
<223> OTHER INFORMATION: crRNA-GFP-1 31

<400> SEQUENCE: 31
gggcgaggag cuguucaccg guuuuagagc uaugcuguuu ug 42

<210> SEQ ID NO 32
<211> LENGTH: 75
<212> TYPE: RNA
<213> ORGANISM: Artificial Sequence
<220> FEATURE:
<223> OTHER INFORMATION: TracrRNA 32

<400> SEQUENCE: 32
aaacagcaua gcaaguuaaa auaaggcuag uccguuauca acuugaaaaa guggcaccga 60
gucggugcuu uuuuu 75

<210> SEQ ID NO 33
<211> LENGTH: 42
<212> TYPE: DNA
<213> ORGANISM: Artificial Sequence
<220> FEATURE:
<223> OTHER INFORMATION: crRNA-GFP-3 33
<220> FEATURE:
<221> NAME/KEY: misc_feature
<222> LOCATION: (20)..(42)
<223> OTHER INFORMATION: deoxyribonucleic acid

<400> SEQUENCE: 33
gggcgaggag ctgttcaccg guuuuagagc uaugcuguuu ug 42

<210> SEQ ID NO 34
<211> LENGTH: 42
<212> TYPE: RNA
<213> ORGANISM: Artificial Sequence
<220> FEATURE:
<223> OTHER INFORMATION: crRNA-GFP-4 34
<220> FEATURE:
<221> NAME/KEY: misc_feature
<222> LOCATION: (10)..(42)
<223> OTHER INFORMATION: deoxyribonucleic

<400> SEQUENCE: 34
gggcgaggag cuguucaccg guuuuagagc uaugcuguuu ug 42

<210> SEQ ID NO 35
<211> LENGTH: 42
<212> TYPE: DNA
<213> ORGANISM: Artificial Sequence
<220> FEATURE:
<223> OTHER INFORMATION: crRNA-GFP-7 35
<220> FEATURE:
<221> NAME/KEY: misc_feature
<222> LOCATION: (18)..(42)
<223> OTHER INFORMATION: deoxyribonucleic

<400> SEQUENCE: 35
gggcgaggag ctgttcaccg guuuuagagc uaugcuguuu ug 42

<210> SEQ ID NO 36
<211> LENGTH: 43
<212> TYPE: DNA
<213> ORGANISM: Artificial Sequence
<220> FEATURE:
<223> OTHER INFORMATION: crRNA-GFP-8 36
<220> FEATURE:
<221> NAME/KEY: misc_feature
<222> LOCATION: (16)..(42)
<223> OTHER INFORMATION: deoxyribonucleic

<400> SEQUENCE: 36
gggcgaggag ctgttcaccg guuuuagarg cuaugcuguu uug 43

<210> SEQ ID NO 37
<211> LENGTH: 42
<212> TYPE: DNA
<213> ORGANISM: Artificial Sequence
<220> FEATURE:
<223> OTHER INFORMATION: crRNA-GFP-9 37
<220> FEATURE:
<221> NAME/KEY: misc_feature
<222> LOCATION: (14)..(42)

<223> OTHER INFORMATION: deoxyribonucleic

<400> SEQUENCE: 37
gggcgaggag ctgtucaccg guuuuagagc uaugcuguuu ug 42

<210> SEQ ID NO 38
<211> LENGTH: 42
<212> TYPE: DNA
<213> ORGANISM: Artificial Sequence
<220> FEATURE:
<223> OTHER INFORMATION: crRNA-GFP-10 38
<220> FEATURE:
<221> NAME/KEY: misc_feature
<222> LOCATION: (12)..(42)
<223> OTHER INFORMATION: deoxyribonucleic

<400> SEQUENCE: 38
gggcgaggag ctguucaccg guuuuagagc uaugcuguuu ug 42

<210> SEQ ID NO 39
<211> LENGTH: 42
<212> TYPE: RNA
<213> ORGANISM: Artificial Sequence
<220> FEATURE:
<223> OTHER INFORMATION: crRNA-GFP-11 39
<220> FEATURE:
<221> NAME/KEY: misc_feature
<222> LOCATION: (8)..(42)
<223> OTHER INFORMATION: deoxyribonucleic

<400> SEQUENCE: 39
gggcgaggag cuguucaccg guuuuagagc uaugcuguuu ug 42

<210> SEQ ID NO 40
<211> LENGTH: 42
<212> TYPE: RNA
<213> ORGANISM: Artificial Sequence
<220> FEATURE:
<223> OTHER INFORMATION: crRNA-GFP-12 40
<220> FEATURE:
<221> NAME/KEY: misc_feature
<222> LOCATION: (6)..(42)
<223> OTHER INFORMATION: deoxyribonucleic

<400> SEQUENCE: 40
gggcgaggag cuguucaccg guuuuagagc uaugcuguuu ug 42

<210> SEQ ID NO 41
<211> LENGTH: 42
<212> TYPE: RNA
<213> ORGANISM: Artificial Sequence
<220> FEATURE:
<223> OTHER INFORMATION: crRNA-GFP-13 41
<220> FEATURE:
<221> NAME/KEY: misc_feature
<222> LOCATION: (4)..(42)
<223> OTHER INFORMATION: deoxyribonucleic

<400> SEQUENCE: 41
gggcgaggag cuguucaccg guuuuagagc uaugcuguuu ug 42

<210> SEQ ID NO 42
<211> LENGTH: 42
<212> TYPE: RNA
<213> ORGANISM: Artificial Sequence
<220> FEATURE:
<223> OTHER INFORMATION: crRNA-GFP-14 42
<220> FEATURE:
<221> NAME/KEY: misc_feature
<222> LOCATION: (1)..(41)
<223> OTHER INFORMATION: deoxyribonucleic

<400> SEQUENCE: 42
gggcgaggag cuguucaccg guuuuagagc uaugcuguuu ug 42

<210> SEQ ID NO 43
<211> LENGTH: 101
<212> TYPE: RNA
<213> ORGANISM: Artificial Sequence
<220> FEATURE:
<223> OTHER INFORMATION: 2F GFP-12 43
<220> FEATURE:
<221> NAME/KEY: misc_feature
<222> LOCATION: (30)..(32)
<223> OTHER INFORMATION: fluorinated base
<220> FEATURE:
<221> NAME/KEY: misc_feature
<222> LOCATION: (34)..(35)
<223> OTHER INFORMATION: fluorinated base
<220> FEATURE:
<221> NAME/KEY: misc_feature
<222> LOCATION: (37)..(39)
<223> OTHER INFORMATION: fluorinated base
<220> FEATURE:
<221> NAME/KEY: misc_feature
<222> LOCATION: (69)..(80)
<223> OTHER INFORMATION: fluorinated base
<220> FEATURE:
<221> NAME/KEY: misc_feature
<222> LOCATION: (83)..(83)
<223> OTHER INFORMATION: fluorinated base
<220> FEATURE:
<221> NAME/KEY: misc_feature
<222> LOCATION: (85)..(86)
<223> OTHER INFORMATION: fluorinated base
<220> FEATURE:
<221> NAME/KEY: misc_feature
<222> LOCATION: (90)..(91)
<223> OTHER INFORMATION: fluorinated base
<220> FEATURE:
<221> NAME/KEY: misc_feature
<222> LOCATION: (94)..(94)
<223> OTHER INFORMATION: fluorinated base
<220> FEATURE:
<221> NAME/KEY: misc_feature
<222> LOCATION: (96)..(101)
<223> OTHER INFORMATION: fluorinated base

<400> SEQUENCE: 43
gggcgaggag cuguucaccg guuuuagagc uagaaauagc aaguuaaaau aaggcuaguc 60
cguuaucaac uugaaaaagu ggcaccgagu cggugcuuuu u 101

<210> SEQ ID NO 44
<211> LENGTH: 101
<212> TYPE: RNA
<213> ORGANISM: Artificial Sequence
<220> FEATURE:
<223> OTHER INFORMATION: s GFP-33 44
<220> FEATURE:
<221> NAME/KEY: misc_feature
<222> LOCATION: (21)..(101)
<223> OTHER INFORMATION: phosphorothioate
<220> FEATURE:
<221> NAME/KEY: misc_feature
<222> LOCATION: (21)..(101)
<223> OTHER INFORMATION: phosphorothioate modified pentose sugar

<400> SEQUENCE: 44
gggcgaggag cuguucaccg guuuuagagc uagaaauagc aaguuaaaau aaggcuaguc 60
cguuaucaac uugaaaaagu ggcaccgagu cggugcuuuu u 101

```
<210> SEQ ID NO 45
<211> LENGTH: 101
<212> TYPE: RNA
<213> ORGANISM: Artificial Sequence
<220> FEATURE:
<223> OTHER INFORMATION: GFP sgRNA45

<400> SEQUENCE: 45

gggcgaggag cuguucaccg guuuuagagc uagaaauagc aaguuaaaau aaggcuaguc     60

cguuaucaac uugaaaaagu ggcaccgagu cggugcuuuu u                        101


<210> SEQ ID NO 46
<211> LENGTH: 101
<212> TYPE: RNA
<213> ORGANISM: Artificial Sequence
<220> FEATURE:
<223> OTHER INFORMATION: n GFP-35 46
<220> FEATURE:
<221> NAME/KEY: misc_feature
<222> LOCATION: (20)..(20)
<223> OTHER INFORMATION: 0-methylated base

<400> SEQUENCE: 46

gggcgaggag cuguucaccg guuuuagagc uagaaauagc aaguuaaaau aaggcuaguc     60

cguuaucaac uugaaaaagu ggcaccgagu cggugcuuuu u                        101


<210> SEQ ID NO 47
<211> LENGTH: 101
<212> TYPE: RNA
<213> ORGANISM: Artificial Sequence
<220> FEATURE:
<223> OTHER INFORMATION: n GFP-36 47
<220> FEATURE:
<221> NAME/KEY: misc_feature
<222> LOCATION: (20)..(20)
<223> OTHER INFORMATION: 0-methylated base
<220> FEATURE:
<221> NAME/KEY: misc_feature
<222> LOCATION: (26)..(27)
<223> OTHER INFORMATION: 0-methylated base
<220> FEATURE:
<221> NAME/KEY: misc_feature
<222> LOCATION: (29)..(33)
<223> OTHER INFORMATION: 0-methylated base
<220> FEATURE:
<221> NAME/KEY: misc_feature
<222> LOCATION: (34)..(35)
<223> OTHER INFORMATION: 0-methylated base
<220> FEATURE:
<221> NAME/KEY: misc_feature
<222> LOCATION: (38)..(39)
<223> OTHER INFORMATION: 0-methylated base

<400> SEQUENCE: 47

gggcgaggag cuguucaccg guuuuagagc uagaaauagc aaguuaaaau aaggcuaguc     60

cguuaucaac uugaaaaagu ggcaccgagu cggugcuuuu u                        101


<210> SEQ ID NO 48
<211> LENGTH: 101
<212> TYPE: RNA
<213> ORGANISM: Artificial Sequence
<220> FEATURE:
<223> OTHER INFORMATION: n GFP-39 48
<220> FEATURE:
<221> NAME/KEY: misc_feature
<222> LOCATION: (70)..(79)
<223> OTHER INFORMATION: phosphorothioate
<220> FEATURE:
<221> NAME/KEY: misc_feature
```

<222> LOCATION: (70)..(79)
<223> OTHER INFORMATION: phosphorothioate modified pentose sugar
<220> FEATURE:
<221> NAME/KEY: misc_feature
<222> LOCATION: (82)..(82)
<223> OTHER INFORMATION: phosphorothioate
<220> FEATURE:
<221> NAME/KEY: misc_feature
<222> LOCATION: (84)..(90)
<223> OTHER INFORMATION: phosphorothioate
<220> FEATURE:
<221> NAME/KEY: misc_feature
<222> LOCATION: (92)..(101)
<223> OTHER INFORMATION: phosphorothioate

<400> SEQUENCE: 48
gggcgaggag cuguucaccg guuuuagagc uagaaauagc aaguuaaaau aaggcuaguc 60
cguuaucaac uugaaaaagu ggcaccgagu cggugcuuuu u 101

<210> SEQ ID NO 49
<211> LENGTH: 101
<212> TYPE: RNA
<213> ORGANISM: Artificial Sequence
<220> FEATURE:
<223> OTHER INFORMATION: n GFP-40 49
<220> FEATURE:
<221> NAME/KEY: misc_feature
<222> LOCATION: (20)..(20)
<223> OTHER INFORMATION: Phosphorothioate
<220> FEATURE:
<221> NAME/KEY: misc_feature
<222> LOCATION: (20)..(20)
<223> OTHER INFORMATION: Phosphorothioate modified pentose sugar
<220> FEATURE:
<221> NAME/KEY: misc_feature
<222> LOCATION: (26)..(27)
<223> OTHER INFORMATION: Phosphorothioate
<220> FEATURE:
<221> NAME/KEY: misc_feature
<222> LOCATION: (29)..(32)
<223> OTHER INFORMATION: Phosphorothioate
<220> FEATURE:
<221> NAME/KEY: misc_feature
<222> LOCATION: (34)..(34)
<223> OTHER INFORMATION: Phosphorothioate
<220> FEATURE:
<221> NAME/KEY: misc_feature
<222> LOCATION: (38)..(38)
<223> OTHER INFORMATION: Phosphorothioate

<400> SEQUENCE: 49
gggcgaggag cuguucaccg guuuuagagc uagaaauagc aaguuaaaau aaggcuaguc 60
cguuaucaac uugaaaaagu ggcaccgagu cggugcuuuu u 101

<210> SEQ ID NO 50
<211> LENGTH: 101
<212> TYPE: RNA
<213> ORGANISM: Artificial Sequence
<220> FEATURE:
<223> OTHER INFORMATION: n GFP-CS 50
<220> FEATURE:
<221> NAME/KEY: misc_feature
<222> LOCATION: (21)..(21)
<223> OTHER INFORMATION: 0-methylated base
<220> FEATURE:
<221> NAME/KEY: misc_feature
<222> LOCATION: (36)..(36)
<223> OTHER INFORMATION: 0-methylated base
<220> FEATURE:
<221> NAME/KEY: misc_feature
<222> LOCATION: (37)..(39)
<223> OTHER INFORMATION: 0-methylated base
<220> FEATURE:

<221> NAME/KEY: misc_feature
<222> LOCATION: (45)..(45)
<223> OTHER INFORMATION: 0-methylated base
<220> FEATURE:
<221> NAME/KEY: misc_feature
<222> LOCATION: (47)..(47)
<223> OTHER INFORMATION: 0-methylated base
<220> FEATURE:
<221> NAME/KEY: misc_feature
<222> LOCATION: (49)..(49)
<223> OTHER INFORMATION: 0-methylated base
<220> FEATURE:
<221> NAME/KEY: misc_feature
<222> LOCATION: (61)..(61)
<223> OTHER INFORMATION: 0-methylated base

<400> SEQUENCE: 50
gggcgaggag cuguucaccg guuuuagagc uagaaauagc aaguuaaaau aaggcuaguc 60
cguuaucaac uugaaaaagu ggcaccgagu cggugcuuuu u 101

<210> SEQ ID NO 51
<211> LENGTH: 42
<212> TYPE: RNA
<213> ORGANISM: Artificial Sequence
<220> FEATURE:
<223> OTHER INFORMATION: n GFP-17 51
<220> FEATURE:
<221> NAME/KEY: misc_feature
<222> LOCATION: (1)..(1)
<223> OTHER INFORMATION: 0-methylated base

<400> SEQUENCE: 51
gggcgaggag cuguucaccg guuuuagagc uaugcuguuu ug 42

<210> SEQ ID NO 52
<211> LENGTH: 42
<212> TYPE: RNA
<213> ORGANISM: Artificial Sequence
<220> FEATURE:
<223> OTHER INFORMATION: n GFP-18 52
<220> FEATURE:
<221> NAME/KEY: misc_feature
<223> OTHER INFORMATION: 0-methylated base

<400> SEQUENCE: 52
gggcgaggag cuguucaccg guuuuagagc uaugcuguuu ug 42

<210> SEQ ID NO 53
<211> LENGTH: 42
<212> TYPE: RNA
<213> ORGANISM: Artificial Sequence
<220> FEATURE:
<223> OTHER INFORMATION: n GFP-19 53
<220> FEATURE:
<221> NAME/KEY: misc_feature
<222> LOCATION: (1)..(1)
<223> OTHER INFORMATION: 0-methylated base

<400> SEQUENCE: 53
gggcgaggag cuguucaccg guuuuagagc uaugcuguuu ug 42

<210> SEQ ID NO 54
<211> LENGTH: 42
<212> TYPE: RNA
<213> ORGANISM: Artificial Sequence
<220> FEATURE:
<223> OTHER INFORMATION: n GFP-20 54
<220> FEATURE:
<221> NAME/KEY: misc_feature
<222> LOCATION: (1)..(1)

<223> OTHER INFORMATION: 0-methylated base
<220> FEATURE:
<221> NAME/KEY: misc_feature
<222> LOCATION: (5)..(6)
<223> OTHER INFORMATION: 0-methylated base
<220> FEATURE:
<221> NAME/KEY: misc_feature
<222> LOCATION: (8)..(8)
<223> OTHER INFORMATION: 0-methylated base

<400> SEQUENCE: 54
gggcgaggag cuguucaccg guuuuagagc uaugcuguuu ug 42

<210> SEQ ID NO 55
<211> LENGTH: 42
<212> TYPE: RNA
<213> ORGANISM: Artificial Sequence
<220> FEATURE:
<223> OTHER INFORMATION: n GFP-21 55
<220> FEATURE:
<221> NAME/KEY: misc_feature
<222> LOCATION: (1)..(2)
<223> OTHER INFORMATION: 0-methylated base
<220> FEATURE:
<221> NAME/KEY: misc_feature
<222> LOCATION: (6)..(6)
<223> OTHER INFORMATION: 0-methylated base
<220> FEATURE:
<221> NAME/KEY: misc_feature
<222> LOCATION: (8)..(8)
<223> OTHER INFORMATION: 0-methylated base
<220> FEATURE:
<221> NAME/KEY: misc_feature
<222> LOCATION: (10)..(10)
<223> OTHER INFORMATION: 0-methylated base

<400> SEQUENCE: 55
gggcgaggag cuguucaccg guuuuagagc uaugcuguuu ug 42

<210> SEQ ID NO 56
<211> LENGTH: 42
<212> TYPE: RNA
<213> ORGANISM: Artificial Sequence
<220> FEATURE:
<223> OTHER INFORMATION: nf GFP-22 56
<220> FEATURE:
<221> NAME/KEY: misc_feature
<222> LOCATION: (1)..(20)
<223> OTHER INFORMATION: fluorinated base

<400> SEQUENCE: 56
gggcgaggag cuguucaccg guuuuagagc uaugcuguuu ug 42

<210> SEQ ID NO 57
<211> LENGTH: 42
<212> TYPE: RNA
<213> ORGANISM: Artificial Sequence
<220> FEATURE:
<223> OTHER INFORMATION: nf GFP-23 57
<220> FEATURE:
<221> NAME/KEY: misc_feature
<222> LOCATION: (11)..(20)
<223> OTHER INFORMATION: fluorinated base

<400> SEQUENCE: 57
gggcgaggag cuguucaccg guuuuagagc uaugcuguuu ug 42

<210> SEQ ID NO 58
<211> LENGTH: 42
<212> TYPE: RNA
<213> ORGANISM: Artificial Sequence
<220> FEATURE:
<223> OTHER INFORMATION: nf GFP-24 58
<220> FEATURE:
<221> NAME/KEY: misc_feature
<222> LOCATION: (1)..(10)
<223> OTHER INFORMATION: fluorinated base

<400> SEQUENCE: 58
gggcgaggag cuguucaccg guuuuagagc uaugcuguuu ug 42

<210> SEQ ID NO 59
<211> LENGTH: 42
<212> TYPE: RNA
<213> ORGANISM: Artificial Sequence
<220> FEATURE:
<223> OTHER INFORMATION: nf GFP-25 59
<220> FEATURE:
<221> NAME/KEY: misc_feature
<222> LOCATION: (2)..(3)
<223> OTHER INFORMATION: fluorinated base
<220> FEATURE:
<221> NAME/KEY: misc_feature
<222> LOCATION: (8)..(11)
<223> OTHER INFORMATION: fluorinated base
<220> FEATURE:
<221> NAME/KEY: misc_feature
<222> LOCATION: (13)..(14)
<223> OTHER INFORMATION: fluorinated base
<220> FEATURE:
<221> NAME/KEY: misc_feature
<222> LOCATION: (17)..(18)
<223> OTHER INFORMATION: fluorinated base

<400> SEQUENCE: 59
gggcgaggag cuguucaccg guuuuagagc uaugcuguuu ug 42

<210> SEQ ID NO 60
<211> LENGTH: 42
<212> TYPE: RNA
<213> ORGANISM: Artificial Sequence
<220> FEATURE:
<223> OTHER INFORMATION: nf GFP-26 60
<220> FEATURE:
<221> NAME/KEY: misc_feature
<222> LOCATION: (1)..(1)
<223> OTHER INFORMATION: fluorinated base
<220> FEATURE:
<221> NAME/KEY: misc_feature
<222> LOCATION: (4)..(7)
<223> OTHER INFORMATION: fluorinated base
<220> FEATURE:
<221> NAME/KEY: misc_feature
<222> LOCATION: (12)..(12)
<223> OTHER INFORMATION: fluorinated base
<220> FEATURE:
<221> NAME/KEY: misc_feature
<222> LOCATION: (15)..(16)
<223> OTHER INFORMATION: fluorinated base
<220> FEATURE:
<221> NAME/KEY: misc_feature
<222> LOCATION: (19)..(20)
<223> OTHER INFORMATION: fluorinated base

<400> SEQUENCE: 60
gggcgaggag cuguucaccg guuuuagagc uaugcuguuu ug 42

<210> SEQ ID NO 61
<211> LENGTH: 42
<212> TYPE: RNA
<213> ORGANISM: Artificial Sequence
<220> FEATURE:
<223> OTHER INFORMATION: s GFP-27 61
<220> FEATURE:

<221> NAME/KEY: misc_feature
<222> LOCATION: (1)..(19)
<223> OTHER INFORMATION: phosphorothioate modified pentose sugar

<400> SEQUENCE: 61
gggcgaggag cuguucaccg guuuuagagc uaugcuguuu ug 42

<210> SEQ ID NO 62
<211> LENGTH: 42
<212> TYPE: RNA
<213> ORGANISM: Artificial Sequence
<220> FEATURE:
<223> OTHER INFORMATION: s GFP-28 62
<220> FEATURE:
<221> NAME/KEY: misc_feature
<222> LOCATION: (2)..(2)
<223> OTHER INFORMATION: Phosphorothioate modified pentose sugar
<220> FEATURE:
<221> NAME/KEY: misc_feature
<222> LOCATION: (6)..(10)
<223> OTHER INFORMATION: Phosphorothioate modified pentose sugar

<400> SEQUENCE: 62
gggcgaggag cuguucaccg guuuuagagc uaugcuguuu ug 42

<210> SEQ ID NO 63
<211> LENGTH: 42
<212> TYPE: RNA
<213> ORGANISM: Artificial Sequence
<220> FEATURE:
<223> OTHER INFORMATION: s GFP-29 63
<220> FEATURE:
<221> NAME/KEY: misc_feature
<222> LOCATION: (1)..(1)
<223> OTHER INFORMATION: Phosphorothioate modified pentose sugar
<220> FEATURE:
<221> NAME/KEY: misc_feature
<222> LOCATION: (3)..(5)
<223> OTHER INFORMATION: Phosphorothioate modified pentose sugar
<220> FEATURE:
<221> NAME/KEY: misc_feature
<222> LOCATION: (11)..(12)
<223> OTHER INFORMATION: Phosphorothioate modified pentose sugar

<400> SEQUENCE: 63
gggcgaggag cuguucaccg guuuuagagc uaugcuguuu ug 42

<210> SEQ ID NO 64
<211> LENGTH: 42
<212> TYPE: RNA
<213> ORGANISM: Artificial Sequence
<220> FEATURE:
<223> OTHER INFORMATION: n GFP-30 64

<400> SEQUENCE: 64
gggcgaggag cuguucaccg guuuuagagc uaugcuguuu ug 42

<210> SEQ ID NO 65
<211> LENGTH: 42
<212> TYPE: RNA
<213> ORGANISM: Artificial Sequence
<220> FEATURE:
<223> OTHER INFORMATION: s GFP-31 65
<220> FEATURE:
<221> NAME/KEY: misc_feature
<222> LOCATION: (1)..(1)
<223> OTHER INFORMATION: phosphorothioate modified pentose sugar
<220> FEATURE:
<221> NAME/KEY: misc_feature
<222> LOCATION: (4)..(6)
<223> OTHER INFORMATION: phosphorothioate modified pentose sugar

```
<220> FEATURE:
<221> NAME/KEY: misc_feature
<222> LOCATION: (8)..(8)
<223> OTHER INFORMATION: phosphorothioate modified pentose sugar

<400> SEQUENCE: 65

gggcgaggag cuguucaccg guuuuagagc uaugcuguuu ug                    42


<210> SEQ ID NO 66
<211> LENGTH: 42
<212> TYPE: RNA
<213> ORGANISM: Artificial Sequence
<220> FEATURE:
<223> OTHER INFORMATION: s GFP-32 66
<220> FEATURE:
<221> NAME/KEY: misc_feature
<222> LOCATION: (2)..(3)
<223> OTHER INFORMATION: phosphorothioate modified pentose sugar
<220> FEATURE:
<221> NAME/KEY: misc_feature
<222> LOCATION: (6)..(11)
<223> OTHER INFORMATION: phosphorothioate modified pentose sugar
<220> FEATURE:
<221> NAME/KEY: misc_feature
<222> LOCATION: (13)..(14)
<223> OTHER INFORMATION: phosphorothioate modified pentose sugar
<220> FEATURE:
<221> NAME/KEY: misc_feature
<222> LOCATION: (17)..(18)
<223> OTHER INFORMATION: phosphorothioate modified pentose sugar

<400> SEQUENCE: 66

gggcgaggag cuguucaccg guuuuagagc uaugcuguuu ug                    42


<210> SEQ ID NO 67
<211> LENGTH: 42
<212> TYPE: RNA
<213> ORGANISM: Artificial Sequence
<220> FEATURE:
<223> OTHER INFORMATION: HY-VEGFA 67

<400> SEQUENCE: 67

gacccccucc accccgccuc guuuuagagc uaugcuguuu ug                    42


<210> SEQ ID NO 68
<211> LENGTH: 42
<212> TYPE: RNA
<213> ORGANISM: Artificial Sequence
<220> FEATURE:
<223> OTHER INFORMATION: HY-VEGFA_M 68
<220> FEATURE:
<221> NAME/KEY: misc_feature
<222> LOCATION: (2)..(3)
<223> OTHER INFORMATION: phosphorothioate modified pentose sugar
<220> FEATURE:
<221> NAME/KEY: misc_feature
<222> LOCATION: (6)..(11)
<223> OTHER INFORMATION: phosphorothioate modified pentose sugar
<220> FEATURE:
<221> NAME/KEY: misc_feature
<222> LOCATION: (12)..(13)
<223> OTHER INFORMATION: phosphorothioate modified pentose sugar
<220> FEATURE:
<221> NAME/KEY: misc_feature
<222> LOCATION: (15)..(16)
<223> OTHER INFORMATION: phosphorothioate modified pentose sugar

<400> SEQUENCE: 68

gacccccucc accccgccuc guuuuagagc uaugcuguuu ug                    42


<210> SEQ ID NO 69
```

<211> LENGTH: 42
<212> TYPE: RNA
<213> ORGANISM: Artificial Sequence
<220> FEATURE:
<223> OTHER INFORMATION: HY-EMX1 69

<400> SEQUENCE: 69
gaguccgagc agaagaagaa guuuuagagc uaugcuguuu ug 42

<210> SEQ ID NO 70
<211> LENGTH: 42
<212> TYPE: RNA
<213> ORGANISM: Artificial Sequence
<220> FEATURE:
<223> OTHER INFORMATION: HY-EMX1_M 70
<220> FEATURE:
<221> NAME/KEY: misc_feature
<222> LOCATION: (2)..(3)
<223> OTHER INFORMATION: phosphorothioate modified pentose sugar
<220> FEATURE:
<221> NAME/KEY: misc_feature
<222> LOCATION: (6)..(11)
<223> OTHER INFORMATION: phosphorothioate modified pentose sugar
<220> FEATURE:
<221> NAME/KEY: misc_feature
<222> LOCATION: (13)..(14)
<223> OTHER INFORMATION: phosphorothioate modified pentose sugar
<220> FEATURE:
<221> NAME/KEY: misc_feature
<222> LOCATION: (17)..(18)
<223> OTHER INFORMATION: phosphorothioate modified pentose sugar

<400> SEQUENCE: 70
gaguccgagc agaagaagaa guuuuagagc uaugcuguuu ug 42

<210> SEQ ID NO 71
<211> LENGTH: 42
<212> TYPE: RNA
<213> ORGANISM: Artificial Sequence
<220> FEATURE:
<223> OTHER INFORMATION: HY-HBB 71

<400> SEQUENCE: 71
cuugccccac agggcaguaa guuuuagagc uaugcuguuu ug 42

<210> SEQ ID NO 72
<211> LENGTH: 42
<212> TYPE: RNA
<213> ORGANISM: Artificial Sequence
<220> FEATURE:
<223> OTHER INFORMATION: HY-HBB_M 72
<220> FEATURE:
<221> NAME/KEY: misc_feature
<222> LOCATION: (2)..(3)
<223> OTHER INFORMATION: phosphorothioate modified pentose sugar
<220> FEATURE:
<221> NAME/KEY: misc_feature
<222> LOCATION: (6)..(11)
<223> OTHER INFORMATION: phosphorothioate modified pentose sugar
<220> FEATURE:
<221> NAME/KEY: misc_feature
<222> LOCATION: (13)..(14)
<223> OTHER INFORMATION: phosphorothioate modified pentose sugar
<220> FEATURE:
<221> NAME/KEY: misc_feature
<222> LOCATION: (17)..(18)
<223> OTHER INFORMATION: phosphorothioate modified pentose sugar

<400> SEQUENCE: 72
cuugccccac agggcaguaa guuuuagagc uaugcuguuu ug 42

<210> SEQ ID NO 73
<211> LENGTH: 101
<212> TYPE: RNA
<213> ORGANISM: Artificial Sequence
<220> FEATURE:
<223> OTHER INFORMATION: GFP-42 73
<220> FEATURE:
<221> NAME/KEY: misc_feature
<222> LOCATION: (1)..(1)
<223> OTHER INFORMATION: phosphorothioate modified pentose sugar
<220> FEATURE:
<221> NAME/KEY: misc_feature
<222> LOCATION: (94)..(94)
<223> OTHER INFORMATION: phosphorothioate modified pentose sugar

<400> SEQUENCE: 73
gggcgaggag cuguucaccg guuuuagagc uagaaauagc aaguuaaaau aaggcuaguc 60
cguuaucaac uugaaaaagu ggcaccgagu cggugcuuuu u 101

<210> SEQ ID NO 74
<211> LENGTH: 101
<212> TYPE: RNA
<213> ORGANISM: Artificial Sequence
<220> FEATURE:
<223> OTHER INFORMATION: s GFP- 43 74
<220> FEATURE:
<221> NAME/KEY: misc_feature
<222> LOCATION: (2)..(3)
<223> OTHER INFORMATION: phosphorothioate modified pentose sugar
<220> FEATURE:
<221> NAME/KEY: misc_feature
<222> LOCATION: (6)..(11)
<223> OTHER INFORMATION: phosphorothioate modified pentose sugar
<220> FEATURE:
<221> NAME/KEY: misc_feature
<222> LOCATION: (13)..(14)
<223> OTHER INFORMATION: phosphorothioate modified pentose sugar
<220> FEATURE:
<221> NAME/KEY: misc_feature
<222> LOCATION: (17)..(18)
<223> OTHER INFORMATION: phosphorothioate modified pentose sugar
<220> FEATURE:
<221> NAME/KEY: misc_feature
<222> LOCATION: (20)..(20)
<223> OTHER INFORMATION: phosphorothioate modified pentose sugar
<220> FEATURE:
<221> NAME/KEY: misc_feature
<222> LOCATION: (26)..(26)
<223> OTHER INFORMATION: phosphorothioate modified pentose sugar
<220> FEATURE:
<221> NAME/KEY: misc_feature
<222> LOCATION: (29)..(32)
<223> OTHER INFORMATION: phosphorothioate modified pentose sugar
<220> FEATURE:
<221> NAME/KEY: misc_feature
<222> LOCATION: (34)..(34)
<223> OTHER INFORMATION: phosphorothioate modified pentose sugar
<220> FEATURE:
<221> NAME/KEY: misc_feature
<222> LOCATION: (38)..(38)
<223> OTHER INFORMATION: phosphorothioate modified pentose sugar
<220> FEATURE:
<221> NAME/KEY: misc_feature
<222> LOCATION: (40)..(41)
<223> OTHER INFORMATION: phosphorothioate modified pentose sugar

<400> SEQUENCE: 74
gggcgaggag cuguucaccg guuuuagagc uagaaauagc aaguuaaaau aaggcuaguc 60
cguuaucaac uugaaaaagu ggcaccgagu cggugcuuuu u 101

<210> SEQ ID NO 75
<211> LENGTH: 7
<212> TYPE: PRT

<213> ORGANISM: Artificial Sequence
<220> FEATURE:
<223> OTHER INFORMATION: SV40 75

<400> SEQUENCE: 75

Pro Lys Lys Lys Arg Lys Val
1               5

<210> SEQ ID NO 76
<211> LENGTH: 16
<212> TYPE: PRT
<213> ORGANISM: Artificial Sequence
<220> FEATURE:
<223> OTHER INFORMATION: NLS 76

<400> SEQUENCE: 76

Lys Arg Pro Ala Ala Thr Lys Lys Ala Gly Gln Ala Lys Lys Lys Lys
1               5                   10                  15

<210> SEQ ID NO 77
<211> LENGTH: 9
<212> TYPE: PRT
<213> ORGANISM: Artificial Sequence
<220> FEATURE:
<223> OTHER INFORMATION: c-myc NLS 77

<400> SEQUENCE: 77

Pro Ala Ala Lys Arg Val Lys Leu Asp
1               5

<210> SEQ ID NO 78
<211> LENGTH: 11
<212> TYPE: PRT
<213> ORGANISM: Artificial Sequence
<220> FEATURE:
<223> OTHER INFORMATION: c-myc NLS 78

<400> SEQUENCE: 78

Arg Gln Arg Arg Asn Glu Leu Lys Arg Ser Pro
1               5                   10

<210> SEQ ID NO 79
<211> LENGTH: 38
<212> TYPE: PRT
<213> ORGANISM: Artificial Sequence
<220> FEATURE:
<223> OTHER INFORMATION: hRNPAI M9 NLS 79

<400> SEQUENCE: 79

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
            20                  25                  30

Arg Asn Gln Gly Gly Tyr
        35

<210> SEQ ID NO 80
<211> LENGTH: 42
<212> TYPE: PRT
<213> ORGANISM: Artificial Sequence
<220> FEATURE:
<223> OTHER INFORMATION: hRNPAI M9 NLS 80

<400> SEQUENCE: 80

Arg Met Arg Ile Glx Phe Lys Asn Lys Gly Lys Asp Thr Ala Glu Leu
1               5                   10                  15

```
Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40


<210> SEQ ID NO 81
<211> LENGTH: 8
<212> TYPE: PRT
<213> ORGANISM: Artificial Sequence
<220> FEATURE:
<223> OTHER INFORMATION: importin-alpha 81

<400> SEQUENCE: 81

Val Ser Arg Lys Arg Pro Arg Pro
1               5


<210> SEQ ID NO 82
<211> LENGTH: 8
<212> TYPE: PRT
<213> ORGANISM: Artificial Sequence
<220> FEATURE:
<223> OTHER INFORMATION: VSRKRPRP 82

<400> SEQUENCE: 82

Pro Pro Lys Lys Ala Arg Glu Asp
1               5


<210> SEQ ID NO 83
<211> LENGTH: 8
<212> TYPE: PRT
<213> ORGANISM: Artificial Sequence
<220> FEATURE:
<223> OTHER INFORMATION: myoma T protein 83

<400> SEQUENCE: 83

Pro Gln Pro Lys Lys Lys Pro Leu
1               5


<210> SEQ ID NO 84
<211> LENGTH: 12
<212> TYPE: PRT
<213> ORGANISM: Artificial Sequence
<220> FEATURE:
<223> OTHER INFORMATION: human p53 84

<400> SEQUENCE: 84

Ser Ala Leu Ile Lys Lys Lys Lys Lys Met Ala Pro
1               5                   10


<210> SEQ ID NO 85
<211> LENGTH: 20
<212> TYPE: DNA
<213> ORGANISM: Artificial Sequence
<220> FEATURE:
<223> OTHER INFORMATION: Mouse sgRNA-1 85

<400> SEQUENCE: 85

gcacccatac cttggagcaa                                                20


<210> SEQ ID NO 86
<211> LENGTH: 20
<212> TYPE: DNA
<213> ORGANISM: Artificial Sequence
<220> FEATURE:
<223> OTHER INFORMATION: sgRNA-2 86
```

<400> SEQUENCE: 86
cccatacctt ggagcaacgg 20

<210> SEQ ID NO 87
<211> LENGTH: 20
<212> TYPE: DNA
<213> ORGANISM: Artificial Sequence
<220> FEATURE:
<223> OTHER INFORMATION: sgRNA-3 87

<400> SEQUENCE: 87
gctcgccctc ccgtcccagg 20

<210> SEQ ID NO 88
<211> LENGTH: 20
<212> TYPE: DNA
<213> ORGANISM: Artificial Sequence
<220> FEATURE:
<223> OTHER INFORMATION: Human sgRNA-1 88

<400> SEQUENCE: 88
gttggtcccc aaagtcccca 20

<210> SEQ ID NO 89
<211> LENGTH: 20
<212> TYPE: DNA
<213> ORGANISM: Artificial Sequence
<220> FEATURE:
<223> OTHER INFORMATION: sgRNA-2 89

<400> SEQUENCE: 89
gctccggcag cagatggcaa 20

<210> SEQ ID NO 90
<211> LENGTH: 20
<212> TYPE: DNA
<213> ORGANISM: Artificial Sequence
<220> FEATURE:
<223> OTHER INFORMATION: sgRNA-3 90

<400> SEQUENCE: 90
tctttgactc taaggcccaa 20

<210> SEQ ID NO 91
<211> LENGTH: 20
<212> TYPE: DNA
<213> ORGANISM: Artificial Sequence
<220> FEATURE:
<223> OTHER INFORMATION: Human sgRNA-1 91

<400> SEQUENCE: 91
catgtggcct ggtcaacaag 20

<210> SEQ ID NO 92
<211> LENGTH: 20
<212> TYPE: DNA
<213> ORGANISM: Artificial Sequence
<220> FEATURE:
<223> OTHER INFORMATION: sgRNA-2 92

<400> SEQUENCE: 92
tgtgctggct tccatgaagg 20

<210> SEQ ID NO 93
<211> LENGTH: 20

<212> TYPE: DNA
<213> ORGANISM: Artificial Sequence
<220> FEATURE:
<223> OTHER INFORMATION: sgRNA-3 93

<400> SEQUENCE: 93
tagatcgaag acatgtggct 20

<210> SEQ ID NO 94
<211> LENGTH: 20
<212> TYPE: DNA
<213> ORGANISM: Artificial Sequence
<220> FEATURE:
<223> OTHER INFORMATION: Human sgRNA-1 94

<400> SEQUENCE: 94
tgaaaacaag agcaaggccg 20

<210> SEQ ID NO 95
<211> LENGTH: 20
<212> TYPE: DNA
<213> ORGANISM: Artificial Sequence
<220> FEATURE:
<223> OTHER INFORMATION: sgRNA-2 95

<400> SEQUENCE: 95
gcgccgtagc ctcagcctga 20

<210> SEQ ID NO 96
<211> LENGTH: 20
<212> TYPE: DNA
<213> ORGANISM: Artificial Sequence
<220> FEATURE:
<223> OTHER INFORMATION: sgRNA-3 96

<400> SEQUENCE: 96
ggcgcatgtg aactccctgg 20

<210> SEQ ID NO 97
<211> LENGTH: 20
<212> TYPE: DNA
<213> ORGANISM: Artificial Sequence
<220> FEATURE:
<223> OTHER INFORMATION: sgRNA-1 97

<400> SEQUENCE: 97
ggtcagctac tgggacaccg 20

<210> SEQ ID NO 98
<211> LENGTH: 20
<212> TYPE: DNA
<213> ORGANISM: Artificial Sequence
<220> FEATURE:
<223> OTHER INFORMATION: sgRNA-2 98

<400> SEQUENCE: 98
agtgatgttg aggaagagga 20

<210> SEQ ID NO 99
<211> LENGTH: 20
<212> TYPE: DNA
<213> ORGANISM: Artificial Sequence
<220> FEATURE:
<223> OTHER INFORMATION: sgRNA-3 99

<400> SEQUENCE: 99
gagcttcctg aattaaactt 20

<210> SEQ ID NO 100
<211> LENGTH: 20
<212> TYPE: DNA
<213> ORGANISM: Artificial Sequence
<220> FEATURE:
<223> OTHER INFORMATION: Human sgRNA-1 100

<400> SEQUENCE: 100
catagacccc tgttgtaaga 20

<210> SEQ ID NO 101
<211> LENGTH: 20
<212> TYPE: DNA
<213> ORGANISM: Artificial Sequence
<220> FEATURE:
<223> OTHER INFORMATION: sgRNA-2 101

<400> SEQUENCE: 101
aggaagtcag aatctgggca 20

<210> SEQ ID NO 102
<211> LENGTH: 20
<212> TYPE: DNA
<213> ORGANISM: Artificial Sequence
<220> FEATURE:
<223> OTHER INFORMATION: sgRNA-3 102

<400> SEQUENCE: 102
tggcttgcct tggatttcag 20

<210> SEQ ID NO 103
<211> LENGTH: 20
<212> TYPE: DNA
<213> ORGANISM: Artificial Sequence
<220> FEATURE:
<223> OTHER INFORMATION: Human sgRNA-1 103

<400> SEQUENCE: 103
ggtaggggaa gaccaccgag 20

<210> SEQ ID NO 104
<211> LENGTH: 20
<212> TYPE: DNA
<213> ORGANISM: Artificial Sequence
<220> FEATURE:
<223> OTHER INFORMATION: sgRNA-2 104

<400> SEQUENCE: 104
gtatttctac tgcgacgagg 20

<210> SEQ ID NO 105
<211> LENGTH: 20
<212> TYPE: DNA
<213> ORGANISM: Artificial Sequence
<220> FEATURE:
<223> OTHER INFORMATION: sgRNA-3 105

<400> SEQUENCE: 105
cttcggggag acaacgacgg 20

<210> SEQ ID NO 106
<211> LENGTH: 20
<212> TYPE: DNA
<213> ORGANISM: Artificial Sequence
<220> FEATURE:
<223> OTHER INFORMATION: Human sgRNA-1 106

<400> SEQUENCE: 106
tcccttctca ggattcctac 20

<210> SEQ ID NO 107
<211> LENGTH: 20
<212> TYPE: DNA
<213> ORGANISM: Artificial Sequence
<220> FEATURE:
<223> OTHER INFORMATION: sgRNA-2 107

<400> SEQUENCE: 107
agatattcac cattataggt 20

<210> SEQ ID NO 108
<211> LENGTH: 20
<212> TYPE: DNA
<213> ORGANISM: Artificial Sequence
<220> FEATURE:
<223> OTHER INFORMATION: sgRNA-3 108

<400> SEQUENCE: 108
aattactact tgcttcctgt 20

<210> SEQ ID NO 109
<211> LENGTH: 20
<212> TYPE: DNA
<213> ORGANISM: Artificial Sequence
<220> FEATURE:
<223> OTHER INFORMATION: Human sgRNA-1 109

<400> SEQUENCE: 109
ggtcggtctc cgagtccccg 20

<210> SEQ ID NO 110
<211> LENGTH: 20
<212> TYPE: DNA
<213> ORGANISM: Artificial Sequence
<220> FEATURE:
<223> OTHER INFORMATION: sgRNA-2 110

<400> SEQUENCE: 110
gatgatgtac ctctgccagc 20

<210> SEQ ID NO 111
<211> LENGTH: 20
<212> TYPE: DNA
<213> ORGANISM: Artificial Sequence
<220> FEATURE:
<223> OTHER INFORMATION: sgRNA-3 111

<400> SEQUENCE: 111
tcagatcgtg cacgtccgcg 20

<210> SEQ ID NO 112
<211> LENGTH: 42
<212> TYPE: DNA
<213> ORGANISM: Artificial Sequence
<220> FEATURE:
<223> OTHER INFORMATION: Cas-protein 112

<400> SEQUENCE: 112
guuuuagagc uagaaauagc aaguuaaaau aaggcuaguc cg 42

<210> SEQ ID NO 113
<211> LENGTH: 42
<212> TYPE: DNA
<213> ORGANISM: Artificial Sequence
<220> FEATURE:
<223> OTHER INFORMATION: Cas-protein 113
<220> FEATURE:
<221> NAME/KEY: misc_feature
<222> LOCATION: (1)..(1)
<223> OTHER INFORMATION: n is a, c, g, t or u
<220> FEATURE:
<221> NAME/KEY: misc_feature
<222> LOCATION: (5)..(22)
<223> OTHER INFORMATION: n is a, c, g, t or u
<220> FEATURE:
<221> NAME/KEY: misc_feature
<222> LOCATION: (26)..(26)
<223> OTHER INFORMATION: n is a, c, g, t or u
<220> FEATURE:
<221> NAME/KEY: misc_feature
<222> LOCATION: (28)..(30)
<223> OTHER INFORMATION: n is a, c, g, t or u
<220> FEATURE:
<221> NAME/KEY: misc_feature
<222> LOCATION: (32)..(37)
<223> OTHER INFORMATION: n is a, c, g, t or u
<220> FEATURE:
<221> NAME/KEY: misc_feature
<222> LOCATION: (39)..(41)
<223> OTHER INFORMATION: n is a, c, g, t or u

<400> SEQUENCE: 113
nuuunnnnnn nnnnnnnnnn nnguunannn annnnnngnn ng 42

<210> SEQ ID NO 114
<211> LENGTH: 39
<212> TYPE: DNA
<213> ORGANISM: Artificial Sequence
<220> FEATURE:
<223> OTHER INFORMATION: nucleic acid 114

<400> SEQUENCE: 114
uuaucaacuu gaaaaagugg caccgagucg gugcuuuuu 39

<210> SEQ ID NO 115
<211> LENGTH: 39
<212> TYPE: DNA
<213> ORGANISM: Artificial Sequence
<220> FEATURE:
<223> OTHER INFORMATION: nucleic acid 115
<220> FEATURE:
<221> NAME/KEY: misc_feature
<222> LOCATION: (4)..(5)
<223> OTHER INFORMATION: n is a, c, g, t or u
<220> FEATURE:
<221> NAME/KEY: misc_feature
<222> LOCATION: (7)..(39)
<223> OTHER INFORMATION: n is a, c, g, t or u

<400> SEQUENCE: 115
uuannannnn nnnnnnnnnn nnnnnnnnnn nnnnnnnnn 39

<210> SEQ ID NO 116
<211> LENGTH: 42
<212> TYPE: DNA
<213> ORGANISM: Artificial Sequence
<220> FEATURE:
<223> OTHER INFORMATION: HY-VTM3 116
<220> FEATURE:
<221> NAME/KEY: misc_feature
<222> LOCATION: (1)..(3)
<223> OTHER INFORMATION: phosphorothioate modified pentose sugar
<220> FEATURE:
<221> NAME/KEY: misc_feature
<222> LOCATION: (6)..(11)
<223> OTHER INFORMATION: phosphorothioate modified pentose sugar
<220> FEATURE:
<221> NAME/KEY: misc_feature
<222> LOCATION: (13)..(14)
<223> OTHER INFORMATION: phosphorothioate modified pentose sugar
<220> FEATURE:
<221> NAME/KEY: misc_feature
<222> LOCATION: (17)..(18)
<223> OTHER INFORMATION: phosphorothioate modified pentose sugar

<400> SEQUENCE: 116
gacccccucc accccgccuc guuuuagagc uaugcuguuu ug 42

<210> SEQ ID NO 117
<211> LENGTH: 42
<212> TYPE: DNA
<213> ORGANISM: Artificial Sequence
<220> FEATURE:
<223> OTHER INFORMATION: HY-VTM4 117
<220> FEATURE:
<221> NAME/KEY: misc_feature
<222> LOCATION: (1)..(3)
<223> OTHER INFORMATION: phosphorothioate modified pentose sugar
<220> FEATURE:
<221> NAME/KEY: misc_feature
<222> LOCATION: (6)..(11)
<223> OTHER INFORMATION: phosphorothioate modified pentose sugar
<220> FEATURE:
<221> NAME/KEY: misc_feature
<222> LOCATION: (13)..(14)
<223> OTHER INFORMATION: phosphorothioate modified pentose sugar
<220> FEATURE:
<221> NAME/KEY: misc_feature
<222> LOCATION: (17)..(18)
<223> OTHER INFORMATION: phosphorothioate modified pentose sugar

<400> SEQUENCE: 117
gacccccucc accccgccuc guuuuagagc uaugcuguuu ug 42

<210> SEQ ID NO 118
<211> LENGTH: 42
<212> TYPE: DNA
<213> ORGANISM: Artificial Sequence
<220> FEATURE:
<223> OTHER INFORMATION: HY-VTM6 118
<220> FEATURE:
<221> NAME/KEY: misc_feature
<222> LOCATION: (1)..(11)
<223> OTHER INFORMATION: phosphorothioate modified pentose sugar
<220> FEATURE:
<221> NAME/KEY: misc_feature
<222> LOCATION: (13)..(14)
<223> OTHER INFORMATION: phosphorothioate modified pentose sugar
<220> FEATURE:
<221> NAME/KEY: misc_feature
<222> LOCATION: (17)..(18)
<223> OTHER INFORMATION: phosphorothioate modified pentose sugar

<400> SEQUENCE: 118
gacccccucc accccgccuc guuuuagagc uaugcuguuu ug 42

<210> SEQ ID NO 119
<211> LENGTH: 42
<212> TYPE: RNA
<213> ORGANISM: Artificial Sequence
<220> FEATURE:
<223> OTHER INFORMATION: HY-EMXM3 119
<220> FEATURE:
<221> NAME/KEY: misc_feature
<222> LOCATION: (1)..(3)

<223> OTHER INFORMATION: phosphorothioate modified pentose sugar
<220> FEATURE:
<221> NAME/KEY: misc_feature
<222> LOCATION: (6)..(11)
<223> OTHER INFORMATION: phosphorothioate modified pentose sugar
<220> FEATURE:
<221> NAME/KEY: misc_feature
<222> LOCATION: (13)..(14)
<223> OTHER INFORMATION: phosphorothioate modified pentose sugar
<220> FEATURE:
<221> NAME/KEY: misc_feature
<222> LOCATION: (17)..(18)
<223> OTHER INFORMATION: phosphorothioate modified pentose sugar

<400> SEQUENCE: 119
gaguccgagc agaagaagaa guuuuagagc uaugcuguuu ug 42

<210> SEQ ID NO 120
<211> LENGTH: 42
<212> TYPE: RNA
<213> ORGANISM: Artificial Sequence
<220> FEATURE:
<223> OTHER INFORMATION: HY-EMXM4 120
<220> FEATURE:
<221> NAME/KEY: misc_feature
<222> LOCATION: (1)..(3)
<223> OTHER INFORMATION: fluorinated base
<220> FEATURE:
<221> NAME/KEY: misc_feature
<222> LOCATION: (6)..(11)
<223> OTHER INFORMATION: fluorinated base
<220> FEATURE:
<221> NAME/KEY: misc_feature
<222> LOCATION: (13)..(14)
<223> OTHER INFORMATION: fluorinated base
<220> FEATURE:
<221> NAME/KEY: misc_feature
<222> LOCATION: (17)..(18)
<223> OTHER INFORMATION: fluorinated base

<400> SEQUENCE: 120
gaguccgagc agaagaagaa guuuuagagc uaugcuguuu ug 42

<210> SEQ ID NO 121
<211> LENGTH: 42
<212> TYPE: RNA
<213> ORGANISM: Artificial Sequence
<220> FEATURE:
<223> OTHER INFORMATION: HY-EMXM5 121
<220> FEATURE:
<221> NAME/KEY: misc_feature
<222> LOCATION: (1)..(1)
<223> OTHER INFORMATION: phosphorothioate modified pentose sugar
<220> FEATURE:
<221> NAME/KEY: misc_feature
<222> LOCATION: (3)..(8)
<223> OTHER INFORMATION: phosphorothioate modified pentose sugar
<220> FEATURE:
<221> NAME/KEY: misc_feature
<222> LOCATION: (10)..(11)
<223> OTHER INFORMATION: phosphorothioate modified pentose sugar
<220> FEATURE:
<221> NAME/KEY: misc_feature
<222> LOCATION: (14)..(15)
<223> OTHER INFORMATION: phosphorothioate modified pentose sugar

<400> SEQUENCE: 121
gaguccgagc agaagaagaa guuuuagagc uaugcuguuu ug 42

<210> SEQ ID NO 122
<211> LENGTH: 42
<212> TYPE: RNA
<213> ORGANISM: Artificial Sequence
<220> FEATURE:
<223> OTHER INFORMATION: HY-EMXM6 122
<220> FEATURE:
<221> NAME/KEY: misc_feature
<222> LOCATION: (1)..(11)
<223> OTHER INFORMATION: phosphorothioate modified pentose sugar
<220> FEATURE:
<221> NAME/KEY: misc_feature
<222> LOCATION: (13)..(14)
<223> OTHER INFORMATION: phosphorothioate modified pentose sugar
<220> FEATURE:
<221> NAME/KEY: misc_feature
<222> LOCATION: (17)..(18)
<223> OTHER INFORMATION: phosphorothioate modified pentose sugar

<400> SEQUENCE: 122
gaguccgagc agaagaagaa guuuuagagc uaugcuguuu ug 42

<210> SEQ ID NO 123
<211> LENGTH: 42
<212> TYPE: RNA
<213> ORGANISM: Artificial Sequence
<220> FEATURE:
<223> OTHER INFORMATION: HBBM3 crRNA

<400> SEQUENCE: 123
cuugccccac agggcaguaa guuuuagagc uaugcuguuu ug 42

<210> SEQ ID NO 124
<211> LENGTH: 42
<212> TYPE: RNA
<213> ORGANISM: Artificial Sequence
<220> FEATURE:
<223> OTHER INFORMATION: HY-HBBM4

<400> SEQUENCE: 124
cuugccccac agggcaguaa guuuuagagc uaugcuguuu ug 42

<210> SEQ ID NO 125
<211> LENGTH: 42
<212> TYPE: RNA
<213> ORGANISM: Artificial Sequence
<220> FEATURE:
<223> OTHER INFORMATION: HY-HBBM5
<220> FEATURE:
<221> NAME/KEY: misc_feature
<222> LOCATION: (1)..(3)
<223> OTHER INFORMATION: phosphorothioated deoxyribonucleoside

<400> SEQUENCE: 125
cuugccccac agggcaguaa guuuuagagc uaugcuguuu ug 42

<210> SEQ ID NO 126
<211> LENGTH: 42
<212> TYPE: RNA
<213> ORGANISM: Artificial Sequence
<220> FEATURE:
<223> OTHER INFORMATION: PC-9 cRNA

<400> SEQUENCE: 126
ggcugaugag gccgcacaug guuuuagagc uaugcuguuu ug 42

<210> SEQ ID NO 127
<211> LENGTH: 42
<212> TYPE: RNA
<213> ORGANISM: Artificial Sequence
<220> FEATURE:
<223> OTHER INFORMATION: HY-PC9M1
<220> FEATURE:

<221> NAME/KEY: misc_feature
<222> LOCATION: (6)..(7)
<223> OTHER INFORMATION: phosphorothioated ribnucleoside

<400> SEQUENCE: 127
ggcugaugag gccgcacaug guuuuagagc uaugcuguuu ug 42

<210> SEQ ID NO 128
<211> LENGTH: 42
<212> TYPE: RNA
<213> ORGANISM: Artificial Sequence
<220> FEATURE:
<223> OTHER INFORMATION: HY-PC9M2
<220> FEATURE:
<221> NAME/KEY: misc_feature
<222> LOCATION: (8)..(11)
<223> OTHER INFORMATION: fluorinated nucleotide

<400> SEQUENCE: 128
ggcugaugag gccgcacaug guuuuagagc uaugcuguuu ug 42

<210> SEQ ID NO 129
<211> LENGTH: 100
<212> TYPE: RNA
<213> ORGANISM: Artificial Sequence
<220> FEATURE:
<223> OTHER INFORMATION: sgHBB1

<400> SEQUENCE: 129
cuugccccac agggcaguaa guuuuagagc uagaaauagc aaguuaaaau aaggcuaguc 60
cguuaucaac uugaaaaagu ggcaccgagu cggugcuuuu 100

<210> SEQ ID NO 130
<211> LENGTH: 100
<212> TYPE: RNA
<213> ORGANISM: Artificial Sequence
<220> FEATURE:
<223> OTHER INFORMATION: sgHBB2
<220> FEATURE:
<221> NAME/KEY: misc_feature
<222> LOCATION: (82)..(100)
<223> OTHER INFORMATION: deoxyribonucleic nucleoside

<400> SEQUENCE: 130
cuugccccac agggcaguaa guuuuagagc uagaaauagc aaguuaaaau aaggcuaguc 60
cguuaucaac uugaaaaagu ggcaccgagu cggugcuuuu 100

<210> SEQ ID NO 131
<211> LENGTH: 100
<212> TYPE: RNA
<213> ORGANISM: Artificial Sequence
<220> FEATURE:
<223> OTHER INFORMATION: sgHBB3
<220> FEATURE:
<221> NAME/KEY: misc_feature
<222> LOCATION: (1)..(3)
<223> OTHER INFORMATION: 2'-O-methylation

<400> SEQUENCE: 131
cuugccccac agggcaguaa guuuuagagc uagaaauagc aaguuaaaau aaggcuaguc 60
cguuaucaac uugaaaaagu ggcaccgagu cggugcuuuu 100

<210> SEQ ID NO 132
<211> LENGTH: 100
<212> TYPE: RNA
<213> ORGANISM: Artificial Sequence
<220> FEATURE:
<223> OTHER INFORMATION: HBB4
<220> FEATURE:
<221> NAME/KEY: misc_feature
<222> LOCATION: (6)..(10)
<223> OTHER INFORMATION: phosphorothioate modified nucleoside

<400> SEQUENCE: 132
cuugccccac agggcaguaa guuuuagagc uagaaauagc aaguuaaaau aaggcuaguc 60
cguuaucaac uugaaaaagu ggcaccgagu cggugcuuuu 100

<210> SEQ ID NO 133
<211> LENGTH: 100
<212> TYPE: RNA
<213> ORGANISM: Artificial Sequence
<220> FEATURE:
<223> OTHER INFORMATION: sgHBB5
<220> FEATURE:
<221> NAME/KEY: misc_feature
<222> LOCATION: (1)..(3)
<223> OTHER INFORMATION: fluorinated nucleoside

<400> SEQUENCE: 133
cuugccccac agggcaguaa guuuuagagc uagaaauagc aaguuaaaau aaggcuaguc 60
cguuaucaac uugaaaaagu ggcaccgagu cggugcuuuu 100

<210> SEQ ID NO 134
<211> LENGTH: 42
<212> TYPE: RNA
<213> ORGANISM: Artificial Sequence
<220> FEATURE:
<223> OTHER INFORMATION: HYVT1
<220> FEATURE:
<221> NAME/KEY: misc_feature
<222> LOCATION: (1)..(42)
<223> OTHER INFORMATION: deoxyribonucleotsides with RNA base

<400> SEQUENCE: 134
gacccccucc accccgccuc guuuuagagc uaugcuguuu ug 42

<210> SEQ ID NO 135
<211> LENGTH: 42
<212> TYPE: DNA
<213> ORGANISM: Artificial sequence
<220> FEATURE:
<223> OTHER INFORMATION: HYVT2
<220> FEATURE:
<221> NAME/KEY: misc_feature
<222> LOCATION: (1)..(10)
<223> OTHER INFORMATION: deoxyribonucleic acids
<220> FEATURE:
<221> NAME/KEY: misc_feature
<222> LOCATION: (11)..(42)
<223> OTHER INFORMATION: ribonucleic bases

<400> SEQUENCE: 135
gaccccctcc accccgccuc guuuuagagc uaugcuguuu ug 42

<210> SEQ ID NO 136
<211> LENGTH: 95
<212> TYPE: RNA
<213> ORGANISM: Artificial Sequence
<220> FEATURE:
<223> OTHER INFORMATION: Guide RNA

<400> SEQUENCE: 136
ggaaauuagg ugcgcuuggc guuuuagagc uagaaauagc aaguuaaaau aaggcuagcc 60
guuaucaacu uaaaaagugg cacccagucg gugcu 95

<210> SEQ ID NO 137
<211> LENGTH: 20
<212> TYPE: DNA
<213> ORGANISM: Artificial Sequence
<220> FEATURE:
<223> OTHER INFORMATION: Target DNA for guide RNA

<400> SEQUENCE: 137
gccaagcgca cctaatttcc 20

<210> SEQ ID NO 138
<211> LENGTH: 69
<212> TYPE: RNA
<213> ORGANISM: Artificial Sequence
<220> FEATURE:
<223> OTHER INFORMATION: Guide RNA

<400> SEQUENCE: 138
acgcguuuua gagcuagaaa uagcaaguua aaauaaggcu aguccguuau caacuugaaa 60
aaguguucc 69

<210> SEQ ID NO 139
<211> LENGTH: 20
<212> TYPE: DNA
<213> ORGANISM: Artificial Sequence
<220> FEATURE:
<223> OTHER INFORMATION: sgRNA

<400> SEQUENCE: 139
gcacccatac cttggagcaa 20

<210> SEQ ID NO 140
<211> LENGTH: 20
<212> TYPE: DNA
<213> ORGANISM: Artificial Sequence
<220> FEATURE:
<223> OTHER INFORMATION: sgRNA

<400> SEQUENCE: 140
gcaaacttga tggcaaaccg 20

<210> SEQ ID NO 141
<211> LENGTH: 20
<212> TYPE: DNA
<213> ORGANISM: Artificial Sequence
<220> FEATURE:
<223> OTHER INFORMATION: sgRNA

<400> SEQUENCE: 141
gcacctgaag agtatcacag 20

<210> SEQ ID NO 142
<211> LENGTH: 20
<212> TYPE: DNA
<213> ORGANISM: Artificial Sequence
<220> FEATURE:
<223> OTHER INFORMATION: sgRNA

<400> SEQUENCE: 142
tgtcttgtaa aagaacccag 20